United States Patent
Okano et al.

(10) Patent No.: US 12,274,745 B2
(45) Date of Patent: Apr. 15, 2025

(54) CONJUGATE OF CAPRIN-1 ANTIBODY LINKED TO IMMUNE ACTIVATOR FOR CANCER TREATMENT

(71) Applicant: TORAY INDUSTRIES, INC., Tokyo (JP)

(72) Inventors: Fumiyoshi Okano, Kamakura (JP); Takanori Saito, Kamakura (JP)

(73) Assignee: TORAY INDUSTRIES, INC., Tokyo (JP)

(*) Notice: Subject to any disclaimer, the term of this patent is extended or adjusted under 35 U.S.C. 154(b) by 528 days.

(21) Appl. No.: 16/344,689

(22) PCT Filed: Oct. 27, 2017

(86) PCT No.: PCT/JP2017/038986
§ 371 (c)(1),
(2) Date: Apr. 24, 2019

(87) PCT Pub. No.: WO2018/079740
PCT Pub. Date: May 3, 2018

(65) Prior Publication Data
US 2020/0054762 A1 Feb. 20, 2020

(30) Foreign Application Priority Data
Oct. 28, 2016 (JP) .................. 2016-211376

(51) Int. Cl.
| C07K 16/46 | (2006.01) |
| A61K 31/4745 | (2006.01) |
| A61K 39/39 | (2006.01) |
| A61K 39/395 | (2006.01) |
| A61K 47/68 | (2017.01) |
| A61P 35/02 | (2006.01) |

(52) U.S. Cl.
CPC .......... *A61K 39/39* (2013.01); *A61K 31/4745* (2013.01); *A61K 39/3955* (2013.01); *A61K 47/6803* (2017.08); *A61K 47/6849* (2017.08); *A61P 35/02* (2018.01)

(58) Field of Classification Search
None
See application file for complete search history.

(56) References Cited

U.S. PATENT DOCUMENTS

| 8,951,528 | B2 | 2/2015 | Stoermer et al. | |
| 10,548,988 | B2* | 2/2020 | Li | A61P 35/02 |
| 2011/0123492 | A1 | 5/2011 | Okano et al. | |
| 2011/0256144 | A1 | 10/2011 | Okano et al. | |
| 2012/0301476 | A1 | 11/2012 | Okano et al. | |
| 2012/0321641 | A1 | 12/2012 | Okano et al. | |
| 2014/0154261 | A1 | 6/2014 | Okano et al. | |
| 2014/0314771 | A1 | 10/2014 | Hoves et al. | |
| 2015/0141625 | A1* | 5/2015 | Stoermer | A61K 47/6843 530/391.9 |
| 2015/0174268 | A1 | 6/2015 | Li | |
| 2016/0297889 | A1 | 10/2016 | Okano et al. | |
| 2017/0290923 | A1* | 10/2017 | Li | C07K 16/2818 |

FOREIGN PATENT DOCUMENTS

| CN | 102112146 A | 6/2011 | |
| CN | 102387808 A | 3/2012 | |
| CN | 102821788 A | 12/2012 | |
| CN | 103118678 A | 5/2013 | |
| CN | 103717739 A | 4/2014 | |
| CN | 104220095 A | 12/2014 | |
| CN | 104411329 A | 3/2015 | |
| CN | 104995213 A | 10/2015 | |
| CN | 105452294 A | 3/2016 | |
| EP | 2 399 595 A1 | 12/2011 | |
| EP | 2 532 365 A1 | 12/2012 | |
| EP | 2 740 794 A1 | 6/2014 | |
| EP | 2 818 483 A1 | 12/2014 | |
| EP | 2 832 365 A1 | 2/2015 | |
| JP | 2013-531043 A | 8/2013 | |
| JP | 2015-524399 A | 8/2015 | |
| JP | 2016-516798 A | 6/2016 | |
| KR | 10-2015-0002617 A | 1/2015 | |
| KR | 10-2015-0054768 A | 5/2015 | |
| RU | 2567657 C2 | 11/2015 | |
| WO | WO 2010/016525 A1 | 2/2010 | |
| WO | WO 2010/016526 A1 | 2/2010 | |
| WO | WO 2011/096528 A1 | 8/2011 | |
| WO | WO 2012/009611 A9 | 1/2012 | |
| WO | WO 2013/018891 A1 | 2/2013 | |
| WO | WO 2013/147169 A1 | 10/2013 | |
| WO | WO-2014012479 A1 * | 1/2014 | ......... A61K 31/4745 |

(Continued)

OTHER PUBLICATIONS

UniProtKB-Q14444, CAPR1_Human, version 179, Retrieved onine from <URL:https://www.uniprot.org/uniprot/Q14444>, [retrieved on Mar. 20, 2022], Feb. 23, 2022.*

Lesnova et al., Difluoromethylornithine (DFMO), an Inhibitor of Polyamine Biosynthesis, and Antioxidant N-Acetylcysteine Potentiate Immune Response in Miceto the Recombinant Hepatitis C Virus NS5B Protein, . Int. J. Mol. Sci. 22, 6892. doi.org/10.3390/ijms2213689, 2021.*

Gordon et al., Synthetic TLR Agonists Reveal Functional Differences between Human TLR7 and TLR8 J. Immunol. 174:1259-68, 2005.*

(Continued)

*Primary Examiner* — Claire Kaufman

(74) *Attorney, Agent, or Firm* — Birch, Stewart, Kolasch & Birch, LLP

(57) ABSTRACT

The present invention provides a conjugate of an antibody or a fragment thereof linked to an immune activator, wherein the antibody or the fragment thereof has immunological reactivity with a CAPRIN-1 protein, and a pharmaceutical composition comprising the conjugate as an active ingredient for treatment and/or prevention of a cancer.

11 Claims, No Drawings

Specification includes a Sequence Listing.

(56) References Cited

FOREIGN PATENT DOCUMENTS

| WO | WO 2014/173814 A1 | | 10/2014 |
|---|---|---|---|
| WO | WO 2015/020212 A1 | | 2/2015 |
| WO | WO 2015/103989 | * | 7/2015 |
| WO | WO 2016/034085 A1 | | 3/2016 |
| WO | WO. 2018/009916 A1 | | 1/2018 |

OTHER PUBLICATIONS

Gadd et al.,, Targeted Activation of Toll-Like Receptors: Conjugation of a Toll-Like Receptor 7 Agonist to a Monoclonal Antibody Maintains Antigen Binding and Specificity, Bioconjugate Chem. 26(8):1743-1752, 2015.*
Kawasaki et al., Toll-like receptor signaling pathways, Front. Immunol. 5:461, doi.org/10.3389/fimmu.2014.00461, Sep. 25, 2014.*
Fargion et al., Heterogeneity of Cell Surface Antigen Expression of Human Small Cell Lung Cancer Detected by Monoclonal Antibodies, Canc. Res. 46(5):2633-2638, May 1986.*
Brockoff et al., Differential impact of Cetuximab, Pertuzumab and Trastuzumab on BT474 and SK-BR-3 breast cancer cell proliferation, Cell Prolif. 48:488-507, 2007.*
Kaczanowska et al., TLR agonists: our best frenemy in cancer immunotherapy, J. Leukoc. Biol. 93:847-863, 2013.*
Li et al., Inhibition of non-small cell lung cancer (NSCLC) growth by a novel small molecular inhibitor of EGFR, doi: 10.18632/oncotarget.3155, Oncotarget, 6(9): 6749-6761, Mar. 30, 2015.*
Cho et al., Cetuximab response of lung cancer-derived EGF receptor mutants is associated with asymmetric dimerization, doi: 10.1158/0008-5472.CAN-13-1145, Canc. Res. 73(22): 6770-6779, Nov. 15, 2013.*
Khongorzul et al., Antibody-Drug Conjugates: A Comprehensive ReviewMol. Canc. Res. 18(1):3-19, 2020.*
The Human Protein Atlas, ErbB2, Cell Line, Retrived onine: <URL:https://www.proteinatlas.org/ENSG00000141736-ERBB2/cell+line>. [retrieved on Apr. 16, 2024], 2024.*
The Human Protein Atlas, Caprin-1, Cell Line, Retrived onine: <URL:https://www.proteinatlas.org/ENSG00000135387-CAPRIN1/ cell+line#lymphoma>. [retrieved on Apr. 16, 2024], 2024.*
The Human Protein Atlas, EGFR, Cell Line, Retrived onine: <URL:https://www.proteinatlas.org/ENSG00000146648-EGFR/cell+line>. [retrieved on Apr. 16, 2024], 2024.*

Cheadle E. et al. "A TLR7 agonist enhances the anti-tumour efficacy of obinutuzumab through an NK cell/CD4 dependent mechanism in a murine lymphoma model", European Journal of Cancer, Jul. 2016, vol. 61, Suppl. 1, S211 Abs. No. 910, total 1 page.
Jain et al. "Current ADC Linker Chemistry", Pharm Res., Nov. 2015, 32 (11): 3526-40, total 15 pages.
Thomas et al. "Antibody-drug conjugates for cancer therapy", Lancet Oncol, Jun. 2016, 17: e254-62, total 9 pages.
Van de Donk et al. "Brentuximab vedotin", MAbs, 2012, 4 (4): 458-65, total 8 pages.
Verma et al. "Trastuzumab Emtansine for HER2-Positive Advanced Breast Cancer", The New England Journal of Medicine, Nov. 8, 2012, vol. 367, No. 19, (8), pp. 1783-1791, total 9 pages.
Decision to Grant issued Dec. 7, 2021, in Russian Patent Application No. 2019116174/10(030927).
Extended European Search Report issued May 13, 2020, in European Patent Application No. 17864888.7.
Galluzzi et al., "Trial Watch: Experimental Toll-like receptor agonists for cancer therapy," OncoImmunology (2012) vol. 1, No. 5, pp. 699-739.
Office Action issued Jul. 9, 2021, in Russian Patent Application No. 2019116174/10(030927).
Sabile et al., "Caprin-1, a novel Cyr61-interacting protein, promotes osteosarcoma tumor growth and lung metastasis in mice," Biochimica et Biophysica Acta (2013), vol. 1832, pp. 1173-1182.
Yao et al., "Methods to Design and Synthesize Antibody-Drug Conjugates (ADCs)," Int. J. Mol. Sci. (2016), vol. 17, No. 194, pp. 1-16.
International Search Report mailed Jan. 23, 2018, in PCT/JP2017/038986.
Written Opinion of the International Searching Authority mailed Jan. 23, 2018, in PCT/JP2017/038986.
European Communication pursuant to Article 94(3) EPC for corresponding European Application No. 17864888.7, dated Jun. 9, 2023.
English translation of Mexican Office Action for Mexican Application No. MX/a/2019/004779, dated Mar. 22, 2023.
Smits et al., "The Use of TLR7 and TLR8 Ligands for the Enhancement of Cancer Immunotherapy," The Oncologist, vol. 13, 2008, pp. 859-875.
Office Action issued Mar. 14, 2022, in Chinese Patent Application No. 201780066545.4.

* cited by examiner

SEQUENCE LISTING

```
<160> NUMBER OF SEQ ID NOS: 309

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)

<400> SEQUENCE: 1
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccacccttg cccctcagc tgcccactcg tgatttccag cggcctccgc     180 gcgcgcacg atg ccc tcg gcc acc agc cac agc ggg agc ggc agc aag tcg    231
           Met Pro Ser Ala Thr Ser His Ser Gly Ser Gly Ser Lys Ser
             1               5                  10 tcc gga ccg cca ccg ccg tcg ggt tcc tcc ggg agt gag gcg gcc gcg       279
Ser Gly Pro Pro Pro Pro Ser Gly Ser Ser Gly Ser Glu Ala Ala Ala
 15                  20                  25                  30 gga gcc ggg gcc gcc gcg ccg gct tct cag cac ccc gca acc ggc acc       327
Gly Ala Gly Ala Ala Ala Pro Ala Ser Gln His Pro Ala Thr Gly Thr
                 35                  40                  45 ggc gct gtc cag acc gag gcc atg aag cag att ctc ggg gtg atc gac       375
Gly Ala Val Gln Thr Glu Ala Met Lys Gln Ile Leu Gly Val Ile Asp
             50                  55                  60 aag aaa ctt cgg aac ctg gag aag aaa aag ggt aag ctt gat gat tac       423
Lys Lys Leu Arg Asn Leu Glu Lys Lys Lys Gly Lys Leu Asp Asp Tyr
 65                  70                  75 cag gaa cga atg aac aaa ggg gaa agg ctt aat caa gat cag ctg gat       471
Gln Glu Arg Met Asn Lys Gly Glu Arg Leu Asn Gln Asp Gln Leu Asp
 80                  85                  90 gcc gtt tct aag tac cag gaa gtc aca aat aat ttg gag ttt gca aaa       519
Ala Val Ser Lys Tyr Gln Glu Val Thr Asn Asn Leu Glu Phe Ala Lys
 95                 100                 105                 110 gaa tta cag agg agt ttc atg gca cta agt caa gat att cag aaa aca       567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa       615
Ile Lys Lys Thr Ala Arg Arg Glu Gln Leu Met Arg Glu Glu Ala Glu
                130                 135                 140 cag aaa cgt tta aaa act gta ctt gag cta cag tat gtt ttg gac aaa       663
Gln Lys Arg Leu Lys Thr Val Leu Glu Leu Gln Tyr Val Leu Asp Lys
            145                 150                 155 ttg gga gat gat gaa gtg cgg act gac ctg aaa caa ggt ttg aat gga       711
Leu Gly Asp Asp Glu Val Arg Thr Asp Leu Lys Gln Gly Leu Asn Gly
        160                 165                 170 gtg cca ata ttg tcc gaa gag gag ttg tca ttg ttg gat gaa ttc tat       759
Val Pro Ile Leu Ser Glu Glu Glu Leu Ser Leu Leu Asp Glu Phe Tyr
175                 180                 185                 190
```

```
                                                       -continued aag cta gta gac cct gaa cgg gac atg agc ttg agg ttg aat gaa cag      807
Lys Leu Val Asp Pro Glu Arg Asp Met Ser Leu Arg Leu Asn Glu Gln
            195                 200                 205 tat gaa cat gcc tcc att cac ctg tgg gac ctg ctg gaa ggg aag gaa      855
Tyr Glu His Ala Ser Ile His Leu Trp Asp Leu Leu Glu Gly Lys Glu
        210                 215                 220 aaa cct gta tgt gga acc acc tat aaa gtt cta aag gaa att gtt gag      903
Lys Pro Val Cys Gly Thr Thr Tyr Lys Val Leu Lys Glu Ile Val Glu
    225                 230                 235 cgt gtt ttt cag tca aac tac ttt gac agc acc cac aac cac cag aat      951
Arg Val Phe Gln Ser Asn Tyr Phe Asp Ser Thr His Asn His Gln Asn
240                 245                 250 ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285 agt gaa gtt gaa tca aca gag tat gta aat aga cag ttc atg gca gaa     1095
Ser Glu Val Glu Ser Thr Glu Tyr Val Asn Arg Gln Phe Met Ala Glu
            290                 295                 300 aca cag ttc acc agt ggt gaa aag gag cag gta gat gag tgg aca gtt     1143
Thr Gln Phe Thr Ser Gly Glu Lys Glu Gln Val Asp Glu Trp Thr Val
        305                 310                 315 gaa acg gtt gag gtg gta aat tca ctc cag cag caa cct cag gct gca     1191
Glu Thr Val Glu Val Val Asn Ser Leu Gln Gln Gln Pro Gln Ala Ala
    320                 325                 330 tcc cct tca gta cca gag ccc cac tct ttg act cca gtg gct cag gca     1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg     1287
Asp Pro Leu Val Arg Arg Gln Arg Val Gln Asp Leu Met Ala Gln Met
                355                 360                 365 cag ggt ccc tat aat ttc ata cag gat tca atg ctg gat ttt gaa aat     1335
Gln Gly Pro Tyr Asn Phe Ile Gln Asp Ser Met Leu Asp Phe Glu Asn
            370                 375                 380 cag aca ctt gat cct gcc att gta tct gca cag cct atg aat cca aca     1383
Gln Thr Leu Asp Pro Ala Ile Val Ser Ala Gln Pro Met Asn Pro Thr
        385                 390                 395 caa aac atg gac atg ccc cag ctg gtt tgc cct cca gtt cat tct gaa     1431
Gln Asn Met Asp Met Pro Gln Leu Val Cys Pro Pro Val His Ser Glu
    400                 405                 410 tct aga ctt gct cag cct aat caa gtt cct gta caa cca gaa gcg aca     1479
Ser Arg Leu Ala Gln Pro Asn Gln Val Pro Val Gln Pro Glu Ala Thr
415                 420                 425                 430 cag gtt cct ttg gta tca tcc aca agt gag ggg tac aca gca tct caa     1527
Gln Val Pro Leu Val Ser Ser Thr Ser Glu Gly Tyr Thr Ala Ser Gln
                435                 440                 445 ccc ttg tac cag cct tct cat gct aca gag caa cga cca cag aag gaa     1575
Pro Leu Tyr Gln Pro Ser His Ala Thr Glu Gln Arg Pro Gln Lys Glu
            450                 455                 460 cca att gat cag att cag gca aca atc tct tta aat aca gac cag act     1623
Pro Ile Asp Gln Ile Gln Ala Thr Ile Ser Leu Asn Thr Asp Gln Thr
        465                 470                 475 aca gca tca tca tcc ctt cct gct gcg tct cag cct caa gta ttt cag     1671
Thr Ala Ser Ser Ser Leu Pro Ala Ala Ser Gln Pro Gln Val Phe Gln
    480                 485                 490 gct ggg aca agc aaa cct tta cat agc agt gga atc aat gta aat gca     1719
Ala Gly Thr Ser Lys Pro Leu His Ser Ser Gly Ile Asn Val Asn Ala
```

-continued

| | |
|---|---|
| gct cca ttc caa tcc atg caa acg gtg ttc aat atg aat gcc cca gtt<br>Ala Pro Phe Gln Ser Met Gln Thr Val Phe Asn Met Asn Ala Pro Val<br>                      515                            520                            525 | 1767 |
| cct cct gtt aat gaa cca gaa act tta aaa cag caa aat cag tac cag<br>Pro Pro Val Asn Glu Pro Glu Thr Leu Lys Gln Gln Asn Gln Tyr Gln<br>                      530                            535                          540 | 1815 |
| gcc agt tat aac cag agc ttt tct agt cag cct cac caa gta gaa caa<br>Ala Ser Tyr Asn Gln Ser Phe Ser Ser Gln Pro His Gln Val Glu Gln<br>                      545                            550                          555 | 1863 |
| aca gag ctt cag caa gaa cag ctt caa aca gtg gtt ggc act tac cat<br>Thr Glu Leu Gln Gln Glu Gln Leu Gln Thr Val Val Gly Thr Tyr His<br>            560                            565                          570 | 1911 |
| ggt tcc cca gac cag tcc cat caa gtg act ggt aac cac cag cag cct<br>Gly Ser Pro Asp Gln Ser His Gln Val Thr Gly Asn His Gln Gln Pro<br>575                      580                            585                          590 | 1959 |
| cct cag cag aac act gga ttt cca cgt agc aat cag ccc tat tac aat<br>Pro Gln Gln Asn Thr Gly Phe Pro Arg Ser Asn Gln Pro Tyr Tyr Asn<br>                      595                            600                          605 | 2007 |
| agt cgt ggt gtg tct cgt gga ggc tcc cgt ggt gct aga ggc ttg atg<br>Ser Arg Gly Val Ser Arg Gly Gly Ser Arg Gly Ala Arg Gly Leu Met<br>            610                            615                          620 | 2055 |
| aat gga tac cgg ggc cct gcc aat gga ttc aga gga gga tat gat ggt<br>Asn Gly Tyr Arg Gly Pro Ala Asn Gly Phe Arg Gly Gly Tyr Asp Gly<br>                      625                            630                          635 | 2103 |
| tac cgc cct tca ttc tct aac act cca aac agt ggt tat aca cag tct<br>Tyr Arg Pro Ser Phe Ser Asn Thr Pro Asn Ser Gly Tyr Thr Gln Ser<br>            640                            645                          650 | 2151 |
| cag ttc agt gct ccc cgg gat tac tct ggc tat caa cgg gat gga tat<br>Gln Phe Ser Ala Pro Arg Asp Tyr Ser Gly Tyr Gln Arg Asp Gly Tyr<br>655                      660                            665                          670 | 2199 |
| cag cag aat ttc aag cga ggc tct ggg cag agt gga cca cgg gga gcc<br>Gln Gln Asn Phe Lys Arg Gly Ser Gly Gln Ser Gly Pro Arg Gly Ala<br>                      675                            680                          685 | 2247 |
| cca cga ggt cgt gga ggg ccc cca aga ccc aac aga ggg atg ccg caa<br>Pro Arg Gly Arg Gly Gly Pro Pro Arg Pro Asn Arg Gly Met Pro Gln<br>            690                            695                          700 | 2295 |
| atg aac act cag caa gtg aat taa tctgattcac aggattatgt ttaatcgcca<br>Met Asn Thr Gln Gln Val Asn<br>            705 | 2349 |
| aaaacacact ggccagtgta ccataatatg ttaccagaag agttattatc tatttgttct | 2409 |
| ccctttcagg aaacttattg taaagggact gttttcatcc cataaagaca ggactacaat | 2469 |
| tgtcagcttt ctattacctg gatatggaag gaaactattt ttactctgca tgttctgtcc | 2529 |
| taagcgtcat cttgagcctt gcacatgata ctcagattcc tcacccttgc ttaggagtaa | 2589 |
| aacaatatac tttacagggt gataataatc tccatagtta tttgaagtgg cttgaaaaag | 2649 |
| gcaagattga cttttatgac attggataaa atctacaaat cagccctcga gttattcaat | 2709 |
| gataactgac aaactaaatt atttccctag aaaggaagat gaaggagtg gagtgtggtt | 2769 |
| tggcagaaca actgcatttc acagcttttc cagttaaatt ggagcactga acgttcagat | 2829 |
| gcataccaaa ttatgcatgg gtcctaatca cacatataag gctggctacc agctttgaca | 2889 |
| cagcactgtt catctggcca aacaactgtg gttaaaaaca catgtaaaat gcttttttaac | 2949 |
| agctgatact gtataagaca aagccaagat gcaaaattag gctttgattg gcacttttg | 3009 |
| aaaaatatgc aacaaatatg ggatgtaatc cggatggccg cttctgtact taatgtgaaa | 3069 |
| tatttagata ccttttgaa cacttaacag tttctttgag acaatgactt tgtaaggat | 3129 |

```
tggtactatc tatcattcct tatgacatgt acattgtctg tcactaatcc ttggattttg    3189
ctgtattgtc acctaaattg gtacaggtac tgatgaaaat ctctagtgga taatcataac    3249
actctcggtc acatgttttt ccttcagctt gaaagctttt ttttaaaagg aaaagatacc    3309
aaatgcctgc tgctaccacc cttttcaatt gctatctttt gaaaggcacc agtatgtgtt    3369
ttagattgat ttccctgttt cagggaaatc acggacagta gtttcagttc tgatggtata    3429
agcaaaacaa ataaaacgtt tataaaagtt gtatcttgaa acactggtgt tcaacagcta    3489
gcagcttatg tgattcaccc catgccacgt tagtgtcaca aattttatgg tttatctcca    3549
gcaacatttc tctagtactt gcacttatta tcttttgtct aatttaacct taactgaatt    3609
ctccgtttct cctggaggca tttatattca gtgataattc cttcccttag atgcataggg    3669
agagtctcta aatttgatgg aaatggacac ttgagtagtg acttagcctt atgtactctg    3729
ttggaatttg tgctagcagt ttgagcacta gttctgtgtg cctaggaagt taatgctgct    3789
tattgtctca ttctgacttc atggagaatt aatcccacct ttaagcaaag gctactaagt    3849
taatggtatt ttctgtgcag aaattaaatt ttattttcag catttagccc aggaattctt    3909
ccagtaggtg ctcagctatt taaaaacaaa actattctca aacattcatc attagacaac    3969
tggagttttt gctggttttg taacctacca aaatggatag gctgttgaac attccacatt    4029
caaaagtttt gtagggtggt gggaaatggg ggatcttcaa tgtttatttt aaaataaaat    4089
aaaataagtt cttgacttt tctcatgtgtg gttgtggtac atcatattgg aagggttaac    4149
ctgttacttt ggcaaatgag tatttttttg ctagcacctc cccttgcgtg ctttaaatga    4209
catctgcctg ggatgtacca caaccatatg ttacctgtat cttaggggaa tggataaaat    4269
atttgtggtt tactgggtaa tccctagatg atgtatgctt gcagtcctat ataaaactaa    4329
atttgctatc tgtgtagaaa ataatttcat gacatttaca atcaggactg aagtaagttc    4389
ttcacacagt gacctctgaa tcagtttcag agaagggatg ggggagaaaa tgccttctag    4449
gttttgaact tctatgcatt agtgcagatg ttgtgaatgt gtaaaggtgt tcatagtttg    4509
actgtttcta tgtatgtttt ttcaaagaat tgttccttt tttgaactat aattttctt    4569 tttttggtta ttttaccatc acagtttaaa tgtatatctt ttatgtctct actcagacca    4629
tattttaaaa ggggtgcctc attatggggc agagaacttt tcaataagtc tcattaagat    4689
ctgaatcttg gttctaagca ttctgtataa tatgtgattc cttgtcctag ctgcagaagg    4749
cctttgtttt ggtcaaatgc atattttagc agagtttcaa ggaaatgatt gtcacacatg    4809
tcactgtagc ctcttggtgt agcaagctca catacaaaat acttttgtat atgcataata    4869
taaatcatct catgtggata tgaaacttct ttttaaaac ttaaaaaggt agaatgttat    4929
tgattacctt gattagggca gttttatttc cagatcctaa taattcctaa aaaatatgga    4989
aaagtttttt ttcaatcatt gtaccttgat attaaaacaa atatccttta agtatttcta    5049
atcagttagc ttctacagtt cttttgtctc cttttatatg cagctcttac gtgggagact    5109
tttccactta aaggagacat agaatgtgtg cttattctca gaaggttcat taactgaggt    5169
gatgagttaa caactagttg agcagtcagc ttcctaagtg ttttaggaca tttgttcatt    5229
atattttccg tcatataact agaggaagtg gaatgcagat aagtgccgaa ttcaaaccct    5289
tcattttatg tttaagctcc tgaatctgca ttccacttgg gttgttttta agcattctaa    5349
attttagttg attataagtt agatttcaca gaatcagtat tgcccttgat cttgtccttt    5409
ttatggagtt aacggggagg aagacccctc aggaaaacga aagtaaattg ttaaggctca    5469
```

```
tcttcatacc tttttccatt ttgaatccta caaaaatact gcaaaagact agtgaatgtt    5529
taaaattaca ctagattaaa taatatgaaa gtc                                 5562
```

<210> SEQ ID NO 2
<211> LENGTH: 709
<212> TYPE: PRT
<213> ORGANISM: Homo sapiens

<400> SEQUENCE: 2

```
Met Pro Ser Ala Thr Ser His Ser Gly Ser Gly Lys Ser Ser Gly
1               5                   10                  15

Pro Pro Pro Pro Ser Gly Ser Ser Gly Ser Glu Ala Ala Gly Ala
                20                  25                  30

Gly Ala Ala Ala Pro Ala Ser Gln His Pro Ala Thr Gly Thr Gly Ala
            35                  40                  45

Val Gln Thr Glu Ala Met Lys Gln Ile Leu Gly Val Ile Asp Lys Lys
        50                  55                  60

Leu Arg Asn Leu Glu Lys Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
                100                 105                 110

Gln Arg Ser Phe Met Ala Leu Ser Gln Asp Ile Gln Lys Thr Ile Lys
                115                 120                 125

Lys Thr Ala Arg Arg Glu Gln Leu Met Arg Glu Glu Ala Glu Gln Lys
130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
                180                 185                 190

Val Asp Pro Glu Arg Asp Met Ser Leu Arg Leu Asn Glu Gln Tyr Glu
                195                 200                 205

His Ala Ser Ile His Leu Trp Asp Leu Leu Glu Gly Lys Glu Lys Pro
        210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
                260                 265                 270

Pro Glu Ala Glu Pro Glu Pro Ala Glu Glu Tyr Thr Glu Gln Ser Glu
            275                 280                 285

Val Glu Ser Thr Glu Tyr Val Asn Arg Gln Phe Met Ala Glu Thr Gln
        290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
                340                 345                 350

Leu Val Arg Arg Gln Arg Val Gln Asp Leu Met Ala Gln Met Gln Gly
```

```
                        355                 360                 365
Pro Tyr Asn Phe Ile Gln Asp Ser Met Leu Asp Phe Glu Asn Gln Thr
370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Arg Gly Gly Pro Pro Arg Pro Asn Arg Gly Met Pro Gln Met Asn
    690                 695                 700

Thr Gln Gln Val Asn
705

<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)

<400> SEQUENCE: 3
```

-continued

```
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccacccttg cccctcagc tgcccactcg tgatttccag cggcctccgc      180 gcgcgcacg atg ccc tcg gcc acc agc cac agc ggg agc ggc agc aag tcg    231
          Met Pro Ser Ala Thr Ser His Ser Gly Ser Gly Ser Lys Ser
          1               5                   10 tcc gga ccg cca ccg ccg tcg ggt tcc tcc ggg agt gag gcg gcc gcg      279
Ser Gly Pro Pro Pro Pro Ser Gly Ser Ser Gly Ser Glu Ala Ala Ala
15                  20                  25                  30 gga gcc ggg gcc gcc gcg ccg gct tct cag cac ccc gca acc ggc acc      327
Gly Ala Gly Ala Ala Ala Pro Ala Ser Gln His Pro Ala Thr Gly Thr
                35                  40                  45 ggc gct gtc cag acc gag gcc atg aag cag att ctc ggg gtg atc gac      375
Gly Ala Val Gln Thr Glu Ala Met Lys Gln Ile Leu Gly Val Ile Asp
        50                  55                  60 aag aaa ctt cgg aac ctg gag aag aaa aag ggt aag ctt gat gat tac      423
Lys Lys Leu Arg Asn Leu Glu Lys Lys Lys Gly Lys Leu Asp Asp Tyr
    65                  70                  75 cag gaa cga atg aac aaa ggg gaa agg ctt aat caa gat cag ctg gat      471
Gln Glu Arg Met Asn Lys Gly Glu Arg Leu Asn Gln Asp Gln Leu Asp
80                  85                  90 gcc gtt tct aag tac cag gaa gtc aca aat aat ttg gag ttt gca aaa      519
Ala Val Ser Lys Tyr Gln Glu Val Thr Asn Asn Leu Glu Phe Ala Lys
95                  100                 105                 110 gaa tta cag agg agt ttc atg gca cta agt caa gat att cag aaa aca      567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa      615
Ile Lys Lys Thr Ala Arg Arg Glu Gln Leu Met Arg Glu Glu Ala Glu
        130                 135                 140 cag aaa cgt tta aaa act gta ctt gag cta cag tat gtt ttg gac aaa      663
Gln Lys Arg Leu Lys Thr Val Leu Glu Leu Gln Tyr Val Leu Asp Lys
    145                 150                 155 ttg gga gat gat gaa gtg cgg act gac ctg aaa caa ggt ttg aat gga      711
Leu Gly Asp Asp Glu Val Arg Thr Asp Leu Lys Gln Gly Leu Asn Gly
160                 165                 170 gtg cca ata ttg tcc gaa gag gag ttg tca ttg ttg gat gaa ttc tat      759
Val Pro Ile Leu Ser Glu Glu Glu Leu Ser Leu Leu Asp Glu Phe Tyr
175                 180                 185                 190 aag cta gta gac cct gaa cgg gac atg agc ttg agg ttg aat gaa cag      807
Lys Leu Val Asp Pro Glu Arg Asp Met Ser Leu Arg Leu Asn Glu Gln
                195                 200                 205 tat gaa cat gcc tcc att cac ctg tgg gac ctg ctg gaa ggg aag gaa      855
Tyr Glu His Ala Ser Ile His Leu Trp Asp Leu Leu Glu Gly Lys Glu
        210                 215                 220 aaa cct gta tgt gga acc acc tat aaa gtt cta aag gaa att gtt gag      903
Lys Pro Val Cys Gly Thr Thr Tyr Lys Val Leu Lys Glu Ile Val Glu
    225                 230                 235 cgt gtt ttt cag tca aac tac ttt gac agc acc cac aac cac cag aat      951
Arg Val Phe Gln Ser Asn Tyr Phe Asp Ser Thr His Asn His Gln Asn
240                 245                 250 ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285 agt gaa gtt gaa tca aca gag tat gta aat aga cag ttc atg gca gaa     1095
Ser Glu Val Glu Ser Thr Glu Tyr Val Asn Arg Gln Phe Met Ala Glu
```

-continued

```
Ser Glu Val Glu Ser Thr Glu Tyr Val Asn Arg Gln Phe Met Ala Glu
            290                 295                 300 aca cag ttc acc agt ggt gaa aag gag cag gta gat gag tgg aca gtt      1143
Thr Gln Phe Thr Ser Gly Glu Lys Glu Gln Val Asp Glu Trp Thr Val
            305                 310                 315 gaa acg gtt gag gtg gta aat tca ctc cag cag caa cct cag gct gca      1191
Glu Thr Val Glu Val Val Asn Ser Leu Gln Gln Gln Pro Gln Ala Ala
        320                 325                 330 tcc cct tca gta cca gag ccc cac tct ttg act cca gtg gct cag gca      1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg      1287
Asp Pro Leu Val Arg Arg Gln Arg Val Gln Asp Leu Met Ala Gln Met
                355                 360                 365 cag ggt ccc tat aat ttc ata cag gat tca atg ctg gat ttt gaa aat      1335
Gln Gly Pro Tyr Asn Phe Ile Gln Asp Ser Met Leu Asp Phe Glu Asn
            370                 375                 380 cag aca ctt gat cct gcc att gta tct gca cag cct atg aat cca aca      1383
Gln Thr Leu Asp Pro Ala Ile Val Ser Ala Gln Pro Met Asn Pro Thr
        385                 390                 395 caa aac atg gac atg ccc cag ctg gtt tgc cct cca gtt cat tct gaa      1431
Gln Asn Met Asp Met Pro Gln Leu Val Cys Pro Pro Val His Ser Glu
400                 405                 410 tct aga ctt gct cag cct aat caa gtt cct gta caa cca gaa gcg aca      1479
Ser Arg Leu Ala Gln Pro Asn Gln Val Pro Val Gln Pro Glu Ala Thr
415                 420                 425                 430 cag gtt cct ttg gta tca tcc aca agt gag ggg tac aca gca tct caa      1527
Gln Val Pro Leu Val Ser Ser Thr Ser Glu Gly Tyr Thr Ala Ser Gln
                435                 440                 445 ccc ttg tac cag cct tct cat gct aca gag caa cga cca cag aag gaa      1575
Pro Leu Tyr Gln Pro Ser His Ala Thr Glu Gln Arg Pro Gln Lys Glu
            450                 455                 460 cca att gat cag att cag gca aca atc tct tta aat aca gac cag act      1623
Pro Ile Asp Gln Ile Gln Ala Thr Ile Ser Leu Asn Thr Asp Gln Thr
        465                 470                 475 aca gca tca tca tcc ctt cct gct gcg tct cag cct caa gta ttt cag      1671
Thr Ala Ser Ser Ser Leu Pro Ala Ala Ser Gln Pro Gln Val Phe Gln
480                 485                 490 gct ggg aca agc aaa cct tta cat agc agt gga atc aat gta aat gca      1719
Ala Gly Thr Ser Lys Pro Leu His Ser Ser Gly Ile Asn Val Asn Ala
495                 500                 505                 510 gct cca ttc caa tcc atg caa acg gtg ttc aat atg aat gcc cca gtt      1767
Ala Pro Phe Gln Ser Met Gln Thr Val Phe Asn Met Asn Ala Pro Val
                515                 520                 525 cct cct gtt aat gaa cca gaa act tta aaa cag caa aat cag tac cag      1815
Pro Pro Val Asn Glu Pro Glu Thr Leu Lys Gln Gln Asn Gln Tyr Gln
            530                 535                 540 gcc agt tat aac cag agc ttt tct agt cag cct cac caa gta gaa caa      1863
Ala Ser Tyr Asn Gln Ser Phe Ser Ser Gln Pro His Gln Val Glu Gln
        545                 550                 555 aca gag ctt cag caa gaa cag ctt caa aca gtg gtt ggc act tac cat      1911
Thr Glu Leu Gln Gln Glu Gln Leu Gln Thr Val Val Gly Thr Tyr His
560                 565                 570 ggt tcc cca gac cag tcc cat caa gtg act ggt aac cac cag cag cct      1959
Gly Ser Pro Asp Gln Ser His Gln Val Thr Gly Asn His Gln Gln Pro
575                 580                 585                 590 cct cag cag aac act gga ttt cca cgt agc aat cag ccc tat tac aat      2007
Pro Gln Gln Asn Thr Gly Phe Pro Arg Ser Asn Gln Pro Tyr Tyr Asn
                595                 600                 605
```

| | |
|---|---|
| agt cgt ggt gtg tct cgt gga ggc tcc cgt ggt gct aga ggc ttg atg<br>Ser Arg Gly Val Ser Arg Gly Gly Ser Arg Gly Ala Arg Gly Leu Met<br>610               615              620 | 2055 |
| aat gga tac cgg ggc cct gcc aat gga ttc aga gga gga tat gat ggt<br>Asn Gly Tyr Arg Gly Pro Ala Asn Gly Phe Arg Gly Gly Tyr Asp Gly<br>625               630              635 | 2103 |
| tac cgc cct tca ttc tct aac act cca aac agt ggt tat aca cag tct<br>Tyr Arg Pro Ser Phe Ser Asn Thr Pro Asn Ser Gly Tyr Thr Gln Ser<br>640               645              650 | 2151 |
| cag ttc agt gct ccc cgg gat tac tct ggc tat caa cgg gat gga tat<br>Gln Phe Ser Ala Pro Arg Asp Tyr Ser Gly Tyr Gln Arg Asp Gly Tyr<br>655               660             665              670 | 2199 |
| cag cag aat ttc aag cga ggc tct ggg cag agt gga cca cgg gga gcc<br>Gln Gln Asn Phe Lys Arg Gly Ser Gly Gln Ser Gly Pro Arg Gly Ala<br>675               680              685 | 2247 |
| cca cga ggt aat att ttg tgg tgg tga tcctagctcc taagtggagc<br>Pro Arg Gly Asn Ile Leu Trp Trp<br>690 | 2294 |
| ttctgttctg gccttggaag agctgttaat agtctgcatg ttaggaatac atttatcctt | 2354 |
| tccagacttg ttgctaggga ttaaatgaaa tgctctgttt ctaaaactta atcttggacc | 2414 |
| caaattttaa ttttttgaatg atttaatttt ccctgttact atataaactg tcttgaaaac | 2474 |
| tagaacatat tctcttctca gaaaagtgt ttttccaact gaaaattatt tttcaggtcc | 2534 |
| taaaacctgc taaatgtttt taggaagtac ttactgaaac atttttgtaa gacatttttg | 2594 |
| gaatgagatt gaacatttat ataaatttat tattcctctt tcattttttt gaaacatgcc | 2654 |
| tattatattt tagggccaga cacccttttaa tggccggata agccatagtt aacatttaga | 2714 |
| gaaccattta gaagtgatag aactaatgga atttgcaatg cctttttggac ctctattagt | 2774 |
| gatataaata tcaagttatt tctgactttt aaacaaaact cccaaattcc taacttattg | 2834 |
| agctatactt aaaaaaaatt acaggtttag agagttttt gtttttcttt tactgttgga | 2894 |
| aaactacttc ccattttggc aggaagttaa cctatttaac aattagagct agcatttcat | 2954 |
| gtagtctgaa attctaaatg gttctctgat ttgagggagg ttaaacatca aacaggtttc | 3014 |
| ctctattggc cataacatgt ataaaatgtg tgttaaggag gaattacaac gtactttgat | 3074 |
| ttgaatacta gtagaaactg gccaggaaaa aggtacattt ttctaaaaat taatggatca | 3134 |
| cttgggaatt actgacttga ctagaagtat caaaggatgt ttgcatgtga atgtgggtta | 3194 |
| tgttctttcc caccttgtag catattcgat gaaagttgag ttaactgata gctaaaaatc | 3254 |
| tgttttaaca gcatgtaaaa agttatttta tctgttaaaa gtcattatac agttttgaat | 3314 |
| gttatgtagt ttctttttaa cagtttaggt aataaggtct gttttcattc tggtgctttt | 3374 |
| attaattttg atagtatgat gttacttact actgaaatgt aagctagagt gtacactaga | 3434 |
| atgtaagctc catgagagca ggtaccttgt ctgtcttctc tgctgtatct attcccaacg | 3494 |
| cttgatgatg gtgcctggca catagtaggc actcaataaa tatttgttga atgaatgaa | 3553 |

<210> SEQ ID NO 4
<211> LENGTH: 694
<212> TYPE: PRT
<213> ORGANISM: Homo sapiens

<400> SEQUENCE: 4

Met Pro Ser Ala Thr Ser His Ser Gly Ser Gly Ser Lys Ser Ser Gly
1             5                 10               15

Pro Pro Pro Pro Ser Gly Ser Ser Gly Ser Glu Ala Ala Ala Gly Ala
               20               25              30

```
Gly Ala Ala Ala Pro Ala Ser Gln His Pro Ala Thr Gly Thr Gly Ala
            35                  40                  45
Val Gln Thr Glu Ala Met Lys Gln Ile Leu Gly Val Ile Asp Lys Lys
 50                  55                  60
Leu Arg Asn Leu Glu Lys Lys Gly Lys Leu Asp Asp Tyr Gln Glu
 65                  70                  75                  80
Arg Met Asn Lys Gly Glu Arg Leu Asn Gln Asp Gln Leu Asp Ala Val
                     85                  90                  95
Ser Lys Tyr Gln Glu Val Thr Asn Asn Leu Glu Phe Ala Lys Glu Leu
                    100                 105                 110
Gln Arg Ser Phe Met Ala Leu Ser Gln Asp Ile Gln Lys Thr Ile Lys
                115                 120                 125
Lys Thr Ala Arg Arg Glu Gln Leu Met Arg Glu Ala Glu Gln Lys
            130                 135                 140
Arg Leu Lys Thr Val Leu Glu Leu Gln Tyr Val Leu Asp Lys Leu Gly
145                 150                 155                 160
Asp Asp Glu Val Arg Thr Asp Leu Lys Gln Gly Leu Asn Gly Val Pro
                    165                 170                 175
Ile Leu Ser Glu Glu Glu Leu Ser Leu Leu Asp Glu Phe Tyr Lys Leu
                180                 185                 190
Val Asp Pro Glu Arg Asp Met Ser Leu Arg Leu Asn Glu Gln Tyr Glu
            195                 200                 205
His Ala Ser Ile His Leu Trp Asp Leu Leu Glu Gly Lys Glu Lys Pro
        210                 215                 220
Val Cys Gly Thr Thr Tyr Lys Val Leu Lys Glu Ile Val Glu Arg Val
225                 230                 235                 240
Phe Gln Ser Asn Tyr Phe Asp Ser Thr His Asn His Gln Asn Gly Leu
                    245                 250                 255
Cys Glu Glu Glu Glu Ala Ala Ser Ala Pro Ala Val Glu Asp Gln Val
                260                 265                 270
Pro Glu Ala Glu Pro Glu Pro Ala Glu Tyr Thr Glu Gln Ser Glu
            275                 280                 285
Val Glu Ser Thr Glu Tyr Val Asn Arg Gln Phe Met Ala Glu Thr Gln
290                 295                 300
Phe Thr Ser Gly Glu Lys Glu Gln Val Asp Glu Trp Thr Val Glu Thr
305                 310                 315                 320
Val Glu Val Val Asn Ser Leu Gln Gln Gln Pro Gln Ala Ala Ser Pro
                    325                 330                 335
Ser Val Pro Glu Pro His Ser Leu Thr Pro Val Ala Gln Ala Asp Pro
                340                 345                 350
Leu Val Arg Arg Gln Arg Val Gln Asp Leu Met Ala Gln Met Gln Gly
            355                 360                 365
Pro Tyr Asn Phe Ile Gln Asp Ser Met Leu Asp Phe Glu Asn Gln Thr
370                 375                 380
Leu Asp Pro Ala Ile Val Ser Ala Gln Pro Met Asn Pro Thr Gln Asn
385                 390                 395                 400
Met Asp Met Pro Gln Leu Val Cys Pro Pro Val His Ser Glu Ser Arg
                    405                 410                 415
Leu Ala Gln Pro Asn Gln Val Pro Val Gln Pro Glu Ala Thr Gln Val
                420                 425                 430
Pro Leu Val Ser Ser Thr Ser Glu Gly Tyr Thr Ala Ser Gln Pro Leu
            435                 440                 445
```

```
Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Asn Ile Leu Trp Trp
    690

<210> SEQ ID NO 5
<211> LENGTH: 1605
<212> TYPE: DNA
<213> ORGANISM: Canis familiaris
<220> FEATURE:
<221> NAME/KEY: CDS
<222> LOCATION: (46)..(1392)

<400> SEQUENCE: 5
gtcacaaata acttggagtt tgcaaaagaa ttacagagga gtttc atg gca tta agt      57
                                                 Met Ala Leu Ser
                                                   1 caa gat att cag aaa aca ata aag aag act gca cgt cgg gag cag ctt       105
Gln Asp Ile Gln Lys Thr Ile Lys Lys Thr Ala Arg Arg Glu Gln Leu
  5              10                  15                  20 atg aga gag gaa gcg gaa caa aaa cgt tta aaa act gta ctt gag ctc      153
Met Arg Glu Glu Ala Glu Gln Lys Arg Leu Lys Thr Val Leu Glu Leu
                25                  30                  35 cag tat gtt ttg gac aaa ttg gga gat gat gaa gtg aga act gac ctg      201
Gln Tyr Val Leu Asp Lys Leu Gly Asp Asp Glu Val Arg Thr Asp Leu
            40                  45                  50 aag caa ggt ttg aat gga gtg cca ata ttg tct gaa gaa gaa ttg tcg      249
Lys Gln Gly Leu Asn Gly Val Pro Ile Leu Ser Glu Glu Glu Leu Ser
        55                  60                  65
```

| | |
|---|---|
| ttg ttg gat gaa ttc tac aaa tta gca gac cct gaa cgg gac atg agc<br>Leu Leu Asp Glu Phe Tyr Lys Leu Ala Asp Pro Glu Arg Asp Met Ser<br>    70                          75                          80 | 297 |
| ttg agg ttg aat gag cag tat gaa cat gct tcc att cac ctg tgg gac<br>Leu Arg Leu Asn Glu Gln Tyr Glu His Ala Ser Ile His Leu Trp Asp<br>85                        90                        95                        100 | 345 |
| ttg ctg gaa gga aag gaa aag tct gta tgt gga aca acc tat aaa gca<br>Leu Leu Glu Gly Lys Glu Lys Ser Val Cys Gly Thr Thr Tyr Lys Ala<br>                    105                      110                      115 | 393 |
| cta aag gaa att gtt gag cgt gtt ttc cag tca aat tac ttt gac agc<br>Leu Lys Glu Ile Val Glu Arg Val Phe Gln Ser Asn Tyr Phe Asp Ser<br>                    120                      125                      130 | 441 |
| act cac aac cac cag aat ggg cta tgt gag gaa gaa gag gca gcc tca<br>Thr His Asn His Gln Asn Gly Leu Cys Glu Glu Glu Glu Ala Ala Ser<br>                 135                      140                      145 | 489 |
| gca cct aca gtt gaa gac cag gta gct gaa gct gag cct gag cca gca<br>Ala Pro Thr Val Glu Asp Gln Val Ala Glu Ala Glu Pro Glu Pro Ala<br>150                        155                        160 | 537 |
| gaa gaa tac act gaa caa agt gaa gtt gaa tca aca gag tat gta aat<br>Glu Glu Tyr Thr Glu Gln Ser Glu Val Glu Ser Thr Glu Tyr Val Asn<br>165                        170                      175                  180 | 585 |
| aga caa ttt atg gca gaa aca cag ttc agc agt ggt gaa aag gag cag<br>Arg Gln Phe Met Ala Glu Thr Gln Phe Ser Ser Gly Glu Lys Glu Gln<br>                    185                      190                      195 | 633 |
| gta gat gag tgg acg gtc gaa aca gtg gag gtg gtg aat tca ctc cag<br>Val Asp Glu Trp Thr Val Glu Thr Val Glu Val Val Asn Ser Leu Gln<br>              200                      205                      210 | 681 |
| cag caa cct cag gct gcg tct cct tca gta cca gag ccc cac tct ttg<br>Gln Gln Pro Gln Ala Ala Ser Pro Ser Val Pro Glu Pro His Ser Leu<br>                    215                      220                      225 | 729 |
| act ccg gtg gct cag gca gat ccc ctt gtg aga aga cag cga gtc cag<br>Thr Pro Val Ala Gln Ala Asp Pro Leu Val Arg Arg Gln Arg Val Gln<br>              230                      235                      240 | 777 |
| gac ctt atg gcg cag atg cag ggg ccc tat aat ttc ata cag gat tca<br>Asp Leu Met Ala Gln Met Gln Gly Pro Tyr Asn Phe Ile Gln Asp Ser<br>245                        250                        255                  260 | 825 |
| atg ctg gat ttt gaa aac cag aca ctc gat cct gcc att gta tct gca<br>Met Leu Asp Phe Glu Asn Gln Thr Leu Asp Pro Ala Ile Val Ser Ala<br>                    265                      270                      275 | 873 |
| cag cct atg aat ccg aca caa aac atg gac atg ccc cag ctg gtt tgc<br>Gln Pro Met Asn Pro Thr Gln Asn Met Asp Met Pro Gln Leu Val Cys<br>                 280                      285                      290 | 921 |
| cct cca gtt cat tct gaa tct aga ctt gct caa cct aat caa gtt cct<br>Pro Pro Val His Ser Glu Ser Arg Leu Ala Gln Pro Asn Gln Val Pro<br>              295                      300                      305 | 969 |
| gta caa cca gaa gct aca cag gtt cct ttg gtt tca tcc aca agt gag<br>Val Gln Pro Glu Ala Thr Gln Val Pro Leu Val Ser Ser Thr Ser Glu<br>              310                      315                      320 | 1017 |
| ggg tat aca gca tct caa ccc ttg tac cag cct tct cat gct aca gag<br>Gly Tyr Thr Ala Ser Gln Pro Leu Tyr Gln Pro Ser His Ala Thr Glu<br>325                        330                      335                  340 | 1065 |
| caa cga cca caa aag gaa cca att gac cag att cag gca aca atc tct<br>Gln Arg Pro Gln Lys Glu Pro Ile Asp Gln Ile Gln Ala Thr Ile Ser<br>                    345                      350                      355 | 1113 |
| tta aat aca gac cag act aca gcg tca tca tcc ctt ccg gct gct tct<br>Leu Asn Thr Asp Gln Thr Thr Ala Ser Ser Ser Leu Pro Ala Ala Ser<br>                 360                      365                      370 | 1161 |
| cag cct cag gta ttc cag gct ggg aca agc aaa cca tta cat agc agt<br>Gln Pro Gln Val Phe Gln Ala Gly Thr Ser Lys Pro Leu His Ser Ser<br>              375                      380                      385 | 1209 |

```
gga atc aat gta aat gca gct cca ttc caa tcc atg caa acg gtg ttc      1257
Gly Ile Asn Val Asn Ala Ala Pro Phe Gln Ser Met Gln Thr Val Phe
    390                 395                 400 aat atg aat gcc cca gtt cct cct gtt aat gaa cca gaa act ttg aaa      1305
Asn Met Asn Ala Pro Val Pro Pro Val Asn Glu Pro Glu Thr Leu Lys
405                 410                 415                 420 caa caa aat cag tac cag gcc agt tat aac cag agc ttt tct agt cag      1353
Gln Gln Asn Gln Tyr Gln Ala Ser Tyr Asn Gln Ser Phe Ser Ser Gln
                425                 430                 435 cct cac caa gta gaa caa aca gag gga tgc cgc aaa tga acactcagca       1402
Pro His Gln Val Glu Gln Thr Glu Gly Cys Arg Lys
                440                 445 agtgaattaa tctgattcac aggattatgt ttaaacgcca aaacacact ggccagtgta     1462 ccataatatg ttaccagaag agttattatc tatttgttct cccttcagg aaacttattg     1522 taaagggact gttttcatcc cataaagaca ggactacaat tgtcagcttt atattacctg    1582
gaaaaaaaaa aaaaaaaaaa aaa                                            1605
```

<210> SEQ ID NO 6
<211> LENGTH: 448
<212> TYPE: PRT
<213> ORGANISM: Canis familiaris

<400> SEQUENCE: 6

```
Met Ala Leu Ser Gln Asp Ile Gln Lys Thr Ile Lys Lys Thr Ala Arg
1               5                   10                  15

Arg Glu Gln Leu Met Arg Glu Glu Ala Glu Gln Lys Arg Leu Lys Thr
            20                  25                  30

Val Leu Glu Leu Gln Tyr Val Leu Asp Lys Leu Gly Asp Asp Glu Val
        35                  40                  45

Arg Thr Asp Leu Lys Gln Gly Leu Asn Gly Val Pro Ile Leu Ser Glu
    50                  55                  60

Glu Glu Leu Ser Leu Leu Asp Glu Phe Tyr Lys Leu Ala Asp Pro Glu
65                  70                  75                  80

Arg Asp Met Ser Leu Arg Leu Asn Glu Gln Tyr Glu His Ala Ser Ile
            85                  90                  95

His Leu Trp Asp Leu Leu Glu Gly Lys Glu Lys Ser Val Cys Gly Thr
            100                 105                 110

Thr Tyr Lys Ala Leu Lys Glu Ile Val Glu Arg Val Phe Gln Ser Asn
        115                 120                 125

Tyr Phe Asp Ser Thr His Asn His Gln Asn Gly Leu Cys Glu Glu Glu
    130                 135                 140

Glu Ala Ser Ala Pro Thr Val Glu Asp Gln Val Ala Glu Ala Glu
145                 150                 155                 160

Pro Glu Pro Ala Glu Glu Tyr Thr Glu Gln Ser Glu Val Glu Ser Thr
            165                 170                 175

Glu Tyr Val Asn Arg Gln Phe Met Ala Glu Thr Gln Phe Ser Ser Gly
        180                 185                 190

Glu Lys Glu Gln Val Asp Glu Trp Thr Val Glu Thr Val Glu Val Val
    195                 200                 205

Asn Ser Leu Gln Gln Gln Pro Gln Ala Ala Ser Pro Ser Val Pro Glu
    210                 215                 220

Pro His Ser Leu Thr Pro Val Ala Gln Ala Asp Pro Leu Val Arg Arg
225                 230                 235                 240

Gln Arg Val Gln Asp Leu Met Ala Gln Met Gln Gly Pro Tyr Asn Phe
```

-continued

```
                    245                 250                 255
Ile Gln Asp Ser Met Leu Asp Phe Glu Asn Gln Thr Leu Asp Pro Ala
            260                 265                 270
Ile Val Ser Ala Gln Pro Met Asn Pro Thr Gln Asn Met Asp Met Pro
        275                 280                 285
Gln Leu Val Cys Pro Pro Val His Ser Glu Ser Arg Leu Ala Gln Pro
    290                 295                 300
Asn Gln Val Pro Val Gln Pro Glu Ala Thr Gln Val Pro Leu Val Ser
305                 310                 315                 320
Ser Thr Ser Glu Gly Tyr Thr Ala Ser Gln Pro Leu Tyr Gln Pro Ser
                325                 330                 335
His Ala Thr Glu Gln Arg Pro Gln Lys Glu Pro Ile Asp Gln Ile Gln
            340                 345                 350
Ala Thr Ile Ser Leu Asn Thr Asp Gln Thr Thr Ala Ser Ser Ser Leu
        355                 360                 365
Pro Ala Ala Ser Gln Pro Gln Val Phe Gln Ala Gly Thr Ser Lys Pro
    370                 375                 380
Leu His Ser Ser Gly Ile Asn Val Asn Ala Ala Pro Phe Gln Ser Met
385                 390                 395                 400
Gln Thr Val Phe Asn Met Asn Ala Pro Val Pro Val Asn Glu Pro
                405                 410                 415
Glu Thr Leu Lys Gln Gln Asn Gln Tyr Gln Ala Ser Tyr Asn Gln Ser
            420                 425                 430
Phe Ser Ser Gln Pro His Gln Val Glu Gln Thr Glu Gly Cys Arg Lys
        435                 440                 445

<210> SEQ ID NO 7
<211> LENGTH: 4154
<212> TYPE: DNA
<213> ORGANISM: Canis familiaris
<220> FEATURE:
<221> NAME/KEY: CDS
<222> LOCATION: (1)..(2154)

<400> SEQUENCE: 7 atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
                20                  25                  30 ggg gcg gcg ggg gcg gcg ggg gcc ggg gcg gct gcg ccc gcc tcc cag     144
Gly Ala Ala Gly Ala Ala Gly Ala Gly Ala Ala Ala Pro Ala Ser Gln
            35                  40                  45 cac ccc gcg acc ggc acc ggc gct gtc cag acc gag gcc atg aag cag     192
His Pro Ala Thr Gly Thr Gly Ala Val Gln Thr Glu Ala Met Lys Gln
        50                  55                  60 atc ctc ggg gtg atc gac aag aaa ctc cgg aac ctg gag aag aaa aag     240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt     288
Gly Lys Leu Asp Asp Tyr Gln Glu Arg Met Asn Lys Gly Glu Arg Leu
                85                  90                  95 aat caa gat cag ctg gat gcc gta tct aag tac cag gaa gtc aca aat     336
Asn Gln Asp Gln Leu Asp Ala Val Ser Lys Tyr Gln Glu Val Thr Asn
            100                 105                 110 aac ttg gag ttt gca aaa gaa tta cag agg agt ttc atg gca tta agt     384
Asn Leu Glu Phe Ala Lys Glu Leu Gln Arg Ser Phe Met Ala Leu Ser
```

```
              115                 120                 125
caa gat att cag aaa aca ata aag aag act gca cgt cgg gag cag ctt      432
Gln Asp Ile Gln Lys Thr Ile Lys Lys Thr Ala Arg Arg Glu Gln Leu
        130                 135                 140 atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205 ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220 ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240 cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255 act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270 gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285 gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300 aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380 atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415 cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430 gta caa cca gaa gct aca cag gtt cct ttg gtt tca tcc aca agt gag     1344
Val Gln Pro Glu Ala Thr Gln Val Pro Leu Val Ser Ser Thr Ser Glu
```

```
          Val Gln Pro Glu Ala Thr Gln Val Pro Leu Val Ser Ser Thr Ser Glu
                  435                 440                 445 gggtat acagcatct caacccttg tac cagcct tct catgct aca gag            1392
Gly Tyr Thr Ala Ser Gln Pro Leu Tyr Gln Pro Ser His Ala Thr Glu
        450                 455                 460 caa cga cca caa aag gaa cca att gac cag att cag gca aca atc tct    1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct    1488
Leu Asn Thr Asp Gln Thr Thr Ala Ser Ser Ser Leu Pro Ala Ala Ser
                        485                 490                 495 cag cct cag gta ttc cag gct ggg aca agc aaa cca tta cat agc agt    1536
Gln Pro Gln Val Phe Gln Ala Gly Thr Ser Lys Pro Leu His Ser Ser
                500                 505                 510 gga atc aat gta aat gca gct cca ttc caa tcc atg caa acg gtg ttc    1584
Gly Ile Asn Val Asn Ala Ala Pro Phe Gln Ser Met Gln Thr Val Phe
        515                 520                 525 aat atg aat gcc cca gtt cct cct gtt aat gaa cca gaa act ttg aaa    1632
Asn Met Asn Ala Pro Val Pro Pro Val Asn Glu Pro Glu Thr Leu Lys
530                 535                 540 caa caa aat cag tac cag gcc agt tat aac cag agc ttt tct agt cag    1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca    1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act    1776
Val Val Gly Thr Tyr His Gly Ser Gln Asp Gln Pro His Gln Val Thr
                580                 585                 590 ggt aac cat cag cag cct ccc cag cag aac act gga ttt cca cgt agc    1824
Gly Asn His Gln Gln Pro Pro Gln Gln Asn Thr Gly Phe Pro Arg Ser
        595                 600                 605 agt cag ccc tat tac aat agt cgt ggt gtg tct cgt ggt ggt tcc cgt    1872
Ser Gln Pro Tyr Tyr Asn Ser Arg Gly Val Ser Arg Gly Gly Ser Arg
        610                 615                 620 ggt gct aga ggc tta atg aat gga tac agg ggc cct gcc aat gga ttc    1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac    1968
Arg Gly Gly Tyr Asp Gly Tyr Arg Pro Ser Phe Ser Asn Thr Pro Asn
                        645                 650                 655 agt ggt tat aca cag tct cag ttc agt gct ccc cgg gac tac tct ggc    2016
Ser Gly Tyr Thr Gln Ser Gln Phe Ser Ala Pro Arg Asp Tyr Ser Gly
                660                 665                 670 tat cag cgg gat gga tat cag cag aat ttc aag cga ggc tct ggg cag    2064
Tyr Gln Arg Asp Gly Tyr Gln Gln Asn Phe Lys Arg Gly Ser Gly Gln
                675                 680                 685 agt gga cca cgg gga gcc cca cga ggt cgt gga ggg ccc cca aga ccc    2112
Ser Gly Pro Arg Gly Ala Pro Arg Gly Arg Gly Gly Pro Pro Arg Pro
        690                 695                 700 aac aga ggg atg ccg caa atg aac act cag caa gtg aat taa             2154
Asn Arg Gly Met Pro Gln Met Asn Thr Gln Gln Val Asn
705                 710                 715 tctgattcac aggattatgt ttaaacgcca aaaacacact ggccagtgta ccataatatg   2214
ttaccagaag agttattatc tatttgttct ccctttcagg aaacttattg taaagggact   2274
gttttcatcc cataaagaca ggactacaat tgtcagcttt atattacctg gatatggaag   2334
gaaactattt ttattctgca tgttcttcct aagcgtcatc ttgagcctlg cacatgatac   2394
```

```
tcagattcct caccettgct taggagtaaa acataataca ctttacaggg tgatatctcc    2454
atagttattt gaagtggctt ggaaaaagca agattaactt ctgacattgg ataaaaatca    2514
acaaatcagc cctagagtta ttcaaatggt aattgacaaa aactaaaata tttcccttcg    2574
agaaggagtg gaatgtggtt tggcagaaca actgcatttc acagcttttc cggttaaatt    2634
ggagcactaa acgtttagat gcataccaaa ttatgcatgg gcccttaata taaaaggctg    2694
gctaccagct tgacacagc actattcatc ctctggccaa acaactgtgg ttaaacaaca     2754
catgtaaatt gctttttaac agctgatact ataataagac aaagccaaaa tgcaaaaatt   2814
gggctttgat tggcactttt tgaaaaatat gcaacaaata tgggatgtaa tctggatggc    2874
cgcttctgta cttaatgtga agtatttaga taccttttg aacacttaac agtttcttct    2934
gacaatgact tttgtaagga ttggtactat ctatcattcc ttataatgta cattgtctgt    2994
cactaatcct cagatcttgc tgtattgtca cctaaattgg tacaggtact gatgaaaata    3054
tctaatggat aatcataaca ctcttggtca catgtttttc ctgcagcctg aaggttttta    3114
aaagaaaaag atatcaaatg cctgctgcta ccaccctttt aaattgctat cttttgaaaa    3174
gcaccagtat gtgttttaga ttgatttccc tattttaggg aaatgacaga cagtagtttc    3234
agttctgatg gtataagcaa aacaaataaa acatgtttat aaaagttgta tcttgaaaca    3294
ctggtgttca acagctagca gcttatgtgg ttcacccat gcattgttag tgtttcagat     3354
tttatggtta tctccagcag ctgttttctgt agtacttgca tttatctttt gtctaaccct   3414
aatattctca cggaggcatt tatattcaaa gtggtgatcc cttcacttag acgcataggg    3474
agagtcacaa gtttgatgaa gaggacagtg tagtaattta tatgctgttg gaatttgtgc    3534
tagcagtttg agcactagtt ctgtgtgcct atgaacttaa tgctgcttgt catattccac    3594
tttgacttca tggagaatta atcccatcta ctcagcaaag gctatactaa tactaagtta    3654
atggtatttt ctgtgcagaa attgaatttt gttttattag catttagcta aggaattttt    3714
ccagtaggtg ctcagctact aaagaaaaac aaaaacaaga cacaaaacta ttctcaaaca    3774
ttcattgtta gacaactgga gttttttgctg gttttgtaac ctactaaaat ggataggctg   3834
ttgaacattc cacattcaaa agttttttgt agggtggtgg ggaagggggg gtgtcttcaa    3894
tgtttatttt aaaataaaat aagttcttga cttttctcat gtgtggttgt ggtacatcat    3954
attggaaggg ttatctgttt acttttgcaa atgagtattt ctcttgctag cacctcccgt    4014
tgtgcgcttt aaatgacatc tgcctgggat gtaccacaac catatgttag ctgtattta     4074
tggggaatag ataaaatatt cgtggtttat tgggtaatcc ctagatgtgt atgcttacaa    4134
tcctatatat aaaactaaat                                                4154

<210> SEQ ID NO 8
<211> LENGTH: 717
<212> TYPE: PRT
<213> ORGANISM: Canis familiaris

<400> SEQUENCE: 8

Met Pro Ser Ala Thr Ser Leu Ser Gly Ser Gly Ser Lys Ser Ser Gly
1               5                   10                  15

Pro Pro Pro Ser Gly Ser Ser Gly Ser Glu Ala Ala Ala Ala
            20                  25                  30

Gly Ala Ala Gly Ala Ala Gly Ala Gly Ala Ala Pro Ala Ser Gln
        35                  40                  45

His Pro Ala Thr Gly Thr Gly Ala Val Gln Thr Glu Ala Met Lys Gln
    50                  55                  60
```

-continued

```
Ile Leu Gly Val Ile Asp Lys Lys Leu Arg Asn Leu Glu Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Val Thr Asn
                    100                 105                 110

Asn Leu Glu Phe Ala Lys Glu Leu Gln Arg Ser Phe Met Ala Leu Ser
            115                 120                 125

Gln Asp Ile Gln Lys Thr Ile Lys Lys Thr Ala Arg Arg Glu Gln Leu
        130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Leu Ser
                    180                 185                 190

Leu Leu Asp Glu Phe Tyr Lys Leu Ala Asp Pro Glu Arg Asp Met Ser
            195                 200                 205

Leu Arg Leu Asn Glu Gln Tyr Glu His Ala Ser Ile His Leu Trp Asp
        210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
                    260                 265                 270

Ala Pro Thr Val Glu Asp Gln Val Ala Glu Ala Glu Pro Glu Pro Ala
            275                 280                 285

Glu Glu Tyr Thr Glu Gln Ser Glu Val Glu Ser Thr Glu Tyr Val Asn
        290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
                    340                 345                 350

Thr Pro Val Ala Gln Ala Asp Pro Leu Val Arg Arg Gln Arg Val Gln
            355                 360                 365

Asp Leu Met Ala Gln Met Gln Gly Pro Tyr Asn Phe Ile Gln Asp Ser
        370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
                    420                 425                 430

Val Gln Pro Glu Ala Thr Gln Val Pro Leu Val Ser Ser Thr Ser Glu
            435                 440                 445

Gly Tyr Thr Ala Ser Gln Pro Leu Tyr Gln Pro Ser His Ala Thr Glu
        450                 455                 460

Gln Arg Pro Gln Lys Glu Pro Ile Asp Gln Ile Gln Ala Thr Ile Ser
465                 470                 475                 480
```

-continued

```
Leu Asn Thr Asp Gln Thr Thr Ala Ser Ser Ser Leu Pro Ala Ala Ser
            485                 490                 495

Gln Pro Gln Val Phe Gln Ala Gly Thr Ser Lys Pro Leu His Ser Ser
        500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
        610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Gly Pro Pro Arg Pro
    690                 695                 700

Asn Arg Gly Met Pro Gln Met Asn Thr Gln Gln Val Asn
705                 710                 715

<210> SEQ ID NO 9
<211> LENGTH: 4939
<212> TYPE: DNA
<213> ORGANISM: Canis familiaris
<220> FEATURE:
<221> NAME/KEY: CDS
<222> LOCATION: (1)..(2109)

<400> SEQUENCE: 9 atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
                20                  25                  30 ggg gcg gcg ggg gcg gcg ggg gcc ggg gcg gct gcg ccc gcc tcc cag     144
Gly Ala Ala Gly Ala Ala Gly Ala Gly Ala Ala Pro Ala Ser Gln
                35                  40                  45 cac ccc gcg acc ggc acc ggc gct gtc cag acc gag gcc atg aag cag     192
His Pro Ala Thr Gly Thr Gly Ala Val Gln Thr Glu Ala Met Lys Gln
    50                  55                  60 atc ctc ggg gtg atc gac aag aaa ctc cgg aac ctg gag aag aaa aag     240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt     288
Gly Lys Leu Asp Asp Tyr Gln Glu Arg Met Asn Lys Gly Glu Arg Leu
                85                  90                  95
```

```
aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110 aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125 caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140 atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205 ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220 ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240 cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255 act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270 gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285 gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300 aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380 atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc     1248
Gln Pro Met Asn Pro Thr Gln Asn Met Asp Met Pro Gln Leu Val Cys
```

-continued

|     |     |     | 405 |     |     |     | 410 |     |     |     | 415 |     |     |      |
|-----|-----|-----|-----|-----|-----|-----|-----|-----|-----|-----|-----|-----|-----|------|
| cct | cca | gtt | cat | tct | gaa | tct | aga | ctt | gct | caa | cct | aat | caa | gtt cct |
| Pro | Pro | Val | His | Ser | Glu | Ser | Arg | Leu | Ala | Gln | Pro | Asn | Gln | Val Pro |
|     |     |     | 420 |     |     |     | 425 |     |     |     | 430 |     |     | 1296 |

```
gta caa cca gaa gct aca cag gtt cct ttg gtt tca tcc aca agt gag      1344
Val Gln Pro Glu Ala Thr Gln Val Pro Leu Val Ser Ser Thr Ser Glu
            435                 440                 445 ggg tat aca gca tct caa ccc ttg tac cag cct tct cat gct aca gag      1392
Gly Tyr Thr Ala Ser Gln Pro Leu Tyr Gln Pro Ser His Ala Thr Glu
450                 455                 460 caa cga cca caa aag gaa cca att gac cag att cag gca aca atc tct      1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct      1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt      1536
Gln Pro Gln Val Phe Gln Ala Gly Thr Ser Lys Pro Leu His Ser Ser
            500                 505                 510 gga atc aat gta aat gca gct cca ttc caa tcc atg caa acg gtg ttc      1584
Gly Ile Asn Val Asn Ala Ala Pro Phe Gln Ser Met Gln Thr Val Phe
            515                 520                 525 aat atg aat gcc cca gtt cct cct gtt aat gaa cca gaa act ttg aaa      1632
Asn Met Asn Ala Pro Val Pro Pro Val Asn Glu Pro Glu Thr Leu Lys
530                 535                 540 caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca      1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act      1776
Val Val Gly Thr Tyr His Gly Ser Gln Asp Gln Pro His Gln Val Thr
            580                 585                 590 ggt aac cat cag cag cct ccc cag cag aac act gga ttt cca cgt agc      1824
Gly Asn His Gln Gln Pro Pro Gln Gln Asn Thr Gly Phe Pro Arg Ser
            595                 600                 605 agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
610                 615                 620 ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag      2064
Tyr Gln Arg Asp Gly Tyr Gln Gln Asn Phe Lys Arg Gly Ser Gly Gln
            675                 680                 685 agt gga cca cgg gga gcc cca cga ggt aat att ttg tgg tgg tga          2109
Ser Gly Pro Arg Gly Ala Pro Arg Gly Asn Ile Leu Trp Trp
            690                 695                 700 tcctagctcc taagtggagc ttctgttctg gccttggaag agctgttcca tagtctgcat   2169
gtaggttaca tgttaggaat acatttatca ttaccagact tgttgctagg gattaaatga   2229
aatgctctgt ttctaaaact tctcttgaac ccaaatttaa ttttttgaat gactttccct   2289
```

-continued

```
gttactatat aaattgtctt gaaaactaga acatttctcc tcctcagaaa aagtgttttt    2349
ccaactgcaa attattttc aggtcctaaa acctgctaaa tgttttagg aagtacttac     2409 tgaaacattt ttgtaagaca tttttggaat gagattgaac atttatataa atttattatt   2469
attcctcttt cattttgaa catgcatatt atatttagg gtcagaaatc ctttaatggc     2529
caaataagcc atagttacat ttagagaacc atttagaagt gatagaacta actgaaattt   2589
caatgccttt ggatcattaa tagcgatata aatttcaaat tgtttctgac ttttaaataa   2649
aacatccaaa atcctaacta acttcctgaa ctatatttaa aaattacagg tttaaggagt   2709
ttctggtttt ttttctctta ccataggaaa actgtttcct gtttggccag gaagtcaacc   2769
tgtgtaataa ttagaagtag catttcatat gatctgaagt tctaaatggt tctctgattt   2829
aagggaagtt aaattgaata ggtttcctct agttattggc cataacatgt ataaaatgta   2889
tattaaggag gaatacaaag tactttgatt tcaatgctag tagaaactgg ccagcaaaaa   2949
ggtgcatttt attttaaat taatggatca cttgggaatt actgacttga agtatcaaag    3009
gatatttgca tgtgaatgtg ggttatgttc tttctcacct tgtagcatat tctatgaaag   3069
ttgagttgac tggtagctaa aaatctgttt taacagcatg taaaaagtta ttttatctgt   3129
tacaagtcat tatacaattt tgaatgttat gtagtttctt tttaacagtt taggtaacaa   3189
ggtctgtttt tcattctggt gcttttatta attttgatag tatgatgtta cttactactg   3249
aaatgtaagc tagagtgtac actagaatgt aagctccatg agagcaggta ccttgtctgt   3309
cttcactgct gtatctattt ccaacgcctg atgacagtgc ctgacacata gtaggcactc   3369
aataaatact tgttgaatga atgaatgaat gagtactggt ggaatactcc attagctcta   3429
ctcttctttt agctagagaa catgagcaaa tttgcgcatg acaacttcca ggacaggtga   3489
acactgaaga attgacctct taaacctaat aatgtggtga caagctgccc acatgcttct   3549
tgacttcaga tgaaaatctg cttgaaggca aagcaaataa tatttgaaag aaaaaccaaa   3609
tgccattttt gtcttctagg tcgtggaggg cccccaagac ccaacagagg gatgccgcaa   3669
atgaacactc agcaagtgaa ttaatctgat tcacaggatt atgtttaaac gccaaaaaca   3729
cactggccag tgtaccataa tatgttacca gaagagttat tatctatttg ttctcccttt   3789
caggaaactt attgtaaagg gactgttttc atcccataaa gacaggacta caattgtcag   3849
ctttatatta cctggatatg gaaggaaact attttttattc tgcatgttct tcctaagcgt   3909
catcttgagc cttgcacatg atactcagat tcctcaccct tgcttaggag taaaacataa   3969
tacactttac agggtgatat ctccatagtt atttgaagtg gcttggaaaa agcaagatta   4029
acttctgaca ttggataaaa atcaacaaat cagccctaga gttattcaaa tggtaattga   4089
caaaaactaa atatttccc ttcgagaagg agtggaatgt ggtttggcag aacaactgca    4149
tttcacagct tttccggtta aattggagca ctaaacgttt agatgcatac caaattatgc   4209
atgggccctt aatataaaag gctggctacc agctttgaca cagcactatt catcctctgg   4269
ccaaacaact gtggttaaac aacacatgta aattgctttt taacagctga tactataata   4329
agacaaagcc aaaatgcaaa aattgggctt tgattggcac tttttgaaaa atatgcaaca   4389
aatatgggat gtaatctgga tggccgcttc tgtacttaat gtgaagtatt tagataccttt  4449 tttgaacact taacagtttc ttctgacaat gacttttgta aggattggta ctatctatca   4509
ttccttataa tgtacattgt ctgtcactaa tcctcagatc ttgctgtatt gtcacctaaa   4569
ttggtacagg tactgatgaa aatatctaat ggataatcat aacactcttg gtcacatgtt   4629
```

-continued

```
tttcctgcag cctgaaggtt tttaaaagaa aaagatatca aatgcctgct gctaccaccc     4689
ttttaaattg ctatcttttg aaaagcacca gtatgtgttt tagattgatt tccctatttt     4749
agggaaatga cagacagtag tttcagttct gatggtataa gcaaaacaaa taaaacatgt     4809
ttataaaagt tgtatcttga aacactggtg ttcaacagct agcagcttat gtggttcacc     4869
ccatgcattg ttagtgtttc agattttatg gttatctcca gcagctgttt ctgtagtact     4929
tgcatttatc                                                            4939
```

<210> SEQ ID NO 10
<211> LENGTH: 702
<212> TYPE: PRT
<213> ORGANISM: Canis familiaris

<400> SEQUENCE: 10

```
Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Leu Ser
            180                 185                 190

Leu Leu Asp Glu Phe Tyr Lys Leu Ala Asp Pro Glu Arg Asp Met Ser
    195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
            260                 265                 270

Ala Pro Thr Val Glu Asp Gln Val Ala Glu Ala Glu Pro Glu Pro Ala
    275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320
```

```
Val Asp Glu Trp Thr Val Glu Thr Val Glu Val Asn Ser Leu Gln
            325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
            355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
            405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
            435                 440                 445

Gly Tyr Thr Ala Ser Gln Pro Leu Tyr Gln Pro Ser His Ala Thr Glu
            450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Leu Pro Ala Ala Ser
            485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
            515                 520                 525

Asn Met Asn Ala Pro Val Pro Pro Val Asn Glu Pro Glu Thr Leu Lys
            530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
            565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
            595                 600                 605

Ser Gln Pro Tyr Tyr Asn Ser Arg Gly Val Ser Arg Gly Gly Ser Arg
            610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
            645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
            675                 680                 685

Ser Gly Pro Arg Gly Ala Pro Arg Gly Asn Ile Leu Trp Trp
            690                 695                 700

<210> SEQ ID NO 11
<211> LENGTH: 3306
<212> TYPE: DNA
<213> ORGANISM: Canis familiaris
<220> FEATURE:
```

-continued

```
<221> NAME/KEY: CDS
<222> LOCATION: (1)..(2040)

<400> SEQUENCE: 11 atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
 1               5                  10                  15 ccg ccg ccc ccg tcg ggt tcc tcc ggg agc gag gcg gcg gcg gcg           96
Pro Pro Pro Pro Ser Gly Ser Ser Gly Ser Glu Ala Ala Ala Ala
             20                  25                  30 ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
         35                  40                  45 cac ccc gcg acc ggc acc ggc gct gtc cag acc gag gcc atg aag cag      192
His Pro Ala Thr Gly Thr Gly Ala Val Gln Thr Glu Ala Met Lys Gln
 50                  55                  60 atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
 65                  70                  75                  80 ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                 85                  90                  95 aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110 aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125 caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140 atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205 ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220 ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240 cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255 act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270 gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285 gaa gaa tac act gaa caa agt gaa gtt gaa tca aca gag tat gta aat      912
Glu Glu Tyr Thr Glu Gln Ser Glu Val Glu Ser Thr Glu Tyr Val Asn
```

-continued

| | | |
|---|---|---|
| 290 | 295 | 300 |

| | | |
|---|---|---|
| aga caa ttt atg gca gaa aca cag ttc agc agt ggt gaa aag gag cag<br>Arg Gln Phe Met Ala Glu Thr Gln Phe Ser Ser Gly Glu Lys Glu Gln<br>305                      310                    315                    320 | 960 |

```
aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380 atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415 cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430 gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445 ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                 455                 460 caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510 gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525 aat atg aat gcc cca gtt cct cct gtt aat gaa cca gaa act ttg aaa     1632
Asn Met Asn Ala Pro Val Pro Pro Val Asn Glu Pro Glu Thr Leu Lys
    530                 535                 540 caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act     1776
Val Val Gly Thr Tyr His Gly Ser Gln Asp Gln Pro His Gln Val Thr
            580                 585                 590 ggt aac cat cag cag cct ccc cag cag aac act gga ttt cca cgt agc     1824
Gly Asn His Gln Gln Pro Pro Gln Gln Asn Thr Gly Phe Pro Arg Ser
        595                 600                 605 agt cag ccc tat tac aat agt cgt ggt gtg tct cgt ggt ggt tcc cgt     1872
```

```
Ser Gln Pro Tyr Tyr Asn Ser Arg Gly Val Ser Arg Gly Gly Ser Arg
        610                 615                 620 ggt gct aga ggc tta atg aat gga tac agg ggc cct gcc aat gga ttc     1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac     1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc     2016
Ser Gly Tyr Thr Gln Ser Gln Phe Ser Ala Pro Arg Asp Tyr Ser Gly
            660                 665                 670 tat cag cgg gga tgc cgc aaa tga acactcagca agtgaattaa tctgattcac    2070
Tyr Gln Arg Gly Cys Arg Lys
            675 aggattatgt ttaaacgcca aaaacacact ggccagtgta ccataatatg ttaccagaag   2130 agttattatc tatttgttct ccctttcagg aaacttattg taaagggact gttttcatcc   2190 cataaagaca ggactacaat tgtcagcttt atattacctg gatatggaag gaaactattt   2250 ttattctgca tgttcttcct aagcgtcatc ttgagccttg cacatgatac tcagattcct   2310 cacccttgct taggagtaaa acataataca ctttacaggg tgatatctcc atagttattt   2370 gaagtggctt ggaaaaagca agattaactt ctgacattgg ataaaaatca acaaatcagc   2430 cctagagtta tcaaatggt aattgacaaa aactaaaata tttcccttcg agaaggagtg    2490 gaatgtggtt tggcagaaca actgcatttc acagctttc cggttaaatt ggagcactaa    2550 acgtttagat gcataccaaa ttatgcatgg gcccttaata taaaaggctg gctaccagct   2610 ttgacacagc actattcatc ctctggccaa acaactgtgg ttaaacaaca catgtaaatt   2670 gcttttttaac agctgatact ataataagac aaagccaaaa tgcaaaaatt gggctttgat  2730 tggcactttt tgaaaaatat gcaacaaata tgggatgtaa tctggatggc cgcttctgta   2790 cttaatgtga agtatttaga taccttttg aacacttaac agtttcttct gacaatgact    2850 tttgtaagga ttggtactat ctatcattcc ttataatgta cattgtctgt cactaatcct   2910 cagatcttgc tgtattgtca cctaaattgg tacaggtact gatgaaaata tctaatggat   2970 aatcataaca ctcttggtca catgttttc ctgcagcctg aaggttttta aaagaaaaag    3030 atatcaaatg cctgctgcta ccaccctttt aaattgctat cttttgaaaa gcaccagtat   3090 gtgttttaga ttgatttccc tattttaggg aaatgacaga cagtagtttc agttctgatg   3150 gtataagcaa acaaataaa acatgtttat aaaagttgta tcttgaaaca ctggtgttca    3210 acagctagca gcttatgtgg ttcaccccat gcattgttag tgtttcagat tttatggtta   3270 tctccagcag ctgtttctgt agtacttgca tttatc                             3306

<210> SEQ ID NO 12
<211> LENGTH: 679
<212> TYPE: PRT
<213> ORGANISM: Canis familiaris

<400> SEQUENCE: 12

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
```

```
                    50                  55                  60
Ile Leu Gly Val Ile Asp Lys Lys Leu Arg Asn Leu Glu Lys Lys
65                  70                  75                  80

Gly Lys Leu Asp Asp Tyr Gln Glu Arg Met Asn Lys Gly Glu Arg Leu
                    85                  90                  95

Asn Gln Asp Gln Leu Asp Ala Val Ser Lys Tyr Gln Glu Val Thr Asn
                100                 105                 110

Asn Leu Glu Phe Ala Lys Glu Leu Gln Arg Ser Phe Met Ala Leu Ser
                115                 120                 125

Gln Asp Ile Gln Lys Thr Ile Lys Lys Thr Ala Arg Arg Glu Gln Leu
                130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Leu Ser
                180                 185                 190

Leu Leu Asp Glu Phe Tyr Lys Leu Ala Asp Pro Glu Arg Asp Met Ser
                195                 200                 205

Leu Arg Leu Asn Glu Gln Tyr Glu His Ala Ser Ile His Leu Trp Asp
                210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
                260                 265                 270

Ala Pro Thr Val Glu Asp Gln Val Ala Glu Ala Glu Pro Glu Pro Ala
                275                 280                 285

Glu Glu Tyr Thr Glu Gln Ser Glu Val Glu Ser Thr Glu Tyr Val Asn
                290                 295                 300

Arg Gln Phe Met Ala Glu Thr Gln Phe Ser Ser Gly Glu Lys Glu Gln
305                 310                 315                 320

Val Asp Glu Trp Thr Val Thr Val Glu Val Val Asn Ser Leu Gln
                325                 330                 335

Gln Gln Pro Gln Ala Ala Ser Pro Ser Val Pro Glu Pro His Ser Leu
                340                 345                 350

Thr Pro Val Ala Gln Ala Asp Pro Leu Val Arg Arg Gln Arg Val Gln
                355                 360                 365

Asp Leu Met Ala Gln Met Gln Gly Pro Tyr Asn Phe Ile Gln Asp Ser
                370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
                420                 425                 430

Val Gln Pro Glu Ala Thr Gln Val Pro Leu Val Ser Ser Thr Ser Glu
                435                 440                 445

Gly Tyr Thr Ala Ser Gln Pro Leu Tyr Gln Pro Ser His Ala Thr Glu
                450                 455                 460

Gln Arg Pro Gln Lys Glu Pro Ile Asp Gln Ile Gln Ala Thr Ile Ser
465                 470                 475                 480
```

```
Leu Asn Thr Asp Gln Thr Thr Ala Ser Ser Ser Leu Pro Ala Ala Ser
            485                 490                 495

Gln Pro Gln Val Phe Gln Ala Gly Thr Ser Lys Pro Leu His Ser Ser
        500                 505                 510

Gly Ile Asn Val Asn Ala Ala Pro Phe Gln Ser Met Gln Thr Val Phe
            515                 520                 525

Asn Met Asn Ala Pro Val Pro Pro Val Asn Glu Pro Glu Thr Leu Lys
        530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
            610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Gly Cys Arg Lys
            675

<210> SEQ ID NO 13
<211> LENGTH: 2281
<212> TYPE: DNA
<213> ORGANISM: Canis familiaris
<220> FEATURE:
<221> NAME/KEY: CDS
<222> LOCATION: (1)..(2154)

<400> SEQUENCE: 13 atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
            20                  25                  30 ggg gcg gcg ggg gcg gcg ggg gcc ggg gcg gct gcg ccc gcc tcc cag     144
Gly Ala Ala Gly Ala Ala Gly Ala Gly Ala Ala Pro Ala Ser Gln
        35                  40                  45 cac ccc gcg acc ggc acc ggc gct gtc cag acc gag gcc atg aag cag     192
His Pro Ala Thr Gly Thr Gly Ala Val Gln Thr Glu Ala Met Lys Gln
    50                  55                  60 atc ctc ggg gtg atc gac aag aaa ctc cgg aac ctg gag aag aaa aag     240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt     288
Gly Lys Leu Asp Asp Tyr Gln Glu Arg Met Asn Lys Gly Glu Arg Leu
                85                  90                  95 aat caa gat cag ctg gat gcc gta tct aag tac cag gaa gtc aca aat     336
Asn Gln Asp Gln Leu Asp Ala Val Ser Lys Tyr Gln Glu Val Thr Asn
            100                 105                 110
```

```
aac ttg gag ttt gca aaa gaa tta cag agg agt ttc atg gca tta agt       384
Asn Leu Glu Phe Ala Lys Glu Leu Gln Arg Ser Phe Met Ala Leu Ser
        115                 120                 125 caa gat att cag aaa aca ata aag aag act gca cgt cgg gag cag ctt       432
Gln Asp Ile Gln Lys Thr Ile Lys Lys Thr Ala Arg Arg Glu Gln Leu
130                 135                 140 atg aga gag gaa gcg gaa caa aaa cgt tta aaa act gta ctt gag ctc       480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg       528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg       576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc       624
Leu Leu Asp Glu Phe Tyr Lys Leu Ala Asp Pro Glu Arg Asp Met Ser
        195                 200                 205 ttg agg ttg aat gag cag tat gaa cat gct tcc att cac ctg tgg gac       672
Leu Arg Leu Asn Glu Gln Tyr Glu His Ala Ser Ile His Leu Trp Asp
210                 215                 220 ttg ctg gaa gga aag gaa aag tct gta tgt gga aca acc tat aaa gca       720
Leu Leu Glu Gly Lys Glu Lys Ser Val Cys Gly Thr Thr Tyr Lys Ala
225                 230                 235                 240 cta aag gaa att gtt gag cgt gtt ttc cag tca aat tac ttt gac agc       768
Leu Lys Glu Ile Val Glu Arg Val Phe Gln Ser Asn Tyr Phe Asp Ser
                245                 250                 255 act cac aac cac cag aat ggg cta tgt gag gaa gaa gag gca gcc tca       816
Thr His Asn His Gln Asn Gly Leu Cys Glu Glu Glu Glu Ala Ala Ser
            260                 265                 270 gca cct aca gtt gaa gac cag gta gct gaa gct gag cct gag cca gca       864
Ala Pro Thr Val Glu Asp Gln Val Ala Glu Ala Glu Pro Glu Pro Ala
        275                 280                 285 gaa gaa tac act gaa caa agt gaa gtt gaa tca aca gag tat gta aat       912
Glu Glu Tyr Thr Glu Gln Ser Glu Val Glu Ser Thr Glu Tyr Val Asn
290                 295                 300 aga caa ttt atg gca gaa aca cag ttc agc agt ggt gaa aag gag cag       960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag      1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg      1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag      1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca      1152
Asp Leu Met Ala Gln Met Gln Gly Pro Tyr Asn Phe Ile Gln Asp Ser
370                 375                 380 atg ctg gat ttt gaa aac cag aca ctc gat cct gcc att gta tct gca      1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc      1248
Gln Pro Met Asn Pro Thr Gln Asn Met Asp Met Pro Gln Leu Val Cys
                405                 410                 415 cct cca gtt cat tct gaa tct aga ctt gct caa cct aat caa gtt cct      1296
Pro Pro Val His Ser Glu Ser Arg Leu Ala Gln Pro Asn Gln Val Pro
            420                 425                 430
```

```
gta caa cca gaa gct aca cag gtt cct ttg gtt tca tcc aca agt gag    1344
Val Gln Pro Glu Ala Thr Gln Val Pro Leu Val Ser Ser Thr Ser Glu
            435                 440                 445 ggg tat aca gca tct caa ccc ttg tac cag cct tct cat gct aca gag    1392
Gly Tyr Thr Ala Ser Gln Pro Leu Tyr Gln Pro Ser His Ala Thr Glu
    450                 455                 460 caa cga cca caa aag gaa cca att gac cag att cag gca aca atc tct    1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct    1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt    1536
Gln Pro Gln Val Phe Gln Ala Gly Thr Ser Lys Pro Leu His Ser Ser
            500                 505                 510 gga atc aat gta aat gca gct cca ttc caa tcc atg caa acg gtg ttc    1584
Gly Ile Asn Val Asn Ala Ala Pro Phe Gln Ser Met Gln Thr Val Phe
        515                 520                 525 aat atg aat gcc cca gtt cct cct gtt aat gaa cca gaa act ttg aaa    1632
Asn Met Asn Ala Pro Val Pro Pro Val Asn Glu Pro Glu Thr Leu Lys
    530                 535                 540 caa caa aat cag tac cag gcc agt tat aac cag agc ttt tct agt cag    1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca    1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act    1776
Val Val Gly Thr Tyr His Gly Ser Gln Asp Gln Pro His Gln Val Thr
            580                 585                 590 ggt aac cat cag cag cct ccc cag cag aac act gga ttt cca cgt agc    1824
Gly Asn His Gln Gln Pro Pro Gln Gln Asn Thr Gly Phe Pro Arg Ser
        595                 600                 605 agt cag ccc tat tac aat agt cgt ggt gtg tct cgt ggt ggt tcc cgt    1872
Ser Gln Pro Tyr Tyr Asn Ser Arg Gly Val Ser Arg Gly Gly Ser Arg
    610                 615                 620 ggt gct aga ggc tta atg aat gga tac agg ggc cct gcc aat gga ttc    1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac    1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc    2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag    2064
Tyr Gln Arg Asp Gly Tyr Gln Gln Asn Phe Lys Arg Gly Ser Gly Gln
        675                 680                 685 agt gga cca cgg gga gcc cca cga ggt cgt gga ggg ccc cca aga ccc    2112
Ser Gly Pro Arg Gly Ala Pro Arg Gly Arg Gly Gly Pro Pro Arg Pro
    690                 695                 700 aac aga ggg atg ccg caa atg aac act cag caa gtg aat taa             2154
Asn Arg Gly Met Pro Gln Met Asn Thr Gln Gln Val Asn
705                 710                 715 tctgattcac aggattatgt ttaaacgcca aaaacacact ggccagtgta ccataatatg   2214
ttaccagaag agttattatc tatttggact gttttcatcc cataaagaca ggactacaat   2274
tgtcagc                                                             2281
```

<210> SEQ ID NO 14
<211> LENGTH: 717
<212> TYPE: PRT
<213> ORGANISM: Canis familiaris

<400> SEQUENCE: 14

```
Met Pro Ser Ala Thr Ser Leu Ser Gly Ser Gly Ser Lys Ser Ser Gly
 1               5                  10                  15

Pro Pro Pro Ser Gly Ser Ser Gly Ser Glu Ala Ala Ala Ala
            20                  25                  30

Gly Ala Ala Gly Ala Ala Gly Ala Gly Ala Ala Pro Ala Ser Gln
            35                  40                  45

His Pro Ala Thr Gly Thr Gly Ala Val Gln Thr Glu Ala Met Lys Gln
        50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
            260                 265                 270

Ala Pro Thr Val Glu Asp Gln Val Ala Glu Glu Pro Glu Pro Ala
        275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
        355                 360                 365

Asp Leu Met Ala Gln Met Gln Gly Pro Tyr Asn Phe Ile Gln Asp Ser
    370                 375                 380
```

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
            405                 410                 415

Pro Pro Val His Ser Glu Ser Arg Leu Ala Gln Pro Asn Gln Val Pro
        420                 425                 430

Val Gln Pro Glu Ala Thr Gln Val Pro Leu Val Ser Thr Ser Ser Glu
    435                 440                 445

Gly Tyr Thr Ala Ser Gln Pro Leu Tyr Gln Pro Ser His Ala Thr Glu
450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Pro Pro Arg Pro
    690                 695                 700

Asn Arg Gly Met Pro Gln Met Asn Thr Gln Gln Val Asn
705                 710                 715

<210> SEQ ID NO 15
<211> LENGTH: 3386
<212> TYPE: DNA
<213> ORGANISM: Bos taurus
<220> FEATURE:
<221> NAME/KEY: CDS
<222> LOCATION: (82)..(2208)

<400> SEQUENCE: 15
cgcgtctcgc cccgtccacc gattgactcg ccgtcttgt ccttcctccc gctctttctt      60
ctctcccctt acggtttcaa g atg cct tcg gcc acc agc cac agc gga agc     111
                         Met Pro Ser Ala Thr Ser His Ser Gly Ser -continued

|   |   |   | 1 |   |   |   |   | 5 |   |   |   |   | 10 |   |   |   |
|---|---|---|---|---|---|---|---|---|---|---|---|---|---|---|---|---|

```
ggc agc aag tcg tcc gga ccg cca ccg ccg tcg ggt tcc tcc ggg aat    159
Gly Ser Lys Ser Ser Gly Pro Pro Pro Pro Ser Gly Ser Ser Gly Asn
             15                  20                  25 gag gcg ggg gcc ggg gcc gcc gcg ccg gct tcc caa cac ccc atg acc    207
Glu Ala Gly Ala Gly Ala Ala Ala Pro Ala Ser Gln His Pro Met Thr
         30                  35                  40 ggc acc ggg gct gtc cag acc gag gcc atg aag cag att ctc ggg gtg    255
Gly Thr Gly Ala Val Gln Thr Glu Ala Met Lys Gln Ile Leu Gly Val
     45                  50                  55 atc gac aag aaa ctt cgg aac ctg gag aag aaa aag ggc aag ctt gat    303
Ile Asp Lys Lys Leu Arg Asn Leu Glu Lys Lys Lys Gly Lys Leu Asp
 60                  65                  70 gat tat cag gaa cga atg aac aaa ggg gaa agg ctt aat caa gat cag    351
Asp Tyr Gln Glu Arg Met Asn Lys Gly Glu Arg Leu Asn Gln Asp Gln
 75                  80                  85                  90 ctg gat gcc gtg tct aag tac cag gaa gtc aca aat aac ttg gag ttt    399
Leu Asp Ala Val Ser Lys Tyr Gln Glu Val Thr Asn Asn Leu Glu Phe
                 95                 100                 105 gca aaa gaa tta cag agg agt ttc atg gca tta agc caa gat att cag    447
Ala Lys Glu Leu Gln Arg Ser Phe Met Ala Leu Ser Gln Asp Ile Gln
             110                 115                 120 aaa aca ata aag aag aca gca cgt cgg gag cag ctt atg aga gag gaa    495
Lys Thr Ile Lys Lys Thr Ala Arg Arg Glu Gln Leu Met Arg Glu Glu
         125                 130                 135 gct gaa cag aaa cgt tta aaa aca gta ctt gag ctg cag tat gtt ttg    543
Ala Glu Gln Lys Arg Leu Lys Thr Val Leu Glu Leu Gln Tyr Val Leu
     140                 145                 150 gac aaa cta gga gat gat gaa gtg aga act gac ctg aag caa ggt ttg    591
Asp Lys Leu Gly Asp Asp Glu Val Arg Thr Asp Leu Lys Gln Gly Leu
155                 160                 165                 170 aat gga gtg cca ata ttg tct gaa gag gag ttg tcg ttg tta gat gag    639
Asn Gly Val Pro Ile Leu Ser Glu Glu Glu Leu Ser Leu Leu Asp Glu
                 175                 180                 185 ttc tac aaa tta gca gac cct gaa cga gac atg agc ttg agg ttg aat    687
Phe Tyr Lys Leu Ala Asp Pro Glu Arg Asp Met Ser Leu Arg Leu Asn
             190                 195                 200 gag cag tat gaa cat gcc tcc att cac ctg tgg gac ttg ctg gaa gga    735
Glu Gln Tyr Glu His Ala Ser Ile His Leu Trp Asp Leu Leu Glu Gly
         205                 210                 215 aag gaa aaa cct gta tgt gga aca act tat aaa gct cta aag gaa att    783
Lys Glu Lys Pro Val Cys Gly Thr Thr Tyr Lys Ala Leu Lys Glu Ile
     220                 225                 230 gtt gag cgt gtt ttc cag tca aac tac ttt gac agc acc cac aac cac    831
Val Glu Arg Val Phe Gln Ser Asn Tyr Phe Asp Ser Thr His Asn His
235                 240                 245                 250 cag aat ggt ctg tgt gag gaa gag gca gcc tca gca cct aca gtt        879
Gln Asn Gly Leu Cys Glu Glu Glu Ala Ala Ser Ala Pro Thr Val
                 255                 260                 265 gaa gac cag gca gct gaa gct gaa cct gag cca gtg gaa gaa tat act    927
Glu Asp Gln Ala Ala Glu Ala Glu Pro Glu Pro Val Glu Glu Tyr Thr
             270                 275                 280 gaa caa aat gag gtt gaa tca aca gag tat gta aat aga caa ttt atg    975
Glu Gln Asn Glu Val Glu Ser Thr Glu Tyr Val Asn Arg Gln Phe Met
         285                 290                 295 gca gaa aca cag ttc agc agt ggt gaa aag gag cag gta gat gat tgg   1023
Ala Glu Thr Gln Phe Ser Ser Gly Glu Lys Glu Gln Val Asp Asp Trp
     300                 305                 310 aca gtt gaa aca gtt gag gtg gta aat tca ctc cag cag caa cct cag   1071
```

```
Thr Val Glu Thr Val Glu Val Val Asn Ser Leu Gln Gln Gln Pro Gln
315                 320                 325                 330 gct gca tct cct tca gta cca gaa ccc cac tct ttg acc cca gtg gct    1119
Ala Ala Ser Pro Ser Val Pro Glu Pro His Ser Leu Thr Pro Val Ala
                335                 340                 345 caa gcc gat ccc ctc gtg aga aga cag cga gta cag gac ctt atg gca    1167
Gln Ala Asp Pro Leu Val Arg Arg Gln Arg Val Gln Asp Leu Met Ala
            350                 355                 360 caa atg cag ggg ccc tat aat ttc ata cag gat tca atg ttg gat ttt    1215
Gln Met Gln Gly Pro Tyr Asn Phe Ile Gln Asp Ser Met Leu Asp Phe
        365                 370                 375 gaa aac cag aca ctt gat cct gcc att gta tct gca cag ccg atg aat    1263
Glu Asn Gln Thr Leu Asp Pro Ala Ile Val Ser Ala Gln Pro Met Asn
380                 385                 390 cca gca cag aac atg gac ata ccc cag ctg gtt tgc cct cca gtt cat    1311
Pro Ala Gln Asn Met Asp Ile Pro Gln Leu Val Cys Pro Pro Val His
395                 400                 405                 410 tct gaa tct aga ctt gct caa cct aat caa gtt tct gta cag cca gaa    1359
Ser Glu Ser Arg Leu Ala Gln Pro Asn Gln Val Ser Val Gln Pro Glu
                415                 420                 425 gct aca cag gtt cct ttg gtt tca tcc aca agt gag gga tat aca gca    1407
Ala Thr Gln Val Pro Leu Val Ser Ser Thr Ser Glu Gly Tyr Thr Ala
            430                 435                 440 tct caa ccc ttg tac caa cct tct cat gct act gac caa cga cca caa    1455
Ser Gln Pro Leu Tyr Gln Pro Ser His Ala Thr Asp Gln Arg Pro Gln
        445                 450                 455 aag gaa ccg att gat cag att cag gcg acg atc tct tta aat aca gac    1503
Lys Glu Pro Ile Asp Gln Ile Gln Ala Thr Ile Ser Leu Asn Thr Asp
460                 465                 470 cag act aca gca tca tca tcc ctt cct gct gct tct cag cct caa gtg    1551
Gln Thr Thr Ala Ser Ser Ser Leu Pro Ala Ala Ser Gln Pro Gln Val
475                 480                 485                 490 ttc cag gct ggg aca agc aaa cct tta cat agc agt gga atc aat gta    1599
Phe Gln Ala Gly Thr Ser Lys Pro Leu His Ser Ser Gly Ile Asn Val
                495                 500                 505 aat gca gct cca ttc caa tcc atg caa acg gta ttc aat atg aat gcc    1647
Asn Ala Ala Pro Phe Gln Ser Met Gln Thr Val Phe Asn Met Asn Ala
            510                 515                 520 cca gtt cct cct gtt aat gaa cca gaa act tta aaa cag caa aat cag    1695
Pro Val Pro Pro Val Asn Glu Pro Glu Thr Leu Lys Gln Gln Asn Gln
        525                 530                 535 tac cag gcc agt tac aac cag agc ttt tcc agt cag cct cac caa gta    1743
Tyr Gln Ala Ser Tyr Asn Gln Ser Phe Ser Ser Gln Pro His Gln Val
540                 545                 550 gaa caa aca gag ctt cag caa gaa cag ctt caa aca gtg gtt ggc act    1791
Glu Gln Thr Glu Leu Gln Gln Glu Gln Leu Gln Thr Val Val Gly Thr
555                 560                 565                 570 tat cat ggt tct cag gac cag ccc cat caa gtg act ggt aac cac cag    1839
Tyr His Gly Ser Gln Asp Gln Pro His Gln Val Thr Gly Asn His Gln
                575                 580                 585 cag cct cct cag cag aac act gga ttt cca cgt agc aat cag ccc tat    1887
Gln Pro Pro Gln Gln Asn Thr Gly Phe Pro Arg Ser Asn Gln Pro Tyr
            590                 595                 600 tac aac agt cgt ggt gtg tct cgt gga ggt tcc cgt ggt gct aga ggc    1935
Tyr Asn Ser Arg Gly Val Ser Arg Gly Gly Ser Arg Gly Ala Arg Gly
        605                 610                 615 ttg atg aat gga tac aga gga cct gct aat gga ttc aga gga gga tat    1983
Leu Met Asn Gly Tyr Arg Gly Pro Ala Asn Gly Phe Arg Gly Gly Tyr
620                 625                 630
```

```
gat ggt tac cgc cct tca ttc tct act aac act cca aac agt ggt tat    2031
Asp Gly Tyr Arg Pro Ser Phe Ser Thr Asn Thr Pro Asn Ser Gly Tyr
635                 640                 645                 650 aca caa tct caa ttc agt gct ccc cgg gac tac tct ggc tat cag cgg    2079
Thr Gln Ser Gln Phe Ser Ala Pro Arg Asp Tyr Ser Gly Tyr Gln Arg
            655                 660                 665 gat gga tat cag cag aat ttc aag cga ggc tct ggg cag agt gga cca    2127
Asp Gly Tyr Gln Gln Asn Phe Lys Arg Gly Ser Gly Gln Ser Gly Pro
        670                 675                 680 cgg gga gcc cca cga ggt cgt gga ggg ccc cca aga ccc aac aga ggg    2175
Arg Gly Ala Pro Arg Gly Arg Gly Gly Pro Pro Arg Pro Asn Arg Gly
    685                 690                 695 atg ccg caa atg aac act cag caa gtg aat taa tctgattcac aggattatgt  2228
Met Pro Gln Met Asn Thr Gln Gln Val Asn
    700                 705 ttaatcgcca aaaacacact ggccagtgta ccataatatg ttaccagaag agttattatc  2288
tatttgttct ccctttcagg aaacttattg taaagggact gttttcatcc cataaagaca  2348
ggactacaat tgtcagcttt atattacctg gatatgaagg gaaactattt ttactctgca  2408
tgttctgtcc taagcgtcat cttgagcctt gcacatgata ctcagattcc tcacccttgc  2468
ttaggagtaa aacataatat actttaatgg ggtgatatct ccatagttat ttgaagtggc  2528
ttggataaag caagactgac ttctgacatt ggataaaatc tacaaatcag ccctagagtc  2588
attcagtggt aactgacaaa actaaaatat ttcccttgaa aggaagatgg aaggagtgga  2648
gtgtggtttg gcagaacaac tgcatttcac agcttttcca cttaaattgg agcactgaac  2708
atttagatgc ataccgaatt atgcatgggc cctaatcaca cagacaaggc tggtgccagc  2768
cttaggcttg acacggcagt gttcacccte tggccagacg actgtggttc aagacacatg  2828
taaattgctt tttaacagct gatactgtat aagacaaagc caaatgcaa aattaggctt   2888 tgattggcac ttttcgaaaa atatgcaaca attaagggat ataatctgga tggccgcttc  2948
tgtacttaat gtgaaatatt tagataccct tcaaacactt aacagtttct ttgacaatga  3008
gttttgtaag gattggtagt aaatatcatt ccttatgacg tacattgtct gtcactaatc  3068
cttggatctt gctgtattgt cacctaaatt ggtacaggta ctgatgaaaa tctaatggat  3128
aatcataaca ctcttggtta catgtttttc ctgcagcctg aaagttttta taagaaaaag  3188
acatcaaatg cctgctgctg ccacccttt  aaattgctat cttttgaaaa gcaccagtat  3248
gtgttttaga ttgatttccc tattttaggg aaatgacagt cagtagtttc acttctgatg  3308
gtataagcaa acaaataaaa catgtttata aaaaaaaaa aaaaaaaaa aaaaaaaaaa   3368 aaaaaaaaa aaaaaaaa                                                 3386

<210> SEQ ID NO 16
<211> LENGTH: 708
<212> TYPE: PRT
<213> ORGANISM: Bos taurus

<400> SEQUENCE: 16

Met Pro Ser Ala Thr Ser His Ser Gly Ser Gly Ser Lys Ser Ser Gly
1               5                   10                  15

Pro Pro Pro Pro Ser Gly Ser Ser Gly Asn Glu Ala Gly Ala Gly Ala
            20                  25                  30

Ala Ala Pro Ala Ser Gln His Pro Met Thr Gly Thr Gly Ala Val Gln
        35                  40                  45

Thr Glu Ala Met Lys Gln Ile Leu Gly Val Ile Asp Lys Lys Leu Arg
    50                  55                  60
```

```
Asn Leu Glu Lys Lys Lys Gly Lys Leu Asp Asp Tyr Gln Glu Arg Met
 65                  70                  75                  80

Asn Lys Gly Glu Arg Leu Asn Gln Asp Gln Leu Asp Ala Val Ser Lys
                 85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Glu Val Arg Thr Asp Leu Lys Gln Gly Leu Asn Gly Val Pro Ile Leu
                165                 170                 175

Ser Glu Glu Glu Leu Ser Leu Leu Asp Glu Phe Tyr Lys Leu Ala Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Ala Ala Glu
            260                 265                 270

Ala Glu Pro Glu Pro Val Glu Glu Tyr Thr Glu Gln Asn Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Asp Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ala Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Ala Gln Asn Met Asp
385                 390                 395                 400

Ile Pro Gln Leu Val Cys Pro Pro Val His Ser Glu Ser Arg Leu Ala
                405                 410                 415

Gln Pro Asn Gln Val Ser Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Asp Gln Arg Pro Gln Lys Glu Pro Ile Asp Gln
    450                 455                 460

Ile Gln Ala Thr Ile Ser Leu Asn Thr Asp Gln Thr Thr Ala Ser Ser
465                 470                 475                 480
```

```
Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Val Asn
        515                 520                 525

Glu Pro Glu Thr Leu Lys Gln Asn Gln Tyr Gln Ala Ser Tyr Asn
    530                 535                 540

Gln Ser Phe Ser Ser Gln Pro His Gln Val Glu Gln Thr Glu Leu Gln
545                 550                 555                 560

Gln Glu Gln Leu Gln Thr Val Val Gly Thr Tyr His Gly Ser Gln Asp
                565                 570                 575

Gln Pro His Gln Val Thr Gly Asn His Gln Gln Pro Gln Gln Asn
            580                 585                 590

Thr Gly Phe Pro Arg Ser Asn Gln Pro Tyr Tyr Asn Ser Arg Gly Val
                595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Thr Asn Thr Pro Asn Ser Gly Tyr Thr Ser Gln Phe Ser
                645                 650                 655

Ala Pro Arg Asp Tyr Ser Tyr Gln Arg Asp Gly Tyr Gln Gln Asn
            660                 665                 670

Phe Lys Arg Gly Ser Gly Gln Ser Gly Pro Arg Gly Ala Pro Arg Gly
                675                 680                 685

Arg Gly Gly Pro Pro Arg Pro Asn Arg Gly Met Pro Gln Met Asn Thr
    690                 695                 700

Gln Gln Val Asn
705

<210> SEQ ID NO 17
<211> LENGTH: 3150
<212> TYPE: DNA
<213> ORGANISM: Equus caballus
<220> FEATURE:
<221> NAME/KEY: CDS
<222> LOCATION: (1)..(1917)

<400> SEQUENCE: 17 atg gag ggc aag ctc gat gat tac caa gag cga atg aac aaa gga gaa    48
Met Glu Gly Lys Leu Asp Asp Tyr Gln Glu Arg Met Asn Lys Gly Glu
1               5                   10                  15 agg ctt aat cag gat cag ctg gat gct gtg tct aag tac cag gaa gtc    96
Arg Leu Asn Gln Asp Gln Leu Asp Ala Val Ser Lys Tyr Gln Glu Val
            20                  25                  30 aca aat aac ttg gag ttt gcg aaa gaa ttg cag agg agt ttc atg gcg   144
Thr Asn Asn Leu Glu Phe Ala Lys Glu Leu Gln Arg Ser Phe Met Ala
        35                  40                  45 ttg agt cag gat att cag aaa aca ata aag aag acg gca cgt cgg gag   192
Leu Ser Gln Asp Ile Gln Lys Thr Ile Lys Lys Thr Ala Arg Arg Glu
    50                  55                  60 cag ctt atg aga gaa gaa gct gaa cag aaa cgt tta aaa act gta ctt   240
Gln Leu Met Arg Glu Glu Ala Glu Gln Lys Arg Leu Lys Thr Val Leu
65                  70                  75                  80 gag ctg cag tat gtt ttg gac aaa ttg gga gat gaa gaa gtg cga act   288
Glu Leu Gln Tyr Val Leu Asp Lys Leu Gly Asp Glu Glu Val Arg Thr
                85                  90                  95
```

```
gac ctg aaa caa ggt ttg aat gga gtg cca ata ctc tct gaa gaa gag      336
Asp Leu Lys Gln Gly Leu Asn Gly Val Pro Ile Leu Ser Glu Glu Glu
            100                 105                 110 ttg tcg ctg ttg gat gag ttc tac aag tta gca gac cct gta cgg gac      384
Leu Ser Leu Leu Asp Glu Phe Tyr Lys Leu Ala Asp Pro Val Arg Asp
        115                 120                 125 atg agc ttg agg ttg aat gag cag tat gag cat gcc tcc att cac ctg      432
Met Ser Leu Arg Leu Asn Glu Gln Tyr Glu His Ala Ser Ile His Leu
130                 135                 140 tgg gac ttg ctg gaa ggg aag gaa aaa tct gtc tgt gga aca acc tat      480
Trp Asp Leu Leu Glu Gly Lys Glu Lys Ser Val Cys Gly Thr Thr Tyr
145                 150                 155                 160 aaa gct ctg agg gaa att gtt gag cgt gtt ttc cag tcc aac tac ttt      528
Lys Ala Leu Arg Glu Ile Val Glu Arg Val Phe Gln Ser Asn Tyr Phe
                165                 170                 175 gac agc acc cac aac cac cag aat ggg ctc tgt gag gag gaa gag gct      576
Asp Ser Thr His Asn His Gln Asn Gly Leu Cys Glu Glu Glu Glu Ala
            180                 185                 190 acc tca gct cca aca gct gaa gac cag gga gct gaa gct gaa cct gag      624
Thr Ser Ala Pro Thr Ala Glu Asp Gln Gly Ala Glu Ala Glu Pro Glu
        195                 200                 205 cca gca gaa gaa tac act gaa caa agt gaa gtt gaa tca aca gag tat      672
Pro Ala Glu Glu Tyr Thr Glu Gln Ser Glu Val Glu Ser Thr Glu Tyr
210                 215                 220 gta aat aga cag ttt atg gca gaa gcg cag ttc agt ggt gag aag gag      720
Val Asn Arg Gln Phe Met Ala Glu Ala Gln Phe Ser Gly Glu Lys Glu
225                 230                 235                 240 cag gtg gat gag tgg aca gtc gag acg gtc gag gtg gta aat tca ctc      768
Gln Val Asp Glu Trp Thr Val Glu Thr Val Glu Val Val Asn Ser Leu
                245                 250                 255 cag cag caa cct cag gct gca tct cct tca gta ccg gag ccc cac tct      816
Gln Gln Gln Pro Gln Ala Ala Ser Pro Ser Val Pro Glu Pro His Ser
            260                 265                 270 ttg act cca gtg gct cag gca gat ccc ctt gtg aga aga cag cga gta      864
Leu Thr Pro Val Ala Gln Ala Asp Pro Leu Val Arg Arg Gln Arg Val
        275                 280                 285 cag gac ctt atg gcg caa atg cag ggg ccc tat aat ttc ata cag gat      912
Gln Asp Leu Met Ala Gln Met Gln Gly Pro Tyr Asn Phe Ile Gln Asp
290                 295                 300 tca atg ctg gat ttt gaa aac cag aca ctt gat cct gcc att gta tct      960
Ser Met Leu Asp Phe Glu Asn Gln Thr Leu Asp Pro Ala Ile Val Ser
305                 310                 315                 320 gca cag cct atg aat cca gca cag aat atg gac atg ccc cag ctg gtt     1008
Ala Gln Pro Met Asn Pro Ala Gln Asn Met Asp Met Pro Gln Leu Val
                325                 330                 335 tgc cct cca gtt cat gct gaa tct aga ctt gct caa cct aat caa gtt     1056
Cys Pro Pro Val His Ala Glu Ser Arg Leu Ala Gln Pro Asn Gln Val
            340                 345                 350 cct gta caa cca gaa gct aca cag gtt cct ttg gtt tca tcc aca agt     1104
Pro Val Gln Pro Glu Ala Thr Gln Val Pro Leu Val Ser Ser Thr Ser
        355                 360                 365 gag ggg tat aca gca tct cag ccc ttg tac cag cct tct cat gct aca     1152
Glu Gly Tyr Thr Ala Ser Gln Pro Leu Tyr Gln Pro Ser His Ala Thr
370                 375                 380 gag caa cga ccg caa aag gaa ccg act gac cag atc cag gca aca atc     1200
Glu Gln Arg Pro Gln Lys Glu Pro Thr Asp Gln Ile Gln Ala Thr Ile
385                 390                 395                 400 tct tta aat aca gac cag act aca gca tca tca tcc ctt cct gct gct     1248
Ser Leu Asn Thr Asp Gln Thr Thr Ala Ser Ser Ser Leu Pro Ala Ala
```

-continued

```
                    405                 410                 415
tct cag cct cag gtg ttc cag gct ggg aca agc aaa cct tta cac agc       1296
Ser Gln Pro Gln Val Phe Gln Ala Gly Thr Ser Lys Pro Leu His Ser
            420                 425                 430 agt ggg atc aat gta aat gca gcg cca ttc cag tcc atg caa acg gtg       1344
Ser Gly Ile Asn Val Asn Ala Ala Pro Phe Gln Ser Met Gln Thr Val
            435                 440                 445 ttc aac atg aat gcc ccg gtt cct cct gtt aat gaa cca gaa act tta       1392
Phe Asn Met Asn Ala Pro Val Pro Pro Val Asn Glu Pro Glu Thr Leu
450                 455                 460 aaa cag caa aat cag tac cag gcc agc tat aac cag agc ttt tcc agt       1440
Lys Gln Gln Asn Gln Tyr Gln Ala Ser Tyr Asn Gln Ser Phe Ser Ser
465                 470                 475                 480 ccg cct cac caa gta gag cag aca gag ctt ccg caa gag cag ctt cag       1488
Pro Pro His Gln Val Glu Gln Thr Glu Leu Pro Gln Glu Gln Leu Gln
                485                 490                 495 acg gtg gtt ggt act tac cat gct tcc caa gac cag ccc cat caa gtg       1536
Thr Val Val Gly Thr Tyr His Ala Ser Gln Asp Gln Pro His Gln Val
            500                 505                 510 acc ggt aac cac cag cag cct ccc cag cag aac act ggg ttt cca cgt       1584
Thr Gly Asn His Gln Gln Pro Pro Gln Gln Asn Thr Gly Phe Pro Arg
            515                 520                 525 agc agt cag ccc tat tac aac agt cgt ggt gtg tct cgt gga ggc tcc       1632
Ser Ser Gln Pro Tyr Tyr Asn Ser Arg Gly Val Ser Arg Gly Gly Ser
            530                 535                 540 cgt ggt gct aga ggc ttg atg aat gga tac agg ggc cct gcc aat gga       1680
Arg Gly Ala Arg Gly Leu Met Asn Gly Tyr Arg Gly Pro Ala Asn Gly
545                 550                 555                 560 ttc aga gga gga tat gat ggt tac cgc cct tcg ttc tct aac act cca       1728
Phe Arg Gly Gly Tyr Asp Gly Tyr Arg Pro Ser Phe Ser Asn Thr Pro
                565                 570                 575 aac agc ggt tac aca cag tct cag ttc agt gct ccc cgg gac tac tct       1776
Asn Ser Gly Tyr Thr Gln Ser Gln Phe Ser Ala Pro Arg Asp Tyr Ser
            580                 585                 590 ggc tat cag cgg gat gga tat cag cag aat ttc aag cga ggc tct ggg       1824
Gly Tyr Gln Arg Asp Gly Tyr Gln Gln Asn Phe Lys Arg Gly Ser Gly
            595                 600                 605 cag agt gga ccc cgg gga gcc cca cga ggt cgt gga ggg ccc cca aga       1872
Gln Ser Gly Pro Arg Gly Ala Pro Arg Gly Arg Gly Gly Pro Pro Arg
            610                 615                 620 ccc aac aga ggg atg ccg caa atg aac act cag caa gtg aat taa           1917
Pro Asn Arg Gly Met Pro Gln Met Asn Thr Gln Gln Val Asn
625                 630                 635 tctgattcac aggattatct ttaatcgcca aaacacactg gccagtgtac cataatatgt     1977
taccagaaga gttattatct atttgttctc cctttcagga aacttattgt aaagggactg    2037 tttcatccc ataaagacag gactacagtt gtcagcttta tattacctgg atatggaagg    2097
aaactatttt tactctgcat gttctgtcct aagcgtcatc ttgagccttg cacatgatac    2157
tcagattcct ttcccttgct taggagtaaa acataatata ctttatgggg tgataatatc    2217
tccatagtta tttgaagtgg cttggaaaaa gcaagattga cttttgacat tggataaaat    2277
ctacaaatca gccctagagt ttcatggtca ttcacaaaac taaatatttt cccttgaaag    2337
gaagatggaa ggactggagt gtggtttggc agaacaactg catttcacag cttttcctat    2397
taaattggag cactgaatgt taaatgcata ccaaattatg catgggccct taatcacaca    2457
tacatggcta ccagctttga cacagcacta ttcatcctct ggccaaacga ctgtggttaa    2517
aaacacgtgt aaattgcttt ttaacagctg atactgtaaa agacaaagct aaaatgcaaa    2577
```

```
attaggcttt cattggcact tttcgaaaaa tatgcaacaa atttgggatg taatctggat    2637
ggccacttct gtacttaatg tgaagtattt agatacottt ttgaacactt aacagtttct    2697
tcgacaatga cttttgtaag gattggtagt atatatcatt ccttatgaca tacattgtct    2757
gttgctaatc cttggatctt gctgtattgt cacctaaatt ggtacaggta ctgatgaaaa    2817
tctctcatgg ataaacctaa cactcttcgt cacatgtttt tcctgcagcc tgaaggtttt    2877
taaaaggaaa agatatcaaa tgcctgctgc taccacccctt ttaaattgct atcttttgaa    2937
aagcaccagt atgtgttttt agattgattt ccctatttta gggaaatgac agtcagtagt    2997
ttcagttctg atggtataag caaagcaaat aaaacgtgtt tataaaagtt gtatcttgaa    3057
acactggtgt tcaacagcta gcagcttctg tggttcaccc cctgccttgt tagtgttacc    3117
catttatggt tatctccagc agcaatttct cta                                 3150
```

<210> SEQ ID NO 18
<211> LENGTH: 638
<212> TYPE: PRT
<213> ORGANISM: Equus caballus

<400> SEQUENCE: 18

```
Met Glu Gly Lys Leu Asp Asp Tyr Gln Glu Arg Met Asn Lys Gly Glu
1               5                   10                  15

Arg Leu Asn Gln Asp Gln Leu Asp Ala Val Ser Lys Tyr Gln Glu Val
            20                  25                  30

Thr Asn Asn Leu Glu Phe Ala Lys Glu Leu Gln Arg Ser Phe Met Ala
        35                  40                  45

Leu Ser Gln Asp Ile Gln Lys Thr Ile Lys Lys Thr Ala Arg Arg Glu
    50                  55                  60

Gln Leu Met Arg Glu Glu Ala Glu Gln Lys Arg Leu Lys Thr Val Leu
65                  70                  75                  80

Glu Leu Gln Tyr Val Leu Asp Lys Leu Gly Asp Glu Glu Val Arg Thr
                85                  90                  95

Asp Leu Lys Gln Gly Leu Asn Gly Val Pro Ile Leu Ser Glu Glu Glu
            100                 105                 110

Leu Ser Leu Leu Asp Glu Phe Tyr Lys Leu Ala Asp Pro Val Arg Asp
        115                 120                 125

Met Ser Leu Arg Leu Asn Glu Gln Tyr Glu His Ala Ser Ile His Leu
    130                 135                 140

Trp Asp Leu Leu Glu Gly Lys Glu Lys Ser Val Cys Gly Thr Thr Tyr
145                 150                 155                 160

Lys Ala Leu Arg Glu Ile Val Glu Arg Val Phe Gln Ser Asn Tyr Phe
                165                 170                 175

Asp Ser Thr His Asn His Gln Asn Gly Leu Cys Glu Glu Glu Ala
            180                 185                 190

Thr Ser Ala Pro Thr Ala Glu Asp Gln Gly Ala Glu Ala Glu Pro Glu
        195                 200                 205

Pro Ala Glu Glu Tyr Thr Glu Gln Ser Glu Val Glu Ser Thr Glu Tyr
    210                 215                 220

Val Asn Arg Gln Phe Met Ala Glu Ala Gln Phe Ser Gly Glu Lys Glu
225                 230                 235                 240

Gln Val Asp Glu Trp Thr Val Glu Thr Val Glu Val Asn Ser Leu
                245                 250                 255

Gln Gln Gln Pro Gln Ala Ala Ser Pro Ser Val Pro Glu Pro His Ser
            260                 265                 270
```

Leu Thr Pro Val Ala Gln Ala Asp Pro Leu Val Arg Gln Arg Val
         275                 280                 285

Gln Asp Leu Met Ala Gln Met Gln Gly Pro Tyr Asn Phe Ile Gln Asp
    290                 295                 300

Ser Met Leu Asp Phe Glu Asn Gln Thr Leu Asp Pro Ala Ile Val Ser
305                 310                 315                 320

Ala Gln Pro Met Asn Pro Ala Gln Asn Met Asp Met Pro Gln Leu Val
                325                 330                 335

Cys Pro Pro Val His Ala Glu Ser Arg Leu Ala Gln Pro Asn Gln Val
            340                 345                 350

Pro Val Gln Pro Glu Ala Thr Gln Val Pro Leu Val Ser Ser Thr Ser
        355                 360                 365

Glu Gly Tyr Thr Ala Ser Gln Pro Leu Tyr Gln Pro Ser His Ala Thr
    370                 375                 380

Glu Gln Arg Pro Gln Lys Glu Pro Thr Asp Gln Ile Gln Ala Thr Ile
385                 390                 395                 400

Ser Leu Asn Thr Asp Gln Thr Thr Ala Ser Ser Leu Pro Ala Ala
                405                 410                 415

Ser Gln Pro Gln Val Phe Gln Ala Gly Thr Ser Lys Pro Leu His Ser
            420                 425                 430

Ser Gly Ile Asn Val Asn Ala Ala Pro Phe Gln Ser Met Gln Thr Val
        435                 440                 445

Phe Asn Met Asn Ala Pro Val Pro Val Asn Glu Pro Glu Thr Leu
    450                 455                 460

Lys Gln Gln Asn Gln Tyr Gln Ala Ser Tyr Asn Gln Ser Phe Ser Ser
465                 470                 475                 480

Pro Pro His Gln Val Glu Gln Thr Glu Leu Pro Gln Glu Gln Leu Gln
                485                 490                 495

Thr Val Val Gly Thr Tyr His Ala Ser Gln Asp Gln Pro His Gln Val
            500                 505                 510

Thr Gly Asn His Gln Gln Pro Pro Gln Gln Asn Thr Gly Phe Pro Arg
        515                 520                 525

Ser Ser Gln Pro Tyr Tyr Asn Ser Arg Gly Val Ser Arg Gly Gly Ser
    530                 535                 540

Arg Gly Ala Arg Gly Leu Met Asn Gly Tyr Arg Gly Pro Ala Asn Gly
545                 550                 555                 560

Phe Arg Gly Gly Tyr Asp Gly Tyr Arg Pro Ser Phe Ser Asn Thr Pro
                565                 570                 575

Asn Ser Gly Tyr Thr Gln Ser Gln Phe Ser Ala Pro Arg Asp Tyr Ser
            580                 585                 590

Gly Tyr Gln Arg Asp Gly Tyr Gln Gln Asn Phe Lys Arg Gly Ser Gly
        595                 600                 605

Gln Ser Gly Pro Arg Gly Ala Pro Arg Gly Arg Gly Pro Pro Arg
    610                 615                 620

Pro Asn Arg Gly Met Pro Gln Met Asn Thr Gln Gln Val Asn
625                 630                 635

<210> SEQ ID NO 19
<211> LENGTH: 6181
<212> TYPE: DNA
<213> ORGANISM: Mus musculus
<220> FEATURE:
<221> NAME/KEY: CDS
<222> LOCATION: (179)..(2302)

<400> SEQUENCE: 19

```
gctggctggc taagtccctc ccgcgccggc tcttgtccca ctaggagcag ctcagagccg      60
cgggacagg gcgaagcggc ctgcgcccac ggagcgcacg tctctgttct caacgcagca     120
ccacccttgc cccctcggc tgccactcc agacgtccag cggctccgcg cgcgcacg        178 atg ccc tcg gcc acc agc cac agc gga agc ggc agc aaa tcg tcg gga      226
Met Pro Ser Ala Thr Ser His Ser Gly Ser Gly Ser Lys Ser Ser Gly
1               5                   10                  15 ccg ccg ccg ccg tcc ggt tcc tcc ggg agt gag gcg gcg gcc ggg gca      274
Pro Pro Pro Pro Ser Gly Ser Ser Gly Ser Glu Ala Ala Ala Gly Ala
                20                  25                  30 gct gcg ccg gct tct cag cat ccg gca acc ggc acc ggc gcc gtc cag      322
Ala Ala Pro Ala Ser Gln His Pro Ala Thr Gly Thr Gly Ala Val Gln
            35                  40                  45 acc gag gcc atg aag cag att ctc ggc gta atc gac aag aaa ctt cgg      370
Thr Glu Ala Met Lys Gln Ile Leu Gly Val Ile Asp Lys Lys Leu Arg
        50                  55                  60 aac ctg gag aag aaa aag ggt aaa ctt gat gat tac cag gaa cga atg      418
Asn Leu Glu Lys Lys Lys Gly Lys Leu Asp Asp Tyr Gln Glu Arg Met
65                  70                  75                  80 aat aaa ggg gaa agg ctc aat caa gac cag ctg gat gcc gta tct aag      466
Asn Lys Gly Glu Arg Leu Asn Gln Asp Gln Leu Asp Ala Val Ser Lys
                85                  90                  95 tac cag gaa gtc aca aat aat ttg gag ttt gca aag gaa tta cag agg      514
Tyr Gln Glu Val Thr Asn Asn Leu Glu Phe Ala Lys Glu Leu Gln Arg
            100                 105                 110 agt ttc atg gca tta agt caa gat att cag aaa aca ata aag aag aca      562
Ser Phe Met Ala Leu Ser Gln Asp Ile Gln Lys Thr Ile Lys Lys Thr
        115                 120                 125 gca cgt cgg gaa cag ctt atg aga gaa gaa gca gaa cag aag cgc tta      610
Ala Arg Arg Glu Gln Leu Met Arg Glu Glu Ala Glu Gln Lys Arg Leu
    130                 135                 140 aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160 gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175 tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190 cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205 tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
    210                 215                 220 gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240 tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255 gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270 gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285
```

-continued

```
tca aca gag tat gtc aat agg cag ttc atg gca gaa aca cag ttc agc      1090
Ser Thr Glu Tyr Val Asn Arg Gln Phe Met Ala Glu Thr Gln Phe Ser
    290             295                 300 agt ggt gag aag gag caa gtg gat gag tgg aca gtt gaa aca gtt gag      1138
Ser Gly Glu Lys Glu Gln Val Asp Glu Trp Thr Val Glu Thr Val Glu
305                 310                 315                 320 gtt gta aac tca ctc cag cag caa cct cag gct gcg tcc cct tca gtc      1186
Val Val Asn Ser Leu Gln Gln Gln Pro Gln Ala Ala Ser Pro Ser Val
                325                 330                 335 cca gag ccc cac tct ttg act cca gtg gct cag tca gat cca ctt gtg      1234
Pro Glu Pro His Ser Leu Thr Pro Val Ala Gln Ser Asp Pro Leu Val
            340                 345                 350 aga agg cag cgt gta caa gat ctt atg gca caa atg caa ggg ccc tat      1282
Arg Arg Gln Arg Val Gln Asp Leu Met Ala Gln Met Gln Gly Pro Tyr
        355                 360                 365 aat ttc ata cag gat tca atg ttg gat ttt gaa aat cag acg ctt gat      1330
Asn Phe Ile Gln Asp Ser Met Leu Asp Phe Glu Asn Gln Thr Leu Asp
    370                 375                 380 cct gcc att gta tcc gca cag cct atg aac cct acc cag aac atg gat      1378
Pro Ala Ile Val Ser Ala Gln Pro Met Asn Pro Thr Gln Asn Met Asp
385                 390                 395                 400 atg cct cag ctg gtt tgc cct cag gtt cat tct gaa tct aga ctt gcc      1426
Met Pro Gln Leu Val Cys Pro Gln Val His Ser Glu Ser Arg Leu Ala
                405                 410                 415 caa tct aat caa gtt cct gta caa cca gaa gcc aca cag gtt cct ttg      1474
Gln Ser Asn Gln Val Pro Val Gln Pro Glu Ala Thr Gln Val Pro Leu
            420                 425                 430 gtt tca tcc aca agt gag ggg tat aca gca tct cag ccc ttg tac cag      1522
Val Ser Ser Thr Ser Glu Gly Tyr Thr Ala Ser Gln Pro Leu Tyr Gln
        435                 440                 445 cca tct cat gct acg gag cag cgg ccg cag aaa gag cca atg gat cag      1570
Pro Ser His Ala Thr Glu Gln Arg Pro Gln Lys Glu Pro Met Asp Gln
    450                 455                 460 att cag gca aca ata tct ttg aat aca gac cag act aca gca tcc tca      1618
Ile Gln Ala Thr Ile Ser Leu Asn Thr Asp Gln Thr Thr Ala Ser Ser
465                 470                 475                 480 tcc ctt cct gct gct tct cag cct caa gtg ttc cag gct ggg aca agt      1666
Ser Leu Pro Ala Ala Ser Gln Pro Gln Val Phe Gln Ala Gly Thr Ser
                485                 490                 495 aaa cct ttg cac agc agt gga atc aat gta aat gca gct cca ttc cag      1714
Lys Pro Leu His Ser Ser Gly Ile Asn Val Asn Ala Ala Pro Phe Gln
            500                 505                 510 tcc atg caa acg gtg ttc aat atg aat gct cca gtc cct cct gct aat      1762
Ser Met Gln Thr Val Phe Asn Met Asn Ala Pro Val Pro Pro Ala Asn
        515                 520                 525 gaa cca gaa acg tta aaa caa cag agt cag tac cag gcc act tat aac      1810
Glu Pro Glu Thr Leu Lys Gln Gln Ser Gln Tyr Gln Ala Thr Tyr Asn
    530                 535                 540 cag agt ttt tcc agt cag cct cac caa gtg gaa caa aca gag ctt caa      1858
Gln Ser Phe Ser Ser Gln Pro His Gln Val Glu Gln Thr Glu Leu Gln
545                 550                 555                 560 caa gac caa ctg caa acg gtg gtt ggc act tac cat gga tcc cag gac      1906
Gln Asp Gln Leu Gln Thr Val Val Gly Thr Tyr His Gly Ser Gln Asp
                565                 570                 575 cag cct cat caa gtg cct ggt aac cac cag caa ccc cca cag cag aac      1954
Gln Pro His Gln Val Pro Gly Asn His Gln Gln Pro Pro Gln Gln Asn
            580                 585                 590 act ggc ttt cca cgt agc agt cag cct tat tac aac agt cgt ggg gta      2002
Thr Gly Phe Pro Arg Ser Ser Gln Pro Tyr Tyr Asn Ser Arg Gly Val
```

|  |  |  |  |  |  |  |  |  |  |  |  |  |  |  |  |
|---|---|---|---|---|---|---|---|---|---|---|---|---|---|---|---|
|  |  |  | 595 |  |  |  |  | 600 |  |  |  |  | 605 |  |  |
| tct | cga | gga | ggg | tct | cgt | ggt | gcc | aga | ggc | ttg | atg | aat | gga | tac | agg | 2050 |
| Ser | Arg | Gly | Gly | Ser | Arg | Gly | Ala | Arg | Gly | Leu | Met | Asn | Gly | Tyr | Arg |
|  |  | 610 |  |  |  | 615 |  |  |  |  | 620 |
| ggc | cct | gcc | aat | gga | ttt | aga | gga | gga | tat | gat | ggt | tac | cgc | cct | tca | 2098 |
| Gly | Pro | Ala | Asn | Gly | Phe | Arg | Gly | Gly | Tyr | Asp | Gly | Tyr | Arg | Pro | Ser |
| 625 |  |  |  | 630 |  |  |  |  | 635 |  |  |  |  | 640 |
| ttc | tcg | aac | act | cca | aac | agt | ggt | tat | tca | cag | tct | cag | ttc | act | gct | 2146 |
| Phe | Ser | Asn | Thr | Pro | Asn | Ser | Gly | Tyr | Ser | Gln | Ser | Gln | Phe | Thr | Ala |
|  |  |  |  | 645 |  |  |  |  | 650 |  |  |  |  | 655 |
| ccc | cgg | gac | tac | tct | ggt | tac | cag | cgg | gat | gga | tat | cag | cag | aat | ttc | 2194 |
| Pro | Arg | Asp | Tyr | Ser | Gly | Tyr | Gln | Arg | Asp | Gly | Tyr | Gln | Gln | Asn | Phe |
|  |  | 660 |  |  |  | 665 |  |  |  |  | 670 |
| aag | cga | ggc | tct | ggg | cag | agt | gga | cca | cgg | gga | gcc | cca | cga | ggt | cgt | 2242 |
| Lys | Arg | Gly | Ser | Gly | Gln | Ser | Gly | Pro | Arg | Gly | Ala | Pro | Arg | Gly | Arg |
| 675 |  |  |  |  | 680 |  |  |  |  | 685 |
| gga | ggg | ccc | cca | aga | ccc | aac | aga | ggg | atg | ccg | caa | atg | aac | act | cag | 2290 |
| Gly | Gly | Pro | Pro | Arg | Pro | Asn | Arg | Gly | Met | Pro | Gln | Met | Asn | Thr | Gln |
|  |  | 690 |  |  |  | 695 |  |  |  |  | 700 |
| caa | gtg | aat | taa | tgtgatacac | aggattatgt | ttaatcgcca | aaaacacact |  |  |  |  |  |  |  |  | 2342 |
| Gln | Val | Asn |
| 705 |

```
ggccagtgta ccataatatg ttaccagaag agttattatc tatttgttct cccttttcagg    2402
aaacttattg taaagggact gttttcatcc cataaagaca ggactgcaat tgtcagcttt    2462
acattacctg gatatggaag gaaactattt ttattctgca tgttctgtcc taagcgtcat    2522
cttgagcctt gcacacaata caatactcag attcctcacc cttgcttagg agtaaaacat    2582
tatatactta tggggtgata atatctccat agttagttga agtggcttgg aaaaaaaatg    2642
caagattgaa ttttttgacct tggataaaat ctacaatcag ccctagaact attcagtggt    2702
aattgacaaa gttaaagcat tttctttgaa aggaagatgg aaggagtgga gtgtggttta    2762
gcaaaactgc atttcatagc tttcccatta aattggagca ccgacagatt aaaagcatac    2822
caaattatgc atgggtcctt actcacacaa gtgaggctgg ctaccagcct tgacatagca    2882
ctcactagtc ttctggccaa acgactgtga ttaaaacaca tgtaaattgc tctttagtag    2942
tggatactgt gtaagacaaa gccaaattgc aaatcaggct ttgattggct cttctggaaa    3002
atatgcatca aatatggggg ataatctgga tgggctgctg ctgtgctcaa tgtgaactat    3062
ttagatacct ttgaacacact taacagtttc tctgaacaat gacttacatg gggattggtc    3122
ctgtttgtca ttcctcacca taattgcatt gtcatcacta atccttggat cttgctgtat    3182
tgttactcaa attggtaata ggtactgatg gaaatcgcta atggatggat aatcataaca    3242
cttttggtca catgttttct cctgcagcct gaaagttctt aaagaaaaag atatcaaatg    3302
cctgctgcta ccacccttttt aaattgctat ctttagaaaa gcaccggtat gtgttttaga    3362
ttcatttccc tgttttaggg aaatgacagg cagtagtttc agttctgatg gcaaaacaaa    3422
taaaaacatg tttctaaaag ttgtatcttg aaacactggt gttcaacagc tagcagctaa    3482
agtaattcaa cccatgcatt gctagtgtca cagcctttgg ttatgtctag tagctgtttc    3542
tgaagtattt tcatttatct tttgtcaaat ttaaccctgt ttgaattctc tccttttcctc    3602
aaggagacac ttatgttcaa agtgttgatt ctttgcctta ggtgcataga gagtagacag    3662
tttggagatg gaaaggttag cagtgactta gccatatgtt ctgtgttgga atttgtgcta    3722
gcagtttgag cactagctct gcgtgcctat gaactgaatg ctgcttgtcc cattccattt    3782
tatgtcatgg agaaataatt ccacttggta acacaaaggc taagttaatg ttatttttctg    3842
```

```
tacagaaatt aaattttact tttagccttt tgtaaacttt ttttttttt ttccaagccg    3902
gtatcagcta ctcaaaacaa ttctcagata ttcatcatta gacaactgga gttttgctg    3962
gttttgtagc ctactaaaac tgctgaggct gttgaacatt ccacattcaa aagttttgta   4022
gggtggtgga taatggggaa gcttcaatgt ttattttaaa ataaataaaa taagttcttg   4082
acttttctca tgtgtggtta tggtacatca tattggaagg gttatctgtt acttttgcc    4142
aagactattt tgccagcacc tacacttgtg tgctttaaaa gacaactacc tgggatgtac   4202
cacaaccata tgttaattgt attttattgg gatggataaa atgtttgtgg tttattggat   4262
aatccctaga tggtgtgtta cgtgtgtaga atataatttt atgatagtaa gaaagcaaaa   4322
ttgaagaaaa taagtttagt attgaatttg agttctgaag tgaattcagg gaatgtctca   4382
cgtttcgggc ttctacccaa agtgtagggc agaaggtgta aaagttgttt gtagtttgac   4442
ttgtttattt tttaagttgc ttattccttt caacagcaac atatcattag ctgtcattct   4502
accattgcag ttctagtgag ttttaacgtc tgcattcaag actgttttaa aagcaacctc   4562
actggacaga gaactgctaa agtcttttcc ttaagatctg agtctttgtt actcagtatc   4622
ttctataata tgcaaatgct tgtctagagg cagaagacct tttgtttggt caagtgtgta   4682
ttttaccaga gtacagggaa ctgatggtcc tacatgtctc ttagtgtagt aagactataa   4742
aatcttttgt acatgcacaa ttcacagtat gtttagatac cacgtgtata atgcccccc    4802
ctcccccagg tagcatgcca ttgatgactt tttgcttagg gccatttat taccagggcc    4862
ttaatattcc taaaagatg atttttttttc atcctttctc ctcttttgat cattgtatct   4922
tgatattaaa aacatgacct tccaatgatt gtagtaaatt aacttctata gttcttttgt   4982
ctctatatgt attcatatat atgctattgt atagagactt caaggagaca tggagatgca   5042
tgcttattct caggttcatt cactaaggtg cttggcagac aaccagtttc taagtgcaga   5102
atgtagttaa gcagcttcat atatgtgcca ggcaatttgt tttgttaaat tttcatctac   5162
ttaaggaaat agggtattgt agcttaggct gatcataccc ttcatttcaa ccttaagctc   5222
tcaacctgca tccatccgac ttgagctatt aagtacttta gttttatcga gtataagtta   5282
acagaaaaag taaattaagc tttgccttta ctattttgaa tttatataca ttctggaaaa   5342
acttagaaac tgttgtatat ttcattagat taaattatat gaaaatgtga ttgtttatag   5402
caaagcctgt gagttgcata caccctaagg aaaactcctt aagtgctcct tgaagagaga   5462
agaaacaatt ctgggtctgg tcttttttaag aacaaagcta gactactgta tgttagcact   5522
gtacattaat agtctgttgt gaagcttgag cagtttcctg catagccttg atccttcacc   5582
gttggcattg aaaatagcag tatccctgat gtacttaaaa cttaaagtca ggttttggta   5642
tatttatttg taagtcttaa tttcctctaa atactatatc tctttagcga gacaacctga   5702
aatttattag cacatttggg tatctcttgc ttggcattat ggccagtgtt aactattcag   5762
tggtgaaaaa attaccccctc aagacactgg agtgacccca gatgtgtgta gtaagtggca   5822
tggttcaact gtgtggttaa tgataaatat atgacttagt cggtatgatc tggaaagact   5882
tgattgaaag ataattcagc tgacataagg atgagtgagg agtggcaaac tggataaaag   5942
agtcaagaga cctgtattcc agtgactcct gttttgttta agcattagca agatctgtct   6002
ggggaaactg gatagggcag ttttcttcca tgtttagttt ttgtctcaac atttggaagc   6062
tattgaaggt tttaaaatgg tgtgtattgt ttttttttgg ggggggggtg gccagaatag   6122
tgggtcatct aataaaactg ccatttaaaa gatcaaaaaa aaaaaaaaaa aaaaaaaa     6181
```

<210> SEQ ID NO 20
<211> LENGTH: 707
<212> TYPE: PRT
<213> ORGANISM: Mus musculus

<400> SEQUENCE: 20

Met Pro Ser Ala Thr Ser His Ser Gly Ser Gly Ser Lys Ser Ser Gly
1               5                   10                  15

Pro Pro Pro Ser Gly Ser Ser Gly Ser Glu Ala Ala Gly Ala
            20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
50                  55                  60

Asn Leu Glu Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
                100                 105                 110

Ser Phe Met Ala Leu Ser Gln Asp Ile Gln Lys Thr Ile Lys Lys Thr
            115                 120                 125

Ala Arg Arg Glu Gln Leu Met Arg Glu Ala Glu Gln Lys Arg Leu
130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
            195                 200                 205

Ser Ile His Leu Trp Asp Leu Leu Glu Gly Lys Glu Lys Pro Val Cys
210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
            275                 280                 285

Ser Thr Glu Tyr Val Asn Arg Gln Phe Met Ala Glu Thr Gln Phe Ser
290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
            355                 360                 365

Asn Phe Ile Gln Asp Ser Met Leu Asp Phe Glu Asn Gln Thr Leu Asp
370                 375                 380

```
Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705

<210> SEQ ID NO 21
<211> LENGTH: 6141
<212> TYPE: DNA
<213> ORGANISM: Mus musculus
<220> FEATURE:
<221> NAME/KEY: CDS
<222> LOCATION: (139)..(2262)

<400> SEQUENCE: 21
cccaccgcgc gcgcgcgtag ccgcctgccc gcccgcccgc tgcgcgtttt gtcccgcgtc      60
tctccccgtc cgtctcctga cttgctggtc ttgtccttcc ctcccgcttt tttcctctcc     120
```

| | | |
|---|---|---|
| tctcttctcg gtctaaag atg ccc tcg gcc acc agc cac agc gga agc ggc<br>                              Met Pro Ser Ala Thr Ser His Ser Gly Ser Gly<br>                              1               5                    10 | | 171 |
| agc aaa tcg tcg gga ccg ccg ccg tcc ggt tcc tcc ggg agt gag<br>Ser Lys Ser Ser Gly Pro Pro Pro Ser Gly Ser Ser Gly Ser Glu<br>             15                  20                  25 | | 219 |
| gcg gcg gcc ggg gca gct gcg ccg gct tct cag cat ccg gca acc ggc<br>Ala Ala Ala Gly Ala Ala Ala Pro Ala Ser Gln His Pro Ala Thr Gly<br>         30                    35                    40 | | 267 |
| acc ggc gcc gtc cag acc gag gcc atg aag cag att ctc ggc gta atc<br>Thr Gly Ala Val Gln Thr Glu Ala Met Lys Gln Ile Leu Gly Val Ile<br> 45                     50                    55 | | 315 |
| gac aag aaa ctt cgg aac ctg gag aag aaa aag ggt aaa ctt gat gat<br>Asp Lys Lys Leu Arg Asn Leu Glu Lys Lys Lys Gly Lys Leu Asp Asp<br>60                  65                  70                    75 | | 363 |
| tac cag gaa cga atg aat aaa ggg gaa agg ctc aat caa gac cag ctg<br>Tyr Gln Glu Arg Met Asn Lys Gly Glu Arg Leu Asn Gln Asp Gln Leu<br>                    80                    85                    90 | | 411 |
| gat gcc gta tct aag tac cag gaa gtc aca aat aat ttg gag ttt gca<br>Asp Ala Val Ser Lys Tyr Gln Glu Val Thr Asn Asn Leu Glu Phe Ala<br>             95                  100                105 | | 459 |
| aag gaa tta cag agg agt ttc atg gca tta agt caa gat att cag aaa<br>Lys Glu Leu Gln Arg Ser Phe Met Ala Leu Ser Gln Asp Ile Gln Lys<br>          110                    115                    120 | | 507 |
| aca ata aag aag aca gca cgt cgg gaa cag ctt atg aga gaa gaa gca<br>Thr Ile Lys Lys Thr Ala Arg Arg Glu Gln Leu Met Arg Glu Glu Ala<br>       125                    130                    135 | | 555 |
| gaa cag aag cgc tta aaa act gta ctt gag tta cag tat gta ttg gat<br>Glu Gln Lys Arg Leu Lys Thr Val Leu Glu Leu Gln Tyr Val Leu Asp<br>140                   145                    150                   155 | | 603 |
| aag ctg gga gat gat gat gtg aga aca gat ctg aaa caa ggt ttg agt<br>Lys Leu Gly Asp Asp Asp Val Arg Thr Asp Leu Lys Gln Gly Leu Ser<br>                   160                    165                    170 | | 651 |
| gga gtg cca ata ttg tct gag gag gag ttg tca ttg ctg gat gag ttc<br>Gly Val Pro Ile Leu Ser Glu Glu Glu Leu Ser Leu Leu Asp Glu Phe<br>                175                    180                    185 | | 699 |
| tac aag ctc gta gat cct gag cgt gac atg agt tta agg tta aat gag<br>Tyr Lys Leu Val Asp Pro Glu Arg Asp Met Ser Leu Arg Leu Asn Glu<br>          190                    195                    200 | | 747 |
| cag tat gaa cat gcc tca att cac ttg tgg gat ttg ctg gaa ggg aaa<br>Gln Tyr Glu His Ala Ser Ile His Leu Trp Asp Leu Leu Glu Gly Lys<br>       205                    210                    215 | | 795 |
| gaa aag cct gtg tgt gga aca acc tat aaa gct cta aag gaa att gtt<br>Glu Lys Pro Val Cys Gly Thr Thr Tyr Lys Ala Leu Lys Glu Ile Val<br>220                   225                    230                   235 | | 843 |
| gag cgt gtt ttc cag tca aac tac ttt gat agc act cac aat cat caa<br>Glu Arg Val Phe Gln Ser Asn Tyr Phe Asp Ser Thr His Asn His Gln<br>                240                    245                    250 | | 891 |
| aat ggg ttg tgt gag gag gaa gag gcg gct tca gcg ccc aca gtg gag<br>Asn Gly Leu Cys Glu Glu Glu Glu Ala Ala Ser Ala Pro Thr Val Glu<br>          255                    260                    265 | | 939 |
| gac cag gta gct gaa gct gaa cct gag cca gcg gaa gaa tac aca gag<br>Asp Gln Val Ala Glu Ala Glu Pro Glu Pro Ala Glu Glu Tyr Thr Glu<br>               270                    275                    280 | | 987 |
| caa agt gag gtt gaa tca aca gag tat gtc aat agg cag ttc atg gca<br>Gln Ser Glu Val Glu Ser Thr Glu Tyr Val Asn Arg Gln Phe Met Ala<br>       285                    290                    295 | | 1035 |
| gaa aca cag ttc agc agt ggt gag aag gag caa gtg gat gag tgg aca<br>Glu Thr Gln Phe Ser Ser Gly Glu Lys Glu Gln Val Asp Glu Trp Thr<br>300                   305                    310                   315 | | 1083 |

```
gtt gaa aca gtt gag gtt gta aac tca ctc cag cag caa cct cag gct     1131
Val Glu Thr Val Glu Val Val Asn Ser Leu Gln Gln Gln Pro Gln Ala
            320                 325                 330 gcg tcc cct tca gtc cca gag ccc cac tct ttg act cca gtg gct cag     1179
Ala Ser Pro Ser Val Pro Glu Pro His Ser Leu Thr Pro Val Ala Gln
                335                 340                 345 tca gat cca ctt gtg aga agg cag cgt gta caa gat ctt atg gca caa     1227
Ser Asp Pro Leu Val Arg Arg Gln Arg Val Gln Asp Leu Met Ala Gln
            350                 355                 360 atg caa ggg ccc tat aat ttc ata cag gat tca atg ttg gat ttt gaa     1275
Met Gln Gly Pro Tyr Asn Phe Ile Gln Asp Ser Met Leu Asp Phe Glu
        365                 370                 375 aat cag acg ctt gat cct gcc att gta tcc gca cag cct atg aac cct     1323
Asn Gln Thr Leu Asp Pro Ala Ile Val Ser Ala Gln Pro Met Asn Pro
380                 385                 390                 395 acc cag aac atg gat atg cct cag ctg gtt tgc cct cag gtt cat tct     1371
Thr Gln Asn Met Asp Met Pro Gln Leu Val Cys Pro Gln Val His Ser
                400                 405                 410 gaa tct aga ctt gcc caa tct aat caa gtt cct gta caa cca gaa gcc     1419
Glu Ser Arg Leu Ala Gln Ser Asn Gln Val Pro Val Gln Pro Glu Ala
            415                 420                 425 aca cag gtt cct ttg gtt tca tcc aca agt gag ggg tat aca gca tct     1467
Thr Gln Val Pro Leu Val Ser Ser Thr Ser Glu Gly Tyr Thr Ala Ser
        430                 435                 440 cag ccc ttg tac cag cca tct cat gct acg gag cag cgg ccg cag aaa     1515
Gln Pro Leu Tyr Gln Pro Ser His Ala Thr Glu Gln Arg Pro Gln Lys
    445                 450                 455 gag cca atg gat cag att cag gca aca ata tct ttg aat aca gac cag     1563
Glu Pro Met Asp Gln Ile Gln Ala Thr Ile Ser Leu Asn Thr Asp Gln
460                 465                 470                 475 act aca gca tcc tca tcc ctt cct gct gct tct cag cct caa gtg ttc     1611
Thr Thr Ala Ser Ser Ser Leu Pro Ala Ala Ser Gln Pro Gln Val Phe
                480                 485                 490 cag gct ggg aca agt aaa cct ttg cac agc agt gga atc aat gta aat     1659
Gln Ala Gly Thr Ser Lys Pro Leu His Ser Ser Gly Ile Asn Val Asn
            495                 500                 505 gca gct cca ttc cag tcc atg caa acg gtg ttc aat atg aat gct cca     1707
Ala Ala Pro Phe Gln Ser Met Gln Thr Val Phe Asn Met Asn Ala Pro
        510                 515                 520 gtc cct cct gct aat gaa cca gaa acg tta aaa caa cag agt cag tac     1755
Val Pro Pro Ala Asn Glu Pro Glu Thr Leu Lys Gln Gln Ser Gln Tyr
    525                 530                 535 cag gcc act tat aac cag agt ttt tcc agt cag cct cac caa gtg gaa     1803
Gln Ala Thr Tyr Asn Gln Ser Phe Ser Ser Gln Pro His Gln Val Glu
540                 545                 550                 555 caa aca gag ctt caa caa gac caa ctg caa acg gtg gtt ggc act tac     1851
Gln Thr Glu Leu Gln Gln Asp Gln Leu Gln Thr Val Val Gly Thr Tyr
                560                 565                 570 cat gga tcc cag gac cag cct cat caa gtg cct ggt aac cac cag caa     1899
His Gly Ser Gln Asp Gln Pro His Gln Val Pro Gly Asn His Gln Gln
            575                 580                 585 ccc cca cag cag aac act ggc ttt cca cgt agc agt cag cct tat tac     1947
Pro Pro Gln Gln Asn Thr Gly Phe Pro Arg Ser Ser Gln Pro Tyr Tyr
        590                 595                 600 aac agt cgt ggg gta tct cga gga ggg tct cgt ggt gcc aga ggc ttg     1995
Asn Ser Arg Gly Val Ser Arg Gly Gly Ser Arg Gly Ala Arg Gly Leu
    605                 610                 615 atg aat gga tac agg ggc cct gcc aat gga ttt aga gga gga tat gat     2043
Met Asn Gly Tyr Arg Gly Pro Ala Asn Gly Phe Arg Gly Gly Tyr Asp
```

```
                620           625           630           635
ggt tac cgc cct tca ttc tcg aac act cca aac agt ggt tat tca cag       2091
Gly Tyr Arg Pro Ser Phe Ser Asn Thr Pro Asn Ser Gly Tyr Ser Gln
                640                   645                   650 tct cag ttc act gct ccc cgg gac tac tct ggt tac cag cgg gat gga       2139
Ser Gln Phe Thr Ala Pro Arg Asp Tyr Ser Gly Tyr Gln Arg Asp Gly
            655                   660                   665 tat cag cag aat ttc aag cga ggc tct ggg cag agt gga cca cgg gga       2187
Tyr Gln Gln Asn Phe Lys Arg Gly Ser Gly Gln Ser Gly Pro Arg Gly
        670                   675                   680 gcc cca cga ggt cgt gga ggg ccc cca aga ccc aac aga ggg atg ccg       2235
Ala Pro Arg Gly Arg Gly Gly Pro Pro Arg Pro Asn Arg Gly Met Pro
    685                   690                   695 caa atg aac act cag caa gtg aat taa tgtgatacac aggattatgt             2282
Gln Met Asn Thr Gln Gln Val Asn
700                 705 ttaatcgcca aaacacact ggccagtgta ccataatatg ttaccagaag agttattatc      2342
tatttgttct ccctttcagg aaacttattg taaagggact gttttcatcc cataaagaca     2402
ggactgcaat tgtcagcttt acattacctg gatatggaag gaaactattt ttattctgca    2462
tgttctgtcc taagcgtcat cttgagcctt gcacacaata caatactcag attcctcacc    2522
cttgcttagg agtaaaacat tatatactta tggggtgata atatctccat agttagttga    2582
agtggcttgg aaaaaaaatg caagattgaa ttttttgacct tggataaaat ctacaatcag   2642
ccctagaact attcagtggt aattgacaaa gttaaagcat tttctttgaa aggaagatgg    2702
aaggagtgga gtgtggttta gcaaaactgc atttcatagc tttcccatta aattggagca    2762
ccgacagatt aaaagcatac caaattatgc atgggtcctt actcacacaa gtgaggctgg    2822
ctaccagcct tgacatagca ctcactagtc ttctggccaa acgactgtga ttaaaacaca    2882
tgtaaattgc tctttagtag tggatactgt gtaagacaaa gccaaattgc aaatcaggct    2942
ttgattggct cttctggaaa atatgcatca aatatggggg ataatctgga tgggctgctg    3002
ctgtgctcaa tgtgaactat ttagatacct ttggaacact taacagtttc tctgaacaat    3062
gacttacatg gggattggtc ctgtttgtca ttcctcacca taattgcatt gtcatcacta    3122
atccttggat cttgctgtat tgttactcaa attggtaata ggtactgatg gaaatcgcta    3182
atggatggat aatcataaca cttttggtca catgttttct cctgcagcct gaaagttctt    3242
aaagaaaaag atatcaaatg cctgctgcta ccacccttt aaattgctat ctttagaaaa     3302
gcaccggtat gtgttttaga ttcatttccc tgttttaggg aaatgacagg cagtagtttc    3362
agttctgatg gcaaaacaaa taaaaacatg tttctaaaag ttgtatcttg aaacactggt    3422
gttcaacagc tagcagctaa agtaattcaa cccatgcatt gctagtgtca cagcctttgg    3482
ttatgtctag tagctgtttc tgaagtattt tcatttatct tttgtcaaat ttaaccctgt    3542
ttgaattctc tccttttcctc aaggagacac ttatgttcaa agtgttgatt ctttgcctta   3602
ggtgcataga gagtagacag tttggagatg gaaaggttag cagtgactta gccatatgtt    3662
ctgtgttgga atttgtgcta gcagtttgag cactagctct gcgtgcctat gaactgaatg    3722
ctgcttgtcc cattccattt tatgtcatgg agaaataatt ccacttggta acacaaaggc    3782
taagttaatg ttattttctg tacagaaatt aaattttact tttagccttt tgtaaacttt    3842
tttttttttt ttccaagccg gtatcagcta ctcaaaacaa ttctcagata ttcatcatta    3902
gacaactgga gttttgctg gttttgtagc ctactaaaac tgctgaggct gttgaacatt     3962
ccacattcaa aagttttgta gggtggtgga taatgggaa gcttcaatgt ttattttaaa     4022
```

```
ataaataaaa taagttcttg acttttctca tgtgtggtta tggtacatca tattggaagg    4082
gttatctgtt tacttttgcc aagactattt tgccagcacc tacacttgtg tgctttaaaa    4142
gacaactacc tgggatgtac cacaaccata tgttaattgt attttattgg gatggataaa    4202
atgtttgtgg tttattggat aatccctaga tggtgtgtta cgtgtgtaga atataatttt    4262
atgatagtaa gaaagcaaaa ttgaagaaaa taagtttagt attgaatttg agttctgaag    4322
tgaattcagg gaatgtctca cgtttcgggc ttctacccaa agtgtagggc agaaggtgta    4382
aaagttgttt gtagtttgac ttgtttattt tttaagttgc ttattccttt caacagcaac    4442
atatcattag ctgtcattct accattgcag ttctagtgag ttttaacgtc tgcattcaag    4502
actgttttaa aagcaaccct actggacaga gaactgctaa agtcttttcc ttaagatctg    4562 agtcttgtt actcagtatc ttctataata tgcaaatgct tgtctagagg cagaagacct    4622
tttgtttggt caagtgtgta ttttaccaga gtacagggaa ctgatggtcc tacatgtctc    4682
ttagtgtagt aagactataa aatcttttgt acatgcacaa ttcacagtat gtttagatac    4742
cacgtgtata atgcccccccc ctcccccagg tagcatgcca ttgatgactt tttgcttagg    4802
gccattttat taccagggcc ttaatattcc taaaaagatg attttttttc atcctttctc    4862
ctcttttgat cattgtatct tgatattaaa aacatgacct tccaatgatt gtagtaaatt    4922
aacttctata gttctttttgt ctctatatgt attcatatat atgctattgt atagagactt    4982
caaggagaca tggagatgca tgcttattct caggttcatt cactaaggtg cttggcagac    5042
aaccagtttc taagtgcaga atgtagttaa gcagcttcat atatgtgcca ggcaatttgt    5102
tttgttaaat tttcatctac ttaaggaaat agggtattgt agcttaggct gatcataccc    5162
ttcatttcaa ccttaagctc tcaacctgca tccatccgac ttgagctatt aagtacttta    5222
gttttatcga gtataagtta acagaaaaag taaattaagc tttgccttta ctattttgaa    5282
tttatataca ttctggaaaa acttagaaac tgttgtatat ttcattagat taaattatat    5342
gaaaatgtga ttgtttatag caaagcctgt gagttgcata caccctaagg aaaactcctt    5402
aagtgctcct tgaagagaga agaaacaatt ctgggtctgg tcttttttaag aacaaagcta    5462 gactactgta tgttagcact gtacattaat agtctgttgt gaagcttgag cagtttcctg    5522
catagccttg atccttcacc gttggcattg aaaatagcag tatccctgat gtacttaaaa    5582
cttaaagtca ggttttggta tatttatttg taagtcttaa tttcctctaa atactatatc    5642
tctttagcga gacaacctga aatttattag cacatttggg tatctcttgc ttggcattat    5702
ggccagtgtt aactattcag tggtgaaaaa attacccctc aagacactgg agtgaccccca   5762 gatgtgtgta gtaagtggca tggttcaact gtgtggttaa tgataaatat atgacttagt    5822
cggtatgatc tggaaagact tgattgaaag ataattcagc tgacataagg atgagtgagg    5882
agtggcaaac tggataaaag agtcaagaga cctgtattcc agtgactcct gttttgttta    5942
agcattagca agatctgtct ggggaaactg gatagggcag ttttcttcca tgtttagttt    6002
ttgtctcaac atttggaagc tattgaaggt tttaaaatgg tgtgtattgt tttttttttgg    6062 gggggggtg ccagaatag tgggtcatct aataaaactg ccatttaaaa gatcaaaaaa    6122
aaaaaaaaaa aaaaaaaaa                                                  6141

<210> SEQ ID NO 22
<211> LENGTH: 707
<212> TYPE: PRT
<213> ORGANISM: Mus musculus
```

```
<400> SEQUENCE: 22

Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Pro Gln Ala Ala Ser Pro Ser Val
                325                 330                 335

Pro Glu Pro His Ser Leu Thr Pro Val Ala Gln Ser Asp Pro Leu Val
        340                 345                 350

Arg Arg Gln Arg Val Gln Asp Leu Met Ala Gln Met Gln Gly Pro Tyr
    355                 360                 365

Asn Phe Ile Gln Asp Ser Met Leu Asp Phe Glu Asn Gln Thr Leu Asp
        370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415
```

```
Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
            435                 440                 445

Pro Ser His Ala Thr Glu Gln Arg Pro Gln Lys Glu Pro Met Asp Gln
            450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
            515                 520                 525

Glu Pro Glu Thr Leu Lys Gln Gln Ser Gln Tyr Gln Ala Thr Tyr Asn
            530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Gln Gln Asn
            580                 585                 590

Thr Gly Phe Pro Arg Ser Ser Gln Pro Tyr Tyr Asn Ser Arg Gly Val
            595                 600                 605

Ser Arg Gly Gly Ser Arg Gly Ala Arg Gly Leu Met Asn Gly Tyr Arg
            610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
            675                 680                 685

Gly Gly Pro Pro Arg Pro Asn Arg Gly Met Pro Gln Met Asn Thr Gln
            690                 695                 700

Gln Val Asn
705

<210> SEQ ID NO 23
<211> LENGTH: 6114
<212> TYPE: DNA
<213> ORGANISM: Mus musculus
<220> FEATURE:
<221> NAME/KEY: CDS
<222> LOCATION: (139)..(2235)

<400> SEQUENCE: 23
cccaccgcgc gcgcgcgtag ccgcctgccc gcccgcccgc tgcgcgtttt gtcccgcgtc    60
tctccccgtc cgtctcctga cttgctggtc ttgtccttcc ctcccgcttt tttcctctcc   120
tctcttctcg gtctaaag atg ccc tcg gcc acc agc cac agc gga agc ggc    171
                    Met Pro Ser Ala Thr Ser His Ser Gly Ser Gly
                     1               5                  10 agc aaa tcg tcg gga ccg ccg ccg ccg tcc ggt tcc tcc ggg agt gag    219
Ser Lys Ser Ser Gly Pro Pro Pro Pro Ser Gly Ser Ser Gly Ser Glu
```

-continued

```
                15                  20                  25
gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
             30                  35                  40 acc ggc gcc gtc cag acc gag gcc atg aag cag att ctc ggc gta atc      315
Thr Gly Ala Val Gln Thr Glu Ala Met Lys Gln Ile Leu Gly Val Ile
     45                  50                  55 gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75 tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                 80                  85                  90 gat gcc gta tct aag tac cag gaa gtc aca aat aat ttg gag ttt gca      459
Asp Ala Val Ser Lys Tyr Gln Glu Val Thr Asn Asn Leu Glu Phe Ala
             95                 100                 105 aag gaa tta cag agg agt ttc atg gca tta agt caa gat att cag aaa      507
Lys Glu Leu Gln Arg Ser Phe Met Ala Leu Ser Gln Asp Ile Gln Lys
        110                 115                 120 aca ata aag aag aca gca cgt cgg gaa cag ctt atg aga gaa gaa gca      555
Thr Ile Lys Lys Thr Ala Arg Arg Glu Gln Leu Met Arg Glu Glu Ala
    125                 130                 135 gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155 aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170 gga gtg cca ata ttg tct gag gag gag ttg tca ttg ctg gat gag ttc      699
Gly Val Pro Ile Leu Ser Glu Glu Glu Leu Ser Leu Leu Asp Glu Phe
             175                 180                 185 tac aag ctc gta gat cct gag cgt gac atg agt tta agg tta aat gag      747
Tyr Lys Leu Val Asp Pro Glu Arg Asp Met Ser Leu Arg Leu Asn Glu
        190                 195                 200 cag tat gaa cat gcc tca att cac ttg tgg gat ttg ctg gaa ggg aaa      795
Gln Tyr Glu His Ala Ser Ile His Leu Trp Asp Leu Leu Glu Gly Lys
    205                 210                 215 gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235 gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250 aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
             255                 260                 265 gac cag gta gct gaa gct gaa cct gag cca gcg gaa gaa tac aca gag      987
Asp Gln Val Ala Glu Ala Glu Pro Glu Pro Ala Glu Glu Tyr Thr Glu
        270                 275                 280 caa agt gag gtt gaa tca aca gag tat gtc aat agg cag ttc atg gca     1035
Gln Ser Glu Val Glu Ser Thr Glu Tyr Val Asn Arg Gln Phe Met Ala
    285                 290                 295 gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315 gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330 gcg tcc cct tca gtc cca gag ccc cac tct ttg act cca gtg gct cag     1179
```

-continued

| | | |
|---|---|---|
| Ala Ser Pro Ser Val Pro Glu Pro His Ser Leu Thr Pro Val Ala Gln<br>335                         340                  345 | | |
| tca gat cca ctt gtg aga agg cag cgt gta caa gat ctt atg gca caa<br>Ser Asp Pro Leu Val Arg Arg Gln Arg Val Gln Asp Leu Met Ala Gln<br>      350                     355                     360 | 1227 | |
| atg caa ggg ccc tat aat ttc ata cag acg ctt gat cct gcc att gta<br>Met Gln Gly Pro Tyr Asn Phe Ile Gln Thr Leu Asp Pro Ala Ile Val<br>365                         370                     375 | 1275 | |
| tcc gca cag cct atg aac cct acc cag aac atg gat atg cct cag ctg<br>Ser Ala Gln Pro Met Asn Pro Thr Gln Asn Met Asp Met Pro Gln Leu<br>380                         385                     390                     395 | 1323 | |
| gtt tgc cct cag gtt cat tct gaa tct aga ctt gcc caa tct aat caa<br>Val Cys Pro Gln Val His Ser Glu Ser Arg Leu Ala Gln Ser Asn Gln<br>                 400                     405                     410 | 1371 | |
| gtt cct gta caa cca gaa gcc aca cag gtt cct ttg gtt tca tcc aca<br>Val Pro Val Gln Pro Glu Ala Thr Gln Val Pro Leu Val Ser Ser Thr<br>                 415                     420                     425 | 1419 | |
| agt gag ggg tat aca gca tct cag ccc ttg tac cag cca tct cat gct<br>Ser Glu Gly Tyr Thr Ala Ser Gln Pro Leu Tyr Gln Pro Ser His Ala<br>                 430                     435                     440 | 1467 | |
| acg gag cag cgg ccg cag aaa gag cca atg gat cag att cag gca aca<br>Thr Glu Gln Arg Pro Gln Lys Glu Pro Met Asp Gln Ile Gln Ala Thr<br>445                         450                     455 | 1515 | |
| ata tct ttg aat aca gac cag act aca gca tcc tca tcc ctt cct gct<br>Ile Ser Leu Asn Thr Asp Gln Thr Thr Ala Ser Ser Ser Leu Pro Ala<br>460                         465                     470                     475 | 1563 | |
| gct tct cag cct caa gtg ttc cag gct ggg aca agt aaa cct ttg cac<br>Ala Ser Gln Pro Gln Val Phe Gln Ala Gly Thr Ser Lys Pro Leu His<br>                 480                     485                     490 | 1611 | |
| agc agt gga atc aat gta aat gca gct cca ttc cag tcc atg caa acg<br>Ser Ser Gly Ile Asn Val Asn Ala Ala Pro Phe Gln Ser Met Gln Thr<br>                       495                     500                     505 | 1659 | |
| gtg ttc aat atg aat gct cca gtc cct cct gct aat gaa cca gaa acg<br>Val Phe Asn Met Asn Ala Pro Val Pro Pro Ala Asn Glu Pro Glu Thr<br>510                         515                     520 | 1707 | |
| tta aaa caa cag agt cag tac cag gcc act tat aac cag agt ttt tcc<br>Leu Lys Gln Gln Ser Gln Tyr Gln Ala Thr Tyr Asn Gln Ser Phe Ser<br>525                         530                     535 | 1755 | |
| agt cag cct cac caa gtg gaa caa aca gag ctt caa caa gac caa ctg<br>Ser Gln Pro His Gln Val Glu Gln Thr Glu Leu Gln Gln Asp Gln Leu<br>540                         545                     550                     555 | 1803 | |
| caa acg gtg gtt ggc act tac cat gga tcc cag gac cag cct cat caa<br>Gln Thr Val Val Gly Thr Tyr His Gly Ser Gln Asp Gln Pro His Gln<br>                 560                     565                     570 | 1851 | |
| gtg cct ggt aac cac cag caa ccc cca cag cag aac act ggc ttt cca<br>Val Pro Gly Asn His Gln Gln Pro Pro Gln Gln Asn Thr Gly Phe Pro<br>                 575                     580                     585 | 1899 | |
| cgt agc agt cag cct tat tac aac agt cgt ggg gta tct cga gga ggg<br>Arg Ser Ser Gln Pro Tyr Tyr Asn Ser Arg Gly Val Ser Arg Gly Gly<br>                 590                     595                     600 | 1947 | |
| tct cgt ggt gcc aga ggc ttg atg aat gga tac agg ggc cct gcc aat<br>Ser Arg Gly Ala Arg Gly Leu Met Asn Gly Tyr Arg Gly Pro Ala Asn<br>605                         610                     615 | 1995 | |
| gga ttt aga gga gga tat gat ggt tac cgc cct tca ttc tcg aac act<br>Gly Phe Arg Gly Gly Tyr Asp Gly Tyr Arg Pro Ser Phe Ser Asn Thr<br>620                         625                     630                     635 | 2043 | |
| cca aac agt ggt tat tca cag tct cag ttc act gct ccc cgg gac tac<br>Pro Asn Ser Gly Tyr Ser Gln Ser Gln Phe Thr Ala Pro Arg Asp Tyr<br>                 640                     645                     650 | 2091 | |

-continued

| | |
|---|---|
| tct ggt tac cag cgg gat gga tat cag cag aat ttc aag cga ggc tct<br>Ser Gly Tyr Gln Arg Asp Gly Tyr Gln Gln Asn Phe Lys Arg Gly Ser<br>655 660 665 | 2139 |
| ggg cag agt gga cca cgg gga gcc cca cga ggt cgt gga ggg ccc cca<br>Gly Gln Ser Gly Pro Arg Gly Ala Pro Arg Gly Arg Gly Gly Pro Pro<br>670 675 680 | 2187 |
| aga ccc aac aga ggg atg ccg caa atg aac act cag caa gtg aat taa<br>Arg Pro Asn Arg Gly Met Pro Gln Met Asn Thr Gln Gln Val Asn<br>685 690 695 | 2235 |
| tgtgatacac aggattatgt ttaatcgcca aaaacacact ggccagtgta ccataatatg | 2295 |
| ttaccagaag agttattatc tatttgttct cccttcagg aaacttattg taaagggact | 2355 |
| gttttcatcc cataaagaca ggactgcaat tgtcagcttt acattacctg gatatggaag | 2415 |
| gaaactattt ttattctgca tgttctgtcc taagcgtcat cttgagcctt gcacacaata | 2475 |
| caatactcag attcctcacc cttgcttagg agtaaaacat tatatactta ggggtgata | 2535 |
| atatctccat agttagttga agtggcttgg aaaaaaaatg caagattgaa ttttgacct | 2595 |
| tggataaaat ctacaatcag ccctagaact attcagtggt aattgacaaa gttaaagcat | 2655 |
| tttctttgaa aggaagatgg aaggagtgga gtgtggttta gcaaaactgc atttcatagc | 2715 |
| tttcccatta aattggagca ccgacagatt aaaagcatac caaattatgc atgggtcctt | 2775 |
| actcacacaa gtgaggctgg ctaccagcct tgacatagca ctcactagtc ttctggccaa | 2835 |
| acgactgtga ttaaaacaca gtaaattgc tctttagtag tggatactgt gtaagacaaa | 2895 |
| gccaaattgc aaatcaggct tgattggct cttctggaaa atatgcatca aatatggggg | 2955 |
| ataatctgga tgggctgctg ctgtgctcaa tgtgaactat ttagataccct ttggaacact | 3015 |
| taacagtttc tctgaacaat gacttacatg gggattggtc ctgtttgtca ttcctcacca | 3075 |
| taattgcatt gtcatcacta atccttggat cttgctgtat tgttactcaa attggtaata | 3135 |
| ggtactgatg gaaatcgcta atggatggat aatcataaca cttttggtca catgttttct | 3195 |
| cctgcagcct gaaagttctt aaagaaaaag atatcaaatg cctgctgcta ccacccttt | 3255 |
| aaattgctat cttagaaaa gcaccggtat gtgttttaga ttcatttccc tgttttaggg | 3315 |
| aaatgacagg cagtagttc agttctgatg gcaaaacaaa taaaaacatg tttctaaaag | 3375 |
| ttgtatcttg aaacactggt gttcaacagc tagcagctaa agtaattcaa cccatgcatt | 3435 |
| gctagtgtca cagcctttgg ttatgtctag tagctgtttc tgaagtattt tcatttatct | 3495 |
| tttgtcaaat ttaaccctgt ttgaattctc tcctttcctc aaggagacac ttatgttcaa | 3555 |
| agtgttgatt ctttgcctta ggtgcataga gagtagacag tttggagatg gaaaggttag | 3615 |
| cagtgactta gccatatgtt ctgtgttgga atttgtgcta gcagtttgag cactagctct | 3675 |
| gcgtgcctat gaactgaatg ctgcttgtcc cattccattt tatgtcatgg agaaataatt | 3735 |
| ccacttggta acacaaaggc taagttaatg ttattttctg tacagaaatt aaattttact | 3795 |
| tttagccttt tgtaaacttt ttttttttt ttccaagccg gtatcagcta ctcaaaacaa | 3855 |
| ttctcagata ttcatcatta gacaactgga gttttgctg gttttgtagc ctactaaaac | 3915 |
| tgctgaggct gttgaacatt ccacattcaa aagttttgta gggtggtgga taatggggaa | 3975 |
| gcttcaatgt ttattttaaa ataaataaaa taagttcttg acttttctca tgtgtggtta | 4035 |
| tggtacatca tattggaagg gttatctgtt tacttttgcc aagactattt tgccagcacc | 4095 |
| tacacttgtg tgctttaaaa gacaactacc tgggatgtac cacaaccata tgttaattgt | 4155 |
| attttattgg gatggataaa atgtttgtgg tttattggat aatccctaga tggtgtgtta | 4215 |
| cgtgtgtaga atataatttt atgatagtaa gaaagcaaaa ttgaagaaaa taagtttagt | 4275 |

```
attgaatttg agttctgaag tgaattcagg gaatgtctca cgtttcgggc ttctacccaa      4335
agtgtagggc agaaggtgta aaagttgttt gtagtttgac ttgtttattt tttaagttgc      4395
ttattccttt caacagcaac atatcattag ctgtcattct accattgcag ttctagtgag      4455
ttttaacgtc tgcattcaag actgttttaa aagcaacctc actggacaga gaactgctaa      4515
agtcttttcc ttaagatctg agtctttgtt actcagtatc ttctataata tgcaaatgct      4575
tgtctagagg cagaagacct tttgtttggt caagtgtgta ttttaccaga gtacagggaa      4635
ctgatggtcc tacatgtctc ttagtgtagt aagactataa aatcttttgt acatgcacaa      4695
ttcacagtat gtttagatac cacgtgtata atgcccccc ctcccccagg tagcatgcca       4755
ttgatgactt tttgcttagg gccattttat taccagggcc ttaatattcc taaaaagatg      4815 atttttttc atcctttctc ctcttttgat cattgtatct tgatattaaa acatgacct        4875 tccaatgatt gtagtaaatt aacttctata gttcttttgt ctctatatgt attcatatat     4935
atgctattgt atagagactt caaggagaca tggagatgca tgcttattct caggttcatt     4995
cactaaggtg cttggcagac aaccagtttc taagtgcaga atgtagttaa gcagcttcat     5055
atatgtgcca ggcaatttgt tttgttaaat tttcatctac ttaaggaaat agggtattgt     5115
agcttaggct gatcataccc ttcatttcaa ccttaagctc tcaacctgca tccatccgac     5175
ttgagctatt aagtacttta gttttatcga gtataagtta acagaaaaag taaattaagc     5235
tttgccttta ctattttgaa tttatataca ttctggaaaa acttagaaac tgttgtatat     5295
ttcattagat taaattatat gaaaatgtga ttgtttatag caaagcctgt gagttgcata     5355
caccctaagg aaaactcctt aagtgctcct tgaagagaga agaaacaatt ctgggtctgg     5415 tcttttaag aacaaagcta gactactgta tgttagcact gtacattaat agtctgttgt      5475
gaagcttgag cagtttcctg catagccttg atccttcacc gttggcattg aaaatagcag     5535
tatccctgat gtacttaaaa cttaaagtca ggttttggta tatttatttg taagtcttaa     5595
tttcctctaa atactatatc tctttagcga gacaacctga aatttattag cacatttggg     5655
tatctcttgc ttggcattat ggccagtgtt aactattcag tggtgaaaaa attacccctc     5715
aagacactgg agtgaccca gatgtgtgta gtaagtggca tggttcaact gtgtggttaa      5775
tgataaatat atgacttagt cggtatgatc tggaaagact tgattgaaag ataattcagc     5835
tgacataagg atgagtgagg agtggcaaac tggataaaag agtcaagaga cctgtattcc     5895
agtgactcct gttttgttta agcattagca agatctgtct ggggaaactg gatagggcag     5955
ttttcttcca tgtttagttt ttgtctcaac atttggaagc tattgaaggt tttaaaatgg     6015
tgtgtattgt ttttttttgg gggggggtg gccagaatag tgggtcatct aataaaactg      6075
ccatttaaaa gatcaaaaaa aaaaaaaaa aaaaaaaa                              6114
```

<210> SEQ ID NO 24
<211> LENGTH: 698
<212> TYPE: PRT
<213> ORGANISM: Mus musculus

<400> SEQUENCE: 24

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

```
Thr Glu Ala Met Lys Gln Ile Leu Gly Val Ile Asp Lys Lys Leu Arg
 50                  55                  60
Asn Leu Glu Lys Lys Lys Gly Lys Leu Asp Asp Tyr Gln Glu Arg Met
 65                  70                  75                  80
Asn Lys Gly Glu Arg Leu Asn Gln Asp Gln Leu Asp Ala Val Ser Lys
                     85                  90                  95
Tyr Gln Glu Val Thr Asn Asn Leu Glu Phe Ala Lys Glu Leu Gln Arg
                100                 105                 110
Ser Phe Met Ala Leu Ser Gln Asp Ile Gln Lys Thr Ile Lys Lys Thr
            115                 120                 125
Ala Arg Arg Glu Gln Leu Met Arg Glu Ala Glu Gln Lys Arg Leu
        130                 135                 140
Lys Thr Val Leu Glu Leu Gln Tyr Val Leu Asp Lys Leu Gly Asp Asp
145                 150                 155                 160
Asp Val Arg Thr Asp Leu Lys Gln Gly Leu Ser Gly Val Pro Ile Leu
                165                 170                 175
Ser Glu Glu Glu Leu Ser Leu Leu Asp Glu Phe Tyr Lys Leu Val Asp
            180                 185                 190
Pro Glu Arg Asp Met Ser Leu Arg Leu Asn Glu Gln Tyr Glu His Ala
        195                 200                 205
Ser Ile His Leu Trp Asp Leu Leu Glu Gly Lys Glu Lys Pro Val Cys
210                 215                 220
Gly Thr Thr Tyr Lys Ala Leu Lys Glu Ile Val Glu Arg Val Phe Gln
225                 230                 235                 240
Ser Asn Tyr Phe Asp Ser Thr His Asn His Gln Asn Gly Leu Cys Glu
                245                 250                 255
Glu Glu Glu Ala Ala Ser Ala Pro Thr Val Glu Asp Gln Val Ala Glu
            260                 265                 270
Ala Glu Pro Glu Pro Ala Glu Glu Tyr Thr Glu Gln Ser Glu Val Glu
        275                 280                 285
Ser Thr Glu Tyr Val Asn Arg Gln Phe Met Ala Glu Thr Gln Phe Ser
290                 295                 300
Ser Gly Glu Lys Glu Gln Val Asp Glu Trp Thr Val Glu Thr Val Glu
305                 310                 315                 320
Val Val Asn Ser Leu Gln Gln Gln Pro Gln Ala Ala Ser Pro Ser Val
                325                 330                 335
Pro Glu Pro His Ser Leu Thr Pro Val Ala Gln Ser Asp Pro Leu Val
            340                 345                 350
Arg Arg Gln Arg Val Gln Asp Leu Met Ala Gln Met Gln Gly Pro Tyr
        355                 360                 365
Asn Phe Ile Gln Thr Leu Asp Pro Ala Ile Val Ser Ala Gln Pro Met
370                 375                 380
Asn Pro Thr Gln Asn Met Asp Met Pro Gln Leu Val Cys Pro Gln Val
385                 390                 395                 400
His Ser Glu Ser Arg Leu Ala Gln Ser Asn Val Pro Val Gln Pro
                405                 410                 415
Glu Ala Thr Gln Val Pro Leu Val Ser Ser Thr Ser Glu Gly Tyr Thr
            420                 425                 430
Ala Ser Gln Pro Leu Tyr Gln Pro Ser His Ala Thr Glu Gln Arg Pro
        435                 440                 445
Gln Lys Glu Pro Met Asp Gln Ile Gln Ala Thr Ile Ser Leu Asn Thr
450                 455                 460
```

```
Asp Gln Thr Thr Ala Ser Ser Leu Pro Ala Ser Gln Pro Gln
465                 470                 475                 480

Val Phe Gln Ala Gly Thr Ser Lys Pro Leu His Ser Ser Gly Ile Asn
                485                 490                 495

Val Asn Ala Ala Pro Phe Gln Ser Met Gln Thr Val Phe Asn Met Asn
                500                 505                 510

Ala Pro Val Pro Pro Ala Asn Glu Pro Glu Thr Leu Lys Gln Gln Ser
            515                 520                 525

Gln Tyr Gln Ala Thr Tyr Asn Gln Ser Phe Ser Gln Pro His Gln
530                 535                 540

Val Glu Gln Thr Glu Leu Gln Gln Asp Gln Leu Gln Thr Val Val Gly
545                 550                 555                 560

Thr Tyr His Gly Ser Gln Asp Gln Pro His Gln Val Pro Gly Asn His
                565                 570                 575

Gln Gln Pro Pro Gln Gln Asn Thr Gly Phe Pro Arg Ser Ser Gln Pro
            580                 585                 590

Tyr Tyr Asn Ser Arg Gly Val Ser Arg Gly Ser Arg Gly Ala Arg
            595                 600                 605

Gly Leu Met Asn Gly Tyr Arg Gly Pro Ala Asn Gly Phe Arg Gly Gly
610                 615                 620

Tyr Asp Gly Tyr Arg Pro Ser Phe Ser Asn Thr Pro Asn Ser Gly Tyr
625                 630                 635                 640

Ser Gln Ser Gln Phe Thr Ala Pro Arg Asp Tyr Ser Gly Tyr Gln Arg
                645                 650                 655

Asp Gly Tyr Gln Gln Asn Phe Lys Arg Gly Ser Gly Ser Gly Pro
            660                 665                 670

Arg Gly Ala Pro Arg Gly Arg Gly Gly Pro Pro Arg Pro Asn Arg Gly
                675                 680                 685

Met Pro Gln Met Asn Thr Gln Gln Val Asn
            690                 695
```

```
<210> SEQ ID NO 25
<211> LENGTH: 3548
<212> TYPE: DNA
<213> ORGANISM: Mus musculus
<220> FEATURE:
<221> NAME/KEY: CDS
<222> LOCATION: (179)..(2257)

<400> SEQUENCE: 25
gctggctggc taagtccctc ccgcgccggc tcttgtccca ctaggagcag ctcagagccg    60
cggggacagg gcgaagcggc ctgcgcccac ggagcgcacg tctctgttct caacgcagca   120
ccacccttgc cccctcggc tgcccactcc agacgtccag cggctccgcg cgcgcacg     178 atg ccc tcg gcc acc agc cac agc gga agc ggc agc aaa tcg tcg gga    226
Met Pro Ser Ala Thr Ser His Ser Gly Ser Gly Ser Lys Ser Ser Gly
1               5                   10                  15 ccg ccg ccg ccg tcc ggt tcc tcc ggg agt gag gcg gcg gcc ggg gca    274
Pro Pro Pro Pro Ser Gly Ser Ser Gly Ser Glu Ala Ala Ala Gly Ala
                20                  25                  30 gct gcg ccg gct tct cag cat ccg gca acc ggc acc ggc gcc gtc cag    322
Ala Ala Pro Ala Ser Gln His Pro Ala Thr Gly Thr Gly Ala Val Gln
            35                  40                  45 acc gag gcc atg aag cag att ctc ggc gta atc gac aag aaa ctt cgg    370
Thr Glu Ala Met Lys Gln Ile Leu Gly Val Ile Asp Lys Lys Leu Arg
50                  55                  60 aac ctg gag aag aaa aag ggt aaa ctt gat gat tac cag gaa cga atg    418
```

```
           Asn Leu Glu Lys Lys Lys Gly Lys Leu Asp Asp Tyr Gln Glu Arg Met
            65              70                  75                  80 aat aaa ggg gaa agg ctc aat caa gac cag ctg gat gcc gta tct aag         466
Asn Lys Gly Glu Arg Leu Asn Gln Asp Gln Leu Asp Ala Val Ser Lys
                    85                  90                  95 tac cag gaa gtc aca aat aat ttg gag ttt gca aag gaa tta cag agg         514
Tyr Gln Glu Val Thr Asn Asn Leu Glu Phe Ala Lys Glu Leu Gln Arg
                100                 105                 110 agt ttc atg gca tta agt caa gat att cag aaa aca ata aag aag aca         562
Ser Phe Met Ala Leu Ser Gln Asp Ile Gln Lys Thr Ile Lys Lys Thr
            115                 120                 125 gca cgt cgg gaa cag ctt atg aga gaa gaa gca gaa cag aag cgc tta         610
Ala Arg Arg Glu Gln Leu Met Arg Glu Glu Ala Glu Gln Lys Arg Leu
            130                 135                 140 aaa act gta ctt gag tta cag tat gta ttg gat aag ctg gga gat gat         658
Lys Thr Val Leu Glu Leu Gln Tyr Val Leu Asp Lys Leu Gly Asp Asp
145                 150                 155                 160 gat gtg aga aca gat ctg aaa caa ggt ttg agt gga gtg cca ata ttg         706
Asp Val Arg Thr Asp Leu Lys Gln Gly Leu Ser Gly Val Pro Ile Leu
                165                 170                 175 tct gag gag gag ttg tca ttg ctg gat gag ttc tac aag ctc gta gat         754
Ser Glu Glu Glu Leu Ser Leu Leu Asp Glu Phe Tyr Lys Leu Val Asp
            180                 185                 190 cct gag cgt gac atg agt tta agg tta aat gag cag tat gaa cat gcc         802
Pro Glu Arg Asp Met Ser Leu Arg Leu Asn Glu Gln Tyr Glu His Ala
            195                 200                 205 tca att cac ttg tgg gat ttg ctg gaa ggg aaa gaa aag cct gtg tgt         850
Ser Ile His Leu Trp Asp Leu Leu Glu Gly Lys Glu Lys Pro Val Cys
210                 215                 220 gga aca acc tat aaa gct cta aag gaa att gtt gag cgt gtt ttc cag         898
Gly Thr Thr Tyr Lys Ala Leu Lys Glu Ile Val Glu Arg Val Phe Gln
225                 230                 235                 240 tca aac tac ttt gat agc act cac aat cat caa aat ggg ttg tgt gag         946
Ser Asn Tyr Phe Asp Ser Thr His Asn His Gln Asn Gly Leu Cys Glu
                245                 250                 255 gag gaa gag gcg gct tca gcg ccc aca gtg gag gac cag gta gct gaa         994
Glu Glu Glu Ala Ala Ser Ala Pro Thr Val Glu Asp Gln Val Ala Glu
            260                 265                 270 gct gaa cct gag cca gcg gaa gaa tac aca gag caa agt gag gtt gaa        1042
Ala Glu Pro Glu Pro Ala Glu Glu Tyr Thr Glu Gln Ser Glu Val Glu
            275                 280                 285 tca aca gag tat gtc aat agg cag ttc atg gca gaa aca cag ttc agc        1090
Ser Thr Glu Tyr Val Asn Arg Gln Phe Met Ala Glu Thr Gln Phe Ser
            290                 295                 300 agt ggt gag aag gag caa gtg gat gag tgg aca gtt gaa aca gtt gag        1138
Ser Gly Glu Lys Glu Gln Val Asp Glu Trp Thr Val Glu Thr Val Glu
305                 310                 315                 320 gtt gta aac tca ctc cag cag caa cct cag gct gcg tcc cct tca gtc        1186
Val Val Asn Ser Leu Gln Gln Gln Pro Gln Ala Ala Ser Pro Ser Val
                325                 330                 335 cca gag ccc cac tct ttg act cca gtg gct cag tca gat cca ctt gtg        1234
Pro Glu Pro His Ser Leu Thr Pro Val Ala Gln Ser Asp Pro Leu Val
            340                 345                 350 aga agg cag cgt gta caa gat ctt atg gca caa atg caa ggg ccc tat        1282
Arg Arg Gln Arg Val Gln Asp Leu Met Ala Gln Met Gln Gly Pro Tyr
            355                 360                 365 aat ttc ata cag gat tca atg ttg gat ttt gaa aat cag acg ctt gat        1330
Asn Phe Ile Gln Asp Ser Met Leu Asp Phe Glu Asn Gln Thr Leu Asp
370                 375                 380
```

| | | |
|---|---|---|
| cct gcc att gta tcc gca cag cct atg aac cct acc cag aac atg gat<br>Pro Ala Ile Val Ser Ala Gln Pro Met Asn Pro Thr Gln Asn Met Asp<br>385                      390                    395                    400 | 1378 | |
| atg cct cag ctg gtt tgc cct cag gtt cat tct gaa tct aga ctt gcc<br>Met Pro Gln Leu Val Cys Pro Gln Val His Ser Glu Ser Arg Leu Ala<br>                   405                    410                    415 | 1426 | |
| caa tct aat caa gtt cct gta caa cca gaa gcc aca cag gtt cct ttg<br>Gln Ser Asn Gln Val Pro Val Gln Pro Glu Ala Thr Gln Val Pro Leu<br>               420                    425                    430 | 1474 | |
| gtt tca tcc aca agt gag ggg tat aca gca tct cag ccc ttg tac cag<br>Val Ser Ser Thr Ser Glu Gly Tyr Thr Ala Ser Gln Pro Leu Tyr Gln<br>          435                    440                    445 | 1522 | |
| cca tct cat gct acg gag cag cgg ccg cag aaa gag cca atg gat cag<br>Pro Ser His Ala Thr Glu Gln Arg Pro Gln Lys Glu Pro Met Asp Gln<br>450                      455                    460 | 1570 | |
| att cag gca aca ata tct ttg aat aca gac cag act aca gca tcc tca<br>Ile Gln Ala Thr Ile Ser Leu Asn Thr Asp Gln Thr Thr Ala Ser Ser<br>465                      470                    475                    480 | 1618 | |
| tcc ctt cct gct gct tct cag cct caa gtg ttc cag gct ggg aca agt<br>Ser Leu Pro Ala Ala Ser Gln Pro Gln Val Phe Gln Ala Gly Thr Ser<br>                   485                    490                    495 | 1666 | |
| aaa cct ttg cac agc agt gga atc aat gta aat gca gct cca ttc cag<br>Lys Pro Leu His Ser Ser Gly Ile Asn Val Asn Ala Ala Pro Phe Gln<br>               500                    505                    510 | 1714 | |
| tcc atg caa acg gtg ttc aat atg aat gct cca gtc cct cct gct aat<br>Ser Met Gln Thr Val Phe Asn Met Asn Ala Pro Val Pro Pro Ala Asn<br>          515                    520                    525 | 1762 | |
| gaa cca gaa acg tta aaa caa cag agt cag tac cag gcc act tat aac<br>Glu Pro Glu Thr Leu Lys Gln Gln Ser Gln Tyr Gln Ala Thr Tyr Asn<br>530                      535                    540 | 1810 | |
| cag agt ttt tcc agt cag cct cac caa gtg gaa caa aca gag ctt caa<br>Gln Ser Phe Ser Ser Gln Pro His Gln Val Glu Gln Thr Glu Leu Gln<br>545                      550                    555                    560 | 1858 | |
| caa gac caa ctg caa acg gtg gtt ggc act tac cat gga tcc cag gac<br>Gln Asp Gln Leu Gln Thr Val Val Gly Thr Tyr His Gly Ser Gln Asp<br>                   565                    570                    575 | 1906 | |
| cag cct cat caa gtg cct ggt aac cac cag caa ccc cca cag cag aac<br>Gln Pro His Gln Val Pro Gly Asn His Gln Gln Pro Pro Gln Gln Asn<br>               580                    585                    590 | 1954 | |
| act ggc ttt cca cgt agc agt cag cct tat tac aac agt cgt ggg gta<br>Thr Gly Phe Pro Arg Ser Ser Gln Pro Tyr Tyr Asn Ser Arg Gly Val<br>          595                    600                    605 | 2002 | |
| tct cga gga ggg tct cgt ggt gcc aga ggc ttg atg aat gga tac agg<br>Ser Arg Gly Gly Ser Arg Gly Ala Arg Gly Leu Met Asn Gly Tyr Arg<br>610                      615                    620 | 2050 | |
| ggc cct gcc aat gga ttt aga gga gga tat gat ggt tac cgc cct tca<br>Gly Pro Ala Asn Gly Phe Arg Gly Gly Tyr Asp Gly Tyr Arg Pro Ser<br>625                      630                    635                    640 | 2098 | |
| ttc tcg aac act cca aac agt ggt tat tca cag tct cag ttc act gct<br>Phe Ser Asn Thr Pro Asn Ser Gly Tyr Ser Gln Ser Gln Phe Thr Ala<br>               645                    650                    655 | 2146 | |
| ccc cgg gac tac tct ggt tac cag cgg gat gga tat cag cag aat ttc<br>Pro Arg Asp Tyr Ser Gly Tyr Gln Arg Asp Gly Tyr Gln Gln Asn Phe<br>                   660                    665                    670 | 2194 | |
| aag cga ggc tct ggg cag agt gga cca cgg gga gcc cca cga ggt aat<br>Lys Arg Gly Ser Gly Gln Ser Gly Pro Arg Gly Ala Pro Arg Gly Asn<br>          675                    680                    685 | 2242 | |
| ata ttg tgg tgg tga tcctagctcc tatgtggagc ttctgttctg gccttggaag<br>Ile Leu Trp Trp<br>          690 | 2297 | |

-continued

```
aactgttcat agtccgcatg taggttacat gttaggaata catttatctt ttccagactt   2357
gttgctaaag attaaatgaa atgctctgtt tctaaaattt catcttgaat ccaaatttta   2417
atttttgaat gactttccct gctgttgtct tcaaaatcag aacattttct ctgcctcaga   2477
aaagcgtttt tccaactgga aatttatttt tcaggtctta aaacctgcta aatgttttta   2537
ggaagtacct actgaaactt tttgtaagac atttttggaa cgagcttgaa catttatata   2597
aatttattac cctctttgat ttttgaaaca tgcatattat atttaggctg agaagccctt   2657
caaatggcca gataagccac agttttagct agagaaccat ttagaattga cataactaat   2717
ctaaacttga acacttttag gaccaatgtt agtgttctaa ataccaacat atttctgatg   2777
tttaaacaga tctcccaaat tcttaggacc ttgatgtcat taaaatttag aatgacaagc   2837
ttaagaggct ttagtttcat ttgtttttca agtaatgaaa aataatttct tacatgggca   2897
gatagttaat ttgttgaaca attacaggta gcatttcatg taatctgatg ttctaaatgg   2957
ttctcttatt gaaggaggtt aaagaattag gtttcttaca gtttttggct ggccatgaca   3017
tgtataaaat gtatattaag gaggaattat aaagtacttt aatttgaatg ctagtggcaa   3077
ttgatcatta agaaagtact ttaaagcaaa aggttaatgg gtcatctggg aaaaatactg   3137
aagtatcaaa ggtatttgca tgtgaatgtg ggttatgttc ttctatccca ccttgtagca   3197
tattctatga aagttgagtt aaatgatagc taaaatatct gtttcaacag catgtaaaaa   3257
gttattttaa ctgttacaag tcattataca attttgaatg ttctgtagtt tctttttaac   3317
agtttaggta caaaggtctg ttttcattct ggtgcttttt attaattttg atagtatgat   3377
gtcacttcct attgaaatgt aagctagcgt gtaccttaga atgtgagctc catgagagca   3437
ggtaccttgt ttgtcttcac tgctgtatct attcccaacg cctcatgaca gtgcctggca   3497
catagtaggc actcaataaa tacttgttga atgaatgaaa aaaaaaaaaa a            3548
```

```

<210> SEQ ID NO 26
<211> LENGTH: 692
<212> TYPE: PRT
<213> ORGANISM: Mus musculus

<400> SEQUENCE: 26

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
```

-continued

```
            145                 150                 155                 160
        Asp Val Arg Thr Asp Leu Lys Gln Gly Leu Ser Gly Val Pro Ile Leu
                        165                 170                 175
        Ser Glu Glu Glu Leu Ser Leu Leu Asp Glu Phe Tyr Lys Leu Val Asp
                        180                 185                 190
        Pro Glu Arg Asp Met Ser Leu Arg Leu Asn Glu Gln Tyr Glu His Ala
                        195                 200                 205
        Ser Ile His Leu Trp Asp Leu Leu Glu Gly Lys Glu Lys Pro Val Cys
                        210                 215                 220
        Gly Thr Thr Tyr Lys Ala Leu Lys Glu Ile Val Glu Arg Val Phe Gln
        225                 230                 235                 240
        Ser Asn Tyr Phe Asp Ser Thr His Asn His Gln Asn Gly Leu Cys Glu
                        245                 250                 255
        Glu Glu Glu Ala Ala Ser Ala Pro Thr Val Glu Asp Gln Val Ala Glu
                        260                 265                 270
        Ala Glu Pro Glu Pro Ala Glu Glu Tyr Thr Glu Gln Ser Glu Val Glu
                        275                 280                 285
        Ser Thr Glu Tyr Val Asn Arg Gln Phe Met Ala Glu Thr Gln Phe Ser
                        290                 295                 300
        Ser Gly Glu Lys Glu Gln Val Asp Glu Trp Thr Val Glu Thr Val Glu
        305                 310                 315                 320
        Val Val Asn Ser Leu Gln Gln Pro Gln Ala Ala Ser Pro Ser Val
                        325                 330                 335
        Pro Glu Pro His Ser Leu Thr Pro Val Ala Gln Ser Asp Pro Leu Val
                        340                 345                 350
        Arg Arg Gln Arg Val Gln Asp Leu Met Ala Gln Met Gln Gly Pro Tyr
                        355                 360                 365
        Asn Phe Ile Gln Asp Ser Met Leu Asp Phe Glu Asn Gln Thr Leu Asp
                        370                 375                 380
        Pro Ala Ile Val Ser Ala Gln Pro Met Asn Pro Thr Gln Asn Met Asp
        385                 390                 395                 400
        Met Pro Gln Leu Val Cys Pro Gln Val His Ser Glu Ser Arg Leu Ala
                        405                 410                 415
        Gln Ser Asn Gln Val Pro Val Gln Pro Glu Ala Thr Gln Val Pro Leu
                        420                 425                 430
        Val Ser Ser Thr Ser Glu Gly Tyr Thr Ala Ser Gln Pro Leu Tyr Gln
                        435                 440                 445
        Pro Ser His Ala Thr Glu Gln Arg Pro Gln Lys Glu Pro Met Asp Gln
                        450                 455                 460
        Ile Gln Ala Thr Ile Ser Leu Asn Thr Asp Gln Thr Thr Ala Ser Ser
        465                 470                 475                 480
        Ser Leu Pro Ala Ala Ser Gln Pro Gln Val Phe Gln Ala Gly Thr Ser
                        485                 490                 495
        Lys Pro Leu His Ser Ser Gly Ile Asn Val Asn Ala Ala Pro Phe Gln
                        500                 505                 510
        Ser Met Gln Thr Val Phe Asn Met Asn Ala Pro Val Pro Pro Ala Asn
                        515                 520                 525
        Glu Pro Glu Thr Leu Lys Gln Gln Ser Gln Tyr Gln Ala Thr Tyr Asn
                        530                 535                 540
        Gln Ser Phe Ser Ser Gln Pro His Gln Val Glu Gln Thr Glu Leu Gln
        545                 550                 555                 560
        Gln Asp Gln Leu Gln Thr Val Val Gly Thr Tyr His Gly Ser Gln Asp
                        565                 570                 575
```

```
Gln Pro His Gln Val Pro Gly Asn His Gln Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
                660                 665                 670

Lys Arg Gly Ser Gly Gln Ser Gly Pro Arg Gly Ala Pro Arg Gly Asn
                675                 680                 685

Ile Leu Trp Trp
    690

<210> SEQ ID NO 27
<211> LENGTH: 3508
<212> TYPE: DNA
<213> ORGANISM: Mus musculus
<220> FEATURE:
<221> NAME/KEY: CDS
<222> LOCATION: (139)..(2217)

<400> SEQUENCE: 27
cccaccgcgc gcgcgcgtag ccgcctgccc gcccgcccgc tgcgcgtttt gtcccgcgtc      60
tctccccgtc cgtctcctga cttgctggtc ttgtccttcc ctcccgcttt tttcctctcc     120
tctcttctcg gtctaaag atg ccc tcg gcc acc agc cac agc gga agc ggc        171
                    Met Pro Ser Ala Thr Ser His Ser Gly Ser Gly
                    1               5                   10 agc aaa tcg tcg gga ccg ccg ccg ccg tcc ggt tcc tcc ggg agt gag        219
Ser Lys Ser Ser Gly Pro Pro Pro Pro Ser Gly Ser Ser Gly Ser Glu
                15                  20                  25 gcg gcg gcc ggg gca gct gcg ccg gct tct cag cat ccg gca acc ggc        267
Ala Ala Ala Gly Ala Ala Ala Pro Ala Ser Gln His Pro Ala Thr Gly
            30                  35                  40 acc ggc gcc gtc cag acc gag gcc atg aag cag att ctc ggc gta atc        315
Thr Gly Ala Val Gln Thr Glu Ala Met Lys Gln Ile Leu Gly Val Ile
        45                  50                  55 gac aag aaa ctt cgg aac ctg gag aag aaa aag ggt aaa ctt gat gat        363
Asp Lys Lys Leu Arg Asn Leu Glu Lys Lys Lys Gly Lys Leu Asp Asp
60                  65                  70                  75 tac cag gaa cga atg aat aaa ggg gaa agg ctc aat caa gac cag ctg        411
Tyr Gln Glu Arg Met Asn Lys Gly Glu Arg Leu Asn Gln Asp Gln Leu
                80                  85                  90 gat gcc gta tct aag tac cag gaa gtc aca aat aat ttg gag ttt gca        459
Asp Ala Val Ser Lys Tyr Gln Glu Val Thr Asn Asn Leu Glu Phe Ala
                95                  100                 105 aag gaa tta cag agg agt ttc atg gca tta agt caa gat att cag aaa        507
Lys Glu Leu Gln Arg Ser Phe Met Ala Leu Ser Gln Asp Ile Gln Lys
            110                 115                 120 aca ata aag aag aca gca cgt cgg gaa cag ctt atg aga gaa gaa gca        555
Thr Ile Lys Lys Thr Ala Arg Arg Glu Gln Leu Met Arg Glu Glu Ala
        125                 130                 135 gaa cag aag cgc tta aaa act gta ctt gag tta cag tat gta ttg gat        603
Glu Gln Lys Arg Leu Lys Thr Val Leu Glu Leu Gln Tyr Val Leu Asp
140                 145                 150                 155
```

```
aag ctg gga gat gat gat gtg aga aca gat ctg aaa caa ggt ttg agt    651
Lys Leu Gly Asp Asp Asp Val Arg Thr Asp Leu Lys Gln Gly Leu Ser
            160                 165                 170 gga gtg cca ata ttg tct gag gag gag ttg tca ttg ctg gat gag ttc    699
Gly Val Pro Ile Leu Ser Glu Glu Glu Leu Ser Leu Leu Asp Glu Phe
                175                 180                 185 tac aag ctc gta gat cct gag cgt gac atg agt tta agg tta aat gag    747
Tyr Lys Leu Val Asp Pro Glu Arg Asp Met Ser Leu Arg Leu Asn Glu
                190                 195                 200 cag tat gaa cat gcc tca att cac ttg tgg gat ttg ctg gaa ggg aaa    795
Gln Tyr Glu His Ala Ser Ile His Leu Trp Asp Leu Leu Glu Gly Lys
            205                 210                 215 gaa aag cct gtg tgt gga aca acc tat aaa gct cta aag gaa att gtt    843
Glu Lys Pro Val Cys Gly Thr Thr Tyr Lys Ala Leu Lys Glu Ile Val
220                 225                 230                 235 gag cgt gtt ttc cag tca aac tac ttt gat agc act cac aat cat caa    891
Glu Arg Val Phe Gln Ser Asn Tyr Phe Asp Ser Thr His Asn His Gln
                240                 245                 250 aat ggg ttg tgt gag gag gaa gag gcg gct tca gcg ccc aca gtg gag    939
Asn Gly Leu Cys Glu Glu Glu Glu Ala Ala Ser Ala Pro Thr Val Glu
            255                 260                 265 gac cag gta gct gaa gct gaa cct gag cca gcg gaa gaa tac aca gag    987
Asp Gln Val Ala Glu Ala Glu Pro Glu Pro Ala Glu Glu Tyr Thr Glu
            270                 275                 280 caa agt gag gtt gaa tca aca gag tat gtc aat agg cag ttc atg gca    1035
Gln Ser Glu Val Glu Ser Thr Glu Tyr Val Asn Arg Gln Phe Met Ala
            285                 290                 295 gaa aca cag ttc agc agt ggt gag aag gag caa gtg gat gag tgg aca    1083
Glu Thr Gln Phe Ser Ser Gly Glu Lys Glu Gln Val Asp Glu Trp Thr
300                 305                 310                 315 gtt gaa aca gtt gag gtt gta aac tca ctc cag cag caa cct cag gct    1131
Val Glu Thr Val Glu Val Val Asn Ser Leu Gln Gln Gln Pro Gln Ala
                320                 325                 330 gcg tcc cct tca gtc cca gag ccc cac tct ttg act cca gtg gct cag    1179
Ala Ser Pro Ser Val Pro Glu Pro His Ser Leu Thr Pro Val Ala Gln
            335                 340                 345 tca gat cca ctt gtg aga agg cag cgt gta caa gat ctt atg gca caa    1227
Ser Asp Pro Leu Val Arg Arg Gln Arg Val Gln Asp Leu Met Ala Gln
            350                 355                 360 atg caa ggg ccc tat aat ttc ata cag gat tca atg ttg gat ttt gaa    1275
Met Gln Gly Pro Tyr Asn Phe Ile Gln Asp Ser Met Leu Asp Phe Glu
365                 370                 375 aat cag acg ctt gat cct gcc att gta tcc gca cag cct atg aac cct    1323
Asn Gln Thr Leu Asp Pro Ala Ile Val Ser Ala Gln Pro Met Asn Pro
380                 385                 390                 395 acc cag aac atg gat atg cct cag ctg gtt tgc cct cag gtt cat tct    1371
Thr Gln Asn Met Asp Met Pro Gln Leu Val Cys Pro Gln Val His Ser
                400                 405                 410 gaa tct aga ctt gcc caa tct aat caa gtt cct gta caa cca gaa gcc    1419
Glu Ser Arg Leu Ala Gln Ser Asn Gln Val Pro Val Gln Pro Glu Ala
            415                 420                 425 aca cag gtt cct ttg gtt tca tcc aca agt gag ggg tat aca gca tct    1467
Thr Gln Val Pro Leu Val Ser Ser Thr Ser Glu Gly Tyr Thr Ala Ser
            430                 435                 440 cag ccc ttg tac cag cca tct cat gct acg gag cag cgg ccg cag aaa    1515
Gln Pro Leu Tyr Gln Pro Ser His Ala Thr Glu Gln Arg Pro Gln Lys
            445                 450                 455 gag cca atg gat cag att cag gca aca ata tct ttg aat aca gac cag    1563
Glu Pro Met Asp Gln Ile Gln Ala Thr Ile Ser Leu Asn Thr Asp Gln
```

```
                460                 465                 470                 475
act aca gca tcc tca tcc ctt cct gct gct tct cag cct caa gtg ttc         1611
Thr Thr Ala Ser Ser Ser Leu Pro Ala Ala Ser Gln Pro Gln Val Phe
                    480                 485                 490 cag gct ggg aca agt aaa cct ttg cac agc agt gga atc aat gta aat         1659
Gln Ala Gly Thr Ser Lys Pro Leu His Ser Ser Gly Ile Asn Val Asn
            495                 500                 505 gca gct cca ttc cag tcc atg caa acg gtg ttc aat atg aat gct cca         1707
Ala Ala Pro Phe Gln Ser Met Gln Thr Val Phe Asn Met Asn Ala Pro
        510                 515                 520 gtc cct cct gct aat gaa cca gaa acg tta aaa caa cag agt cag tac         1755
Val Pro Pro Ala Asn Glu Pro Glu Thr Leu Lys Gln Gln Ser Gln Tyr
    525                 530                 535 cag gcc act tat aac cag agt ttt tcc agt cag cct cac caa gtg gaa         1803
Gln Ala Thr Tyr Asn Gln Ser Phe Ser Ser Gln Pro His Gln Val Glu
540                 545                 550                 555 caa aca gag ctt caa caa gac caa ctg caa acg gtg gtt ggc act tac         1851
Gln Thr Glu Leu Gln Gln Asp Gln Leu Gln Thr Val Val Gly Thr Tyr
                560                 565                 570 cat gga tcc cag gac cag cct cat caa gtg cct ggt aac cac cag caa         1899
His Gly Ser Gln Asp Gln Pro His Gln Val Pro Gly Asn His Gln Gln
            575                 580                 585 ccc cca cag cag aac act ggc ttt cca cgt agc agt cag cct tat tac         1947
Pro Pro Gln Gln Asn Thr Gly Phe Pro Arg Ser Ser Gln Pro Tyr Tyr
        590                 595                 600 aac agt cgt ggg gta tct cga gga ggg tct cgt ggt gcc aga ggc ttg         1995
Asn Ser Arg Gly Val Ser Arg Gly Gly Ser Arg Gly Ala Arg Gly Leu
    605                 610                 615 atg aat gga tac agg ggc cct gcc aat gga ttt aga gga gga tat gat         2043
Met Asn Gly Tyr Arg Gly Pro Ala Asn Gly Phe Arg Gly Gly Tyr Asp
620                 625                 630                 635 ggt tac cgc cct tca ttc tcg aac act cca aac agt ggt tat tca cag         2091
Gly Tyr Arg Pro Ser Phe Ser Asn Thr Pro Asn Ser Gly Tyr Ser Gln
                640                 645                 650 tct cag ttc act gct ccc cgg gac tac tct ggt tac cag cgg gat gga         2139
Ser Gln Phe Thr Ala Pro Arg Asp Tyr Ser Gly Tyr Gln Arg Asp Gly
            655                 660                 665 tat cag cag aat ttc aag cga ggc tct ggg cag agt gga cca cgg gga         2187
Tyr Gln Gln Asn Phe Lys Arg Gly Ser Gly Gln Ser Gly Pro Arg Gly
        670                 675                 680 gcc cca cga ggt aat ata ttg tgg tgg tga cctagctcc tatgtggagc            2237
Ala Pro Arg Gly Asn Ile Leu Trp Trp
    685                 690 ttctgttctg gccttggaag aactgttcat agtccgcatg taggttacat gttaggaata      2297
catttatctt ttccagactt gttgctaaag attaaatgaa atgctctgtt tctaaaattt      2357
catcttgaat ccaaatttta attttgaat gactttccct gctgttgtct tcaaaatcag       2417
aacattttct ctgcctcaga aaagcgtttt tccaactgga aatttatttt tcaggtctta      2477
aaacctgcta atgttttta ggaagtacct actgaaactt tttgtaagac attttttggaa     2537 cgagcttgaa catttatata aatttattac cctctttgat ttttgaaaca tgcatattat      2597
atttaggctg agaagcccctt caaatggcca gataagccac agttttagct agagaaccat    2657
ttagaattga cataactaat ctaaacttga acactttag gaccaatgtt agtgttctaa       2717
ataccaacat atttctgatg tttaaacaga tctcccaaat tcttaggacc ttgatgtcat      2777
taaaatttag aatgacaagc ttaagaggct ttagtttcat ttgttttttca agtaatgaaa     2837 aataatttct tacatgggca gatagttaat ttgttgaaca attacaggta gcatttcatg      2897
```

-continued

```
taatctgatg ttctaaatgg ttctcttatt gaaggaggtt aaagaattag gtttcttaca    2957
gttttttggct ggccatgaca tgtataaaat gtatattaag gaggaattat aaagtacttt   3017
aatttgaatg ctagtggcaa ttgatcatta agaaagtact ttaaagcaaa aggttaatgg    3077
gtcatctggg aaaaatactg aagtatcaaa ggtatttgca tgtgaatgtg ggttatgttc    3137
ttctatccca ccttgtagca tattctatga agttgagtt aaatgatagc taaaatatct     3197
gtttcaacag catgtaaaaa gttatttaa ctgttacaag tcattataca attttgaatg     3257
ttctgtagtt tcttttaac agtttaggta caaaggtctg ttttcattct ggtgcttttt     3317
attaattttg atagtatgat gtcacttcct attgaaatgt aagctagcgt gtaccttaga    3377
atgtgagctc catgagagca ggtaccttgt ttgtcttcac tgctgtatct attcccaacg    3437
cctcatgaca gtgcctggca catagtaggc actcaataaa tacttgttga atgaatgaaa    3497
aaaaaaaaaa a                                                         3508
```

<210> SEQ ID NO 28
<211> LENGTH: 692
<212> TYPE: PRT
<213> ORGANISM: Mus musculus

<400> SEQUENCE: 28

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
                20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
        50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255
```

-continued

```
Glu Glu Glu Ala Ala Ser Ala Pro Thr Val Glu Asp Gln Val Ala Glu
                260                 265                 270

Ala Glu Pro Glu Pro Ala Glu Glu Tyr Thr Glu Gln Ser Glu Val Glu
            275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Pro Gln Ala Ala Ser Pro Ser Val
                325                 330                 335

Pro Glu Pro His Ser Leu Thr Pro Val Ala Gln Ser Asp Pro Leu Val
                340                 345                 350

Arg Arg Gln Arg Val Gln Asp Leu Met Ala Gln Met Gln Gly Pro Tyr
            355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Thr Ser Glu Gly Tyr Thr Ala Ser Gln Pro Leu Tyr Gln
    435                 440                 445

Pro Ser His Ala Thr Glu Gln Arg Pro Gln Lys Glu Pro Met Asp Gln
450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
                500                 505                 510

Ser Met Gln Thr Val Phe Asn Met Asn Ala Pro Val Pro Pro Ala Asn
            515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Gln Gln Asn
                580                 585                 590

Thr Gly Phe Pro Arg Ser Ser Gln Pro Tyr Tyr Asn Ser Arg Gly Val
            595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
                660                 665                 670

Lys Arg Gly Ser Gly Gln Ser Gly Pro Arg Gly Ala Pro Arg Gly Asn
```

```
              675                 680                 685

Ile Leu Trp Trp
    690

<210> SEQ ID NO 29
<211> LENGTH: 2109
<212> TYPE: DNA
<213> ORGANISM: Gallus gallus
<220> FEATURE:
<221> NAME/KEY: CDS
<222> LOCATION: (1)..(2109)

<400> SEQUENCE: 29 atg ccc tcg gct acc aac ggc acc atg gcg agc agc agc ggg aag gcg      48
Met Pro Ser Ala Thr Asn Gly Thr Met Ala Ser Ser Ser Gly Lys Ala
1               5                   10                  15 ggc ccg ggc ggc aac gag cag gcc ccg gcg gcg gca gcg gcg gcc ccg      96
Gly Pro Gly Gly Asn Glu Gln Ala Pro Ala Ala Ala Ala Ala Ala Pro
            20                  25                  30 cag gcg tcg ggc ggc agc atc acc tcg gtt cag acc gag gcc atg aag     144
Gln Ala Ser Gly Gly Ser Ile Thr Ser Val Gln Thr Glu Ala Met Lys
        35                  40                  45 cag atc ttg gga gtg atc gac aaa aag ctc cgc aac ctc gag aag aaa     192
Gln Ile Leu Gly Val Ile Asp Lys Lys Leu Arg Asn Leu Glu Lys Lys
    50                  55                  60 aag agc aaa ctt gac gat tac cag gaa cga atg aac aag ggg gaa cgt     240
Lys Ser Lys Leu Asp Asp Tyr Gln Glu Arg Met Asn Lys Gly Glu Arg
65                  70                  75                  80 cta aat caa gat caa ctg gat gca gtg tca aaa tac cag gaa gtg aca     288
Leu Asn Gln Asp Gln Leu Asp Ala Val Ser Lys Tyr Gln Glu Val Thr
                85                  90                  95 aat aac ctg gaa ttc gct aaa gaa ctg cag agg agc ttt atg gca ctg     336
Asn Asn Leu Glu Phe Ala Lys Glu Leu Gln Arg Ser Phe Met Ala Leu
            100                 105                 110 agc caa gat atc cag aaa aca ata aaa aag acg gct cgc agg gag cag     384
Ser Gln Asp Ile Gln Lys Thr Ile Lys Lys Thr Ala Arg Arg Glu Gln
        115                 120                 125 ctg atg aga gaa gag gct gag cag aag cgt tta aag act gtg cta gag     432
Leu Met Arg Glu Glu Ala Glu Gln Lys Arg Leu Lys Thr Val Leu Glu
    130                 135                 140 ctg cag ttc att ttg gac aag ttg ggt gac gat gaa gtg cgc agt gac     480
Leu Gln Phe Ile Leu Asp Lys Leu Gly Asp Asp Glu Val Arg Ser Asp
145                 150                 155                 160 ttg aaa caa gga tca aat gga gta ccg gta ctg aca gag gag gaa ctg     528
Leu Lys Gln Gly Ser Asn Gly Val Pro Val Leu Thr Glu Glu Glu Leu
                165                 170                 175 aca atg ctg gat gaa ttt tac aag cta gtt tac cct gaa agg gac atg     576
Thr Met Leu Asp Glu Phe Tyr Lys Leu Val Tyr Pro Glu Arg Asp Met
            180                 185                 190 aac atg agg ttg aat gag cag tat gag caa gca tct gtt cac ctg tgg     624
Asn Met Arg Leu Asn Glu Gln Tyr Glu Gln Ala Ser Val His Leu Trp
        195                 200                 205 gac tta ctg gaa ggg aag gaa aaa ccc gtt tgt gga aca acc tat aaa     672
Asp Leu Leu Glu Gly Lys Glu Lys Pro Val Cys Gly Thr Thr Tyr Lys
    210                 215                 220 gcc ctg aag gag gtt gtt gaa cgt att ctt caa act agt tac ttt gat     720
Ala Leu Lys Glu Val Val Glu Arg Ile Leu Gln Thr Ser Tyr Phe Asp
225                 230                 235                 240 agc acc cat aac cat cag aac ggg tta tgt gag gaa gaa gag gca gca     768
Ser Thr His Asn His Gln Asn Gly Leu Cys Glu Glu Glu Glu Ala Ala
                245                 250                 255
```

-continued

| | | |
|---|---|---|
| ccc aca cct gca gta gaa gac act gta gca gaa gct gag cct gat cca<br>Pro Thr Pro Ala Val Glu Asp Thr Val Ala Glu Ala Glu Pro Asp Pro<br>           260                      265                   270 | | 816 |
| gca gaa gaa ttt act gaa cct act gaa gtt gaa tcg act gag tat gta<br>Ala Glu Glu Phe Thr Glu Pro Thr Glu Val Glu Ser Thr Glu Tyr Val<br>           275                      280                   285 | | 864 |
| aac aga caa ttc atg gca gag act cag ttc agc agt agt gag aag gaa<br>Asn Arg Gln Phe Met Ala Glu Thr Gln Phe Ser Ser Ser Glu Lys Glu<br>290                      295                      300 | | 912 |
| cag gta gat gag tgg aca gtt gaa acg gtt gag gtt gta aat tca ctg<br>Gln Val Asp Glu Trp Thr Val Glu Thr Val Glu Val Val Asn Ser Leu<br>305                      310                      315                  320 | | 960 |
| cag caa caa aca caa gct aca tct cct cca gtt cct gaa cct cat aca<br>Gln Gln Gln Thr Gln Ala Thr Ser Pro Pro Val Pro Glu Pro His Thr<br>                   325                      330                   335 | | 1008 |
| ctc act act gtg gct caa gca gat cct ctt gtt aga aga cag aga gta<br>Leu Thr Thr Val Ala Gln Ala Asp Pro Leu Val Arg Arg Gln Arg Val<br>                   340                      345                   350 | | 1056 |
| cag gac ctt atg gcc cag atg cag ggt cca tat aac ttc atg cag gac<br>Gln Asp Leu Met Ala Gln Met Gln Gly Pro Tyr Asn Phe Met Gln Asp<br>           355                      360                   365 | | 1104 |
| tct atg ctg gag ttt gag aac cag aca ctt gat cct gcc att gta tct<br>Ser Met Leu Glu Phe Glu Asn Gln Thr Leu Asp Pro Ala Ile Val Ser<br>           370                      375                   380 | | 1152 |
| gca cag ccc atg aat cca gca cag aat ttg gac atg ccg caa atg gtc<br>Ala Gln Pro Met Asn Pro Ala Gln Asn Leu Asp Met Pro Gln Met Val<br>385                      390                      395                  400 | | 1200 |
| tgc cct cca gtt cat act gag tca aga ctt gcc cag cct aat caa gtt<br>Cys Pro Pro Val His Thr Glu Ser Arg Leu Ala Gln Pro Asn Gln Val<br>                   405                      410                   415 | | 1248 |
| cct gtg caa cca gaa gct acg cag gtt ccc ttg gtt tca tct aca agt<br>Pro Val Gln Pro Glu Ala Thr Gln Val Pro Leu Val Ser Ser Thr Ser<br>                   420                      425                   430 | | 1296 |
| gag gga tat aca gcc tcc cag ccc atg tat cag cct tct cat acc aca<br>Glu Gly Tyr Thr Ala Ser Gln Pro Met Tyr Gln Pro Ser His Thr Thr<br>           435                      440                   445 | | 1344 |
| gag caa cgg cca cag aag gaa tcc att gac cag att cag gct tca atg<br>Glu Gln Arg Pro Gln Lys Glu Ser Ile Asp Gln Ile Gln Ala Ser Met<br>450                      455                      460 | | 1392 |
| tca ctg aat gca gac cag acc ccg tca tca tca ctt ccc act gca<br>Ser Leu Asn Ala Asp Gln Thr Pro Ser Ser Ser Leu Pro Thr Ala<br>465                      470                      475                  480 | | 1440 |
| tcc cag ccg caa gtt ttc caa gct gga tct agc aaa cct ttg cat agc<br>Ser Gln Pro Gln Val Phe Gln Ala Gly Ser Ser Lys Pro Leu His Ser<br>                       485                      490                   495 | | 1488 |
| agc gga atc aat gtt aat gca gct cca ttc caa tcc atg caa aca gta<br>Ser Gly Ile Asn Val Asn Ala Ala Pro Phe Gln Ser Met Gln Thr Val<br>                   500                      505                   510 | | 1536 |
| ttc aac atg aat gca cct gtt cct cct gtt aat gag cca gaa gcc ctt<br>Phe Asn Met Asn Ala Pro Val Pro Pro Val Asn Glu Pro Glu Ala Leu<br>           515                      520                   525 | | 1584 |
| aag caa caa aat cag tac cag gcc agt tac aac cag agt ttc tcc aat<br>Lys Gln Gln Asn Gln Tyr Gln Ala Ser Tyr Asn Gln Ser Phe Ser Asn<br>           530                      535                   540 | | 1632 |
| cag cca cac caa gta gaa caa tca gat ctt cag caa gaa cag ctc cag<br>Gln Pro His Gln Val Glu Gln Ser Asp Leu Gln Gln Glu Gln Leu Gln<br>545                      550                      555                  560 | | 1680 |
| aca gtg gtt ggt act tac cat ggt tct ccg gac cag acc cat caa gtg<br>Thr Val Val Gly Thr Tyr His Gly Ser Pro Asp Gln Thr His Gln Val | | 1728 |

```
              565                 570                 575
gca gga aac cac cag caa cct ccc cag cag aat act gga ttt cca cgc    1776
Ala Gly Asn His Gln Gln Pro Pro Gln Gln Asn Thr Gly Phe Pro Arg
            580                 585                 590 aac agt cag cct tat tac aac agt cgg gga gtg tct cgt ggt gga tca    1824
Asn Ser Gln Pro Tyr Tyr Asn Ser Arg Gly Val Ser Arg Gly Gly Ser
            595                 600                 605 cgt ggg act cgt gga ttg atg aat ggt tac agg gga cct gca aat gga    1872
Arg Gly Thr Arg Gly Leu Met Asn Gly Tyr Arg Gly Pro Ala Asn Gly
        610                 615                 620 ttt aga gga gga tat gat ggc tac cgt cct tca ttt tcc aac act ccg    1920
Phe Arg Gly Gly Tyr Asp Gly Tyr Arg Pro Ser Phe Ser Asn Thr Pro
625                 630                 635                 640 aac agt ggt tac acg cag ccc caa ttt aat gct cct cga gat tat tca    1968
Asn Ser Gly Tyr Thr Gln Pro Gln Phe Asn Ala Pro Arg Asp Tyr Ser
                645                 650                 655 aac tac cag cgg gat gga tat cag cag aac ttc aaa cgt ggt tct gga    2016
Asn Tyr Gln Arg Asp Gly Tyr Gln Gln Asn Phe Lys Arg Gly Ser Gly
            660                 665                 670 caa agt ggg cct cgg gga gct cct cga ggt cgt gga ggg ccc cca aga    2064
Gln Ser Gly Pro Arg Gly Ala Pro Arg Gly Arg Gly Gly Pro Pro Arg
        675                 680                 685 cca aac aga ggg atg cct caa atg aac gct cag caa gtg aat taa        2109
Pro Asn Arg Gly Met Pro Gln Met Asn Ala Gln Gln Val Asn
690                 695                 700
```

<210> SEQ ID NO 30
<211> LENGTH: 702
<212> TYPE: PRT
<213> ORGANISM: Gallus gallus

<400> SEQUENCE: 30

```
Met Pro Ser Ala Thr Asn Gly Thr Met Ala Ser Ser Ser Gly Lys Ala
1               5                   10                  15

Gly Pro Gly Gly Asn Glu Gln Ala Pro Ala Ala Ala Ala Ala Ala Pro
            20                  25                  30

Gln Ala Ser Gly Gly Ser Ile Thr Ser Val Gln Thr Glu Ala Met Lys
        35                  40                  45

Gln Ile Leu Gly Val Ile Asp Lys Lys Leu Arg Asn Leu Glu Lys Lys
    50                  55                  60

Lys Ser Lys Leu Asp Asp Tyr Gln Glu Arg Met Asn Lys Gly Glu Arg
65                  70                  75                  80

Leu Asn Gln Asp Gln Leu Asp Ala Val Ser Lys Tyr Gln Glu Val Thr
                85                  90                  95

Asn Asn Leu Glu Phe Ala Lys Glu Leu Gln Arg Ser Phe Met Ala Leu
            100                 105                 110

Ser Gln Asp Ile Gln Lys Thr Ile Lys Lys Thr Ala Arg Arg Glu Gln
        115                 120                 125

Leu Met Arg Glu Glu Ala Glu Gln Lys Arg Leu Lys Thr Val Leu Glu
    130                 135                 140

Leu Gln Phe Ile Leu Asp Lys Leu Gly Asp Asp Glu Val Arg Ser Asp
145                 150                 155                 160

Leu Lys Gln Gly Ser Asn Gly Val Pro Val Leu Thr Glu Glu Leu
                165                 170                 175

Thr Met Leu Asp Glu Phe Tyr Lys Leu Val Tyr Pro Glu Arg Asp Met
            180                 185                 190

Asn Met Arg Leu Asn Glu Gln Tyr Glu Gln Ala Ser Val His Leu Trp
```

-continued

```
                195                 200                 205
Asp Leu Leu Glu Gly Lys Glu Lys Pro Val Cys Gly Thr Thr Tyr Lys
    210                 215                 220

Ala Leu Lys Glu Val Val Glu Arg Ile Leu Gln Thr Ser Tyr Phe Asp
225                 230                 235                 240

Ser Thr His Asn His Gln Asn Gly Leu Cys Glu Glu Glu Glu Ala Ala
                245                 250                 255

Pro Thr Pro Ala Val Glu Asp Thr Val Ala Glu Ala Glu Pro Asp Pro
            260                 265                 270

Ala Glu Glu Phe Thr Glu Pro Thr Glu Val Glu Ser Thr Glu Tyr Val
                275                 280                 285

Asn Arg Gln Phe Met Ala Glu Thr Gln Phe Ser Ser Ser Glu Lys Glu
            290                 295                 300

Gln Val Asp Glu Trp Thr Val Glu Thr Val Glu Val Val Asn Ser Leu
305                 310                 315                 320

Gln Gln Gln Thr Gln Ala Thr Ser Pro Pro Val Pro Glu Pro His Thr
                325                 330                 335

Leu Thr Thr Val Ala Gln Ala Asp Pro Leu Val Arg Arg Gln Arg Val
            340                 345                 350

Gln Asp Leu Met Ala Gln Met Gln Gly Pro Tyr Asn Phe Met Gln Asp
                355                 360                 365

Ser Met Leu Glu Phe Glu Asn Gln Thr Leu Asp Pro Ala Ile Val Ser
            370                 375                 380

Ala Gln Pro Met Asn Pro Ala Gln Asn Leu Asp Met Pro Gln Met Val
385                 390                 395                 400

Cys Pro Pro Val His Thr Glu Ser Arg Leu Ala Gln Pro Asn Gln Val
                405                 410                 415

Pro Val Gln Pro Glu Ala Thr Gln Val Pro Leu Val Ser Ser Thr Ser
            420                 425                 430

Glu Gly Tyr Thr Ala Ser Gln Pro Met Tyr Gln Pro Ser His Thr Thr
                435                 440                 445

Glu Gln Arg Pro Gln Lys Glu Ser Ile Asp Gln Ile Gln Ala Ser Met
            450                 455                 460

Ser Leu Asn Ala Asp Gln Thr Pro Ser Ser Ser Leu Pro Thr Ala
465                 470                 475                 480

Ser Gln Pro Gln Val Phe Gln Ala Gly Ser Ser Lys Pro Leu His Ser
                485                 490                 495

Ser Gly Ile Asn Val Asn Ala Ala Pro Phe Gln Ser Met Gln Thr Val
            500                 505                 510

Phe Asn Met Asn Ala Pro Val Pro Val Asn Glu Pro Glu Ala Leu
                515                 520                 525

Lys Gln Gln Asn Gln Tyr Gln Ala Ser Tyr Asn Gln Ser Phe Ser Asn
            530                 535                 540

Gln Pro His Gln Val Glu Gln Ser Asp Leu Gln Gln Glu Gln Leu Gln
545                 550                 555                 560

Thr Val Val Gly Thr Tyr His Gly Ser Pro Asp Gln Thr His Gln Val
                565                 570                 575

Ala Gly Asn His Gln Gln Pro Pro Gln Gln Asn Thr Gly Phe Pro Arg
            580                 585                 590

Asn Ser Gln Pro Tyr Tyr Asn Ser Arg Gly Val Ser Arg Gly Gly Ser
            595                 600                 605

Arg Gly Thr Arg Gly Leu Met Asn Gly Tyr Arg Gly Pro Ala Asn Gly
            610                 615                 620
```

```
Phe Arg Gly Gly Tyr Asp Gly Tyr Arg Pro Ser Phe Ser Asn Thr Pro
625                 630                 635                 640

Asn Ser Gly Tyr Thr Gln Pro Gln Phe Asn Ala Pro Arg Asp Tyr Ser
            645                 650                 655

Asn Tyr Gln Arg Asp Gly Tyr Gln Asn Phe Lys Arg Gly Ser Gly
        660                 665                 670

Gln Ser Gly Pro Arg Gly Ala Pro Arg Gly Arg Gly Pro Pro Arg
        675                 680                 685

Pro Asn Arg Gly Met Pro Gln Met Asn Ala Gln Gln Val Asn
        690                 695                 700

<210> SEQ ID NO 31
<211> LENGTH: 63
<212> TYPE: PRT
<213> ORGANISM: Homo sapiens

<400> SEQUENCE: 31

Glu Glu Tyr Thr Glu Gln Ser Glu Val Glu Ser Thr Glu Tyr Val Asn
1               5                   10                  15

Arg Gln Phe Met Ala Glu Thr Gln Phe Thr Ser Gly Glu Lys Glu Gln
            20                  25                  30

Val Asp Glu Trp Thr Val Glu Thr Val Glu Val Asn Ser Leu Gln
        35                  40                  45

Gln Gln Pro Gln Ala Ala Ser Pro Ser Val Pro Glu Pro His Ser
        50                  55                  60

<210> SEQ ID NO 32
<211> LENGTH: 18
<212> TYPE: PRT
<213> ORGANISM: Homo sapiens

<400> SEQUENCE: 32

Val Phe Asn Met Asn Ala Pro Val Pro Val Asn Glu Pro Glu Thr
1               5                   10                  15

Leu Lys

<210> SEQ ID NO 33
<211> LENGTH: 16
<212> TYPE: PRT
<213> ORGANISM: Homo sapiens

<400> SEQUENCE: 33

Ala Thr Gln Val Pro Leu Val Ser Ser Thr Ser Glu Gly Tyr Thr Ala
1               5                   10                  15

<210> SEQ ID NO 34
<211> LENGTH: 25
<212> TYPE: PRT
<213> ORGANISM: Homo sapiens

<400> SEQUENCE: 34

Gln Ile Leu Gly Val Ile Asp Lys Lys Leu Arg Asn Leu Glu Lys Lys
1               5                   10                  15

Lys Gly Lys Leu Asp Asp Tyr Gln Glu
            20                  25

<210> SEQ ID NO 35
<211> LENGTH: 23
<212> TYPE: PRT
<213> ORGANISM: Homo sapiens
```

```
<400> SEQUENCE: 35

Pro Arg Gly Arg Gly Gly Pro Pro Arg Pro Asn Arg Gly Met Pro Gln
1               5                   10                  15

Met Asn Thr Gln Gln Val Asn
            20

<210> SEQ ID NO 36
<211> LENGTH: 5
<212> TYPE: PRT
<213> ORGANISM: Gallus gallus

<400> SEQUENCE: 36

Ser Tyr Gln Met Asn
1               5

<210> SEQ ID NO 37
<211> LENGTH: 17
<212> TYPE: PRT
<213> ORGANISM: Gallus gallus

<400> SEQUENCE: 37

Ala Ile Asn Lys Phe Gly Asn Ser Thr Gly His Gly Ala Ala Val Lys
1               5                   10                  15

Gly

<210> SEQ ID NO 38
<211> LENGTH: 19
<212> TYPE: PRT
<213> ORGANISM: Gallus gallus

<400> SEQUENCE: 38

His Ala Tyr Gly Tyr Cys Gly Ser Gly Thr Trp Cys Ala Ala Gly Glu
1               5                   10                  15

Ile Asp Ala

<210> SEQ ID NO 39
<211> LENGTH: 128
<212> TYPE: PRT
<213> ORGANISM: Gallus gallus

<400> SEQUENCE: 39

Ala Val Thr Leu Asp Glu Ser Gly Gly Gly Leu Gln Met Ser Arg Gly
1               5                   10                  15

Gly Leu Ser Leu Val Cys Lys Ala Ser Gly Phe Asp Phe Ser Ser Tyr
            20                  25                  30

Gln Met Asn Trp Ile Arg Gln Ala Pro Gly Lys Gly Leu Glu Phe Val
        35                  40                  45

Ala Ala Ile Asn Lys Phe Gly Asn Ser Thr Gly His Gly Ala Ala Val
    50                  55                  60

Lys Gly Arg Val Thr Ile Ser Arg Asp Asn Gly Gln Ser Thr Val Arg
65                  70                  75                  80

Leu Gln Leu Asn Asn Leu Arg Ala Glu Asp Thr Ala Ile Tyr Phe Cys
                85                  90                  95

Thr Lys His Ala Tyr Gly Tyr Cys Gly Ser Gly Thr Trp Cys Ala Ala
            100                 105                 110

Gly Glu Ile Asp Ala Trp Gly His Gly Thr Glu Val Ile Val Ser Ser
        115                 120                 125
```

<210> SEQ ID NO 40
<211> LENGTH: 9
<212> TYPE: PRT
<213> ORGANISM: Gallus gallus

<400> SEQUENCE: 40

Ser Gly Gly Gly Ser Tyr Ser Tyr Gly
1               5

<210> SEQ ID NO 41
<211> LENGTH: 7
<212> TYPE: PRT
<213> ORGANISM: Gallus gallus

<400> SEQUENCE: 41

Asn Asn Lys Arg Pro Ser Asp
1               5

<210> SEQ ID NO 42
<211> LENGTH: 10
<212> TYPE: PRT
<213> ORGANISM: Gallus gallus

<400> SEQUENCE: 42

Ser Gly Asp Ser Thr Asp Thr Ala Val Phe
1               5                   10

<210> SEQ ID NO 43
<211> LENGTH: 108
<212> TYPE: PRT
<213> ORGANISM: Gallus gallus

<400> SEQUENCE: 43

Gln Ala Ala Ser Thr Gln Pro Ser Ser Val Ser Ala Asn Pro Gly Glu
1               5                   10                  15

Thr Val Glu Ile Thr Cys Ser Gly Gly Gly Ser Tyr Ser Tyr Gly Trp
                20                  25                  30

Phe Gln Gln Lys Ser Pro Gly Ser Ala Pro Val Thr Val Ile Tyr Tyr
            35                  40                  45

Asn Asn Lys Arg Pro Ser Asp Ile Pro Ser Arg Phe Ser Gly Ser Lys
        50                  55                  60

Ser Gly Ser Thr Gly Thr Leu Thr Ile Thr Gly Val Gln Ala Asp Asp
65                  70                  75                  80

Glu Ala Val Tyr Tyr Cys Gly Ser Gly Asp Ser Thr Asp Thr Ala Val
                85                  90                  95

Phe Gly Ala Gly Thr Thr Leu Thr Val Leu Gly Gln
            100                 105

<210> SEQ ID NO 44
<211> LENGTH: 5
<212> TYPE: PRT
<213> ORGANISM: Rabbit

<400> SEQUENCE: 44

Ser His Ser Leu Gly
1               5

<210> SEQ ID NO 45
<211> LENGTH: 16
<212> TYPE: PRT
<213> ORGANISM: Rabbit

<400> SEQUENCE: 45

```
Asp Ile Arg Ser Gly Gly Ser Ala Tyr Tyr Ala Asn Trp Ala Lys Gly
1               5                   10                  15
```

<210> SEQ ID NO 46
<211> LENGTH: 13
<212> TYPE: PRT
<213> ORGANISM: Rabbit

<400> SEQUENCE: 46

```
Thr Asn Gly Pro Ser Asp Leu Thr Asn Arg Leu Asp Leu
1               5                   10
```

<210> SEQ ID NO 47
<211> LENGTH: 121
<212> TYPE: PRT
<213> ORGANISM: Homo sapiens

<400> SEQUENCE: 47

```
Glu Gln Ser Leu Val Glu Ser Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120
```

<210> SEQ ID NO 48
<211> LENGTH: 13
<212> TYPE: PRT
<213> ORGANISM: Rabbit

<400> SEQUENCE: 48

```
Gln Ala Ser Gln Ser Leu Tyr Asn Asn Glu Asn Leu Ala
1               5                   10
```

<210> SEQ ID NO 49
<211> LENGTH: 7
<212> TYPE: PRT
<213> ORGANISM: Rabbit

<400> SEQUENCE: 49

```
Gly Ala Ser Thr Leu Ala Ser
1               5
```

<210> SEQ ID NO 50
<211> LENGTH: 13
<212> TYPE: PRT
<213> ORGANISM: Rabbit

<400> SEQUENCE: 50

```
Leu Gly Glu Phe Ser Cys Gly Ser Ala Asp Cys Phe Ala
1               5                   10
```

<210> SEQ ID NO 51
<211> LENGTH: 112
<212> TYPE: PRT
<213> ORGANISM: Homo sapiens

<400> SEQUENCE: 51

Gln Val Leu Thr Gln Ser Pro Ser Leu Ser Ala Ser Val Gly Asp
1               5                   10                  15

Arg Val Thr Ile Asn Cys Gln Ala Ser Gln Ser Leu Tyr Asn Asn Glu
                20                  25                  30

Asn Leu Ala Trp Phe Gln Gln Lys Pro Gly Lys Val Pro Lys Arg Leu
            35                  40                  45

Ile Tyr Gly Ala Ser Thr Leu Ala Ser Gly Val Ser Ser Arg Phe Ser
        50                  55                  60

Gly Ser Gly Ser Gly Thr Glu Phe Thr Leu Thr Ile Ser Ser Leu Gln
65                  70                  75                  80

Cys Glu Asp Phe Ala Ile Tyr Tyr Cys Leu Gly Glu Phe Ser Cys Gly
                85                  90                  95

Ser Ala Asp Cys Phe Ala Phe Gly Gly Gly Thr Lys Val Glu Ile Lys
                100                 105                 110

<210> SEQ ID NO 52
<211> LENGTH: 4
<212> TYPE: PRT
<213> ORGANISM: Gallus gallus

<400> SEQUENCE: 52

Phe Asp Met Gly
1

<210> SEQ ID NO 53
<211> LENGTH: 17
<212> TYPE: PRT
<213> ORGANISM: Gallus gallus

<400> SEQUENCE: 53

Gln Ile Asn Asp Ala Gly Ser Arg Thr Trp Tyr Ala Thr Ala Val Lys
1               5                   10                  15

Gly

<210> SEQ ID NO 54
<211> LENGTH: 12
<212> TYPE: PRT
<213> ORGANISM: Gallus gallus

<400> SEQUENCE: 54

Gly Ser Gly Tyr Val Gly Ala Gly Ala Ile Asp Ala
1               5                   10

<210> SEQ ID NO 55
<211> LENGTH: 120
<212> TYPE: PRT
<213> ORGANISM: Gallus gallus

<400> SEQUENCE: 55

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Phe
                20                  25                  30

Asp Met Gly Trp Val Arg Gln Ala Pro Gly Lys Gly Leu Glu Phe Val
            35                  40                  45

Ala Gln Ile Asn Asp Ala Gly Ser Arg Thr Trp Tyr Ala Thr Ala Val
 50                  55                  60

Lys Gly Arg Ala Thr Ile Ser Arg Asp Asn Gly Gln Thr Thr Val Arg
 65                  70                  75                  80

Leu Gln Leu Asn Asn Leu Arg Ala Glu Asp Thr Gly Thr Tyr Tyr Cys
                 85                  90                  95

Thr Arg Gly Ser Gly Tyr Val Gly Ala Gly Ala Ile Asp Ala Trp Gly
            100                 105                 110

His Gly Thr Glu Val Ile Val Ser
            115                 120

<210> SEQ ID NO 56
<211> LENGTH: 8
<212> TYPE: PRT
<213> ORGANISM: Gallus gallus

<400> SEQUENCE: 56

Ser Gly Gly Ser Gly Tyr Tyr Gly
1               5

<210> SEQ ID NO 57
<211> LENGTH: 7
<212> TYPE: PRT
<213> ORGANISM: Gallus gallus

<400> SEQUENCE: 57

Asn Asp Lys Arg Pro Ser Asp
1               5

<210> SEQ ID NO 58
<211> LENGTH: 10
<212> TYPE: PRT
<213> ORGANISM: Gallus gallus

<400> SEQUENCE: 58

Arg Tyr Asp Ser Thr Asp Ser Gly Ile Phe
1               5                   10

<210> SEQ ID NO 59
<211> LENGTH: 105
<212> TYPE: PRT
<213> ORGANISM: Gallus gallus

<400> SEQUENCE: 59

Ala Ala Leu Thr Gln Pro Ser Ser Val Ser Ala Asn Pro Gly Glu Thr
1               5                   10                  15

Val Lys Ile Thr Cys Ser Gly Gly Ser Gly Tyr Tyr Gly Trp Tyr Gln
            20                  25                  30

Gln Gln Lys Ser Pro Gly Ser Ala Pro Val Thr Val Ile Tyr Gln Asn
            35                  40                  45

Asp Lys Arg Pro Ser Asp Ile Pro Ser Arg Phe Ser Gly Ser Gly Ser
 50                  55                  60

Gly Ser Thr Asn Thr Leu Thr Ile Thr Gly Val Gln Ala Glu Asp Glu
 65                  70                  75                  80

Ala Val Tyr Phe Cys Gly Arg Tyr Asp Ser Thr Asp Ser Gly Ile Phe
                 85                  90                  95

Gly Ala Gly Thr Thr Leu Thr Val Leu
            100                 105

<210> SEQ ID NO 60
<211> LENGTH: 6
<212> TYPE: PRT
<213> ORGANISM: Oryctolagus cuniculus

<400> SEQUENCE: 60

Gly Ser Tyr Tyr Met Ser
1               5

<210> SEQ ID NO 61
<211> LENGTH: 17
<212> TYPE: PRT
<213> ORGANISM: Oryctolagus cuniculus

<400> SEQUENCE: 61

Tyr Ile Tyr Ile Gly Asp Gly Val Thr Ala Tyr Ala Asn Trp Ala Lys
1               5                   10                  15

Gly

<210> SEQ ID NO 62
<211> LENGTH: 4
<212> TYPE: PRT
<213> ORGANISM: Oryctolagus cuniculus

<400> SEQUENCE: 62

Gly Asn Lys Leu
1

<210> SEQ ID NO 63
<211> LENGTH: 112
<212> TYPE: PRT
<213> ORGANISM: Oryctolagus cuniculus

<400> SEQUENCE: 63

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Gly Ser Tyr
            20                  25                  30

Tyr Met Ser Trp Val Arg Gln Ala Pro Gly Lys Gly Leu Glu Trp Ile
        35                  40                  45

Ala Tyr Ile Tyr Ile Gly Asp Gly Val Thr Ala Tyr Ala Asn Trp Ala
    50                  55                  60

Lys Gly Arg Phe Thr Ile Ser Lys Ala Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Asn Lys Leu Trp Gly Pro Gly Thr Leu Val Thr Val Ser Ser
            100                 105                 110

<210> SEQ ID NO 64
<211> LENGTH: 11
<212> TYPE: PRT
<213> ORGANISM: Oryctolagus cuniculus

<400> SEQUENCE: 64

Gln Ala Ser Gln Ser Ile Ser Ser Tyr Leu Ala
1               5                   10

<210> SEQ ID NO 65
<211> LENGTH: 7

```
<212> TYPE: PRT
<213> ORGANISM: Oryctolagus cuniculus

<400> SEQUENCE: 65

Asp Ala Ser Asn Leu Asp Ser
1               5

<210> SEQ ID NO 66
<211> LENGTH: 14
<212> TYPE: PRT
<213> ORGANISM: Oryctolagus cuniculus

<400> SEQUENCE: 66

Gln Cys Thr Ala Val Ser Ser Ala Thr Ile Tyr Gly Asn Ala
1               5                   10

<210> SEQ ID NO 67
<211> LENGTH: 112
<212> TYPE: PRT
<213> ORGANISM: Oryctolagus cuniculus

<400> SEQUENCE: 67

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Arg Leu Ile
        35                  40                  45

Tyr Asp Ala Ser Asn Leu Asp Ser Gly Val Pro Ser Arg Phe Lys Gly
    50                  55                  60

Ser Gly Ser Gly Thr Asp Phe Thr Ile Thr Ile Ser Asp Leu Glu Cys
65                  70                  75                  80

Ala Asp Ala Ala Thr Tyr Tyr Cys Gln Cys Thr Ala Val Ser Ser Ala
                85                  90                  95

Thr Ile Tyr Gly Asn Ala Phe Gly Gly Gly Thr Glu Val Val Val Lys
            100                 105                 110

<210> SEQ ID NO 68
<211> LENGTH: 127
<212> TYPE: PRT
<213> ORGANISM: Gallus gallus

<400> SEQUENCE: 68

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Gly Tyr
            20                  25                  30

Asp Met Leu Trp Val Arg Gln Ala Pro Gly Lys Gly Leu Glu Trp Val
        35                  40                  45

Ala Gly Ile Gly Ser Thr Gly Gly Thr Asp Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Val Ala Gly Gly Cys Asn Ser Gly Tyr Cys Arg Asp Ser Pro
            100                 105                 110

Gly Ser Ile Asp Ala Trp Gly His Gly Thr Glu Val Ile Val Ser
        115                 120                 125
```

<210> SEQ ID NO 69
<211> LENGTH: 107
<212> TYPE: PRT
<213> ORGANISM: Gallus gallus

<400> SEQUENCE: 69

Ala Val Thr Gln Gln Pro Ala Ser Val Ser Ala Asn Pro Gly Glu Thr
1               5                   10                  15

Val Lys Ile Thr Cys Ser Gly Gly Ser Arg Asn Tyr Tyr Gly Trp
            20                  25                  30

Tyr Gln Gln Lys Ser Pro Gly Ser Val Pro Val Thr Val Ile Tyr Tyr
                35                  40                  45

Asp Asp Gln Arg Pro Ser Asn Ile Pro Ser Arg Phe Ser Gly Ala Leu
            50                  55                  60

Ser Gly Ser Thr Ser Thr Leu Thr Ile Thr Gly Val Gln Ala Asp Asp
65                  70                  75                  80

Glu Ala Val Tyr Phe Cys Gly Ser Ala Asp Ser Asn Thr Tyr Glu Gly
                85                  90                  95

Ser Phe Gly Ala Gly Thr Thr Leu Thr Val Leu
                100                 105

<210> SEQ ID NO 70
<211> LENGTH: 148
<212> TYPE: PRT
<213> ORGANISM: Mus musculus

<400> SEQUENCE: 70

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
            35                  40                  45

Thr Asp Tyr Asn Met Asp Trp Val Lys Gln Ser His Gly Lys Ser Leu
            50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
                100                 105                 110

Tyr Tyr Cys Ala Arg Ser Arg Ser Tyr Asp Tyr Glu Gly Phe Ala Tyr
            115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 71
<211> LENGTH: 105
<212> TYPE: PRT
<213> ORGANISM: Mus musculus

<400> SEQUENCE: 71

Gly Leu Phe Cys Ser Val Glu Arg Cys His Tyr Gln Leu Gln Ser Ser
1               5                   10                  15

Gln Asn Leu Leu Ser Ile Val Asn Arg Tyr His Tyr Met Ser Gly Asn
                20                  25                  30

Pro Pro Lys Leu Leu Val Tyr Pro Ala Leu Leu Ile Tyr Glu Ala Ser
            35                  40                  45

Ile Thr Lys Ser Cys Val Pro Asp Arg Phe Thr Arg Ser Gly Ser Gly
50                  55                  60

Thr Asn Phe Thr Leu Thr Ile Asn Phe Val His Ala Asp Asp Leu Ile
65                  70                  75                  80

Phe Tyr Tyr Cys Gln His Asn Arg Gly Ser Phe Leu Pro Ser Ser Ser
                85                  90                  95

Val Gln Val Pro Arg Arg Ser Asn
            100                 105

<210> SEQ ID NO 72
<211> LENGTH: 109
<212> TYPE: PRT
<213> ORGANISM: Mus musculus

<400> SEQUENCE: 72

Pro Arg Ala Ser Leu Gly Val Ser Glu Thr Leu Leu Cys Thr Ser Gly
1               5                   10                  15

Phe Thr Phe Thr Asp Tyr Tyr Met Ser Trp Val Arg Gln Pro Pro Gly
                20                  25                  30

Lys Ala Leu Glu Trp Leu Gly Phe Ile Arg Asn Lys Ala Asn Gly Tyr
            35                  40                  45

Thr Thr Glu Tyr Ser Ala Ser Val Lys Gly Arg Phe Thr Ile Ser Arg
50                  55                  60

Asp Asn Ser Gln Ser Ile Leu Tyr Leu Gln Met Asn Thr Leu Arg Ala
65                  70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105

<210> SEQ ID NO 73
<211> LENGTH: 94
<212> TYPE: PRT
<213> ORGANISM: Mus musculus

<400> SEQUENCE: 73

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
                20                  25                  30

Leu Ile Lys Tyr Ala Ser Gln Ser Ile Ser Gly Ile Pro Ser Arg Phe
            35                  40                  45

Ser Gly Ser Gly Ser Gly Thr Asp Phe Thr Leu Ser Ile Asn Ser Val
50                  55                  60

Glu Thr Glu Asp Phe Gly Met Tyr Phe Cys Gln Ser Asn Ser Trp
65                  70                  75                  80

Pro Tyr Thr Phe Gly Gly Gly Thr Lys Leu Glu Ile Lys Gln
                85                  90

<210> SEQ ID NO 74
<211> LENGTH: 118
<212> TYPE: PRT
<213> ORGANISM: Mus musculus

<400> SEQUENCE: 74

Ala Ala Glu Leu Val Arg Pro Gly Thr Ser Val Lys Val Ser Cys Lys
1               5                   10                  15

Ala Ser Gly Tyr Ala Phe Thr Asn Tyr Leu Ile Val Trp Ile Lys Gln
            20                  25                  30

Arg Pro Gly Gln Gly Leu Glu Trp Ile Gly Val Ile Ser Pro Gly Ser
        35                  40                  45

Gly Gly Thr Asn Tyr Asn Glu Lys Phe Lys Gly Lys Ala Ile Leu Thr
    50                  55                  60

Ala Asp Lys Ser Ser Ser Thr Ala Tyr Met Gln Leu Ser Ser Leu Thr
65                  70                  75                  80

Ser Asp Glu Phe Ala Val Tyr Phe Cys Ala Arg Glu Lys Ile Tyr Asp
                85                  90                  95

Asp Tyr Tyr Glu Gly Tyr Phe Asp Val Trp Gly Ala Gly Pro Arg His
            100                 105                 110

Leu Leu Ala Ser Leu Ser
        115

<210> SEQ ID NO 75
<211> LENGTH: 107
<212> TYPE: PRT
<213> ORGANISM: Mus musculus

<400> SEQUENCE: 75

Gly Thr Arg Cys Asp Ile Arg Leu Thr Gln Thr Thr Ser Ser Leu Ser
1               5                   10                  15

Ala Ser Leu Gly Asp Arg Val Thr Ile Ser Cys Ser Ala Ser Leu Gly
            20                  25                  30

Ile Gly Asn Tyr Leu Asn Trp Tyr Gln Gln Lys Pro Asp Gly Thr Val
        35                  40                  45

Lys Leu Leu Ile Tyr Tyr Thr Ser Asn Leu His Ser Gly Val Pro Ser
    50                  55                  60

Arg Phe Ser Gly Ser Gly Ser Gly Thr Asp Tyr Ser Leu Thr Ile Ser
65                  70                  75                  80

Asn Leu Glu Pro Glu Asp Ile Ala Thr Tyr Tyr Cys Gln His Tyr Ser
                85                  90                  95

Lys Leu Pro Leu Thr Phe Gly Ala Gly Pro Ser
            100                 105

<210> SEQ ID NO 76
<211> LENGTH: 113
<212> TYPE: PRT
<213> ORGANISM: Mus musculus

<400> SEQUENCE: 76

Gly Ala Glu Leu Val Arg Ser Gly Ala Ser Val Lys Met Ser Cys Lys
1               5                   10                  15

Ala Ser Gly Tyr Ser Phe Thr Asp Tyr Asn Met Tyr Trp Val Lys Gln
            20                  25                  30

Thr Pro Gly Gln Gly Leu Glu Trp Ile Gly Tyr Ile Tyr Pro Gly Asn
        35                  40                  45

Gly Gly Thr Asn Tyr Asn Gln Lys Phe Lys Gly Lys Ala Thr Leu Thr
    50                  55                  60

Ala Asp Thr Ser Ser Ser Thr Ala Tyr Met Gln Ile Ser Ser Leu Thr
65                  70                  75                  80

Ser Glu Asp Ser Ala Val Tyr Phe Cys Ala Arg Asp Tyr Asp Asp Gly 85                  90                  95

Gly Tyr Ala Met Asp Tyr Trp Gly Gln Gly Thr Thr Val Thr Val Ser
                100                 105                 110

Ser

<210> SEQ ID NO 77
<211> LENGTH: 117
<212> TYPE: PRT
<213> ORGANISM: Mus musculus

<400> SEQUENCE: 77

Leu Leu Leu Trp Leu Thr Gly Ala Arg Cys Asp Ile Gln Met Thr Gln
1               5                   10                  15

Ser Pro Ala Ser Leu Ser Ala Ser Val Gly Glu Thr Val Thr Ile Thr
            20                  25                  30

Cys Arg Ala Ser Gly Asn Ile His Asn Tyr Leu Thr Trp Tyr Gln Gln
        35                  40                  45

Lys Gln Gly Lys Ser Pro Gln Leu Leu Val Tyr Asn Ala Lys Thr Leu
    50                  55                  60

Ala Asp Gly Val Pro Ser Arg Phe Ser Gly Ser Gly Ser Gly Thr Gln
65                  70                  75                  80

Tyr Ser Leu Lys Ile Asn Arg Leu Gln Pro Glu Asp Phe Gly Ser Tyr
                85                  90                  95

Tyr Cys Gln His Phe Trp Asn Ile Pro Trp Thr Phe Gly Gly Gly Thr
                100                 105                 110

Lys Leu Asn Ser Arg
        115

<210> SEQ ID NO 78
<211> LENGTH: 114
<212> TYPE: PRT
<213> ORGANISM: Mus musculus

<400> SEQUENCE: 78

Asp Ala Glu Leu Val Lys Pro Gly Ala Ser Val Lys Ile Ser Cys Lys
1               5                   10                  15

Ala Ser Gly Tyr Thr Phe Thr Asp His Ser Ile His Trp Val Gln Gln
            20                  25                  30

Lys Pro Glu Gln Gly Leu Glu Trp Ile Gly Tyr Ile Ser Pro Gly Asn
        35                  40                  45

Gly Asn Ile Lys Tyr Asn Glu Lys Phe Lys Gly Lys Ala Thr Leu Thr
    50                  55                  60

Ala Asp Lys Ser Ser Ser Thr Ala Tyr Met Gln Leu Asn Ser Leu Thr
65                  70                  75                  80

Ser Glu Asp Ser Ala Val Tyr Phe Cys Lys Arg Ser Leu Gly Arg Gly
                85                  90                  95

Gly Pro Tyr Tyr Phe Asp Tyr Trp Gly Gln Gly Thr Thr Val Thr Val
                100                 105                 110

Ser Ser

<210> SEQ ID NO 79
<211> LENGTH: 108
<212> TYPE: PRT
<213> ORGANISM: Mus musculus

<400> SEQUENCE: 79

Asp Ile Val Leu Thr Gln Ala Ala Pro Ser Leu Pro Val Thr Pro Gly

```
               1               5                  10                 15
         Glu Ser Val Ser Ile Ser Cys Arg Ser Ser Lys Ser Leu Leu His Ser
                             20                  25                 30

Asn Gly Asn Thr Tyr Leu Tyr Trp Phe Leu Gln Arg Pro Gly Gln Ser
                     35                  40                  45

Pro Gln Leu Leu Ile Tyr Arg Met Ser Asn Leu Ala Ser Gly Val Pro
                     50                  55                  60

Asp Arg Phe Ser Gly Ser Gly Ser Gly Thr Ala Phe Thr Leu Arg Ile
         65                  70                  75                  80

Ser Arg Val Glu Ala Glu Asp Val Gly Val Tyr Tyr Cys Met Gln His
                             85                  90                  95

Arg Glu Tyr Pro Val Thr Phe Gly Ser Gly Pro Asn
                             100                 105
```

<210> SEQ ID NO 80
<211> LENGTH: 111
<212> TYPE: PRT
<213> ORGANISM: Mus musculus

<400> SEQUENCE: 80

```
         Gln Val Gln Leu Gln Gln Ser Gly Ala Glu Leu Met Lys Pro Gly Ala
         1               5                   10                  15

Ser Val Lys Ile Ser Cys Lys Ala Thr Gly Tyr Thr Phe Ser Ser Tyr
                             20                  25                  30

Trp Ile Glu Trp Val Lys Gln Arg Pro Gly His Gly Leu Glu Trp Ile
                     35                  40                  45

Gly Glu Ile Leu Pro Gly Ser Gly Ser Thr Asn Tyr Asn Glu Lys Phe
                     50                  55                  60

Lys Gly Lys Ala Thr Phe Thr Ala Asp Thr Ser Ser Asn Thr Ala Tyr
         65                  70                  75                  80

Met Gln Leu Ser Ser Leu Thr Ser Glu Asp Ser Ala Val Tyr Tyr Cys
                             85                  90                  95

Ala Ser Tyr Tyr Trp Tyr Phe Asp Val Trp Ala Gln Asp His Val
                             100                 105                 110
```

<210> SEQ ID NO 81
<211> LENGTH: 109
<212> TYPE: PRT
<213> ORGANISM: Mus musculus

<400> SEQUENCE: 81

```
         Ile Val Met Thr Gln Ala Ala Phe Ser Asn Pro Val Thr Leu Gly Thr
         1               5                   10                  15

Ser Ala Ser Ile Ser Cys Arg Ser Ser Lys Asn Leu Leu His Ser Asn
                             20                  25                  30

Gly Ile Thr Tyr Leu Tyr Trp Tyr Leu Gln Arg Pro Gly Gln Ser Pro
                     35                  40                  45

Gln Leu Leu Ile Tyr Arg Val Ser Asn Leu Ala Ser Gly Val Pro Asn
                     50                  55                  60

Arg Phe Ser Gly Ser Glu Ser Gly Thr Asp Phe Thr Leu Arg Ile Ser
         65                  70                  75                  80

Arg Val Glu Ala Glu Asp Val Gly Val Tyr Tyr Cys Ala Gln Leu Leu
                             85                  90                  95

Glu Leu Pro Tyr Thr Ser Glu Gly Thr Lys Arg Trp Glu
                             100                 105
```

```
<210> SEQ ID NO 82
<211> LENGTH: 109
<212> TYPE: PRT
<213> ORGANISM: Mus musculus

<400> SEQUENCE: 82

Gly Gly Gly Leu Val Lys Pro Gly Gly Ser Leu Lys Leu Ser Cys Ala
1               5                   10                  15

Ala Ser Gly Phe Ala Phe Ser Ser Tyr Asp Met Ser Trp Ile Arg Gln
            20                  25                  30

Thr Pro Glu Lys Arg Leu Glu Trp Val Ala Tyr Ile Ser Ser Gly Ala
        35                  40                  45

Gly Ser Thr Tyr Tyr Pro Asp Thr Val Lys Gly Arg Phe Thr Val Ser
    50                  55                  60

Arg Asp Asn Ala Lys Asn Thr Leu Tyr Leu Gln Met Ser Ser Leu Lys
65                  70                  75                  80

Ser Glu Asp Thr Ala Met Tyr Tyr Cys Ala Arg His Phe Tyr Arg Phe
                85                  90                  95

Asp Tyr Trp Gly Gln Gly Thr Thr Val Thr Val Ser Ser
            100                 105

<210> SEQ ID NO 83
<211> LENGTH: 113
<212> TYPE: PRT
<213> ORGANISM: Mus musculus

<400> SEQUENCE: 83

Leu Leu Leu Cys Val Ser Gly Ala Pro Gly Ser Ile Val Met Thr Gln
1               5                   10                  15

Thr Pro Lys Phe Leu Leu Val Ser Ala Gly Asp Arg Ile Thr Ile Thr
            20                  25                  30

Cys Lys Ala Ser Gln Ser Val Ser Asn Asp Val Ala Trp Tyr Gln Gln
        35                  40                  45

Lys Pro Gly Gln Ser Pro Lys Leu Leu Ile Tyr Tyr Ala Ser Asn Arg
    50                  55                  60

Tyr Thr Gly Val Pro Asp Arg Phe Thr Gly Ser Gly Tyr Gly Thr Asp
65                  70                  75                  80

Phe Thr Phe Thr Ile Ser Thr Val Gln Ala Glu Asp Leu Ala Val Tyr
                85                  90                  95

Phe Cys Gln Gln Asp Asp Arg Phe Pro Leu Thr Phe Gly Ala Gly Pro
            100                 105                 110

Ser

<210> SEQ ID NO 84
<211> LENGTH: 112
<212> TYPE: PRT
<213> ORGANISM: Mus musculus

<400> SEQUENCE: 84

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60
```

```
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Thr Gly Ala Trp Phe Ala Tyr Trp Ala Lys Asp Ser Ser Arg His
            100                 105                 110

<210> SEQ ID NO 85
<211> LENGTH: 107
<212> TYPE: PRT
<213> ORGANISM: Mus musculus

<400> SEQUENCE: 85

Gly Val Glu Gly Asp Ile Val Met Thr Gln Ser His Lys Phe Met Ser
  1               5                  10                  15

Thr Ser Val Gly Asp Arg Val Ser Ile Thr Cys Lys Ala Ser Gln Asp
                20                  25                  30

Val Gly Thr Ala Val Ala Trp Tyr Gln Gln Lys Pro Gly Gln Ser Pro
            35                  40                  45

Lys Leu Leu Ile Tyr Trp Ala Ser Thr Arg His Thr Gly Val Pro Asp
 50                  55                  60

Arg Phe Thr Gly Ser Gly Ser Gly Thr Asp Phe Thr Leu Thr Ile Ser
 65                  70                  75                  80

Asn Val Gln Ser Glu Asp Leu Ala Asp Tyr Phe Cys Gln Gln Tyr Ser
                 85                  90                  95

Ser Tyr Pro Leu Thr Phe Gly Ala Gly Pro Ser
            100                 105

<210> SEQ ID NO 86
<211> LENGTH: 118
<212> TYPE: PRT
<213> ORGANISM: Mus musculus

<400> SEQUENCE: 86

Gly Gly Gly Leu Val Gln Pro Gly Gly Ser Met Lys Val Ser Cys Val
  1               5                  10                  15

Ala Ser Gly Phe Ser Phe Ile Asp Phe Trp Met Asn Trp Val Arg Gln
                20                  25                  30

Ser Pro Glu Lys Gly Leu Glu Trp Val Ala Glu Ile Arg Leu Lys Ser
            35                  40                  45

Asn Asn Tyr Ala Thr His Tyr Ala Glu Ser Val Lys Gly Arg Phe Thr
 50                  55                  60

Ile Ser Arg Asp Asp Ser Lys Ser Ser Val Tyr Leu Gln Met Asn Asn
 65                  70                  75                  80

Leu Arg Pro Glu Asp Thr Gly Ile Tyr Tyr Cys Thr Ser Leu Phe Tyr
                 85                  90                  95

Tyr Tyr Asp Gly Thr Ser Gly Phe Ala Tyr Trp Gly Gln Gly Thr Thr
            100                 105                 110

Val Thr Val Leu Leu Lys
            115

<210> SEQ ID NO 87
<211> LENGTH: 109
<212> TYPE: PRT
<213> ORGANISM: Mus musculus

<400> SEQUENCE: 87

Asp Ile Val Met Thr Gln Ser Pro Ser Ser Leu Thr Val Thr Ala Gly
```

```
                1               5                      10                      15
            Glu Lys Val Thr Met His Cys Lys Ser Ser Gln Ser Leu Leu Asn Ser
                            20                      25                      30
            Gly Asp Gln Lys Asn Tyr Leu Thr Trp Tyr Gln Gln Lys Pro Gly Gln
                        35                      40                      45
            Pro Pro Lys Leu Leu Ile Tyr Trp Ala Ser Thr Arg Glu Ser Gly Val
                    50                      55                      60
            Pro Asp Arg Phe Thr Gly Ser Gly Ser Gly Thr Asp Phe Thr Leu Thr
                65                      70                      75                      80
            Ile Ser Ser Val Gln Ala Glu Asp Leu Ala Val Tyr Tyr Cys Gln Asn
                            85                      90                      95
            Asp Tyr Asp Tyr Pro Leu Thr Phe Gly Ala Gly Pro Ser
                            100                     105

<210> SEQ ID NO 88
<211> LENGTH: 148
<212> TYPE: PRT
<213> ORGANISM: Mus musculus

<400> SEQUENCE: 88

Met Glu Trp Ser Gly Val Phe Ile Phe Leu Leu Ser Gly Thr Ala Gly
            1               5                       10                      15
            Val Leu Ser Glu Val Gln Leu His Gln Phe Gly Ala Glu Leu Val Lys
                            20                      25                      30
            Pro Gly Ala Ser Val Lys Ile Ser Cys Lys Ala Ser Gly Tyr Thr Phe
                        35                      40                      45
            Thr Asp Tyr Asn Met Asp Trp Val Lys Gln Ser His Gly Lys Ser Leu
                    50                      55                      60
            Glu Trp Ile Gly Asp Ile Asn Pro Asn Tyr Asp Ser Thr Ser Tyr Asn
                65                      70                      75                      80
            Gln Lys Phe Lys Gly Lys Ala Thr Leu Thr Val Asp Lys Ser Ser Ser
                            85                      90                      95
            Thr Ala Tyr Met Glu Leu Arg Ser Leu Thr Ser Glu Asp Thr Ala Val
                            100                     105                     110
            Tyr Tyr Cys Ala Arg Ser Arg Ser Tyr Asp Tyr Glu Gly Phe Ala Tyr
                            115                     120                     125
            Trp Gly Gln Gly Thr Leu Val Thr Val Ser Ala Ala Lys Thr Thr Pro
                    130                     135                     140
            Pro Ser Val Tyr
            145

<210> SEQ ID NO 89
<211> LENGTH: 139
<212> TYPE: PRT
<213> ORGANISM: Mus musculus

<400> SEQUENCE: 89

Met Ser Val Leu Thr Gln Val Leu Gly Leu Leu Leu Leu Trp Leu Thr
            1               5                       10                      15
            Gly Ala Arg Cys Asp Ile Gln Met Thr Gln Ser Pro Ala Ser Leu Ser
                            20                      25                      30
            Ala Ser Val Gly Glu Thr Val Thr Ile Thr Cys Arg Ala Ser Gly Asn
                        35                      40                      45
            Ile His Asn Tyr Leu Ala Trp Tyr Gln Gln Lys Gln Gly Lys Ser Pro
                    50                      55                      60
            Gln Leu Leu Val Tyr Asn Ala Lys Thr Leu Ala Asp Gly Val Pro Ser
```

```
                65                  70                  75                  80
Arg Phe Ser Gly Ser Gly Ser Gly Thr Gln Tyr Ser Leu Lys Ile Asn
                        85                  90                  95

Ser Leu Gln Pro Glu Asp Phe Gly Ser Tyr Tyr Cys Gln His Phe Trp
                    100                 105                 110

Ser Thr Leu Thr Phe Gly Ala Gly Thr Lys Leu Glu Leu Lys Arg Ala
                115                 120                 125

Asp Ala Ala Pro Thr Val Ser Asn Pro Tyr Asp
            130                 135

<210> SEQ ID NO 90
<211> LENGTH: 100
<212> TYPE: PRT
<213> ORGANISM: Mus musculus

<400> SEQUENCE: 90

Asp Ile Leu Gln Ala Ser Gly Tyr Ser Phe Thr Gly Tyr Thr Met Asn
1               5                   10                  15

Trp Val Lys Gln Ser His Gly Lys Asn Leu Glu Trp Ile Gly Leu Ile
                20                  25                  30

Asn Pro Tyr Asn Gly Gly Thr Ser Tyr Asn Gln Lys Phe Lys Gly Lys
            35                  40                  45

Ala Thr Leu Thr Val Asp Lys Ser Ser Ser Thr Ala Tyr Met Glu Leu
        50                  55                  60

Leu Ser Leu Thr Ser Glu Asp Ser Ala Val Tyr Tyr Cys Ala Arg Trp
65                  70                  75                  80

Gly Val Trp Ser Ala Met Asp Tyr Trp Gly Gln Gly Thr Thr Val Thr
                85                  90                  95

Val Ser Ser Lys
            100

<210> SEQ ID NO 91
<211> LENGTH: 90
<212> TYPE: PRT
<213> ORGANISM: Mus musculus

<400> SEQUENCE: 91

Asp Arg Val Ser Ile Thr Cys Lys Ala Ser Gln Asn Val Arg Thr Ala
1               5                   10                  15

Val Ala Trp Tyr Gln Gln Lys Pro Arg Gln Ser Pro Lys Ala Leu Ile
                20                  25                  30

Tyr Leu Ala Ser Asn Arg Asp Thr Gly Leu Pro Asp Arg Phe Pro Gly
            35                  40                  45

Arg Gly Ser Gly Thr Asp Phe Thr Leu Asn Ile Thr Asn Val Gln Ser
        50                  55                  60

Glu Asp Leu Glu Asp Tyr Phe Cys Leu Gln His Cys Asn Tyr Pro Asn
65                  70                  75                  80

Glu Phe Arg Gly Cys Thr Lys Val Pro Ile
                85                  90

<210> SEQ ID NO 92
<211> LENGTH: 116
<212> TYPE: PRT
<213> ORGANISM: Mus musculus

<400> SEQUENCE: 92

Leu Gln Glu Ser Gly Ala Glu Leu Ala Arg Pro Gly Ala Ser Val Lys
1               5                   10                  15
```

```
Leu Ser Cys Lys Ala Ser Gly Tyr Thr Phe Thr Ser Tyr Trp Met Gln
            20                  25                  30

Trp Val Lys Gln Arg Pro Gly Gln Gly Leu Glu Trp Ile Gly Ala Ile
            35                  40                  45

Tyr Pro Gly Asp Gly Asp Thr Arg Tyr Thr Gln Lys Phe Lys Gly Lys
        50                  55                  60

Ala Thr Leu Thr Ala Asp Lys Ser Ser Ser Thr Ala Tyr Met Gln Leu
65                  70                  75                  80

Ser Ser Leu Ala Ser Glu Asp Ser Ala Val Tyr Tyr Cys Ala Arg Gly
                85                  90                  95

Glu Tyr Gly Asn Tyr Phe Ala Tyr Trp Gly Gln Gly Thr Thr Val Thr
            100                 105                 110

Val Ser Ser Asn
        115

<210> SEQ ID NO 93
<211> LENGTH: 100
<212> TYPE: PRT
<213> ORGANISM: Mus musculus

<400> SEQUENCE: 93

Thr Ser Asp Ala Ser Leu Gly Glu Arg Val Thr Ile Thr Cys Lys Ala
1               5                   10                  15

Ser Gln Asp Ile Asn Ser Tyr Leu Ser Trp Phe Gln Gln Lys Pro Gly
            20                  25                  30

Lys Ser Pro Lys Thr Leu Ile Tyr Arg Ala Asn Arg Leu Val Asp Gly
        35                  40                  45

Val Pro Ser Arg Phe Ser Gly Ser Gly Ser Gly Gln Asp Tyr Ser Leu
    50                  55                  60

Thr Ile Ser Ser Leu Glu Tyr Glu Asp Met Gly Ile Tyr Tyr Cys Leu
65                  70                  75                  80

Gln Tyr Asp Glu Phe Pro Leu Thr Phe Gly Gly Gly Thr Lys Leu Glu
                85                  90                  95

Ile Lys Gln Lys
        100

<210> SEQ ID NO 94
<211> LENGTH: 108
<212> TYPE: PRT
<213> ORGANISM: Mus musculus

<400> SEQUENCE: 94

Ala Trp Leu Ser Gln Leu Ser Cys Thr Ala Ser Gly Phe Asn Ile Lys
1               5                   10                  15

Asp Thr Tyr Met His Trp Val Lys Gln Arg Pro Glu Gln Gly Leu Glu
            20                  25                  30

Trp Ile Gly Arg Ile Asp Pro Ala Asn Gly Asn Thr Lys Tyr Asp Pro
        35                  40                  45

Lys Phe Gln Gly Lys Ala Thr Ile Thr Ala Asp Thr Ser Ser Asn Thr
    50                  55                  60

Ala Tyr Leu Gln Leu Ser Ser Leu Thr Ser Glu Asp Thr Ala Val Tyr
65                  70                  75                  80

Tyr Cys Ala Arg Pro Ile His Tyr Tyr Gly Ser Ser Leu Ala Tyr
                85                  90                  95

Trp Gly Gln Gly Thr Thr Val Thr Val Ser Ser Lys
            100                 105
```

<210> SEQ ID NO 95
<211> LENGTH: 104
<212> TYPE: PRT
<213> ORGANISM: Mus musculus

<400> SEQUENCE: 95

Glu Phe His Ala Val Ser Leu Gly Gln Arg Ala Thr Ile Ser Cys Arg
1               5                   10                  15

Ala Ser Glu Ser Val Asp Ser Tyr Gly Asn Ser Phe Met His Trp Tyr
            20                  25                  30

Gln Gln Lys Pro Gly Gln Pro Pro Lys Leu Leu Ile Tyr Arg Ala Ser
        35                  40                  45

Asn Leu Glu Ser Gly Ile Pro Ala Arg Phe Ser Gly Ser Gly Ser Arg
    50                  55                  60

Thr Asp Phe Thr Leu Thr Ile Asn Pro Val Glu Ala Asp Asp Val Ala
65                  70                  75                  80

Thr Tyr Tyr Cys Gln Gln Ser Asn Glu Asp Pro Gly Arg Ser Glu Val
                85                  90                  95

Val Pro Ser Trp Arg Ser Asn Lys
            100

<210> SEQ ID NO 96
<211> LENGTH: 109
<212> TYPE: PRT
<213> ORGANISM: Mus musculus

<400> SEQUENCE: 96

Pro Arg Ala Ser Leu Gly Val Ser Glu Thr Leu Leu Cys Thr Ser Gly
1               5                   10                  15

Phe Thr Phe Thr Asp Tyr Tyr Met Ser Trp Val Arg Gln Pro Pro Gly
            20                  25                  30

Lys Ala Leu Glu Trp Leu Gly Phe Ile Arg Asn Lys Ala Asn Gly Tyr
        35                  40                  45

Thr Thr Glu Tyr Ser Ala Ser Val Lys Gly Arg Phe Thr Ile Ser Arg
    50                  55                  60

Asp Asn Ser Gln Ser Ile Leu Tyr Leu Gln Met Asn Thr Leu Arg Ala
65                  70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105

<210> SEQ ID NO 97
<211> LENGTH: 94
<212> TYPE: PRT
<213> ORGANISM: Mus musculus

<400> SEQUENCE: 97

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

```
Glu Thr Glu Asp Phe Gly Met Tyr Phe Cys Gln Gln Ser Asn Ser Trp
 65                  70                  75                  80

Pro Tyr Thr Phe Gly Gly Gly Thr Lys Leu Glu Ile Lys Gln
                 85                  90
```

<210> SEQ ID NO 98
<211> LENGTH: 111
<212> TYPE: PRT
<213> ORGANISM: Mus musculus

<400> SEQUENCE: 98

```
Pro Ala Cys Leu Pro Gly Gly Ser Leu Arg Leu Ser Cys Ala Thr Ser
 1               5                  10                  15

Gly Phe Thr Phe Thr Asp Tyr Tyr Met Ser Trp Val Arg Gln Pro Pro
                20                  25                  30

Gly Lys Ala Leu Glu Trp Leu Gly Phe Ile Arg Asn Lys Ala Asn Gly
            35                  40                  45

Tyr Thr Thr Glu Tyr Ser Ala Ser Val Lys Gly Arg Phe Thr Ile Ser
50                   55                  60

Arg Asp Asn Ser Gln Ser Ile Leu Tyr Leu Gln Met Asn Thr Leu Arg
 65                  70                  75                  80

Ala Glu Asp Ser Ala Thr Tyr Tyr Cys Ala Arg Ala Pro Leu Leu Tyr
                85                  90                  95

Tyr Ala Met Asp Tyr Trp Gly Gln Gly Thr Thr Val Thr Val Ser
                100                 105                 110
```

<210> SEQ ID NO 99
<211> LENGTH: 102
<212> TYPE: PRT
<213> ORGANISM: Mus musculus

<400> SEQUENCE: 99

```
Arg Leu Pro Phe Tyr Ser Leu Glu Gln Arg Ala Thr Ile Ser Tyr Arg
 1               5                  10                  15

Ala Ser Lys Asn Val Ser Thr Ser Gly Tyr Ser Tyr Met His Trp Asn
                20                  25                  30

Gln Gln Lys Pro Gly Gln Pro Pro Lys Leu Leu Ile Tyr Leu Val Ser
            35                  40                  45

Asn Leu Glu Ser Gly Val Pro Ala Arg Phe Ser Gly Ser Gly Ser Gly
         50                  55                  60

Thr Asp Phe Thr Leu Asn Ile His Pro Val Glu Glu Glu Asp Ala Ala
 65                  70                  75                  80

Thr Tyr Tyr Cys Gln His Ile Arg Glu Leu Thr Arg Ser Glu Leu Val
                85                  90                  95

Pro Ser Trp Lys Ser Asn
                100
```

<210> SEQ ID NO 100
<211> LENGTH: 101
<212> TYPE: PRT
<213> ORGANISM: Mus musculus

<400> SEQUENCE: 100

```
Val Ser Cys Lys Ala Ser Gly Tyr Thr Phe Thr Ser Tyr Trp Met His
 1               5                  10                  15

Trp Val Lys Gln Arg Pro Gly Gln Gly Leu Glu Trp Ile Gly Met Ile
                20                  25                  30

Asp Pro Ser Asn Ser Glu Thr Arg Leu Asn Gln Lys Phe Lys Asp Lys
```

```
            35                  40                  45
Ala Thr Leu Asn Val Asp Lys Ser Ser Asn Thr Ala Tyr Met Gln Leu
 50                  55                  60

Ser Ser Leu Thr Ser Glu Asp Ser Ala Val Tyr Tyr Cys Ala Arg Gly
 65                  70                  75                  80

Leu Arg His Tyr Trp Tyr Phe Asp Val Trp Gly Gln Gly Thr Thr Val
                     85                  90                  95

Thr Val Ser Ser Lys
                100

<210> SEQ ID NO 101
<211> LENGTH: 99
<212> TYPE: PRT
<213> ORGANISM: Mus musculus

<400> SEQUENCE: 101

Thr Ile Leu Trp Arg Glu Gly Pro Phe Ser Tyr Arg Ala Ser Lys Ser
 1               5                   10                  15

Val Ser Thr Ser Gly Tyr Ser Tyr Met His Trp Asn Gln Gln Lys Pro
                 20                  25                  30

Gly Gln Pro Pro Arg Leu Leu Ile Tyr Leu Val Ser Asn Leu Glu Ser
             35                  40                  45

Gly Val Pro Ala Arg Phe Ser Gly Ser Gly Ser Gly Thr Asp Phe Thr
 50                  55                  60

Leu Asn Ile His Pro Val Glu Glu Asp Ala Ala Thr Tyr Tyr Cys Gln
 65                  70                  75                  80

Gln His Ile Arg Glu Leu Thr Arg Ser Glu Val Pro Ser Trp Arg
                     85                  90                  95

Ser Asn Lys

<210> SEQ ID NO 102
<211> LENGTH: 110
<212> TYPE: PRT
<213> ORGANISM: Mus musculus

<400> SEQUENCE: 102

Gly Gly Gly Leu Val Lys Pro Gly Gly Ser Leu Lys Leu Ser Cys Ala
 1               5                   10                  15

Ala Ser Gly Phe Thr Phe Ser Ser Tyr Gly Met Ser Trp Val Arg Gln
                 20                  25                  30

Thr Pro Glu Lys Arg Leu Glu Trp Val Ala Thr Ile Ser Ser Gly Gly
             35                  40                  45

Ser Tyr Thr Tyr Tyr Pro Asp Ser Val Lys Gly Arg Phe Thr Ile Ser
 50                  55                  60

Arg Asp Asn Ala Lys Asn Thr Leu Tyr Leu Gln Met Ser Ser Leu Arg
 65                  70                  75                  80

Ser Glu Asp Thr Ala Met Tyr Tyr Cys Ala Ser Leu Ala Ser Tyr Tyr
                     85                  90                  95

Phe Asp Tyr Trp Gly Gln Gly Thr Thr Leu Thr Val Ser Ser
                100                 105                 110

<210> SEQ ID NO 103
<211> LENGTH: 113
<212> TYPE: PRT
<213> ORGANISM: Mus musculus

<400> SEQUENCE: 103
```

```
Gly Ala Arg Cys Asp Val Gln Met Ile Gln Ser Pro Ser Ser Leu Ser
1               5                   10                  15

Ala Ser Leu Gly Asp Ile Val Thr Met Thr Cys Gln Ala Ser Gln Gly
            20                  25                  30

Thr Ser Ile Asn Leu Asn Trp Phe Gln Gln Lys Pro Gly Lys Ala Pro
        35                  40                  45

Lys Leu Leu Ile Tyr Gly Ala Ser Ser Leu Glu Asp Gly Val Pro Ser
    50                  55                  60

Arg Phe Ser Gly Ser Cys Phe Gly Thr Asp Phe Thr Leu Thr Ile Ser
65                  70                  75                  80

Ser Leu Glu Asp Glu Asp Met Ala Thr Tyr Phe Cys Leu Gln His Ser
                85                  90                  95

Tyr Leu Pro Pro Leu Thr Phe Gly Ala Gly Thr Lys Leu Glu Leu Lys
                100                 105                 110

Arg

<210> SEQ ID NO 104
<211> LENGTH: 111
<212> TYPE: PRT
<213> ORGANISM: Mus musculus

<400> SEQUENCE: 104

Gly Pro Gly Leu Val Gln Pro Ser Gln Ser Leu Ser Ile Thr Cys Thr
1               5                   10                  15

Val Ser Gly Phe Ser Leu Thr Thr Tyr Asp Leu His Trp Val Arg Gln
            20                  25                  30

Ser Pro Gly Lys Gly Leu Glu Trp Leu Gly Val Ile Trp Ser Gly Gly
        35                  40                  45

Ser Thr Asp Tyr Asn Ala Ala Phe Ile Ser Arg Leu Ser Ile Ser Lys
    50                  55                  60

Asp Asn Ser Lys Ser Gln Val Phe Phe Lys Met Asn Ser Leu Gln Ala
65                  70                  75                  80

Asn Asp Thr Ala Ile Tyr Tyr Cys Ala Arg Asn Tyr Gly Tyr Ser Ala
                85                  90                  95

Trp Phe Ala Tyr Trp Gly Gln Gly Thr Leu Val Thr Val Ser Ala
                100                 105                 110

<210> SEQ ID NO 105
<211> LENGTH: 118
<212> TYPE: PRT
<213> ORGANISM: Mus musculus

<400> SEQUENCE: 105

Pro Ala Ser Ser Asp Val Leu Met Thr Gln Thr Pro Leu Ser Leu
1               5                   10                  15

Pro Val Ser Leu Gly Asp Gln Ala Ser Ile Ser Cys Arg Ser Ser Gln
            20                  25                  30

Ser Ile Val His Ser Asn Gly Asn Thr Tyr Leu Glu Trp Tyr Leu Gln
        35                  40                  45

Lys Pro Gly Gln Ser Pro Lys Leu Leu Ile Tyr Lys Val Ser Asn Arg
    50                  55                  60

Phe Ser Gly Val Pro Asp Arg Phe Ser Gly Ser Gly Ser Gly Thr Asp
65                  70                  75                  80

Phe Thr Leu Lys Ile Ser Arg Val Glu Ala Glu Asp Leu Gly Val Tyr
                85                  90                  95

Tyr Cys Phe Gln Gly Ser His Val Pro Leu Thr Phe Gly Ala Gly Thr
```

Lys Leu Glu Leu Lys Arg
                115

<210> SEQ ID NO 106
<211> LENGTH: 114
<212> TYPE: PRT
<213> ORGANISM: Mus musculus

<400> SEQUENCE: 106

Gly Phe Glu Leu Lys Lys Pro Gly Glu Thr Val Lys Ile Ser Cys Lys
1               5                   10                  15

Ala Ser Gly Tyr Thr Phe Thr Ala Tyr Ser Met His Trp Val Lys Gln
            20                  25                  30

Thr Pro Gly Lys Gly Leu Lys Trp Leu Gly Trp Ile Asn Thr Glu Thr
        35                  40                  45

Gly Glu Pro Thr Tyr Thr Asp Asp Phe Lys Gly Arg Phe Thr Phe Ser
    50                  55                  60

Leu Glu Thr Ser Ala Arg Ile Ala Tyr Leu Gln Ile Asn Asp Leu Lys
65                  70                  75                  80

Asn Glu Asp Thr Ala Thr Tyr Phe Cys Ala Arg Arg Ile Tyr Tyr Phe
                85                  90                  95

Gly Arg Gly Gly Phe Asp Tyr Trp Gly Gln Gly Thr Thr Val Thr Val
            100                 105                 110

Ser Ser

<210> SEQ ID NO 107
<211> LENGTH: 118
<212> TYPE: PRT
<213> ORGANISM: Mus musculus

<400> SEQUENCE: 107

Pro Ala Ser Ser Ser Asp Val Leu Met Thr Gln Thr Pro Leu Ser Leu
1               5                   10                  15

Pro Val Arg Leu Gly Asp Gln Ser Ser Ile Ser Cys Arg Ser Ser Gln
            20                  25                  30

Ser Ile Val His Ser Asn Gly Asn Thr Tyr Leu Glu Trp Tyr Leu Gln
        35                  40                  45

Lys Pro Gly Gln Ser Pro Lys Leu Leu Ile Tyr Lys Val Ser Asn Arg
    50                  55                  60

Phe Ser Gly Val Pro Asp Arg Phe Ser Gly Ser Gly Ser Gly Thr Asp
65                  70                  75                  80

Phe Thr Leu Lys Ile Ser Arg Val Glu Pro Glu Asp Leu Gly Val Tyr
                85                  90                  95

Tyr Cys Phe Gln Gly Ser His Val Pro Tyr Thr Ser Glu Gly Asp Gln
            100                 105                 110

Ala Glu Ile Lys Leu Ala
        115

<210> SEQ ID NO 108
<211> LENGTH: 114
<212> TYPE: PRT
<213> ORGANISM: Mus musculus

<400> SEQUENCE: 108

Gly Gly Gly Leu Val Gln Pro Gly Gly Ser Met Arg Leu Ser Cys Val
1               5                   10                  15

Ala Ser Gly Phe Thr Phe Ser Asn Ser Trp Phe Asn Trp Val Arg Gln
            20                  25                  30

Ser Pro Glu Lys Gly Leu Glu Trp Val Ala Glu Ile Arg Leu Thr Ser
        35                  40                  45

Asp Asn Tyr Ala Ile Tyr Tyr Ala Glu Ser Val Lys Gly Arg Phe Thr
    50                  55                  60

Ile Ser Arg Asp Asp Ser Lys Ser Ser Val Tyr Leu Gln Met Asn Asn
65                  70                  75                  80

Leu Arg Ala Glu Asp Thr Gly Ile Tyr Tyr Cys Thr Arg Pro Glu Thr
                85                  90                  95

Ala Arg Ala Thr Phe Ala Tyr Trp Gly Gln Gly Thr Thr Val Thr Val
            100                 105                 110

Ser Ser

<210> SEQ ID NO 109
<211> LENGTH: 118
<212> TYPE: PRT
<213> ORGANISM: Mus musculus

<400> SEQUENCE: 109

Pro Ala Ser Thr Ser Asp Val Leu Met Thr Gln Thr Pro Leu Ser Leu
1               5                   10                  15

Pro Val Ser Leu Gly Asp Gln Ala Ser Ile Ser Cys Arg Ser Ser Gln
            20                  25                  30

Ser Ile Val His Ser Asn Gly Asn Thr Tyr Leu Glu Trp Tyr Leu Gln
        35                  40                  45

Lys Pro Gly Gln Ser Pro Lys Val Leu Ile Tyr Lys Val Phe Asn Arg
    50                  55                  60

Phe Ser Gly Val Pro Asp Arg Phe Ser Gly Ser Gly Ser Gly Thr Asp
65                  70                  75                  80

Phe Thr Leu Lys Ile Ser Arg Val Glu Ala Glu Asp Leu Gly Val Tyr
                85                  90                  95

Tyr Cys Phe Gln Gly Ser His Val Pro Arg Thr Phe Gly Gly Gly Thr
            100                 105                 110

Lys Leu Asn Gln Thr Gly
        115

<210> SEQ ID NO 110
<211> LENGTH: 111
<212> TYPE: PRT
<213> ORGANISM: Mus musculus

<400> SEQUENCE: 110

Gly Pro Asp Leu Val Lys Pro Gly Ala Ser Val Lys Ile Ser Cys Lys
1               5                   10                  15

Ala Ser Gly Tyr Ser Phe Thr Ala Tyr Tyr Met His Trp Val Lys Gln
            20                  25                  30

Ser His Gly Lys Ser Leu Glu Trp Ile Gly Arg Val Asn Pro Asn Asn
        35                  40                  45

Gly Gly Thr Thr Tyr Asn Gln Lys Phe Lys Gly Lys Ala Ile Leu Thr
    50                  55                  60

Val Asp Lys Ser Ser Ser Thr Ala Tyr Met Glu Leu Arg Ser Leu Thr
65                  70                  75                  80

Phe Glu Asp Ser Ala Val Tyr Tyr Cys Ala Arg Arg Ile Tyr Tyr Gly
                85                  90                  95

Tyr Phe Asp Tyr Trp Gly Gln Gly Thr Thr Val Thr Val Ser Ser

<210> SEQ ID NO 111
<211> LENGTH: 104
<212> TYPE: PRT
<213> ORGANISM: Mus musculus

<400> SEQUENCE: 111

Ala Phe Phe Ala Val Ser Leu Gly Gln Arg Ala Thr Ile Ser Cys Lys
1               5                   10                  15

Ala Ser Gln Ser Val Asp Tyr Asp Gly Asp Ser Tyr Met Asn Trp Tyr
            20                  25                  30

Gln Gln Lys Pro Gly Gln Pro Pro Lys Leu Leu Ile Tyr Val Ala Ser
        35                  40                  45

Asn Leu Glu Ser Gly Val Pro Ala Arg Phe Ser Gly Ser Gly Ser Gly
50                  55                  60

Thr Asp Phe Thr Leu Asn Ile His Pro Val Glu Glu Asp Ala Ala
65                  70                  75                  80

Thr Tyr Tyr Cys Gln Gln Ser Asn Glu Asp Pro Tyr Thr Phe Gly Gly
                85                  90                  95

Gly Thr Lys Leu Glu Ile Lys Gln
            100

<210> SEQ ID NO 112
<211> LENGTH: 106
<212> TYPE: PRT
<213> ORGANISM: Mus musculus

<400> SEQUENCE: 112

Gly Ala Glu Leu Val Lys Pro Gly Ala Ser Val Lys Leu Ser Cys Thr
1               5                   10                  15

Ala Ser Gly Leu Asn Ile Arg Asp Ile Tyr Met His Trp Val Lys Gln
            20                  25                  30

Arg Pro Glu Gln Gly Leu Glu Trp Ile Gly Lys Ile Asp Pro Ala Asn
        35                  40                  45

Gly Asn Thr Lys Tyr Asp Pro Lys Phe Gln Gly Lys Ala Thr Ile Thr
50                  55                  60

Ala Asp Thr Ser Ser Asn Thr Ala Tyr Val Gln Leu Ser Ser Leu Thr
65                  70                  75                  80

Ser Glu Asp Thr Ala Val Tyr Tyr Cys Ala Gly Thr Gly Asp Tyr Trp
                85                  90                  95

Gly Gln Gly Thr Thr Val Thr Val Ser Ser
            100                 105

<210> SEQ ID NO 113
<211> LENGTH: 112
<212> TYPE: PRT
<213> ORGANISM: Mus musculus

<400> SEQUENCE: 113

Gly Thr Cys Gly Asp Ile Val Met Ser Gln Ser Pro Ser Ser Leu Ala
1               5                   10                  15

Val Ser Ala Gly Glu Lys Val Thr Met Ser Cys Lys Ser Ser Gln Ser
            20                  25                  30

Leu Leu Asn Ser Arg Thr Arg Lys Asn Tyr Leu Ala Trp Val Gln His
        35                  40                  45

Lys Pro Gly Gln Ser Pro Arg Leu Leu Ile Tyr Trp Ala Ser Thr Arg
50                  55                  60

Glu Ser Gly Val Pro Asp Arg Phe Thr Gly Ser Gly Ser Gly Thr Asp
65                  70                  75                  80

Phe Thr Leu Thr Ile Ser Ser Val Gln Ala Glu Asp Leu Ala Val Tyr
                85                  90                  95

Tyr Cys Arg Gln Ser Tyr Asn Leu Val Thr Phe Gly Ala Gly Pro Ser
            100                 105                 110

<210> SEQ ID NO 114
<211> LENGTH: 112
<212> TYPE: PRT
<213> ORGANISM: Mus musculus

<400> SEQUENCE: 114

Gly Pro Glu Leu Val Lys Pro Gly Ala Ser Val Lys Met Ser Cys Lys
1               5                   10                  15

Ala Ser Gly Tyr Thr Phe Thr Ser Tyr Val Met His Trp Val Lys Gln
                20                  25                  30

Lys Pro Gly Gln Gly Leu Glu Trp Ile Gly Tyr Ile Asn Pro Tyr Asn
            35                  40                  45

Asp Gly Thr Lys Tyr Asn Glu Lys Phe Lys Gly Lys Ala Thr Leu Thr
        50                  55                  60

Ser Asp Lys Ser Ser Ser Thr Ala Tyr Met Glu Leu Ser Ser Leu Thr
65                  70                  75                  80

Ser Glu Asp Ser Ala Val Tyr Tyr Cys Ala Arg Arg Tyr Tyr Tyr Gly
                85                  90                  95

Ser Ser Gly Gly Tyr Phe Asp Val Trp Ala Gln Asp His Val Arg Thr
            100                 105                 110

<210> SEQ ID NO 115
<211> LENGTH: 108
<212> TYPE: PRT
<213> ORGANISM: Mus musculus

<400> SEQUENCE: 115

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
                20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Ile Lys Arg
            100                 105

<210> SEQ ID NO 116
<211> LENGTH: 113
<212> TYPE: PRT
<213> ORGANISM: Mus musculus

<400> SEQUENCE: 116

Gly Pro Glu Leu Val Lys Pro Gly Ala Ser Val Lys Ile Ser Cys Lys
1               5                   10                  15

Ala Ser Gly Tyr Ser Phe Thr Gly Tyr Phe Met Asn Trp Val Met Gln
            20                  25                  30

Ser His Gly Lys Ser Leu Glu Trp Ile Gly Arg Ile Asn Pro Tyr Asn
        35                  40                  45

Gly Asp Thr Phe Tyr Asn Gln Lys Phe Lys Gly Lys Ala Thr Leu Thr
    50                  55                  60

Val Asp Lys Ser Ser Ser Thr Ala His Met Glu Leu Arg Ser Leu Ala
65                  70                  75                  80

Ser Glu Asp Ser Ala Val Tyr Tyr Cys Ala Arg Arg Ile His Tyr Tyr
                85                  90                  95

Tyr Gly Ser Ser Tyr Tyr Ala Met Asp Tyr Trp Gly Gln Glu Pro His
            100                 105                 110

His

<210> SEQ ID NO 117
<211> LENGTH: 108
<212> TYPE: PRT
<213> ORGANISM: Mus musculus

<400> SEQUENCE: 117

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys Arg
            100                 105

<210> SEQ ID NO 118
<211> LENGTH: 113
<212> TYPE: PRT
<213> ORGANISM: Mus musculus

<400> SEQUENCE: 118

Gly Ala Gly Leu Val Lys Pro Gly Ala Ser Val Lys Leu Ser Cys Lys
1               5                   10                  15

Ala Ser Gly Tyr Thr Phe Thr Glu Tyr Ile Ile His Trp Val Lys Gln
            20                  25                  30

Arg Ser Gly Gln Gly Leu Glu Trp Ile Gly Trp Phe Tyr Pro Gly Ser
        35                  40                  45

Gly Ser Ile Lys Tyr Asn Glu Lys Phe Lys Asp Lys Ala Thr Leu Thr
    50                  55                  60

Ala Asp Lys Ser Ser Thr Val Tyr Met Glu Leu Ser Arg Leu Thr
65                  70                  75                  80

Ser Glu Asp Ser Ala Val Tyr Phe Cys Ala Arg His Glu Val Tyr Tyr
                85                  90                  95

Asp Tyr Asp Lys Ser Met Leu Trp Thr Thr Gly Val Lys Asn Leu Ile
            100                 105                 110

Arg

<210> SEQ ID NO 119
<211> LENGTH: 108
<212> TYPE: PRT
<213> ORGANISM: Mus musculus

<400> SEQUENCE: 119

Ser Pro Ser Ser Leu Ala Val Ser Val Gly Glu Lys Val Thr Met Ser
1               5                   10                  15

Cys Lys Ser Ser Gln Ser Leu Leu Tyr Ser Ser Asn Gln Lys Asn Tyr
            20                  25                  30

Leu Ala Trp Tyr Gln Gln Lys Pro Gly Gln Ser Pro Lys Leu Leu Ile
        35                  40                  45

Tyr Trp Ala Ser Thr Arg Glu Ser Gly Val Pro Asp Arg Phe Thr Gly
    50                  55                  60

Ser Gly Ser Gly Thr Asp Phe Thr Leu Thr Ile Ser Ser Val Lys Ala
65                  70                  75                  80

Glu Asp Leu Ala Val Tyr Tyr Cys Gln Gln Tyr Tyr Ser Tyr Pro Tyr
                85                  90                  95

Thr Phe Gly Gly Gly Thr Lys Leu Glu Ile Lys Arg
            100                 105

<210> SEQ ID NO 120
<211> LENGTH: 113
<212> TYPE: PRT
<213> ORGANISM: Mus musculus

<400> SEQUENCE: 120

Gly Ala Glu Leu Val Arg Pro Gly Thr Ser Val Lys Val Ser Cys Lys
1               5                   10                  15

Ala Ser Val Tyr Ala Phe Thr Asn Tyr Leu Ile Glu Trp Val Lys Gln
            20                  25                  30

Arg Pro Gly Gln Gly Leu Glu Trp Ile Gly Val Ile Asn Pro Lys Ser
        35                  40                  45

Gly Gly Thr Lys Tyr Asn Glu Lys Phe Arg Gly Lys Ala Thr Leu Thr
    50                  55                  60

Ala Asp Lys Ser Ser Ser Thr Ala Tyr Met Gln Leu Ser Ser Leu Thr
65                  70                  75                  80

Ser Gly Asp Ser Ala Val Tyr Phe Cys Ala Ile Thr Gly Thr Asp Tyr
                85                  90                  95

Trp Gly Gln Gly Thr Thr Leu Thr Val Ser Ser Ala Lys Thr Thr Pro
            100                 105                 110

Pro

<210> SEQ ID NO 121
<211> LENGTH: 113
<212> TYPE: PRT
<213> ORGANISM: Mus musculus

<400> SEQUENCE: 121

Gln Gly Thr Arg Cys Asp Ile Gln Met Thr Gln Thr Thr Ser Ser Leu
1               5                   10                  15

Ser Ala Ser Leu Gly Asp Arg Val Thr Ile Ser Cys Ser Ala Ser Gln
            20                  25                  30

Gly Ile Asn Asn Tyr Leu Asn Trp Tyr Gln Gln Lys Pro Asp Gly Thr
        35                  40                  45

Val Lys Leu Leu Ile Tyr Tyr Thr Ser Ser Leu Arg Ser Gly Val Pro

```
                50                  55                  60
Ser Arg Phe Ser Gly Ser Gly Ser Gly Thr Asp Tyr Ser Leu Thr Ile
 65                  70                  75                  80

Ser Asn Leu Glu Pro Glu Asp Val Ala Thr Tyr Tyr Cys Gln Gln Tyr
                 85                  90                  95

Ser Lys Leu Pro Arg Thr Phe Gly Gly Gly Thr Lys Leu Glu Ile Lys
            100                 105                 110

Arg

<210> SEQ ID NO 122
<211> LENGTH: 121
<212> TYPE: PRT
<213> ORGANISM: Homo sapiens

<400> SEQUENCE: 122

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ser Ser His
                20                  25                  30

Ser Leu Gly Trp Val Arg Gln Ala Pro Gly Lys Gly Leu Glu Trp Ile
             35                  40                  45

Gly Asp Ile Arg Ser Gly Gly Ser Ala Tyr Tyr Ala Asn Trp Ala Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Thr
                 85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
            115                 120

<210> SEQ ID NO 123
<211> LENGTH: 112
<212> TYPE: PRT
<213> ORGANISM: Homo sapiens

<400> SEQUENCE: 123

Gln Val Leu Thr Gln Ser Pro Ser Ser Leu Ser Ala Ser Val Gly Asp
 1               5                  10                  15

Arg Val Thr Ile Asn Cys Gln Ala Ser Gln Ser Leu Tyr Asn Asn Glu
                20                  25                  30

Asn Leu Ala Trp Phe Gln Gln Lys Pro Gly Lys Val Pro Lys Arg Leu
             35                  40                  45

Ile Tyr Gly Ala Ser Thr Leu Ala Ser Gly Val Ser Ser Arg Phe Ser
         50                  55                  60

Gly Ser Gly Ser Gly Thr Glu Phe Thr Leu Thr Ile Ser Ser Leu Gln
 65                  70                  75                  80

Cys Glu Asp Phe Ala Ile Tyr Tyr Cys Leu Gly Glu Phe Ser Cys Gly
                 85                  90                  95

Ser Ala Asp Cys Phe Ala Phe Gly Gly Gly Thr Lys Val Glu Ile Lys
            100                 105                 110

<210> SEQ ID NO 124
<211> LENGTH: 121
<212> TYPE: PRT
<213> ORGANISM: Homo sapiens
```

<400> SEQUENCE: 124

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Ser | Leu | Ser | Ser | His |
|---|---|---|---|---|---|---|---|---|---|---|---|---|---|---|---|
| | | | 20 | | | | | 25 | | | | | 30 | | |

| Ser | Leu | Gly | Trp | Val | Arg | Gln | Ala | Pro | Gly | Lys | Gly | Leu | Glu | Trp | Ile |
|---|---|---|---|---|---|---|---|---|---|---|---|---|---|---|---|
| | | 35 | | | | | 40 | | | | | 45 | | | |

| Gly | Asp | Ile | Arg | Ser | Gly | Gly | Ser | Ala | Tyr | Tyr | Ala | Asn | Trp | Ala | Lys |
|---|---|---|---|---|---|---|---|---|---|---|---|---|---|---|---|
| 50 | | | | | 55 | | | | | 60 | | | | | |

| Gly | Arg | Phe | Thr | Ile | Ser | Arg | Asp | Asn | Ser | Lys | Asn | Thr | Leu | Tyr | Leu |
|---|---|---|---|---|---|---|---|---|---|---|---|---|---|---|---|
| 65 | | | | | 70 | | | | | 75 | | | | | 80 |

| Gln | Met | Asn | Ser | Leu | Arg | Ala | Glu | Asp | Thr | Ala | Val | Tyr | Phe | Cys | Thr |
|---|---|---|---|---|---|---|---|---|---|---|---|---|---|---|---|
| | | | | 85 | | | | | 90 | | | | | 95 | |

| Arg | Thr | Asn | Gly | Pro | Ser | Asp | Leu | Thr | Asn | Arg | Leu | Asp | Leu | Trp | Gly |
|---|---|---|---|---|---|---|---|---|---|---|---|---|---|---|---|
| | | | 100 | | | | | 105 | | | | | 110 | | |

| Gln | Gly | Thr | Leu | Val | Thr | Val | Ser | Ser |
|---|---|---|---|---|---|---|---|---|
| | | | 115 | | | | | 120 |

<210> SEQ ID NO 125
<211> LENGTH: 112
<212> TYPE: PRT
<213> ORGANISM: Homo sapiens

<400> SEQUENCE: 125

| Gln | Val | Leu | Thr | Gln | Ser | Pro | Ser | Ser | Leu | Ser | Ala | Ser | Val | Gly | Asp |
|---|---|---|---|---|---|---|---|---|---|---|---|---|---|---|---|
| 1 | | | | 5 | | | | | 10 | | | | | 15 | |

| Arg | Val | Thr | Ile | Asn | Cys | Gln | Ala | Ser | Gln | Ser | Leu | Tyr | Asn | Asn | Glu |
|---|---|---|---|---|---|---|---|---|---|---|---|---|---|---|---|
| | | | 20 | | | | | 25 | | | | | 30 | | |

| Asn | Leu | Ala | Trp | Phe | Gln | Gln | Lys | Pro | Gly | Lys | Val | Pro | Lys | Arg | Leu |
|---|---|---|---|---|---|---|---|---|---|---|---|---|---|---|---|
| | | 35 | | | | | 40 | | | | | 45 | | | |

| Ile | Tyr | Gly | Ala | Ser | Thr | Leu | Ala | Ser | Gly | Val | Ser | Ser | Arg | Phe | Ser |
|---|---|---|---|---|---|---|---|---|---|---|---|---|---|---|---|
| | | 50 | | | | | 55 | | | | | 60 | | | |

| Gly | Ser | Gly | Ser | Gly | Thr | Glu | Phe | Thr | Leu | Thr | Ile | Ser | Ser | Leu | Gln |
|---|---|---|---|---|---|---|---|---|---|---|---|---|---|---|---|
| 65 | | | | | 70 | | | | | 75 | | | | | 80 |

| Cys | Glu | Asp | Phe | Ala | Ile | Tyr | Tyr | Cys | Leu | Gly | Glu | Phe | Ser | Cys | Gly |
|---|---|---|---|---|---|---|---|---|---|---|---|---|---|---|---|
| | | | | 85 | | | | | 90 | | | | | 95 | |

| Ser | Ala | Asp | Cys | Phe | Ala | Phe | Gly | Gly | Thr | Lys | Val | Glu | Ile | Lys |
|---|---|---|---|---|---|---|---|---|---|---|---|---|---|---|
| | | | 100 | | | | | 105 | | | | | 110 | |

<210> SEQ ID NO 126
<211> LENGTH: 121
<212> TYPE: PRT
<213> ORGANISM: Homo sapiens

<400> SEQUENCE: 126

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Ser | Leu | Ser | Ser | His |
|---|---|---|---|---|---|---|---|---|---|---|---|---|---|---|---|
| | | | 20 | | | | | 25 | | | | | 30 | | |

| Ser | Leu | Gly | Trp | Val | Arg | Gln | Ala | Pro | Gly | Lys | Gly | Leu | Glu | Trp | Ile |
|---|---|---|---|---|---|---|---|---|---|---|---|---|---|---|---|
| | | 35 | | | | | 40 | | | | | 45 | | | |

| Gly | Asp | Ile | Arg | Ser | Gly | Gly | Ser | Ala | Tyr | Tyr | Ala | Asn | Trp | Ala | Lys |
|---|---|---|---|---|---|---|---|---|---|---|---|---|---|---|---|
| | | | 50 | | | | | 55 | | | | | 60 | | |

| Gly | Arg | Phe | Thr | Ile | Ser | Arg | Asp | Asn | Ser | Lys | Asn | Thr | Leu | Tyr | Leu |
|---|---|---|---|---|---|---|---|---|---|---|---|---|---|---|---|
| 65 | | | | | 70 | | | | | 75 | | | | | 80 |

```
Gln Met Asn Ser Leu Arg Ala Glu Asp Thr Ala Val Tyr Tyr Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120
```

<210> SEQ ID NO 127
<211> LENGTH: 113
<212> TYPE: PRT
<213> ORGANISM: Homo sapiens

<400> SEQUENCE: 127

```
Glu Gln Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
        35                  40                  45

Leu Ile Tyr Gly Ala Ser Thr Leu Ala Ser Gly Val Ser Ser Arg Phe
    50                  55                  60

Ser Gly Ser Gly Ser Gly Thr Glu Phe Thr Leu Thr Ile Ser Asn Leu
65                  70                  75                  80

Gln Pro Glu Asp Phe Ala Ile Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys
```

<210> SEQ ID NO 128
<211> LENGTH: 121
<212> TYPE: PRT
<213> ORGANISM: Homo sapiens

<400> SEQUENCE: 128

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120
```

<210> SEQ ID NO 129
<211> LENGTH: 113
<212> TYPE: PRT
<213> ORGANISM: Homo sapiens

<400> SEQUENCE: 129

Glu Ile Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
        35                  40                  45

Leu Ile Tyr Gly Ala Ser Thr Leu Ala Ser Gly Val Ser Ser Arg Phe
    50                  55                  60

Ser Gly Ser Gly Ser Gly Thr Glu Phe Thr Leu Thr Ile Ser Asn Leu
65              70                  75                  80

Gln Pro Glu Asp Phe Ala Thr Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys

<210> SEQ ID NO 130
<211> LENGTH: 121
<212> TYPE: PRT
<213> ORGANISM: Homo sapiens

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Tyr Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120

<210> SEQ ID NO 131
<211> LENGTH: 113
<212> TYPE: PRT
<213> ORGANISM: Homo sapiens

<400> SEQUENCE: 131

Glu Ile Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
        35                  40                  45

Leu Ile Tyr Gly Ala Ser Thr Leu Ala Ser Gly Val Ser Ser Arg Phe
    50                  55                  60

Ser Gly Ser Gly Ser Gly Thr Glu Phe Thr Leu Thr Ile Ser Asn Leu
65              70                  75                  80

```
Gln Pro Glu Asp Phe Ala Thr Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys
```

```
<210> SEQ ID NO 132
<211> LENGTH: 121
<212> TYPE: PRT
<213> ORGANISM: Homo sapiens

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120
```

```
<210> SEQ ID NO 133
<211> LENGTH: 113
<212> TYPE: PRT
<213> ORGANISM: Homo sapiens

<400> SEQUENCE: 133

Glu Gln Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
        35                  40                  45

Leu Ile Tyr Gly Ala Ser Thr Leu Ala Ser Gly Val Ser Ser Arg Phe
    50                  55                  60

Ser Gly Ser Gly Ser Gly Thr Glu Phe Thr Leu Thr Ile Ser Asn Leu
65                  70                  75                  80

Gln Pro Glu Asp Phe Ala Ile Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys
```

```
<210> SEQ ID NO 134
<211> LENGTH: 5
<212> TYPE: PRT
<213> ORGANISM: Gallus gallus

<400> SEQUENCE: 134
```

Gly Tyr Asp Met Leu
1               5

<210> SEQ ID NO 135
<211> LENGTH: 17
<212> TYPE: PRT
<213> ORGANISM: Gallus gallus

<400> SEQUENCE: 135

Gly Ile Gly Ser Thr Gly Gly Gly Thr Asp Tyr Gly Ala Ala Val Lys
1               5                   10                  15

Gly

<210> SEQ ID NO 136
<211> LENGTH: 19
<212> TYPE: PRT
<213> ORGANISM: Gallus gallus

<400> SEQUENCE: 136

Val Ala Gly Gly Cys Asn Ser Gly Tyr Cys Arg Asp Ser Pro Gly Ser
1               5                   10                  15

Ile Asp Ala

<210> SEQ ID NO 137
<211> LENGTH: 10
<212> TYPE: PRT
<213> ORGANISM: Gallus gallus

<400> SEQUENCE: 137

Ser Gly Gly Gly Ser Arg Asn Tyr Tyr Gly
1               5                   10

<210> SEQ ID NO 138
<211> LENGTH: 7
<212> TYPE: PRT
<213> ORGANISM: Gallus gallus

<400> SEQUENCE: 138

Asp Asp Gln Arg Pro Ser Asn
1               5

<210> SEQ ID NO 139
<211> LENGTH: 11
<212> TYPE: PRT
<213> ORGANISM: Gallus gallus

<400> SEQUENCE: 139

Ser Ala Asp Ser Asn Thr Tyr Glu Gly Ser Phe
1               5                   10

<210> SEQ ID NO 140
<211> LENGTH: 5
<212> TYPE: PRT
<213> ORGANISM: Mus musculus

<400> SEQUENCE: 140

Asp Tyr Asn Met Asp
1               5

<210> SEQ ID NO 141
<211> LENGTH: 17
<212> TYPE: PRT
<213> ORGANISM: Mus musculus

<400> SEQUENCE: 141

Asp Ile Asn Pro Asn Tyr Asp Ser Thr Ser Tyr Asn Gln Lys Phe Lys
1               5                   10                  15

Gly

<210> SEQ ID NO 142
<211> LENGTH: 11
<212> TYPE: PRT
<213> ORGANISM: Mus musculus

<400> SEQUENCE: 142

Ser Arg Ser Tyr Asp Tyr Glu Gly Phe Ala Tyr
1               5                   10

<210> SEQ ID NO 143
<211> LENGTH: 11
<212> TYPE: PRT
<213> ORGANISM: Mus musculus

<400> SEQUENCE: 143

Leu Ser Ile Val Asn Arg Tyr His Tyr Met Ser
1               5                   10

<210> SEQ ID NO 144
<211> LENGTH: 6
<212> TYPE: PRT
<213> ORGANISM: Mus musculus

<400> SEQUENCE: 144

Glu Ala Ser Ile Thr Lys
1               5

<210> SEQ ID NO 145
<211> LENGTH: 9
<212> TYPE: PRT
<213> ORGANISM: Mus musculus

<400> SEQUENCE: 145

Gln His Asn Arg Gly Ser Phe Leu Pro
1               5

<210> SEQ ID NO 146
<211> LENGTH: 5
<212> TYPE: PRT
<213> ORGANISM: Mus musculus

<400> SEQUENCE: 146

Asp Tyr Tyr Met Ser
1               5

<210> SEQ ID NO 147
<211> LENGTH: 17
<212> TYPE: PRT
<213> ORGANISM: Mus musculus

<400> SEQUENCE: 147

Arg Asn Lys Ala Asn Gly Tyr Thr Thr Glu Tyr Ser Ala Ser Val Lys
1               5                   10                  15

Gly

<210> SEQ ID NO 148
<211> LENGTH: 9
<212> TYPE: PRT

<213> ORGANISM: Mus musculus

<400> SEQUENCE: 148

Ala Arg Ala Asn Trp Ala Phe Asp Tyr
1               5

<210> SEQ ID NO 149
<211> LENGTH: 11
<212> TYPE: PRT
<213> ORGANISM: Mus musculus

<400> SEQUENCE: 149

Arg Ala Ser Gln Ser Ile Ser Asn Tyr Leu His
1               5                   10

<210> SEQ ID NO 150
<211> LENGTH: 7
<212> TYPE: PRT
<213> ORGANISM: Mus musculus

<400> SEQUENCE: 150

Tyr Ala Ser Gln Ser Ile Ser
1               5

<210> SEQ ID NO 151
<211> LENGTH: 7
<212> TYPE: PRT
<213> ORGANISM: Mus musculus

<400> SEQUENCE: 151

Tyr Ala Ser Gln Ser Ile Ser
1               5

<210> SEQ ID NO 152
<211> LENGTH: 5
<212> TYPE: PRT
<213> ORGANISM: Mus musculus

<400> SEQUENCE: 152

Asn Tyr Leu Ile Val
1               5

<210> SEQ ID NO 153
<211> LENGTH: 17
<212> TYPE: PRT
<213> ORGANISM: Mus musculus

<400> SEQUENCE: 153

Val Ile Ser Pro Gly Ser Gly Gly Thr Asn Tyr Asn Glu Lys Phe Lys
1               5                   10                  15

Gly

<210> SEQ ID NO 154
<211> LENGTH: 11
<212> TYPE: PRT
<213> ORGANISM: Mus musculus

<400> SEQUENCE: 154

Glu Lys Ile Tyr Asp Asp Tyr Tyr Glu Gly Tyr
1               5                   10

<210> SEQ ID NO 155
<211> LENGTH: 15
<212> TYPE: PRT

```
<213> ORGANISM: Mus musculus

<400> SEQUENCE: 155

Thr Ile Ser Cys Ser Ala Ser Leu Gly Ile Gly Asn Tyr Leu Asn
1               5                   10                  15

<210> SEQ ID NO 156
<211> LENGTH: 7
<212> TYPE: PRT
<213> ORGANISM: Mus musculus

<400> SEQUENCE: 156

Thr Ser Asn Leu His Ser Gly
1               5

<210> SEQ ID NO 157
<211> LENGTH: 9
<212> TYPE: PRT
<213> ORGANISM: Mus musculus

<400> SEQUENCE: 157

His Tyr Ser Lys Leu Pro Leu Thr Phe
1               5

<210> SEQ ID NO 158
<211> LENGTH: 5
<212> TYPE: PRT
<213> ORGANISM: Mus musculus

<400> SEQUENCE: 158

Asp Tyr Asn Met Tyr
1               5

<210> SEQ ID NO 159
<211> LENGTH: 17
<212> TYPE: PRT
<213> ORGANISM: Mus musculus

<400> SEQUENCE: 159

Tyr Ile Tyr Pro Gly Asn Gly Gly Thr Asn Tyr Asn Gln Lys Phe Lys
1               5                   10                  15

Gly

<210> SEQ ID NO 160
<211> LENGTH: 11
<212> TYPE: PRT
<213> ORGANISM: Mus musculus

<400> SEQUENCE: 160

Asp Tyr Asp Asp Gly Gly Tyr Ala Met Asp Tyr
1               5                   10

<210> SEQ ID NO 161
<211> LENGTH: 15
<212> TYPE: PRT
<213> ORGANISM: Mus musculus

<400> SEQUENCE: 161

Ser Val Gly Glu Thr Val Thr Ile Thr Cys Arg Ala Ser Gly Asn
1               5                   10                  15

<210> SEQ ID NO 162
<211> LENGTH: 7
<212> TYPE: PRT
```

<213> ORGANISM: Mus musculus

<400> SEQUENCE: 162

Asn Ala Lys Thr Leu Ala Asp
1               5

<210> SEQ ID NO 163
<211> LENGTH: 9
<212> TYPE: PRT
<213> ORGANISM: Mus musculus

<400> SEQUENCE: 163

Gln His Phe Trp Asn Ile Pro Trp Thr
1               5

<210> SEQ ID NO 164
<211> LENGTH: 5
<212> TYPE: PRT
<213> ORGANISM: Mus musculus

<400> SEQUENCE: 164

Asp His Ser Ile His
1               5

<210> SEQ ID NO 165
<211> LENGTH: 17
<212> TYPE: PRT
<213> ORGANISM: Mus musculus

<400> SEQUENCE: 165

Tyr Ile Ser Pro Gly Asn Gly Asn Ile Lys Tyr Asn Glu Lys Phe Lys
1               5                   10                  15

Gly

<210> SEQ ID NO 166
<211> LENGTH: 12
<212> TYPE: PRT
<213> ORGANISM: Mus musculus

<400> SEQUENCE: 166

Ser Leu Gly Arg Gly Gly Pro Tyr Tyr Phe Asp Tyr
1               5                   10

<210> SEQ ID NO 167
<211> LENGTH: 16
<212> TYPE: PRT
<213> ORGANISM: Mus musculus

<400> SEQUENCE: 167

Arg Ser Ser Lys Ser Leu Leu His Ser Asn Gly Asn Thr Tyr Leu Tyr
1               5                   10                  15

<210> SEQ ID NO 168
<211> LENGTH: 7
<212> TYPE: PRT
<213> ORGANISM: Mus musculus

<400> SEQUENCE: 168

Arg Met Ser Asn Leu Ala Ser
1               5

<210> SEQ ID NO 169
<211> LENGTH: 9
<212> TYPE: PRT

<213> ORGANISM: Mus musculus

<400> SEQUENCE: 169

Met Gln His Arg Glu Tyr Pro Val Thr
1               5

<210> SEQ ID NO 170
<211> LENGTH: 5
<212> TYPE: PRT
<213> ORGANISM: Mus musculus

<400> SEQUENCE: 170

Ser Tyr Trp Ile Glu
1               5

<210> SEQ ID NO 171
<211> LENGTH: 17
<212> TYPE: PRT
<213> ORGANISM: Mus musculus

<400> SEQUENCE: 171

Glu Ile Leu Pro Gly Ser Gly Ser Thr Asn Tyr Asn Glu Lys Phe Lys
1               5                   10                  15

Gly

<210> SEQ ID NO 172
<211> LENGTH: 11
<212> TYPE: PRT
<213> ORGANISM: Mus musculus

<400> SEQUENCE: 172

Tyr Tyr Trp Tyr Phe Asp Val Trp Ala Gln Asp
1               5                   10

<210> SEQ ID NO 173
<211> LENGTH: 15
<212> TYPE: PRT
<213> ORGANISM: Mus musculus

<400> SEQUENCE: 173

Ser Ser Lys Asn Leu Leu His Ser Asn Gly Ile Thr Tyr Leu Tyr
1               5                   10                  15

<210> SEQ ID NO 174
<211> LENGTH: 7
<212> TYPE: PRT
<213> ORGANISM: Mus musculus

<400> SEQUENCE: 174

Arg Val Ser Asn Leu Ala Ser
1               5

<210> SEQ ID NO 175
<211> LENGTH: 9
<212> TYPE: PRT
<213> ORGANISM: Mus musculus

<400> SEQUENCE: 175

Ala Gln Leu Leu Glu Leu Pro Tyr Thr
1               5

<210> SEQ ID NO 176
<211> LENGTH: 5
<212> TYPE: PRT

<213> ORGANISM: Mus musculus

<400> SEQUENCE: 176

Ser Tyr Asp Met Ser
1               5

<210> SEQ ID NO 177
<211> LENGTH: 17
<212> TYPE: PRT
<213> ORGANISM: Mus musculus

<400> SEQUENCE: 177

Tyr Ile Ser Ser Gly Ala Gly Ser Thr Tyr Tyr Pro Asp Thr Val Lys
1               5                   10                  15

Gly

<210> SEQ ID NO 178
<211> LENGTH: 11
<212> TYPE: PRT
<213> ORGANISM: Mus musculus

<400> SEQUENCE: 178

His Phe Tyr Arg Phe Asp Tyr Trp Gly Gln Gly
1               5                   10

<210> SEQ ID NO 179
<211> LENGTH: 15
<212> TYPE: PRT
<213> ORGANISM: Mus musculus

<400> SEQUENCE: 179

Ser Ala Gly Asp Arg Ile Thr Ile Thr Cys Lys Ala Ser Gln Ser
1               5                   10                  15

<210> SEQ ID NO 180
<211> LENGTH: 7
<212> TYPE: PRT
<213> ORGANISM: Mus musculus

<400> SEQUENCE: 180

Tyr Ala Ser Asn Arg Tyr Thr
1               5

<210> SEQ ID NO 181
<211> LENGTH: 9
<212> TYPE: PRT
<213> ORGANISM: Mus musculus

<400> SEQUENCE: 181

Gln Gln Asp Asp Arg Phe Pro Leu Thr
1               5

<210> SEQ ID NO 182
<211> LENGTH: 5
<212> TYPE: PRT
<213> ORGANISM: Mus musculus

<400> SEQUENCE: 182

Asn Tyr Gly Met Asn
1               5

<210> SEQ ID NO 183
<211> LENGTH: 17
<212> TYPE: PRT

<213> ORGANISM: Mus musculus

<400> SEQUENCE: 183

Trp Ile Asn Thr Tyr Thr Gly Glu Pro Thr Tyr Ala Asp Asp Phe Lys
1               5                   10                  15
Gly

<210> SEQ ID NO 184
<211> LENGTH: 11
<212> TYPE: PRT
<213> ORGANISM: Mus musculus

<400> SEQUENCE: 184

Gly Ala Trp Phe Ala Tyr Trp Ala Lys Asp Ser
1               5                   10

<210> SEQ ID NO 185
<211> LENGTH: 15
<212> TYPE: PRT
<213> ORGANISM: Mus musculus

<400> SEQUENCE: 185

Ser Ile Thr Cys Lys Ala Ser Gln Asp Val Gly Thr Ala Val Ala
1               5                   10                  15

<210> SEQ ID NO 186
<211> LENGTH: 7
<212> TYPE: PRT
<213> ORGANISM: Mus musculus

<400> SEQUENCE: 186

Trp Ala Ser Thr Arg His Thr
1               5

<210> SEQ ID NO 187
<211> LENGTH: 9
<212> TYPE: PRT
<213> ORGANISM: Mus musculus

<400> SEQUENCE: 187

Gln Gln Tyr Ser Ser Tyr Pro Leu Thr
1               5

<210> SEQ ID NO 188
<211> LENGTH: 5
<212> TYPE: PRT
<213> ORGANISM: Mus musculus

<400> SEQUENCE: 188

Asp Phe Trp Met Asn
1               5

<210> SEQ ID NO 189
<211> LENGTH: 19
<212> TYPE: PRT
<213> ORGANISM: Mus musculus

<400> SEQUENCE: 189

Glu Ile Arg Leu Lys Ser Asn Asn Tyr Ala Thr His Tyr Ala Glu Ser
1               5                   10                  15
Val Lys Gly

<210> SEQ ID NO 190

```
<211> LENGTH: 13
<212> TYPE: PRT
<213> ORGANISM: Mus musculus

<400> SEQUENCE: 190

Leu Phe Tyr Tyr Tyr Asp Gly Thr Ser Gly Phe Ala Tyr
1               5                   10

<210> SEQ ID NO 191
<211> LENGTH: 17
<212> TYPE: PRT
<213> ORGANISM: Mus musculus

<400> SEQUENCE: 191

Lys Ser Ser Gln Ser Leu Leu Asn Ser Gly Asp Gln Lys Asn Tyr Leu
1               5                   10                  15

Thr

<210> SEQ ID NO 192
<211> LENGTH: 7
<212> TYPE: PRT
<213> ORGANISM: Mus musculus

<400> SEQUENCE: 192

Trp Ala Ser Thr Arg Glu Ser
1               5

<210> SEQ ID NO 193
<211> LENGTH: 9
<212> TYPE: PRT
<213> ORGANISM: Mus musculus

<400> SEQUENCE: 193

Gln Asn Asp Tyr Asp Tyr Pro Leu Thr
1               5

<210> SEQ ID NO 194
<211> LENGTH: 5
<212> TYPE: PRT
<213> ORGANISM: Mus musculus

<400> SEQUENCE: 194

Asp Tyr Asn Met Asp
1               5

<210> SEQ ID NO 195
<211> LENGTH: 17
<212> TYPE: PRT
<213> ORGANISM: Mus musculus

<400> SEQUENCE: 195

Asp Ile Asn Pro Asn Tyr Asp Ser Thr Ser Tyr Asn Gln Lys Phe Lys
1               5                   10                  15

Gly

<210> SEQ ID NO 196
<211> LENGTH: 11
<212> TYPE: PRT
<213> ORGANISM: Mus musculus

<400> SEQUENCE: 196

Ser Arg Ser Tyr Asp Tyr Glu Gly Phe Ala Tyr
1               5                   10
```

<210> SEQ ID NO 197
<211> LENGTH: 11
<212> TYPE: PRT
<213> ORGANISM: Mus musculus

<400> SEQUENCE: 197

Arg Ala Ser Gly Asn Ile His Asn Tyr Leu Ala
1               5                   10

<210> SEQ ID NO 198
<211> LENGTH: 7
<212> TYPE: PRT
<213> ORGANISM: Mus musculus

<400> SEQUENCE: 198

Asn Ala Lys Thr Leu Ala Asp
1               5

<210> SEQ ID NO 199
<211> LENGTH: 8
<212> TYPE: PRT
<213> ORGANISM: Mus musculus

<400> SEQUENCE: 199

Gln His Phe Trp Ser Thr Leu Thr
1               5

<210> SEQ ID NO 200
<211> LENGTH: 5
<212> TYPE: PRT
<213> ORGANISM: Mus musculus

<400> SEQUENCE: 200

Gly Tyr Thr Met Asn
1               5

<210> SEQ ID NO 201
<211> LENGTH: 16
<212> TYPE: PRT
<213> ORGANISM: Mus musculus

<400> SEQUENCE: 201

Asn Pro Tyr Asn Gly Gly Thr Ser Tyr Asn Gln Lys Phe Lys Gly Lys
1               5                   10                  15

<210> SEQ ID NO 202
<211> LENGTH: 9
<212> TYPE: PRT
<213> ORGANISM: Mus musculus

<400> SEQUENCE: 202

Trp Gly Val Trp Ser Ala Met Asp Tyr
1               5

<210> SEQ ID NO 203
<211> LENGTH: 11
<212> TYPE: PRT
<213> ORGANISM: Mus musculus

<400> SEQUENCE: 203

Lys Ala Ser Gln Asn Val Arg Thr Ala Val Ala
1               5                   10

<210> SEQ ID NO 204

```
<211> LENGTH: 7
<212> TYPE: PRT
<213> ORGANISM: Mus musculus

<400> SEQUENCE: 204

Leu Ala Ser Asn Arg Asp Thr
1               5

<210> SEQ ID NO 205
<211> LENGTH: 9
<212> TYPE: PRT
<213> ORGANISM: Mus musculus

<400> SEQUENCE: 205

Leu Gln His Cys Asn Tyr Pro Asn Glu
1               5

<210> SEQ ID NO 206
<211> LENGTH: 5
<212> TYPE: PRT
<213> ORGANISM: Mus musculus

<400> SEQUENCE: 206

Ser Tyr Trp Met Gln
1               5

<210> SEQ ID NO 207
<211> LENGTH: 17
<212> TYPE: PRT
<213> ORGANISM: Mus musculus

<400> SEQUENCE: 207

Ala Ile Tyr Pro Gly Asp Gly Asp Thr Arg Tyr Thr Gln Lys Phe Lys
1               5                   10                  15

Gly

<210> SEQ ID NO 208
<211> LENGTH: 11
<212> TYPE: PRT
<213> ORGANISM: Mus musculus

<400> SEQUENCE: 208

Ala Arg Gly Glu Tyr Gly Asn Tyr Phe Ala Tyr
1               5                   10

<210> SEQ ID NO 209
<211> LENGTH: 11
<212> TYPE: PRT
<213> ORGANISM: Mus musculus

<400> SEQUENCE: 209

Lys Ala Ser Gln Asp Ile Asn Ser Tyr Leu Ser
1               5                   10

<210> SEQ ID NO 210
<211> LENGTH: 7
<212> TYPE: PRT
<213> ORGANISM: Mus musculus

<400> SEQUENCE: 210

Arg Ala Asn Arg Leu Val Asp
1               5

<210> SEQ ID NO 211
```

```
<211> LENGTH: 9
<212> TYPE: PRT
<213> ORGANISM: Mus musculus

<400> SEQUENCE: 211

Leu Gln Tyr Asp Glu Phe Pro Leu Thr
1               5

<210> SEQ ID NO 212
<211> LENGTH: 5
<212> TYPE: PRT
<213> ORGANISM: Mus musculus

<400> SEQUENCE: 212

Asp Thr Tyr Met His
1               5

<210> SEQ ID NO 213
<211> LENGTH: 17
<212> TYPE: PRT
<213> ORGANISM: Mus musculus

<400> SEQUENCE: 213

Arg Ile Asp Pro Ala Asn Gly Asn Thr Lys Tyr Asp Pro Lys Phe Gln
1               5                   10                  15

Gly

<210> SEQ ID NO 214
<211> LENGTH: 14
<212> TYPE: PRT
<213> ORGANISM: Mus musculus

<400> SEQUENCE: 214

Ala Arg Pro Ile His Tyr Tyr Tyr Gly Ser Ser Leu Ala Tyr
1               5                   10

<210> SEQ ID NO 215
<211> LENGTH: 11
<212> TYPE: PRT
<213> ORGANISM: Mus musculus

<400> SEQUENCE: 215

Ser Val Asp Ser Tyr Gly Asn Ser Phe Met His
1               5                   10

<210> SEQ ID NO 216
<211> LENGTH: 7
<212> TYPE: PRT
<213> ORGANISM: Mus musculus

<400> SEQUENCE: 216

Arg Ala Ser Asn Leu Glu Ser
1               5

<210> SEQ ID NO 217
<211> LENGTH: 9
<212> TYPE: PRT
<213> ORGANISM: Mus musculus

<400> SEQUENCE: 217

Gln Gln Ser Asn Glu Asp Pro Gly Arg
1               5

<210> SEQ ID NO 218
```

```
<211> LENGTH: 5
<212> TYPE: PRT
<213> ORGANISM: Mus musculus

<400> SEQUENCE: 218

Asp Tyr Tyr Met Ser
1               5

<210> SEQ ID NO 219
<211> LENGTH: 17
<212> TYPE: PRT
<213> ORGANISM: Mus musculus

<400> SEQUENCE: 219

Arg Asn Lys Ala Asn Gly Tyr Thr Thr Glu Tyr Ser Ala Ser Val Lys
1               5                   10                  15

Gly

<210> SEQ ID NO 220
<211> LENGTH: 9
<212> TYPE: PRT
<213> ORGANISM: Mus musculus

<400> SEQUENCE: 220

Ala Arg Ala Asn Trp Ala Phe Asp Tyr
1               5

<210> SEQ ID NO 221
<211> LENGTH: 11
<212> TYPE: PRT
<213> ORGANISM: Mus musculus

<400> SEQUENCE: 221

Arg Ala Ser Gln Ser Ile Ser Asn Tyr Leu His
1               5                   10

<210> SEQ ID NO 222
<211> LENGTH: 7
<212> TYPE: PRT
<213> ORGANISM: Mus musculus

<400> SEQUENCE: 222

Tyr Ala Ser Gln Ser Ile Ser
1               5

<210> SEQ ID NO 223
<211> LENGTH: 9
<212> TYPE: PRT
<213> ORGANISM: Mus musculus

<400> SEQUENCE: 223

Gln Gln Ser Asn Ser Trp Pro Tyr Thr
1               5

<210> SEQ ID NO 224
<211> LENGTH: 5
<212> TYPE: PRT
<213> ORGANISM: Mus musculus

<400> SEQUENCE: 224

Asp Tyr Tyr Met Ser
1               5

<210> SEQ ID NO 225
```

```
<211> LENGTH: 17
<212> TYPE: PRT
<213> ORGANISM: Mus musculus

<400> SEQUENCE: 225

Arg Asn Lys Ala Asn Gly Tyr Thr Thr Glu Tyr Ser Ala Ser Val Lys
1               5                   10                  15
Gly

<210> SEQ ID NO 226
<211> LENGTH: 12
<212> TYPE: PRT
<213> ORGANISM: Mus musculus

<400> SEQUENCE: 226

Ala Arg Ala Pro Leu Leu Tyr Tyr Ala Met Asp Tyr
1               5                   10

<210> SEQ ID NO 227
<211> LENGTH: 11
<212> TYPE: PRT
<213> ORGANISM: Mus musculus

<400> SEQUENCE: 227

Asn Val Ser Thr Ser Gly Tyr Ser Tyr Met His
1               5                   10

<210> SEQ ID NO 228
<211> LENGTH: 7
<212> TYPE: PRT
<213> ORGANISM: Mus musculus

<400> SEQUENCE: 228

Leu Val Ser Asn Leu Glu Ser
1               5

<210> SEQ ID NO 229
<211> LENGTH: 8
<212> TYPE: PRT
<213> ORGANISM: Mus musculus

<400> SEQUENCE: 229

Gln His Ile Arg Glu Leu Thr Arg
1               5

<210> SEQ ID NO 230
<211> LENGTH: 5
<212> TYPE: PRT
<213> ORGANISM: Mus musculus

<400> SEQUENCE: 230

Ser Tyr Trp Met His
1               5

<210> SEQ ID NO 231
<211> LENGTH: 17
<212> TYPE: PRT
<213> ORGANISM: Mus musculus

<400> SEQUENCE: 231

Met Ile Asp Pro Ser Asn Ser Glu Thr Arg Leu Asn Gln Lys Phe Lys
1               5                   10                  15
Asp
```

<210> SEQ ID NO 232
<211> LENGTH: 12
<212> TYPE: PRT
<213> ORGANISM: Mus musculus

<400> SEQUENCE: 232

Ala Arg Gly Leu Arg His Tyr Trp Tyr Phe Asp Val
1               5                   10

<210> SEQ ID NO 233
<211> LENGTH: 11
<212> TYPE: PRT
<213> ORGANISM: Mus musculus

<400> SEQUENCE: 233

Ser Val Ser Thr Ser Gly Tyr Ser Tyr Met His
1               5                   10

<210> SEQ ID NO 234
<211> LENGTH: 7
<212> TYPE: PRT
<213> ORGANISM: Mus musculus

<400> SEQUENCE: 234

Leu Val Ser Asn Leu Glu Ser
1               5

<210> SEQ ID NO 235
<211> LENGTH: 9
<212> TYPE: PRT
<213> ORGANISM: Mus musculus

<400> SEQUENCE: 235

Gln His Ile Arg Glu Leu Thr Arg Ser
1               5

<210> SEQ ID NO 236
<211> LENGTH: 5
<212> TYPE: PRT
<213> ORGANISM: Mus musculus

<400> SEQUENCE: 236

Ser Tyr Gly Met Ser
1               5

<210> SEQ ID NO 237
<211> LENGTH: 14
<212> TYPE: PRT
<213> ORGANISM: Mus musculus

<400> SEQUENCE: 237

Trp Val Arg Gln Thr Pro Glu Lys Arg Leu Glu Trp Val Ala
1               5                   10

<210> SEQ ID NO 238
<211> LENGTH: 11
<212> TYPE: PRT
<213> ORGANISM: Mus musculus

<400> SEQUENCE: 238

Leu Ala Ser Tyr Tyr Phe Asp Tyr Trp Gly Gln
1               5                   10

<210> SEQ ID NO 239

```
<211> LENGTH: 15
<212> TYPE: PRT
<213> ORGANISM: Mus musculus

<400> SEQUENCE: 239

Thr Met Thr Cys Gln Ala Ser Gln Gly Thr Ser Ile Asn Leu Asn
1               5                   10                  15

<210> SEQ ID NO 240
<211> LENGTH: 7
<212> TYPE: PRT
<213> ORGANISM: Mus musculus

<400> SEQUENCE: 240

Gly Ala Ser Ser Leu Glu Asp
1               5

<210> SEQ ID NO 241
<211> LENGTH: 11
<212> TYPE: PRT
<213> ORGANISM: Mus musculus

<400> SEQUENCE: 241

Leu Gln His Ser Tyr Leu Pro Pro Leu Thr Phe
1               5                   10

<210> SEQ ID NO 242
<211> LENGTH: 5
<212> TYPE: PRT
<213> ORGANISM: Mus musculus

<400> SEQUENCE: 242

Thr Tyr Asp Leu His
1               5

<210> SEQ ID NO 243
<211> LENGTH: 16
<212> TYPE: PRT
<213> ORGANISM: Mus musculus

<400> SEQUENCE: 243

Val Ile Trp Ser Gly Gly Ser Thr Asp Tyr Asn Ala Ala Phe Ile Ser
1               5                   10                  15

<210> SEQ ID NO 244
<211> LENGTH: 11
<212> TYPE: PRT
<213> ORGANISM: Mus musculus

<400> SEQUENCE: 244

Asn Tyr Gly Tyr Ser Ala Trp Phe Ala Tyr Trp
1               5                   10

<210> SEQ ID NO 245
<211> LENGTH: 15
<212> TYPE: PRT
<213> ORGANISM: Mus musculus

<400> SEQUENCE: 245

Ala Ser Ile Ser Cys Arg Ser Ser Gln Ser Ile Val His Ser Asn
1               5                   10                  15

<210> SEQ ID NO 246
<211> LENGTH: 7
<212> TYPE: PRT
```

<213> ORGANISM: Mus musculus

<400> SEQUENCE: 246

Lys Val Ser Asn Arg Phe Ser
1               5

<210> SEQ ID NO 247
<211> LENGTH: 9
<212> TYPE: PRT
<213> ORGANISM: Mus musculus

<400> SEQUENCE: 247

Phe Gln Gly Ser His Val Pro Leu Thr
1               5

<210> SEQ ID NO 248
<211> LENGTH: 5
<212> TYPE: PRT
<213> ORGANISM: Mus musculus

<400> SEQUENCE: 248

Ala Tyr Ser Met His
1               5

<210> SEQ ID NO 249
<211> LENGTH: 17
<212> TYPE: PRT
<213> ORGANISM: Mus musculus

<400> SEQUENCE: 249

Trp Ile Asn Thr Glu Thr Gly Glu Pro Thr Tyr Thr Asp Asp Phe Lys
1               5                   10                  15

Gly

<210> SEQ ID NO 250
<211> LENGTH: 11
<212> TYPE: PRT
<213> ORGANISM: Mus musculus

<400> SEQUENCE: 250

Arg Ile Tyr Tyr Phe Gly Arg Gly Gly Phe Asp
1               5                   10

<210> SEQ ID NO 251
<211> LENGTH: 15
<212> TYPE: PRT
<213> ORGANISM: Mus musculus

<400> SEQUENCE: 251

Ser Ser Ile Ser Cys Arg Ser Ser Gln Ser Ile Val His Ser Asn
1               5                   10                  15

<210> SEQ ID NO 252
<211> LENGTH: 7
<212> TYPE: PRT
<213> ORGANISM: Mus musculus

<400> SEQUENCE: 252

Lys Val Ser Asn Arg Phe Ser
1               5

<210> SEQ ID NO 253
<211> LENGTH: 9
<212> TYPE: PRT

<213> ORGANISM: Mus musculus

<400> SEQUENCE: 253

Phe Gln Gly Ser His Val Pro Tyr Thr
1               5

<210> SEQ ID NO 254
<211> LENGTH: 5
<212> TYPE: PRT
<213> ORGANISM: Mus musculus

<400> SEQUENCE: 254

Asn Ser Trp Phe Asn
1               5

<210> SEQ ID NO 255
<211> LENGTH: 19
<212> TYPE: PRT
<213> ORGANISM: Mus musculus

<400> SEQUENCE: 255

Glu Ile Arg Leu Thr Ser Asp Asn Tyr Ala Ile Tyr Tyr Ala Glu Ser
1               5                   10                  15

Val Lys Gly

<210> SEQ ID NO 256
<211> LENGTH: 11
<212> TYPE: PRT
<213> ORGANISM: Mus musculus

<400> SEQUENCE: 256

Pro Glu Thr Ala Arg Ala Thr Phe Ala Tyr Trp
1               5                   10

<210> SEQ ID NO 257
<211> LENGTH: 15
<212> TYPE: PRT
<213> ORGANISM: Mus musculus

<400> SEQUENCE: 257

Ala Ser Ile Ser Cys Arg Ser Ser Gln Ser Ile Val His Ser Asn
1               5                   10                  15

<210> SEQ ID NO 258
<211> LENGTH: 7
<212> TYPE: PRT
<213> ORGANISM: Mus musculus

<400> SEQUENCE: 258

Lys Val Phe Asn Arg Phe Ser
1               5

<210> SEQ ID NO 259
<211> LENGTH: 9
<212> TYPE: PRT
<213> ORGANISM: Mus musculus

<400> SEQUENCE: 259

Phe Gln Gly Ser His Val Pro Arg Thr
1               5

<210> SEQ ID NO 260
<211> LENGTH: 5
<212> TYPE: PRT

<213> ORGANISM: Mus musculus

<400> SEQUENCE: 260

Ala Tyr Tyr Met His
1               5

<210> SEQ ID NO 261
<211> LENGTH: 17
<212> TYPE: PRT
<213> ORGANISM: Mus musculus

<400> SEQUENCE: 261

Arg Val Asn Pro Asn Asn Gly Gly Thr Thr Tyr Asn Gln Lys Phe Lys
1               5                   10                  15
Gly

<210> SEQ ID NO 262
<211> LENGTH: 11
<212> TYPE: PRT
<213> ORGANISM: Mus musculus

<400> SEQUENCE: 262

Arg Ile Tyr Tyr Gly Tyr Phe Asp Tyr Trp Gly
1               5                   10

<210> SEQ ID NO 263
<211> LENGTH: 15
<212> TYPE: PRT
<213> ORGANISM: Mus musculus

<400> SEQUENCE: 263

Lys Ala Ser Gln Ser Val Asp Tyr Asp Gly Asp Ser Tyr Met Asn
1               5                   10                  15

<210> SEQ ID NO 264
<211> LENGTH: 7
<212> TYPE: PRT
<213> ORGANISM: Mus musculus

<400> SEQUENCE: 264

Val Ala Ser Asn Leu Glu Ser
1               5

<210> SEQ ID NO 265
<211> LENGTH: 9
<212> TYPE: PRT
<213> ORGANISM: Mus musculus

<400> SEQUENCE: 265

Gln Gln Ser Asn Glu Asp Pro Tyr Thr
1               5

<210> SEQ ID NO 266
<211> LENGTH: 4
<212> TYPE: PRT
<213> ORGANISM: Mus musculus

<400> SEQUENCE: 266

Asp Ile Tyr Met
1

<210> SEQ ID NO 267
<211> LENGTH: 17
<212> TYPE: PRT

<213> ORGANISM: Mus musculus

<400> SEQUENCE: 267

Lys Ile Asp Pro Ala Asn Gly Asn Thr Lys Tyr Asp Pro Lys Phe Gln
1               5                   10                  15
Gly

<210> SEQ ID NO 268
<211> LENGTH: 11
<212> TYPE: PRT
<213> ORGANISM: Mus musculus

<400> SEQUENCE: 268

Thr Gly Asp Tyr Trp Gly Gln Gly Thr Thr Val
1               5                   10

<210> SEQ ID NO 269
<211> LENGTH: 15
<212> TYPE: PRT
<213> ORGANISM: Mus musculus

<400> SEQUENCE: 269

Thr Met Ser Cys Lys Ser Ser Gln Ser Leu Leu Asn Ser Arg Thr
1               5                   10                  15

<210> SEQ ID NO 270
<211> LENGTH: 7
<212> TYPE: PRT
<213> ORGANISM: Mus musculus

<400> SEQUENCE: 270

Trp Ala Ser Thr Arg Glu Ser
1               5

<210> SEQ ID NO 271
<211> LENGTH: 9
<212> TYPE: PRT
<213> ORGANISM: Mus musculus

<400> SEQUENCE: 271

Arg Gln Ser Tyr Asn Leu Val Thr Phe
1               5

<210> SEQ ID NO 272
<211> LENGTH: 5
<212> TYPE: PRT
<213> ORGANISM: Mus musculus

<400> SEQUENCE: 272

Ser Tyr Val Met His
1               5

<210> SEQ ID NO 273
<211> LENGTH: 17
<212> TYPE: PRT
<213> ORGANISM: Mus musculus

<400> SEQUENCE: 273

Tyr Ile Asn Pro Tyr Asn Asp Gly Thr Lys Tyr Asn Glu Lys Phe Lys
1               5                   10                  15
Gly

<210> SEQ ID NO 274

```
<210> SEQ ID NO 274
<211> LENGTH: 11
<212> TYPE: PRT
<213> ORGANISM: Mus musculus

<400> SEQUENCE: 274

Arg Tyr Tyr Tyr Gly Ser Ser Gly Gly Tyr Phe
1               5                   10

<210> SEQ ID NO 275
<211> LENGTH: 15
<212> TYPE: PRT
<213> ORGANISM: Mus musculus

<400> SEQUENCE: 275

Arg Ala Ser Lys Ser Ile Ser Lys Tyr Leu Ala Trp Tyr Gln Glu
1               5                   10                  15

<210> SEQ ID NO 276
<211> LENGTH: 7
<212> TYPE: PRT
<213> ORGANISM: Mus musculus

<400> SEQUENCE: 276

Ser Gly Ser Thr Leu Gln Ser
1               5

<210> SEQ ID NO 277
<211> LENGTH: 9
<212> TYPE: PRT
<213> ORGANISM: Mus musculus

<400> SEQUENCE: 277

Gln Gln His Asn Glu Tyr Pro Tyr Thr
1               5

<210> SEQ ID NO 278
<211> LENGTH: 5
<212> TYPE: PRT
<213> ORGANISM: Mus musculus

<400> SEQUENCE: 278

Gly Tyr Phe Met Asn
1               5

<210> SEQ ID NO 279
<211> LENGTH: 17
<212> TYPE: PRT
<213> ORGANISM: Mus musculus

<400> SEQUENCE: 279

Arg Ile Asn Pro Tyr Asn Gly Asp Thr Phe Tyr Asn Gln Lys Phe Lys
1               5                   10                  15

Gly

<210> SEQ ID NO 280
<211> LENGTH: 11
<212> TYPE: PRT
<213> ORGANISM: Mus musculus

<400> SEQUENCE: 280

Arg Ile His Tyr Tyr Tyr Gly Ser Ser Tyr Tyr
1               5                   10

<210> SEQ ID NO 281
```

```
<211> LENGTH: 15
<212> TYPE: PRT
<213> ORGANISM: Mus musculus

<400> SEQUENCE: 281

Arg Ala Ser Lys Ser Ile Ser Lys Tyr Leu Ala Trp Tyr Gln Glu
1               5                   10                  15

<210> SEQ ID NO 282
<211> LENGTH: 7
<212> TYPE: PRT
<213> ORGANISM: Mus musculus

<400> SEQUENCE: 282

Ser Gly Ser Thr Leu Gln Ser
1               5

<210> SEQ ID NO 283
<211> LENGTH: 9
<212> TYPE: PRT
<213> ORGANISM: Mus musculus

<400> SEQUENCE: 283

Gln Gln His Asn Glu Tyr Pro Trp Thr
1               5

<210> SEQ ID NO 284
<211> LENGTH: 5
<212> TYPE: PRT
<213> ORGANISM: Mus musculus

<400> SEQUENCE: 284

Glu Tyr Ile Ile His
1               5

<210> SEQ ID NO 285
<211> LENGTH: 17
<212> TYPE: PRT
<213> ORGANISM: Mus musculus

<400> SEQUENCE: 285

Trp Phe Tyr Pro Gly Ser Gly Ser Ile Lys Tyr Asn Glu Lys Phe Lys
1               5                   10                  15

Asp

<210> SEQ ID NO 286
<211> LENGTH: 11
<212> TYPE: PRT
<213> ORGANISM: Mus musculus

<400> SEQUENCE: 286

His Glu Val Tyr Tyr Asp Tyr Asp Lys Ser Met
1               5                   10

<210> SEQ ID NO 287
<211> LENGTH: 15
<212> TYPE: PRT
<213> ORGANISM: Mus musculus

<400> SEQUENCE: 287

Leu Tyr Ser Ser Asn Gln Lys Asn Tyr Leu Ala Trp Tyr Gln Gln
1               5                   10                  15

<210> SEQ ID NO 288
```

```
<211> LENGTH: 7
<212> TYPE: PRT
<213> ORGANISM: Mus musculus

<400> SEQUENCE: 288

Trp Ala Ser Thr Arg Glu Ser
1               5

<210> SEQ ID NO 289
<211> LENGTH: 9
<212> TYPE: PRT
<213> ORGANISM: Mus musculus

<400> SEQUENCE: 289

Gln Gln Tyr Tyr Ser Tyr Pro Tyr Thr
1               5

<210> SEQ ID NO 290
<211> LENGTH: 5
<212> TYPE: PRT
<213> ORGANISM: Mus musculus

<400> SEQUENCE: 290

Asn Tyr Leu Ile Glu
1               5

<210> SEQ ID NO 291
<211> LENGTH: 19
<212> TYPE: PRT
<213> ORGANISM: Mus musculus

<400> SEQUENCE: 291

Val Ile Asn Pro Lys Ser Gly Gly Thr Lys Tyr Asn Glu Lys Phe Arg
1               5                   10                  15

Gly Lys Ala

<210> SEQ ID NO 292
<211> LENGTH: 11
<212> TYPE: PRT
<213> ORGANISM: Mus musculus

<400> SEQUENCE: 292

Thr Gly Thr Asp Tyr Trp Gly Gln Gly Thr Thr
1               5                   10

<210> SEQ ID NO 293
<211> LENGTH: 10
<212> TYPE: PRT
<213> ORGANISM: Mus musculus

<400> SEQUENCE: 293

Val Thr Ile Ser Cys Ser Ala Ser Gln Gly
1               5                   10

<210> SEQ ID NO 294
<211> LENGTH: 7
<212> TYPE: PRT
<213> ORGANISM: Mus musculus

<400> SEQUENCE: 294

Tyr Thr Ser Ser Leu Arg Ser
1               5

<210> SEQ ID NO 295
```

-continued

```
<211> LENGTH: 9
<212> TYPE: PRT
<213> ORGANISM: Mus musculus

<400> SEQUENCE: 295

Gln Gln Tyr Ser Lys Leu Pro Arg Thr
1               5

<210> SEQ ID NO 296
<211> LENGTH: 12
<212> TYPE: PRT
<213> ORGANISM: Homo sapiens

<400> SEQUENCE: 296

Phe Thr Ser Gly Glu Lys Glu Gln Val Asp Glu Trp
1               5                   10

<210> SEQ ID NO 297
<211> LENGTH: 16
<212> TYPE: PRT
<213> ORGANISM: Homo sapiens

<400> SEQUENCE: 297

Ala Glu Gln Lys Arg Leu Lys Thr Val Leu Glu Leu Gln Tyr Val Leu
1               5                   10                  15

<210> SEQ ID NO 298
<211> LENGTH: 16
<212> TYPE: PRT
<213> ORGANISM: Homo sapiens

<400> SEQUENCE: 298

Val Glu Arg Val Phe Gln Ser Asn Tyr Phe Asp Ser Thr His Asn His
1               5                   10                  15

<210> SEQ ID NO 299
<211> LENGTH: 16
<212> TYPE: PRT
<213> ORGANISM: Homo sapiens

<400> SEQUENCE: 299

Phe Gln Ser Met Gln Thr Val Phe Asn Met Asn Ala Pro Val Pro Pro
1               5                   10                  15

<210> SEQ ID NO 300
<211> LENGTH: 5
<212> TYPE: PRT
<213> ORGANISM: Mus musculus

<400> SEQUENCE: 300

Thr Asn Ala Met Asn
1               5

<210> SEQ ID NO 301
<211> LENGTH: 17
<212> TYPE: PRT
<213> ORGANISM: Mus musculus

<400> SEQUENCE: 301

Arg Ile Arg Ser Lys Ser Asn Asn Tyr Ala Thr Tyr Tyr Ala Asp Ser
1               5                   10                  15

Val

<210> SEQ ID NO 302
```

```
<211> LENGTH: 11
<212> TYPE: PRT
<213> ORGANISM: Mus musculus

<400> SEQUENCE: 302

Asp Trp Asp Gly Phe Leu Tyr Phe Asp Tyr Trp
1               5                   10

<210> SEQ ID NO 303
<211> LENGTH: 112
<212> TYPE: PRT
<213> ORGANISM: Mus musculus

<400> SEQUENCE: 303

Gly Gly Gly Leu Val Gln Pro Lys Gly Ser Leu Lys Leu Ser Cys Ala
1               5                   10                  15

Ala Ser Gly Phe Thr Phe Asn Thr Asn Ala Met Asn Trp Val Arg Gln
            20                  25                  30

Ala Pro Gly Lys Gly Leu Glu Trp Val Ala Arg Ile Arg Ser Lys Ser
        35                  40                  45

Asn Asn Tyr Ala Thr Tyr Tyr Ala Asp Ser Val Lys Asp Arg Phe Thr
    50                  55                  60

Ile Ser Arg Asp Asp Ser Gln Ser Met Leu Tyr Leu Gln Met Asn Asn
65                  70                  75                  80

Leu Lys Thr Glu Asp Thr Ala Met Tyr Tyr Cys Val Arg Asp Trp Asp
                85                  90                  95

Gly Phe Leu Tyr Phe Asp Tyr Trp Ala Lys His His Leu Thr Leu Phe
            100                 105                 110

<210> SEQ ID NO 304
<211> LENGTH: 15
<212> TYPE: PRT
<213> ORGANISM: Mus musculus

<400> SEQUENCE: 304

Ser Val Ser Thr Ser Gly Tyr Ser Tyr Met His Trp Asn Gln Gln
1               5                   10                  15

<210> SEQ ID NO 305
<211> LENGTH: 7
<212> TYPE: PRT
<213> ORGANISM: Mus musculus

<400> SEQUENCE: 305

Leu Val Ser Asn Leu Glu Ser
1               5

<210> SEQ ID NO 306
<211> LENGTH: 9
<212> TYPE: PRT
<213> ORGANISM: Mus musculus

<400> SEQUENCE: 306

Gln His Ile Arg Glu Leu Thr Arg Ser
1               5

<210> SEQ ID NO 307
<211> LENGTH: 104
<212> TYPE: PRT
<213> ORGANISM: Mus musculus

<400> SEQUENCE: 307
```

```
Thr Gln Ser Pro Ala Ser Leu Ala Val Ser Leu Gly Gln Arg Ala Thr
1               5                   10                  15

Ile Ser Tyr Arg Ala Ser Lys Ser Val Ser Thr Ser Gly Tyr Ser Tyr
                20                  25                  30

Met His Trp Asn Gln Gln Lys Pro Gly Gln Pro Pro Arg Leu Leu Ile
            35                  40                  45

Tyr Leu Val Ser Asn Leu Glu Ser Gly Val Pro Ala Arg Phe Ser Gly
    50                  55                  60

Ser Gly Ser Gly Thr Asp Phe Thr Leu Asn Ile His Pro Val Glu Glu
65                  70                  75                  80

Glu Asp Ala Ala Thr Tyr Tyr Cys Gln His Ile Arg Glu Leu Thr Arg
                85                  90                  95

Ser Glu Gly Gly Pro Ser Trp Lys
                100

<210> SEQ ID NO 308
<211> LENGTH: 14
<212> TYPE: PRT
<213> ORGANISM: Homo sapiens

<400> SEQUENCE: 308

Pro Pro Val Asn Glu Pro Glu Thr Leu Lys Gln Gln Asn Gln
1               5                   10

<210> SEQ ID NO 309
<211> LENGTH: 12
<212> TYPE: PRT
<213> ORGANISM: Homo sapiens

<400> SEQUENCE: 309

Glu Thr Leu Lys Gln Gln Asn Gln Tyr Gln Ala Ser
1               5                   10
```

CONJUGATE OF CAPRIN-1 ANTIBODY LINKED TO IMMUNE ACTIVATOR FOR CANCER TREATMENT

REFERENCE TO SEQUENCE LISTING SUBMITTED VIA EFS-WEB

This application includes an electronically submitted sequence listing in .txt format. The txt file contains a sequence listing entitled "2019 Apr. 24 SequenceListing 1254-0620PUS1" created on Apr. 19, 2019, and is 38,839 bytes in size. The sequence listing contained in this.txt file is part of the specification and is hereby incorporated by reference herein in its entirety.

TECHNICAL FIELD

The present invention relates to a conjugate of an antibody against a CAPRIN-1 protein and an immune activator, and medical use thereof as a therapeutic and/or preventive agent for a cancer, etc.

BACKGROUND ART

Various antibody drugs targeting specific antigenic proteins on cancer cells are applied as therapeutic drugs for cancers with fewer adverse reactions to cancer treatment because of their cancer specificity. For example, cytoplasmic-activation and proliferation-associated protein 1 (CAPRIN-1) is expressed on the cell membrane surface of many solid cancers, and antibodies against this CAPRIN-1 protein have been known to be promising in medical use for the treatment and/or prevention of cancers (Patent Literature 1).

In recent years, studies have been made to enhance the pharmacological effects of the antibody drugs. Particularly, antibody-drug conjugates (ADCs) in which an antibody is conjugated with a drug having the strong ability to directly kill cells have been actively developed (Non Patent Literatures 1 and 2). As examples of ADCs, Kadcyla® (trastuzumab emtansine) comprising an existing antibody drug trastuzumab linked to a drug emtansine (DM1) which exhibits a cell-killing activity, and Adcetris® (brentuximab vedotin) comprising an anti-CD30 monoclonal antibody linked to monomethyl auristatin E (MMAE) are used in the treatment of some cancers. These ADCs have been found to prolong survival rates as compared with conventional treatment methods and found to be useful over existing methods for treating cancers (Non Patent Literatures 3 and 4).

In other cases, studies have also been made in an attempt to enhance pharmacological effects by conjugating immune activators to antibody drugs against cancers. For example, a conjugate of an existing antibody drug trastuzumab or cetuximab with resiquimod, one of the immune activators, or conjugates of an antibody drug rituximab against CD20 as a target antigen with various immune activators have been found to have an effect of enhancing the pharmacological effect of the antibody in animal models (Patent Literatures 2 and 3).

As described above, attempts have been made to enhance the pharmacological effects of antibody drugs against cancers by conjugating various factors to various antibodies. However, antitumor effects strong enough to completely regress various cancers have not yet been obtained. Furthermore, effects of preventing cancer recurrence or metastasis, etc. have not been found.

CITATION LIST

Patent Literature

Patent Literature 1: WO2010/016526
Patent Literature 2: WO2014/012479
Patent Literature 3: U.S. Pat. No. 8,951,528

Non Patent Literature

Non Patent Literature 1: Lancet Oncol 2016; 17: e254-62
Non Patent Literature 2: Pharm Res. 2015 November; 32 (11): 3526-40
Non Patent Literature 3: New England Journal of Medicine 367; 19 (8), 2012, p. 1783-1791.
Non Patent Literature 4: MAbs 2012; 4 (4): 458-65

SUMMARY OF INVENTION

Technical Problem

An object of the present invention is to provide a solution to enhance the antitumor effect of an antibody or a fragment thereof against a CAPRIN-1 protein expressed on the cell membrane surface of cancer cells.

Solution to Problem

The present inventor has conducted diligent studies and consequently completed the present invention by finding that: a conjugate of an antibody or a fragment thereof against a CAPRIN-1 protein and an immune activator exerts a much stronger antitumor effect than that of the antibody against the CAPRIN-1 protein or the fragment thereof used alone; and the effect of enhancing the antitumor effect by conjugating the antibody against the CAPRIN-1 protein or the fragment thereof to the immune activator is much superior to the effect of enhancing the antitumor effect by conjugating an existing antibody drug for a cancer to the immune activator.

Specifically, the present invention has the following features (1) to (14):

(1) A conjugate of an antibody or a fragment thereof linked to an immune activator, wherein the antibody or the fragment thereof has immunological reactivity with a CAPRIN-1 protein having an amino acid sequence represented by any of even-numbered SEQ ID NOs among SEQ ID NOs: 2 to 30 or an amino acid sequence having 80% or more sequence identity to the amino acid sequence.

(2) The conjugate according to (1), wherein the antibody or the fragment thereof has immunological reactivity with a partial polypeptide of the CAPRIN-1 protein, wherein the partial polypeptide has an amino acid sequence represented by any of SEQ ID NOs: 31 to 35 and 296 to 299, 308, and 309 or an amino acid sequence having 80% or more sequence identity to the amino acid sequence.

(3) The conjugate according to (1) or (2), wherein the antibody is a monoclonal antibody or a polyclonal antibody.

(4) The conjugate according to any of (1) to (3), wherein the antibody or the fragment thereof is any of the following (A) to (M):

(A) an antibody or a fragment thereof, which comprises a heavy chain variable region comprising complementarity-determining regions of SEQ ID NOs: 36, 37, and 38 (CDR1, CDR2, and CDR3, respectively) and a light chain variable region comprising complementarity-determining regions of SEQ ID NOs: 40, 41, and 42

(CDR1, CDR2, and CDR3, respectively) and has immunological reactivity with the CAPRIN-1 protein, (B) an antibody or a fragment thereof, which comprises a heavy chain variable region comprising complementarity-determining regions of SEQ ID NOs: 44, 45, and 46 (CDR1, CDR2, and CDR3, respectively) and a light chain variable region comprising complementarity-determining regions of SEQ ID NOs: 48, 49, and 50 (CDR1, CDR2, and CDR3, respectively) and has immunological reactivity with the CAPRIN-1 protein, (C) an antibody or a fragment thereof, which comprises a heavy chain variable region comprising complementarity-determining regions of SEQ ID NOs: 52, 53, and 54 (CDR1, CDR2, and CDR3, respectively) and a light chain variable region comprising complementarity-determining regions of SEQ ID NOs: 56, 57, and 58 (CDR1, CDR2, and CDR3, respectively) and has immunological reactivity with the CAPRIN-1 protein, (D) an antibody or a fragment thereof, which comprises a heavy chain variable region comprising complementarity-determining regions of SEQ ID NOs: 60, 61, and 62 (CDR1, CDR2, and CDR3, respectively) and a light chain variable region comprising complementarity-determining regions of SEQ ID NOs: 64, 65, and 66 (CDR1, CDR2, and CDR3, respectively) and has immunological reactivity with the CAPRIN-1 protein, (E) an antibody or a fragment thereof, which comprises a heavy chain variable region comprising complementarity-determining regions of SEQ ID NOs: 170, 171, and 172 (CDR1, CDR2, and CDR3, respectively) and a light chain variable region comprising complementarity-determining regions of SEQ ID NOs: 173, 174, and 175 (CDR1, CDR2, and CDR3, respectively) and has immunological reactivity with the CAPRIN-1 protein, (F) an antibody or a fragment thereof, which comprises a heavy chain variable region comprising complementarity-determining regions of SEQ ID NOS: 176, 177, and 178 (CDR1, CDR2, and CDR3, respectively) and a light chain variable region comprising complementarity-determining regions of SEQ ID NOs: 179, 180, and 181 (CDR1, CDR2, and CDR3, respectively) and has immunological reactivity with the CAPRIN-1 protein, (G) an antibody or a fragment thereof, which comprises a heavy chain variable region comprising complementarity-determining regions of SEQ ID NOs: 182, 183, and 184 (CDR1, CDR2, and CDR3, respectively) and a light chain variable region comprising complementarity-determining regions of SEQ ID NOs: 185, 186, and 187 (CDR1, CDR2, and CDR3, respectively) and has immunological reactivity with the CAPRIN-1 protein, (H) an antibody or a fragment thereof, which comprises a heavy chain variable region comprising complementarity-determining regions of SEQ ID NOs: 188, 189, and 190 (CDR1, CDR2, and CDR3, respectively) and a light chain variable region comprising complementarity-determining regions of SEQ ID NOs: 191, 192, and 193 (CDR1, CDR2, and CDR3, respectively) and has immunological reactivity with the CAPRIN-1 protein, (I) an antibody or a fragment thereof, which comprises a heavy chain variable region comprising complementarity-determining regions of SEQ ID NOs: 146, 147, and 148 (CDR1, CDR2, and CDR3, respectively) and a light chain variable region comprising complementarity-determining regions of SEQ ID NOs: 149, 150, and 151 (CDR1, CDR2, and CDR3, respectively) and has immunological reactivity with the CAPRIN-1 protein, (J) an antibody or a fragment thereof, which comprises a heavy chain variable region comprising complementarity-determining regions of SEQ ID NOs: 272, 273, and 274 (CDR1, CDR2, and CDR3, respectively) and a light chain variable region comprising complementarity-determining regions of SEQ ID NOs: 275, 276, and 277 (CDR1, CDR2, and CDR3, respectively) and has immunological reactivity with the CAPRIN-1 protein, (K) an antibody or a fragment thereof, which comprises a heavy chain variable region comprising complementarity-determining regions of SEQ ID NOs: 290, 291, and 292 (CDR1, CDR2, and CDR3, respectively) and a light chain variable region comprising complementarity-determining regions of SEQ ID NOs: 293, 294, and 295 (CDR1, CDR2, and CDR3, respectively) and has immunological reactivity with the CAPRIN-1 protein, (L) an antibody or a fragment thereof, which comprises a heavy chain variable region comprising complementarity-determining regions of SEQ ID NOs: 300304, 301302, and 302303 (CDR1, CDR2, and CDR3, respectively) and a light chain variable region comprising complementarity-determining regions of SEQ ID NOs: 304305, 305306, and 306307 (CDR1, CDR2, and CDR3, respectively) and has immunological reactivity with the CAPRIN-1 protein, and (M) an antibody or a fragment thereof, which comprises a heavy chain variable region comprising complementarity-determining regions of SEQ ID NOs: 134, 135, and 136 (CDR1, CDR2, and CDR3, respectively) and a light chain variable region comprising complementarity-determining regions of SEQ ID NOs: 137, 138, and 139 (CDR1, CDR2, and CDR3, respectively) and has immunological reactivity with the CAPRIN-1 protein.

(5) The conjugate according to any of (1) to (4), wherein the antibody or the fragment thereof is any of the following (a) to (al);

(a) an antibody or a fragment thereof, comprising a heavy chain variable region comprising the amino acid sequence of SEQ ID NO: 39 and a light chain variable region comprising the amino acid sequence of SEQ ID NO: 43, (b) an antibody or a fragment thereof, comprising a heavy chain variable region comprising the amino acid sequence of SEQ ID NO: 47 and a light chain variable region comprising the amino acid sequence of SEQ ID NO: 51, (c) an antibody or a fragment thereof, comprising a heavy chain variable region comprising the amino acid sequence of SEQ ID NO: 55 and a light chain variable region comprising the amino acid sequence of SEQ ID NO: 59, (d) an antibody or a fragment thereof, comprising a heavy chain variable region comprising the amino acid sequence of SEQ ID NO: 63 and a light chain variable region comprising the amino acid sequence of SEQ ID NO: 67, (e) an antibody or a fragment thereof, comprising a heavy chain variable region comprising the amino acid sequence of SEQ ID NO: 68 and a light chain variable region comprising the amino acid sequence of SEQ ID NO: 69,
(f) an antibody or a fragment thereof, comprising a heavy chain variable region comprising the amino acid sequence of SEQ ID NO: 70 and a light chain variable region comprising the amino acid sequence of SEQ ID NO: 71,
(g) an antibody or a fragment thereof, comprising a heavy chain variable region comprising the amino acid sequence of SEQ ID NO: 72 and a light chain variable region comprising the amino acid sequence of SEQ ID NO: 73,
(h) an antibody or a fragment thereof, comprising a heavy chain variable region comprising the amino acid sequence of SEQ ID NO: 74 and a light chain variable region comprising the amino acid sequence of SEQ ID NO: 75,
(i) an antibody or a fragment thereof, comprising a heavy chain variable region comprising the amino acid sequence of SEQ ID NO: 76 and a light chain variable region comprising the amino acid sequence of SEQ ID NO: 77,
(j) an antibody or a fragment thereof, comprising a heavy chain variable region comprising the amino acid sequence of SEQ ID NO: 78 and a light chain variable region comprising the amino acid sequence of SEQ ID NO: 79,
(k) an antibody or a fragment thereof, comprising a heavy chain variable region comprising the amino acid sequence of SEQ ID NO: 80 and a light chain variable region comprising the amino acid sequence of SEQ ID NO: 81,
(l) an antibody or a fragment thereof, comprising a heavy chain variable region comprising the amino acid sequence of SEQ ID NO: 82 and a light chain variable region comprising the amino acid sequence of SEQ ID NO: 83,
(m) an antibody or a fragment thereof, comprising a heavy chain variable region comprising the amino acid sequence of SEQ ID NO: 84 and a light chain variable region comprising the amino acid sequence of SEQ ID NO: 85,
(n) an antibody or a fragment thereof, comprising a heavy chain variable region comprising the amino acid sequence of SEQ ID NO: 86 and a light chain variable region comprising the amino acid sequence of SEQ ID NO: 87,
(o) an antibody or a fragment thereof, comprising a heavy chain variable region comprising the amino acid sequence of SEQ ID NO: 88 and a light chain variable region comprising the amino acid sequence of SEQ ID NO: 89,
(p) an antibody or a fragment thereof, comprising a heavy chain variable region comprising the amino acid sequence of SEQ ID NO: 90 and a light chain variable region comprising the amino acid sequence of SEQ ID NO: 91,
(q) an antibody or a fragment thereof, comprising a heavy chain variable region comprising the amino acid sequence of SEQ ID NO: 92 and a light chain variable region comprising the amino acid sequence of SEQ ID NO: 93,
(r) an antibody or a fragment thereof, comprising a heavy chain variable region comprising the amino acid sequence of SEQ ID NO: 94 and a light chain variable region comprising the amino acid sequence of SEQ ID NO: 95,
(s) an antibody or a fragment thereof, comprising a heavy chain variable region comprising the amino acid sequence of SEQ ID NO: 96 and a light chain variable region comprising the amino acid sequence of SEQ ID NO: 97,
(t) an antibody or a fragment thereof, comprising a heavy chain variable region comprising the amino acid sequence of SEQ ID NO: 98 and a light chain variable region comprising the amino acid sequence of SEQ ID NO: 99 (u) an antibody or a fragment thereof, comprising a heavy chain variable region comprising the amino acid sequence of SEQ ID NO: 100 and a light chain variable region comprising the amino acid sequence of SEQ ID NO: 101,
(v) an antibody or a fragment thereof, comprising a heavy chain variable region comprising the amino acid sequence of SEQ ID NO: 102 and a light chain variable region comprising the amino acid sequence of SEQ ID NO: 103,
(w) an antibody or a fragment thereof, comprising a heavy chain variable region comprising the amino acid sequence of SEQ ID NO: 104 and a light chain variable region comprising the amino acid sequence of SEO ID NO: 105
(x) an antibody or a fragment thereof, comprising a heavy chain variable region comprising the amino acid sequence of SEQ ID NO: 106 and a light chain variable region comprising the amino acid sequence of SEQ ID NO: 107,
(y) an antibody or a fragment thereof, comprising a heavy chain variable region comprising the amino acid sequence of SEQ ID NO: 108 and a light chain variable region comprising the amino acid sequence of SEQ ID NO: 109,
(z) an antibody or a fragment thereof, comprising a heavy chain variable region comprising the amino acid sequence of SEQ ID NO: 110 and a light chain variable region comprising the amino acid sequence of SEQ ID NO: 111,
(aa) an antibody or a fragment thereof, comprising a heavy chain variable region comprising the amino acid sequence of SEQ ID NO: 112 and a light chain variable region comprising the amino acid sequence of SEQ ID NO: 113,
(ab) an antibody or a fragment thereof, comprising a heavy chain variable region comprising the amino acid sequence of SEQ ID NO: 114 and a light chain variable region comprising the amino acid sequence of SEQ ID NO: 115,
(ac) an antibody or a fragment thereof, comprising a heavy chain variable region comprising the amino acid sequence of SEQ ID NO: 116 and a light chain variable region comprising the amino acid sequence of SEQ ID NO: 117,
(ad) an antibody or a fragment thereof, comprising a heavy chain variable region comprising the amino acid sequence of SEQ ID NO: 118 and a light chain variable region comprising the amino acid sequence of SEQ ID NO: 119,
(ae) an antibody or a fragment thereof, comprising a heavy chain variable region comprising the amino acid sequence of SEQ ID NO: 120 and a light chain variable region comprising the amino acid sequence of SEQ ID NO: 121, (af) an antibody or a fragment thereof, comprising a heavy chain variable region comprising the amino acid sequence of SEQ ID NO: 122 and a light chain variable region comprising the amino acid sequence of SEQ ID NO: 123, (ag) an antibody or a fragment thereof, comprising a heavy chain variable region comprising the amino acid sequence of SEQ ID NO: 124 and a light chain variable region comprising the amino acid sequence of SEQ ID NO: 125, (ah) an antibody or a fragment thereof, comprising a heavy chain variable region comprising the amino acid sequence of SEQ ID NO: 126 and a light chain variable region comprising the amino acid sequence of SEQ ID NO: 127, (ai) an antibody or a fragment thereof, comprising a heavy chain variable region comprising the amino acid sequence of SEQ ID NO: 128 and a light chain variable region comprising the amino acid sequence of SEQ ID NO: 129, (aj) an antibody or a fragment thereof, comprising a heavy chain variable region comprising the amino acid sequence of SEQ ID NO: 130 and a light chain variable region comprising the amino acid sequence of SEQ ID NO: 131, (ak) an antibody or a fragment thereof, comprising a heavy chain variable region comprising the amino acid sequence of SEQ ID NO: 132 and a light chain variable region comprising the amino acid sequence of SEQ ID NO: 133, and (al) an antibody or a fragment thereof, comprising a heavy chain variable region comprising the amino acid sequence of SEQ ID NO: 303 and a light chain variable region comprising the amino acid sequence of SEQ ID NO: 307.

(6) The conjugate according to any of (1) to (5), wherein the antibody is a human antibody, a humanized antibody, a chimeric antibody, or a single-chain antibody.

(7) The conjugate according to any of (1) to (6), wherein the immune activator is a ligand or an agonist binding to Toll-like receptor (TLR), NOD-like receptor (NLR), RIG-like receptor, or C-type lectin receptor (CLR).

(8) The conjugate according to (7), wherein the Toll-like receptor (TLR) is TLR2, TLR3, TLR4, TLR5, TLR7, TLR8, TLR9, or TLR10.

(9) The conjugate according to (7) or (8), wherein the ligand or the agonist binding to the Toll-like receptor (TLR), or a derivative thereof is any of the following (1) to (vii):

(i) a TLR2-binding ligand or agonist selected from the group consisting of peptidoglycan, lipoprotein, lipopolysaccharide, and zymosan, (ii) a TLR3-binding ligand or agonist selected from the group consisting of poly(I: C) and poly(A: U), (iii) a TLR4-binding ligand or agonist selected from the group consisting of lipopolysaccharide (LPS), HSP60, RS09, and MPLA, (iv) a TLR5-binding ligand or agonist selected from the group consisting of flagellin and FLA, (v) a TLR7- or TLR8-binding ligand or agonist selected from the group consisting of an imidazoquinoline compound and single-stranded RNA, (vi) a TLR9-binding ligand or agonist selected from the group consisting of bacterial DNA, non-methylated CpG DNA, hemozoin, ODN1585, ODN1668, and ODN1826, and (vii) a TLR10-binding ligand or agonist selected from the group consisting of profilin and a uropathogenic bacterium.

(10) The conjugate according to any of (1) to (9), wherein the antibody or the fragment thereof is linked to the immune activator via a linker.

(11) A pharmaceutical composition for the treatment and/or prevention of a cancer, comprising the conjugate according to any of (1) to (10) as an active ingredient.

(12) The pharmaceutical composition according to (11), wherein the cancer is a cancer expressing s CAPRIN-1 protein on the cell membrane surface.

(13) The pharmaceutical composition according to (11) or (12), wherein the cancer is a cancer selected from the group consisting of breast cancer, kidney cancer, pancreatic cancer, colorectal cancer, lung cancer, brain tumor, stomach cancer, uterine cancer, ovary cancer, prostate cancer, bladder cancer, esophagus cancer, leukemia, lymphoma, liver cancer, gallbladder cancer, sarcoma, mastocytoma, melanoma, adrenal cortex cancer, Ewing's tumor, Hodgkin's lymphoma, mesothelioma, multiple myeloma, testicle cancer, thyroid cancer, and head and neck cancer.

(14) A method for treating and/or preventing a cancer, comprising administering the conjugate according to any of (1) to (10) or the pharmaceutical composition according to any of (11) to (13) to a subject.

Advantageous Effects of Invention

The conjugate according to the present invention not only exerts a much stronger antitumor effect than that of an antibody against a CAPRIN-1 protein used alone but is superior in antitumor effect to a known conjugate of an antibody drug for a cancer and an immune activator. Also, the effect of enhancing the antitumor effect by the conjugate according to the present invention is superior to the effect of enhancing the antitumor effect by conjugating an existing antibody drug for a cancer to the immune activator. Thus, the conjugate according to the present invention is effective for the treatment or prevention of a cancer.

DESCRIPTION OF EMBODIMENTS

The conjugate of an antibody or a fragment thereof against a CAPRIN-1 protein (hereinafter, referred to as an "anti-CAPRIN-1 antibody") and an immune activator used in the present invention can be evaluated for its antitumor activity, as mentioned later, by examining in vivo the inhibition of tumor growth in a cancer-bearing animal.

In the present invention, the "conjugate" refers to an antibody linked to an immune activator via a covalent bond. The linking between the antibody and the immune activator may be done by a linker.

The anti-CAPRIN-1 antibody that is a constituent of the conjugate according to the present invention may be a monoclonal antibody or a polyclonal antibody and is preferably a monoclonal antibody. The anti-CAPRIN-1 antibody may be any type of antibody as long as the conjugate of the present invention can exert antitumor activity. The antibody is a recombinant antibody, a human antibody, a humanized antibody, a chimeric antibody, or a non-human animal antibody.

The immune activator that is a constituent of the conjugate according to the present invention can be any factor activating immunocytes and is preferably a ligand or an agonist, or a derivative thereof, binding to Toll-like receptor (TLR), NOD-like receptor (NLR), RIG-like receptor, or C-type lectin receptor (CLR), more preferably a ligand or an agonist, or a derivative thereof, binding to Toll-like receptor (TLR).

The subject to be treated and/or prevented for cancer according to the present invention is a mammal such as a human, a pet animal, livestock, or a sport animal, and a preferred subject is a human.

Hereinafter, the anti-CAPRIN-1 antibody, the immune activator, the conjugate of the anti-CAPRIN-1 antibody and the immune activator, the pharmaceutical composition comprising the conjugate, and the method for treating and/or preventing a cancer using the conjugate, according to the present invention will be described.

<Anti-CAPRIN-1 Antibody>

Among CAPRIN-1 proteins having an amino acid sequence represented by any of even-numbered SEQ ID NOs among SEQ ID NOs: 2 to 30 and having immunological reactivity with the anti-CAPRIN-1 antibody used in the present invention, the amino acid sequences represented by SEQ ID NOs: 6, 8, 10, 12, and 14 are the amino acid sequences of canine CAPRIN-1 proteins; the amino acid sequence represented by SEQ ID NOs: 2 and 4 are the amino acid sequences of human CAPRIN-1 proteins; the amino acid sequence represented by SEQ ID NO: 16 is the amino acid sequence of a bovine CAPRIN-1 protein; the amino acid sequence represented by SEQ ID NO: 18 is the amino acid sequence of an equine CAPRIN-1 protein; the amino acid sequences represented by SEQ ID NOs: 20 to 28 are the amino acid sequences of mouse CAPRIN-1 proteins; and the amino acid sequence represented by SEQ ID NO: 30 is the amino acid sequence of a chicken CAPRIN-1 protein.

The anti-CAPRIN-1 antibody used in the present invention may have immunological reactivity with a variant of the CAPRIN-1 protein having 80% or more, preferably 90% or more, more preferably 95% or more, further preferably 99% or more sequence identity to the amino acid sequence represented by any of even-numbered SEQ ID NOs among SEQ ID NOs: 2 to 30. In this context, the term "% sequence identity" means a percentage (%) of the number of identical amino acids (or bases) to the total number of amino acids (or bases) when two sequences are aligned so that the maximum degree of similarity can be achieved with or without introducing a gap.

In the present invention, the anti-CAPRIN-1 antibody that is used for preparing the conjugate means an antibody or a fragment thereof having immunological reactivity with a full-length CAPRIN-1 protein or a fragment thereof. In this context, the "immunological reactivity" means the property of the antibody binding to the CAPRIN-1 protein or a partial polypeptide thereof in vivo.

The anti-CAPRIN-1 antibody used in the present invention may be a monoclonal antibody or a polyclonal antibody.

The polyclonal antibody having immunological reactivity with the full-length CAPRIN-1 protein or the fragment thereof (anti-CAPRIN-1 polyclonal antibody) can be obtained, for example, by immunizing a mouse, a human antibody-producing mouse, a rat, a rabbit, a chicken, or the like with a naturally occurring CAPRIN-1 protein, or a fusion protein thereof with GST or the like, or a partial peptide thereof and obtaining serum therefrom, and applying the obtained serum to ammonium sulfate precipitation, protein A, protein G, a DEAE ion-exchange column, an affinity column linked to a CAPRIN-1 protein or a partial peptide, or the like.

As for the full-length CAPRIN-1 protein or the fragment thereof to be used in the immunization, the nucleotide sequences and amino acid sequences of CAPRIN-1 and homologs thereof are available, for example, by accessing GenBank (NCBI, USA) and using an algorithm such as BLAST or FASTA (Karlin and Altschul, Proc. Natl. Acad. Sci. USA, 90: 5873-5877, 1993; and Altschul et al., Nucleic Acids Res. 25: 3389-3402, 1997). Also, a method for preparing the CAPRIN-1 protein is available with reference to WO2014/012479, or can be carried out using, for example, cells expressing the CAPRIN-1 protein.

The monoclonal antibody having immunological reactivity with the full-length CAPRIN-1 protein or the fragment thereof (anti-CAPRIN-1 monoclonal antibody) can be obtained, for example, by: administering SK-BR-3 (breast cancer cells expressing CAPRIN-1) or the full-length CAPRIN-1 protein or the fragment thereof, or the like to a mouse for immunization; fusing spleen cells separated from the mouse with myeloma cells; and selecting a clone producing anti-CAPRIN-1 monoclonal antibodies from among the obtained fusion cells (hybridomas). The antibody produced from the hybridoma thus selected can be prepared in the same way as the method for purifying the polyclonal antibody mentioned above.

The antibody used in the present invention includes human antibodies, humanized antibodies, chimeric antibodies, and non-human animal antibodies.

The human antibody can be obtained by: sensitizing EB virus-infected human lymphocytes, with the protein, protein-expressing cells, or lysates thereof; fusing the sensitized lymphocytes with human-derived myeloma cells such as U266 cells; and obtaining an antibody having immunological reactivity with the full-length CAPRIN-1 protein or the fragment thereof from the obtained fusion cells.

The humanized antibody, also called reshaped human antibody, is an engineered antibody. The humanized antibody is constructed by grafting complementarity-determining regions of an antibody derived from an immunized animal onto complementarity-determining regions of a human antibody. A genetic engineering technique commonly used for constructing humanized antibodies is also well-known. Specifically, DNA sequences designed to link complementarity-determining regions of, for example, a mouse or rabbit antibody, to framework regions of a human antibody are synthesized by PCR from several prepared oligonucleotides having overlapping terminal portions. The obtained DNAs are ligated with DNAs encoding human antibody constant regions. The resulting ligation products are incorporated into expression vectors, which are then transferred to hosts for antibody production to obtain the antibody of interest. See, European Patent Application Publication No. EP239400 and International Publication No. WO96/02576). The framework regions of a human antibody connected via the complementarity-determining regions are selected so that the complementarity-determining regions form a favorable antigen-binding site. If necessary, an amino acid in the framework regions of antibody variable regions may be substituted so that the complementarity-determining regions of a reshaped human antibody form an appropriate antigen-binding site (Sato K. et al., Cancer Research 1993, 53: 851-856). In addition, these framework regions may be replaced with framework regions derived from various human antibodies (see WO99/51743).

Antibodies are typically heteromultimeric glycoproteins each comprising at least two heavy chains and two light chains. The antibodies are each composed of two identical light chains and two identical heavy chains. Each heavy chain has a heavy chain variable region at one end, followed by a series of constant regions. Each light chain has a light chain variable region at one end, followed by a series of constant regions. The variable regions contain certain variable regions called complementarity-determining regions (CDRs) and impart binding specificity to the antibody. Portions relatively conserved in the variable regions are called framework regions (FRs). The complete heavy chain and light chain variable regions each contain four FRs connected via three CDRs (CDR1 to CDR3).

The sequences of human-derived heavy chain and light chain constant regions and variable regions are available from, for example, NCBI (USA; GenBank, UniGene, etc.). For example, the following sequences can be referred to: Accession No. J00228 for a human IgG1 heavy chain constant region; Accession No. J00230 for a human IgG2 heavy chain constant region; Accession Nos. V00557, X64135, X64133, etc., for a human light chain κ constant region; and Accession Nos. X64132, X64134, etc., for a human light chain λ constant region.

A chimeric antibody is an antibody prepared from a combination of sequences derived from different animals and may be, for example, an antibody composed of heavy chain and light chain variable regions of a mouse antibody and constant regions of heavy chain and light chain variable regions of a human antibody. The chimeric antibody can be prepared using a method known in the art and is obtained, for example, by: ligating DNAs encoding the antibody V regions to DNAs encoding the human antibody C regions; incorporating the resulting ligation products into expression vectors; and transferring the vectors into hosts for antibody production.

The non-human animal antibody is obtained by immunizing an animal with a sensitizing antigen according to a method known in the art and, as a general method, by intraperitoneally, intracutaneously, or subcutaneously injecting a sensitizing antigen to an animal such as a mouse. For the injection of the sensitizing antigen, the antigen is mixed in an appropriate amount with various adjuvants including CFA (complete Freund's adjuvant), and the mixture is administered to the animal a plurality of times. The animal is immunized and then verified to contain anti-CAPRIN-1 antibodies in serum. The serum can be obtained and applied, as mentioned above, to ammonium sulfate precipitation, protein A, protein G, a DEAE ion-exchange column, an affinity column bound with a CAPRIN-1 protein or a partial peptide, or the like to obtain the non-human animal antibody. In the case of obtaining a monoclonal antibody from a non-human animal, immunocytes can be collected from an immunized animal and subjected to cell fusion with myeloma cells to obtain the monoclonal antibody. The cell fusion between the immunocytes and the myeloma cells can be carried out according to a method known in the art (see Kohler, G. and Milstein, C. Methods Enzymol. (1981) 73, 3-46).

The antibody used in the present invention may be also obtained as a recombinant antibody produced using a genetic engineering technique by cloning genes of the antibody from a hybridoma; incorporating the antibody genes into appropriate vectors; and transferring the vectors into hosts (see Carl, A. K. Borrebaeck, James, W. Larrick, THERAPEUTIC MONOCLONAL ANTIBODIES, Published in the United Kingdom by MACMILLAN PUBLISHERS LTD, 1990).

The anti-CAPRIN-1 antibody that is used for obtaining the conjugate of the present invention may be an antibody in which an amino acid in a variable region (e.g., FR) or a constant region is substituted with another amino acid. The amino acid substitution is the substitution of one or more, for example, less than 15, less than 10, 8 or less, 6 or less, 5 or less, 4 or less, 3 or less, or 2 or less amino acids, preferably 1 to 9 amino acids. The substituted antibody should be an antibody that has the property of specifically binding to the antigen and binding affinity for the antigen equivalent to or greater than those of the corresponding unsubstituted antibody and causes no rejection when applied to humans.

The anti-CAPRIN-1 antibody used in the present invention is expected to have a stronger antitumor effect, the higher binding affinity for the CAPRIN-1 protein on cancer cell surface the antibody has. Its association constant (affinity constant) Ka (kon/koff) is preferably at least $10^7$ $M^{-1}$, at least $10^8 M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$ at least $10^{11}$ $M^{-1}$, at least $5 \times 10^{11}$ $M^{-1}$, at least $10^{12}$ $M^{-1}$, or at least $10^{13}$ $M^{-1}$.

The binding activity of the anti-CAPRIN-1 antibody used in the present invention against effector cells can be improved by substituting one, two or several amino acids in the heavy chain constant region of the antibody or by removing fucose added to N-acetylglucosamine in a N-glycoside-linked sugar chain attached to the heavy chain constant region. Such an antibody may have the amino acid substitution alone or may be in a composition comprising a fucosylated antibody.

The antibody in which one, two or several amino acids in the heavy chain constant region are substituted can be prepared with reference to, for example, WO2004/063351, WO2011/120135, U.S. Pat. No. 8,388,955, WO2011/005481, U.S. Pat. No. 6,737,056, and/or WO2005/063351.

The antibody lacking fucose added to N-acetylglucosamine in a N-glycoside-linked sugar chain in the heavy chain constant region has been removed, or cells producing the antibody, can be prepared with reference to U.S. Pat. No. 6,602,684, European Patent No. 1914244, and/or U.S. Pat. No. 7,579,170. A composition of the antibody lacking fucose added to N-acetylglucosamine in a N-glycoside-linked sugar chain attached to the heavy chain constant region, and the antibody having the fucose, or cells producing the composition can be prepared with reference to, for example, U.S. Pat. No. 8,642,292.

Methods for preparing and purifying the anti-CAPRIN-1 polyclonal antibody, the anti-CAPRIN-1 monoclonal antibody, and the antibody used in the present invention, and a method for preparing the CAPRIN-1 protein or the partial polypeptide thereof to be used in immunization can be carried out with reference to WO2010/016526, WO2011/096517, WO2011/096528, WO2011/096519, WO2011/096533, WO2011/096534, WO2011/096535, WO2013/018886, WO2013/018894, WO2013/018892, WO2013/018891, WO2013/018889, WO2013/018883, WO2013/125636, WO2013/125654, WO2013/125630, WO2013/125640, WO2013/147169, WO2013/147176 and WO2015/020212.

Specific examples of the anti-CAPRIN-1 antibody according to the present invention include anti-CAPRIN-1 antibodies disclosed in WO2010/016526, WO2011/096517, WO2011/096528, WO2011/096519, WO2011/096533, WO2011/096534, WO2011/096535, WO2013/018886, WO2013/018894, WO2013/018892, WO2013/018891, WO2013/018889, WO2013/018883, WO2013/125636, WO2013/125654, WO2013/125630, WO2013/125640, WO2013/147169, WO2013/147176 and WO2015/020212 mentioned above. Preferred examples of the anti-CAPRIN-1 antibody include the following.

An antibody or a fragment thereof having immunological reactivity with the amino acid sequence represented by SEQ ID NO: 2 or SEQ ID NO: 4 or a partial polypeptide of the CAPRIN-1 protein having an amino acid sequence having 80% or more (preferably 85% or more, more preferably 90% or more, further preferably 95% or more, still further preferably 99% or more) sequence identity to the amino acid sequence represented by SEQ ID NO: 2 or SEQ ID NO: 4.

An antibody or a fragment thereof having immunological reactivity with a partial polypeptide of the CAPRIN-1 protein having the amino acid sequence represented by SEQ ID NO: 31 or an amino acid sequence having 80% or more (preferably 85% or more, more preferably 90% or more, further preferably 95% or more) sequence identity to the amino acid sequence. Preferably, an antibody or a fragment thereof which comprises a heavy chain variable region comprising complementarity-determining regions of SEQ ID NOs: 36, 37, and 38 (CDR1, CDR2, and CDR3, respectively) and a light chain variable region comprising complementarity-determining regions of SEQ ID NOs: 40, 41, and 42 (CDR1, CDR2, and CDR3, respectively) and has immunological reactivity with the CAPRIN-1 protein; an antibody or a fragment thereof which comprises a heavy chain variable region comprising complementarity-determining regions of SEQ ID NOs: 140, 141, and 142 (CDR1, CDR2, and CDR3, respectively) and a light chain variable region comprising complementarity-determining regions of SEQ ID NOs: 143, 144, and 145 (CDR1, CDR2, and CDR3, respectively) and has immunological reactivity with the CAPRIN-1 protein; or an antibody or a fragment thereof which comprises a heavy chain variable region comprising complementarity-determining regions of SEQ ID NOs: 164, 165, and 166 (CDR1, CDR2, and CDR3, respectively) and a light chain variable region comprising complementarity-determining regions of SEQ ID NOs: 167, 168, and 169 (CDR1, CDR2, and CDR3, respectively) and has immunological reactivity with the CAPRIN-1 protein. More preferably, an antibody or a fragment thereof comprising a heavy chain variable region comprising the amino acid sequence of SEQ ID NO: 39 and a light chain variable region comprising the amino acid sequence of SEQ ID NO: 43; an antibody or a fragment thereof comprising a heavy chain variable region comprising the amino acid sequence of SEQ ID NO: 70 and a light chain variable region comprising the amino acid sequence of SEQ ID NO: 71; or an antibody or a fragment thereof comprising a heavy chain variable region comprising the amino acid sequence of SEQ ID NO: 78 and a light chain variable region comprising the amino acid sequence of SEQ ID NO: 79.

An antibody or a fragment thereof having immunological reactivity with a partial polypeptide of the CAPRIN-1 protein having the amino acid sequence represented by SEQ ID NO: 33 or an amino acid sequence having 80% or more (preferably 85% or more, more preferably 90% or more, further preferably 95% or more) sequence identity to the amino acid sequence. Preferably, an antibody or a fragment thereof which comprises a heavy chain variable region comprising complementarity-determining regions of SEQ ID NOs: 60, 61, and 62 (CDR1, CDR2, and CDR3, respectively) and a light chain variable region comprising complementarity-determining regions of SEQ ID NOs: 64, 65, and 66 (CDR1, CDR2, and CDR3, respectively) and has immunological reactivity with the CAPRIN-1 protein; or an antibody or a fragment thereof comprising a heavy chain variable region comprising the amino acid sequence of SEQ ID NO: 63 and a light chain variable region comprising the amino acid sequence of SEQ ID NO: 67.

An antibody or a fragment thereof having immunological reactivity with a partial polypeptide of the CAPRIN-1 protein having the amino acid sequence represented by SEQ ID NO: 32 or an amino acid sequence having 80% or more (preferably 85% or more, more preferably 90% or more, further preferably 95% or more) sequence identity to the amino acid sequence. Preferably, an antibody or a fragment thereof which comprises a heavy chain variable region comprising complementarity-determining regions of SEQ ID NOs: 52, 53, and 54 (CDR1, CDR2, and CDR3, respectively) and a light chain variable region comprising complementarity-determining regions of SEQ ID NOs: 56, 57, and 58 (CDR1, CDR2, and CDR3, respectively) and has immunological reactivity with the CAPRIN-1 protein. More preferably, an antibody or a fragment thereof comprising a heavy chain variable region comprising the amino acid sequence of SEQ ID NO: 55 and a light chain variable region comprising the amino acid sequence of SEQ ID NO: 59.

An antibody or a fragment thereof having immunological reactivity with a partial polypeptide of the CAPRIN-1 protein having the amino acid sequence represented by SEQ ID NO: 34 or an amino acid sequence having 80% or more (preferably 85% or more, more preferably 90% or more, further preferably 95% or more) sequence identity to the amino acid sequence. Preferably, an antibody or a fragment thereof which comprises a heavy chain variable region comprising complementarity-determining regions of SEQ ID NOs: 170, 171, and 172 (CDR1, CDR2, and CDR3, respectively) and a light chain variable region comprising complementarity-determining regions of SEQ ID NOs: 173, 174, and 175 (CDR1, CDR2, and CDR3, respectively) and has immunological reactivity with the CAPRIN-1 protein; or an antibody or a fragment thereof which comprises a heavy chain variable region comprising complementarity-determining regions of SEQ ID NOs: 176, 177, and 178 (CDR1, CDR2, and CDR3, respectively) and a light chain variable region comprising complementarity-determining regions of SEQ ID NOs: 179, 180, and 181 (CDR1, CDR2, and CDR3, respectively) and has immunological reactivity with the CAPRIN-1 protein. More preferably, an antibody or a fragment thereof comprising a heavy chain variable region comprising the amino acid sequence of SEQ ID NO: 80 and a light chain variable region comprising the amino acid sequence of SEQ ID NO: 81; or an antibody or a fragment thereof comprising a heavy chain variable region comprising the amino acid sequence of SEQ ID NO: 82 and a light chain variable region comprising the amino acid sequence of SEQ ID NO: 83.

An antibody or a fragment thereof having immunological reactivity with a partial polypeptide of the CAPRIN-1 protein having the amino acid sequence represented by SEQ ID NO: 35 or an amino acid sequence having 80% or more (preferably 85% or more, more preferably 90% or more, further preferably 95% or more) sequence identity to the amino acid sequence. Preferably, an antibody or a fragment thereof which comprises a heavy chain variable region comprising complementarity-determining regions of SEQ ID NOs: 182, 183, and 184 (CDR1, CDR2, and CDR3, respectively) and a light chain variable region comprising complementarity-determining regions of SEQ ID NOs: 185, 186, and 187 (CDR1, CDR2, and CDR3, respectively) and has immunological reactivity with the CAPRIN-1 protein; or an antibody or a fragment thereof which comprises a heavy chain variable region comprising complementarity-determining regions of SEQ ID NOs: 188, 189, and 190 (CDR1, CDR2, and CDR3, respectively) and a light chain variable region comprising complementarity-determining regions of SEQ ID NOs: 191, 192, and 193 (CDR1, CDR2, and CDR3, respectively) and has immunological reactivity with the CAPRIN-1 protein. More preferably, an antibody or a fragment thereof comprising a heavy chain variable region comprising the amino acid sequence of SEQ ID NO: 84 and a light chain variable region comprising the amino acid sequence of SEQ ID NO: 85; or an antibody or a fragment thereof comprising a heavy chain variable region comprising the amino acid sequence of SEQ ID NO: 86 and a light chain variable region comprising the amino acid sequence of SEQ ID NO: 87.

An antibody or a fragment thereof which comprises a heavy chain variable region comprising complementarity-determining regions of SEQ ID NOs: 44, 45, and 46 (CDR1, CDR2, and CDR3, respectively) and a light chain variable region comprising complementarity-determining regions of SEQ ID NOs: 48, 49, and 50 (CDR1, CDR2, and CDR3, respectively) and has immunological reactivity with the CAPRIN-1 protein. Preferably, an antibody or a fragment thereof comprising a heavy chain variable region comprising the amino acid sequence of SEQ ID NO: 47 and a light chain variable region comprising the amino acid sequence of SEQ ID NO: 51.

An antibody or a fragment thereof having immunological reactivity with a partial polypeptide of the CAPRIN-1 protein having the amino acid sequence represented by SEQ ID NO: 296 or an amino acid sequence having 80% or more (preferably 85% or more, more preferably 90% or more, further preferably 95% or more) sequence identity to the amino acid sequence. Preferably, an antibody or a fragment thereof which comprises a heavy chain variable region comprising complementarity-determining regions of SEQ ID NOs: 146, 147, and 148 (CDR1, CDR2, and CDR3, respectively) and a light chain variable region comprising complementarity-determining regions of SEQ ID NOs: 149, 150, and 151 (CDR1, CDR2, and CDR3, respectively) and has immunological reactivity with the CAPRIN-1 protein. More preferably, an antibody or a fragment thereof comprising a heavy chain variable region comprising the amino acid sequence of SEQ ID NO: 72 and a light chain variable region comprising the amino acid sequence of SEQ ID NO: 73.

An antibody or a fragment thereof having immunological reactivity with a partial polypeptide of the CAPRIN-1 protein having the amino acid sequence represented by SEQ ID NO: 297 or an amino acid sequence having 80% or more (preferably 85% or more, more preferably 90% or more, further preferably 95% or more) sequence identity to the amino acid sequence. Preferably, an antibody or a fragment thereof which comprises a heavy chain variable region comprising complementarity-determining regions of SEQ ID NOs: 272, 273, and 274 (CDR1, CDR2, and CDR3, respectively) and a light chain variable region comprising complementarity-determining regions of SEQ ID NOs: 275, 276, and 277 (CDR1, CDR2, and CDR3, respectively) and has immunological reactivity with the CAPRIN-1 protein. More preferably, an antibody or a fragment thereof comprising a heavy chain variable region comprising the amino acid sequence of SEQ ID NO: 114 and a light chain variable region comprising the amino acid sequence of SEQ ID NO: 115.

An antibody or a fragment thereof having immunological reactivity with a partial polypeptide of the CAPRIN-1 protein having the amino acid sequence represented by SEQ ID NO: 298 or an amino acid sequence having 80% or more (preferably 85% or more, more preferably 90% or more, further preferably 95% or more) sequence identity to the amino acid sequence. Preferably, an antibody or a fragment thereof which comprises a heavy chain variable region comprising complementarity-determining regions of SEQ ID NOs: 290, 291, and 292 (CDR1, CDR2, and CDR3, respectively) and a light chain variable region comprising complementarity-determining regions of SEQ ID NOs: 293, 294, and 295 (CDR1, CDR2, and CDR3, respectively) and has immunological reactivity with the CAPRIN-1 protein. More preferably, an antibody or a fragment thereof comprising a heavy chain variable region comprising the amino acid sequence of SEQ ID NO: 120 and a light chain variable region comprising the amino acid sequence of SEQ ID NO: 121.

An antibody or a fragment thereof having immunological reactivity with a partial polypeptide of the CAPRIN-1 protein having the amino acid sequence represented by SEQ ID NO: 299 or an amino acid sequence having 80% or more (preferably 85% or more, more preferably 90% or more, further preferably 95% or more) sequence identity to the amino acid sequence. Preferably, an antibody or a fragment thereof which comprises a heavy chain variable region comprising complementarity-determining regions of SEQ ID NOs: 300, 301, and 302 (CDR1, CDR2, and CDR3, respectively) and a light chain variable region comprising complementarity-determining regions of SEQ ID NOs: 304, 305, and 306 (CDR1, CDR2, and CDR3, respectively) and has immunological reactivity with the CAPRIN-1 protein. More preferably, an antibody or a fragment thereof comprising a heavy chain variable region comprising the amino acid sequence of SEQ ID NO: 303 and a light chain variable region comprising the amino acid sequence of SEQ ID NO: 307.

An antibody or a fragment thereof having immunological reactivity with a partial polypeptide of the CAPRIN-1 protein having the amino acid sequence represented by SEQ ID NO: 308 or an amino acid sequence having 80% or more (preferably 85% or more, more preferably 90% or more, further preferably 95% or more) sequence identity to the amino acid sequence. Preferably, an antibody or a fragment thereof which comprises a heavy chain variable region comprising complementarity-determining regions of SEQ ID NOs: 134, 135, and 136 (CDR1, CDR2, and CDR3, respectively) and a light chain variable region comprising complementarity-determining regions of SEQ ID NOs: 137, 138, and 139 (CDR1, CDR2, and CDR3, respectively) and has immunological reactivity with the CAPRIN-1 protein. More preferably, an antibody or a fragment thereof comprising a heavy chain variable region comprising the amino acid sequence of SEQ ID NO: 68 and a light chain variable region comprising the amino acid sequence of SEQ ID NO: 69.

An antibody or a fragment thereof having immunological reactivity with a partial polypeptide of the CAPRIN-1 protein having the amino acid sequence represented by SEQ ID NO: 309 or an amino acid sequence having 80% or more (preferably 85% or more, more preferably 90% or more, further preferably 95% or more) sequence identity to the amino acid sequence. Preferably, an antibody or a fragment thereof which comprises a heavy chain variable region comprising complementarity-determining regions of SEQ ID NOs: 134, 135, and 136 (CDR1, CDR2, and CDR3, respectively) and a light chain variable region comprising complementarity-determining regions of SEQ ID NOs: 137, 138, and 139 (CDR1, CDR2, and CDR3, respectively) and has immunological reactivity with the CAPRIN-1 protein. More preferably, an antibody or a fragment thereof comprising a heavy chain variable region comprising the amino acid sequence of SEQ ID NO: 68 and a light chain variable region comprising the amino acid sequence of SEQ ID NO: 69.

Also, the following anti-CAPRIN-1 antibodies are preferably used.

An antibody or a fragment thereof comprising a heavy chain variable region comprising the amino acid sequence of SEQ ID NO: 68 and a light chain variable region comprising the amino acid sequence of SEQ ID NO: 69.

An antibody or a fragment thereof comprising a heavy chain variable region comprising the amino acid sequence of SEQ ID NO: 70 and a light chain variable region comprising the amino acid sequence of SEQ ID NO: 71.

An antibody or a fragment thereof comprising a heavy chain variable region comprising the amino acid sequence of SEQ ID NO: 72 and a light chain variable region comprising the amino acid sequence of SEQ ID NO: 73.

An antibody or a fragment thereof comprising a heavy chain variable region comprising the amino acid sequence of SEQ ID NO: 74 and a light chain variable region comprising the amino acid sequence of SEQ ID NO: 75.

An antibody or a fragment thereof comprising a heavy chain variable region comprising the amino acid sequence of SEQ ID NO: 76 and a light chain variable region comprising the amino acid sequence of SEQ ID NO: 77.

An antibody or a fragment thereof comprising a heavy chain variable region comprising the amino acid sequence of SEQ ID NO: 78 and a light chain variable region comprising the amino acid sequence of SEQ ID NO: 79.

An antibody or a fragment thereof comprising a heavy chain variable region comprising the amino acid sequence of SEQ ID NO: 80 and a light chain variable region comprising the amino acid sequence of SEQ ID NO: 81.

An antibody or a fragment thereof comprising a heavy chain variable region comprising the amino acid sequence of SEQ ID NO: 82 and a light chain variable region comprising the amino acid sequence of SEQ ID NO: 83.

An antibody or a fragment thereof comprising a heavy chain variable region comprising the amino acid sequence of SEQ ID NO: 84 and a light chain variable region comprising the amino acid sequence of SEQ ID NO: 85.

An antibody or a fragment thereof comprising a heavy chain variable region comprising the amino acid sequence of SEQ ID NO: 86 and a light chain variable region comprising the amino acid sequence of SEQ ID NO: 87.

An antibody or a fragment thereof comprising a heavy chain variable region comprising the amino acid sequence of SEQ ID NO: 88 and a light chain variable region comprising the amino acid sequence of SEQ ID NO: 89.

An antibody or a fragment thereof comprising a heavy chain variable region comprising the amino acid sequence of SEQ ID NO: 90 and a light chain variable region comprising the amino acid sequence of SEQ ID NO: 91.

An antibody or a fragment thereof comprising a heavy chain variable region comprising the amino acid sequence of SEQ ID NO: 92 and a light chain variable region comprising the amino acid sequence of SEQ ID NO: 93.

An antibody or a fragment thereof comprising a heavy chain variable region comprising the amino acid sequence of SEQ ID NO: 94 and a light chain variable region comprising the amino acid sequence of SEQ ID NO: 95.

An antibody or a fragment thereof comprising a heavy chain variable region comprising the amino acid sequence of SEQ ID NO: 96 and a light chain variable region comprising the amino acid sequence of SEQ ID NO: 97.

An antibody or a fragment thereof comprising a heavy chain variable region comprising the amino acid sequence of SEQ ID NO: 98 and a light chain variable region comprising the amino acid sequence of SEQ ID NO: 99.

An antibody or a fragment thereof comprising a heavy chain variable region comprising the amino acid sequence of SEQ ID NO: 100 and a light chain variable region comprising the amino acid sequence of SEQ ID NO: 101.

An antibody or a fragment thereof comprising a heavy chain variable region comprising the amino acid sequence of SEQ ID NO: 102 and a light chain variable region comprising the amino acid sequence of SEQ ID NO: 103.

An antibody or a fragment thereof comprising a heavy chain variable region comprising the amino acid sequence of SEQ ID NO: 104 and a light chain variable region comprising the amino acid sequence of SEQ ID NO: 105.

An antibody or a fragment thereof comprising a heavy chain variable region comprising the amino acid sequence of SEQ ID NO: 106 and a light chain variable region comprising the amino acid sequence of SEQ ID NO: 107.

An antibody or a fragment thereof comprising a heavy chain variable region comprising the amino acid sequence of SEQ ID NO: 108 and a light chain variable region comprising the amino acid sequence of SEQ ID NO: 109.

An antibody or a fragment thereof comprising a heavy chain variable region comprising the amino acid sequence of SEQ ID NO: 110 and a light chain variable region comprising the amino acid sequence of SEQ ID NO: 111.

An antibody or a fragment thereof comprising a heavy chain variable region comprising the amino acid sequence of SEQ ID NO: 112 and a light chain variable region comprising the amino acid sequence of SEQ ID NO: 113.

An antibody or a fragment thereof comprising a heavy chain variable region comprising the amino acid sequence of SEQ ID NO: 114 and a light chain variable region comprising the amino acid sequence of SEQ ID NO: 115.

An antibody or a fragment thereof comprising a heavy chain variable region comprising the amino acid sequence of SEQ ID NO: 116 and a light chain variable region comprising the amino acid sequence of SEQ ID NO: 117.

An antibody or a fragment thereof comprising a heavy chain variable region comprising the amino acid sequence of SEQ ID NO: 118 and a light chain variable region comprising the amino acid sequence of SEQ ID NO: 119.

An antibody or a fragment thereof comprising a heavy chain variable region comprising the amino acid sequence of SEQ ID NO: 120 and a light chain variable region comprising the amino acid sequence of SEQ ID NO: 121.

An antibody or a fragment thereof comprising a heavy chain variable region comprising the amino acid sequence of SEQ ID NO: 122 and a light chain variable region comprising the amino acid sequence of SEQ ID NO: 123.

An antibody or a fragment thereof comprising a heavy chain variable region comprising the amino acid sequence of SEQ ID NO: 124 and a light chain variable region comprising the amino acid sequence of SEQ ID NO: 125.

An antibody or a fragment thereof comprising a heavy chain variable region comprising the amino acid sequence of SEQ ID NO: 126 and a light chain variable region comprising the amino acid sequence of SEQ ID NO: 127.

An antibody or a fragment thereof comprising a heavy chain variable region comprising the amino acid sequence of SEQ ID NO: 128 and a light chain variable region comprising the amino acid sequence of SEQ ID NO: 129.

An antibody or a fragment thereof comprising a heavy chain variable region comprising the amino acid sequence of SEQ ID NO: 130 and a light chain variable region comprising the amino acid sequence of SEQ ID NO: 131.

An antibody or a fragment thereof comprising a heavy chain variable region comprising the amino acid sequence of SEQ ID NO: 132 and a light chain variable region comprising the amino acid sequence of SEQ ID NO: 133.

An antibody or a fragment thereof comprising a heavy chain variable region comprising the amino acid sequence of SEQ ID NO: 303 and a light chain variable region comprising the amino acid sequence of SEQ ID NO: 307.

In Examples mentioned later, conjugates with an immune activator were prepared using the polyclonal antibody or the monoclonal antibody against the full-length CAPRIN-1 protein or a polypeptide of a partial region thereof expressed on the cell membrane surface of cancer cells, and verified to have a strong antitumor effect.

<Immune Activator>

Herein, the immune activator according to the present invention is a factor activating various immunocytes and means a naturally occurring compound, a nucleic acid, or a naturally occurring compound capable of maintaining or enhancing the immune functions of the cells. In this context, the "immunocytes" are T lymphocytes, B lymphocytes, NK cells, monocytes, dendritic cells, granulocytes, macrophages, myeloid-derived suppressor cells, Langerhans cells and precursor cell groups thereof, and these immunocyte groups present in tumor.

Specific examples of the immune activator used in the present invention include, but are not particularly limited to, ligands or agonists binding to Toll-like receptor (TLR), NOD-like receptor (NLR), RIG-like receptor, or C-type lectin receptor (CLR).

Specific examples of the ligand or the agonist binding to Toll-like receptor (TLR) include ligands or agonists binding to TLR2, TLR3, TLR4, TLR5, TLR7, TLR8, TLR9, or TLR10.

Specific examples of the ligand or the agonist binding to TLR2 include substances selected from the group consisting of peptidoglycan, lipoprotein, lipopolysaccharide, and zymosan.

Specific examples of the ligand or the agonist binding to TLR3 include substances selected from the group consisting of poly(I:C), poly(A:U) polyICLC (Hiltonol), and Ampligen.

Specific examples of the ligand or the agonist binding to TLR4 include substances selected from the group consisting of lipopolysaccharide (LPS), HSP60, RS09, MPLA (monophosphoryl lipid A from *Salmonella minnesota* R595), GLA-SE, G100, and MPLA.

Specific examples of the ligand or the agonist binding to TLR5 include substances selected from the group consisting of flagellin and FLA.

Specific examples of the ligand or the agonist binding to TLR7 or TLR8 include low-molecular compounds such as imidazoquinoline compounds, and single-stranded RNA. Specific examples thereof include Imiquimod, Resiquimod, Loxorbine, 852A, 854A, S-34240, Motolimod (VTX-2337), DSR-6434, GS-9620, ANA773, AZD8848/DSP-3025, GSK2245035, Gardiquimod, CL264, UC-1V150, CL075, CL097, CL307, CL347, 3M-003, 3M-0043, 3M-052, CL264, IV209, ORN R-2176-dT, Poly(dT), ORN R-0006, ORN R-0002, ORN R-2336, PolyU, ORN R-1886, polyG3, DSR6434, RWJ21757, SM324405, p-IMDQ, m-IMDQ and GSK2245035.

Specific examples of the ligand or the agonist binding to TLR9 include substances selected from the group consisting of bacterial DNA, non-methylated CpG DNA, hemozoin, ODN1585, ODN1668, ODN1668, lefitolimod (MGN1703), SD-101, CYT003, CPG7909, DUK-CPG-001, and ODN1826.

Specific examples of the ligand or the agonist binding to TLR10 include substances selected from the group consisting of profilin and uropathogenic bacteria.

Among the ligands or the agonists binding to Toll-like receptor (TLR), the ligand or the agonist binding to TLR7 or TLR8 is preferably used in the present invention. A TLR7- or TLR8-binding ligand or agonist selected from the group consisting of imidazoquinoline compounds and single-stranded RNA is more preferably used as the ligand or the agonist binding to TLR7 or TLR8, and a TLR7- or TLR8-binding ligand or agonist selected from imidazoquinoline compounds is further preferably used.

Preferred specific examples of the imidazoquinoline compound include compounds described in U.S. Pat. No. 8,951,528 and compounds disclosed in WO2015/103989, for example, 1-(2-methylpropyl)-1H-imidazo[4,5-c]quinoline-4-amine (Imiquimod), 1-(4-amino-2-ethylaminomethylimidazo-[4,5-c]quinolin-1-yl)-2-methylpropan-2-ol (Gardiquimod), N-[4-(4-amino-2-ethyl-1H-imidazo[4,5-c]quinolin-1-yl)butyl-]methanesulfonamide (PF-4878691), 4-amino-2-(ethoxymethyl)-a,a-dimethyl-1H-imidazo[4,5-c]quinoline-1-ethanol (Resiquimod), 4-amino-aa-dimethyl-2-methoxyethyl-1H-imidazo[4,5-c]quinoline-1-ethanol, 1-(2-(3-(benzyloxy) propoxy)ethyl)-2-(ethoxymethyl)-1H-imidazo[4,5-c]quinolin-4-amine, 4-amino-2-ethoxymethyl-aa-dimethyl-6,7,8,9-tetrahydro-1H-imidazo[4,5-c]quinoline-1-ethanol, N-(2-{2-[4-amino-2-(2-methoxyethyl)-1H-imidazo[4,5-c]quinolin-1-yl]ethoxy}ethyl)-n'-phenylurea, 1-2-amino-2-methylpropyl)-2-(ethoxymethyl)-1H-imidazo[4,5-c]quinolin-4-amine, 1-{4-[(3,5-dichlorophenyl) sulfonyl]butyl}-2-ethyl-1H-imidazo[4,5-c]quinolin-4-amine, N-(2-{2-[4-amino-2-(ethoxymethyl)-1H-imidazo[4,5-c]quinolin-1-yl]ethoxy}ethyl)-n'-cyclohexylurea, N-{3-[4-amino-2-(ethoxymethyl)-1H-imidazo[4,5-c]quinolin-1-yl]propyl}-n'-(3-cyanophenyl)thiourea, N-[3-(4-amino-2-butyl-1H-imidazo[4,5-c]quinolin-1-yl)-2,2-dimethylpropyl] benzamide, 2-butyl-1-[3-(methylsulfonyl) propyl]-1H-imidazo[4,5-c]quinolin-4-amine, though the imidazoquinoline compound is not limited thereto as long as the imidazoquinoline compound binds to TLR7 or TLR8.

Specific examples of the ligand or the agonist binding to NOD-like receptor (NLR) include M-TriDAP and PGN. Other examples thereof include ligands or agonists against NOD1, for example, Tri-DAP, iE-DAP, and C12-iE. Further examples thereof include ligands or agonists against NOD2, for example, MDP, N-glycosyl-MDP, murabutide, M-TriLyS-D-ASN, M-TriLYS, and L18-MDP.

Specific examples of the ligand or the agonist binding to RIG-like receptor include 5'ppp-dsRNA, poly(dA:dT), poly (dG:dC), and poly(I:C).

Specific examples of the ligand or the agonist binding to C-type lectin receptor (CLR) include trehalose 6,6-dibehenate, zymosan, WGP, HKSC, HKCA, and curdlan AL.

<Conjugate of Anti-CAPRIN-1 Antibody and Immune Activator>

In the present invention, the mode of binding between the anti-CAPRIN-1 antibody and the immune activator in the conjugate of the anti-CAPRIN-1 antibody and the immune activator is not particularly limited as long as it allows antitumor activity against a cancer to be maintained. The mode of binding preferably has a linker structure formed between the anti-CAPRIN-1 antibody and the immune activator.

In this context, the linker means a compound capable of linking the anti-CAPRIN-1 antibody to the immune activator. Any of various linkers known in the art may be used, or an appropriate chemical modification to the structure of the activator may be used for directly binding the antibody to the activator.

The details of the type of the linker and the binding method can be basically in accordance with a method known in the art (see, for example, Greg T. Hermanson Bioconjugate Techniques, Third Edition, WO2004010957, and WO2014/012479).

In an embodiment of the present invention, examples of reactive groups attached to the anti-CAPRIN-1 antibody, the immune activator, and the linker include the following.

Examples of the reactive group attached to the amino acid sequence of the antibody or a glycoprotein modifying an amino acid include primary amine (c-amino group), carboxyl, thiol (sulfhydryl), carbonyl (ketone or aldehyde), and hydroxyl unless a special chemical modification is made. The primary amine exists at the N-terminus of a polypeptide or the side chain of a lysine residue and is positively charged under physiological conditions. The primary amine usually exists outside of the protein and can therefore be used in binding without denaturing the structure of the protein. The carboxyl exists at the C-terminus of a polypeptide or the side chain of aspartic acid or glutamic acid. The sulfhydryl exists at the side chain of cysteine and forms a disulfide bond that maintains the higher-order structure of the protein. The ketone or aldehyde group is generated in a glycoprotein by the oxidation of glycosyl with sodium metaperiodate.

The conjugate of the present invention is prepared by binding the linker to the reactive group of the antibody, binding thereto the immune activator bound with the linker, or directly binding the immune activator to the antibody.

Examples of the reactive groups attached to the linker and the immune activator include the following.

Reactive group capable of reacting with the amine: N-hydroxysuccinimide (NHS) ester, imide ester, pentafluorophenyl ester, hydroxymethyl phosphine, isothiocyanate, isocyanate, acyl azide, N-hydroxyl ester, sulfonyl chloride, aldehyde, glyoxal, epoxide, oxirane, carbonate, aryl, imide ester, carbodiimide, and carboxylic anhydride.

Reactive group capable of reacting with the carboxyl and the amine: carbodiimide, diazoalkane, diazoacetyl compounds, and carbonyldiimidazole.

Reactive group capable of reacting with the thiol: maleimide, haloacetamide, pyridyl disulfide, thiosulfone, vinyl sulfone, haloacetyl, aziridine, acryloyl, and aryl.

Reactive group capable of reacting with the aldehyde: hydrazide and alkoxyamine. Reactive group capable of reacting with the hydroxyl: epoxy, oxirane, carbonyldiimidazole, N,N'-disuccinimidyl carbonate, N-hydroxysuccinimidyl chloroformate, and isocyanate.

Reactive group capable of reacting with the hydroxyl: isocyanate.

Photoreactive reactive group: diaziridine, aryl azide, aryl, benzophenol, and diazo compounds.

Specific examples of the linker having the reactive group include the following.

As a linker having the same reactive group ends, a linker having N-hydroxysuccinimide ester as a reactive group (e.g., Disuccinimidyl Glutarate (DSG), disuccinimidyl suberate (DSS), bis(sulfosuccinimidyl)suberate (BS3), tris-(succinimidyl)aminotriacetate (TSAT), PEGylated bis (sulfosuccinimidyl)suberate (BS(PEG)$_5$, BS(PEG)$_9$), dithiobis (succinimidyl propionate) (DSP), (DTSSP), (EGS), (Sulfo-EGS), (DMA), (DMP), (DMS), (DTBP), (DFDNB), (DST), (BSOCOES), (EGS), (Sulfo-EGS)) and a linker having maleimide as a reactive group (e.g., (BMOE), (BMB), (BMH), (TMEA), (BM(PEG)2), (BM(PEG)$_3$), (DTME), and (DMDB)).

As a linker having different reactive group ends, a linker having NHS ester and maleimide as reactive groups (e.g., AMAS, BMPS, GMBS, Sulfo-MBS, MBS, Sulfo-MBS, SMCC, Sulfo-SMCC, EMCS, Sulfo-EMCS, SMPB, Sulfo-SMPB, SMPH, LC-SMCC, Sulfo-KMUS, SM(PEG)$_2$, SM(PEG)$_4$, SM(PEG)$_6$, SM(PEG)$_8$, SM(PEG)$_{12}$, and SM(PEG)$_{24}$), a linker having NHS ester and pyridyldithiol as reactive groups (e.g., SPDP, LC-SPDP, Sulfo-LC-SPDP, SMPT, PEG4-SPDP, and PEG12-SPDP), a linker having NHS ester and haloacetyl as reactive groups (e.g., SIA, SBAP, SIAB, and Sulfo-SIAB), a linker having NHS ester and aryl azide as reactive groups (e.g., ANB-NOS, Sulfo-SANPAH, and ATFB), a linker having NHS ester and diaziridine as reactive groups (e.g., SDA, Sulfo-SDA, LC-SDA, SDAD, and Sulfo-SDAD), a linker having carbodiimide as reactive groups (e.g., DCC, EDC, EDAC, NHS, and Sulfo-NHS), a linker having maleimide and hydrazide as reactive groups (e.g., BMPH, EMCH, MPBH, and KMUH), a linker having pyridyldithiol and hydrazide as a reactive group (e.g., PDPH), a linker having isocyanate and maleimide as reactive groups (e.g., PMPI), and a linker having NHS ester and psoralen as reactive groups (e.g., SPB).

As other linkers, a linker containing a polypeptide, for example, Fmoc-Ala-Ala-Asn-PAB, Fmoc-Ala-Ala-Asn(Trt)-PAB, Fmoc-PEG$_3$-Ala-Ala-Asn(Trt)-PAB, Fmoc-PEG$_4$-Ala-Ala-Asn(Trt)-PAB, Fmoc-Ala-Ala-Asn-PAB-PNP, Fmoc-Ala-Ala-Asn(Trt)-PAB-PNP, Fmoc-PEG$_3$-Ala-Ala-Asn(Trt)-PAB-PNP, Azide-PEG$_4$-Ala-Ala-Asn(Trt)-PAB-PNP, Mal-PEG$_4$-Ala-Ala-Asn(Trt)-PAB-PNP, Fmoc-Val-Cit-PAB-OH, Val-Cit-PAB-OH, Fmoc-Val-Cit-PAB-PNP, MC-Val-Cit-PAB, MC-Val-Cit-PAB-PNP.

Also, Bis-PEG-acid, PEG Acid (e.g., Acid-PEG-TEMPO, Amino-PEG-acid, Amino-PEG-CH$_2$CO$_2$H, Aminoxy-PEG-acid, Azido-PEG-acid, Carboxy-PEG-sulfonic acid, Fmoc-N-amido-PEG-acid, Fmoc-N-amido-PEG-CH$_2$CO$_2$H, Fmoc-aminooxy-PEG-acid, Hydroxy-PEG-acid, Hydroxy-PEG-CH$_2$CO$_2$H, m-PEG-acid, m-PEG-(CH$_2$)$_3$-acid, Methoxytrityl-N-PEG-acid, N-methyl-N-(t-Boc)-PEG-acid, Propargyl-PEG-acid, Propargyl-PEG-CH$_2$CO$_2$H, Propargyl-PEG-(CH$_2$)$_3$-acid, t-Boc-N-amido-PEG-acid, t-Boc-N-amido-PEG-CH$_2$CO$_2$H, t-Boc-Aminooxy-PEG-acid, Acid-PEG-PFP ester, Miscellaneous PEG acid), PEG PFP ester (e.g., Acid-PEG-PFP ester, Bis-PEG-PFP ester), Bis-PEG-NHS, PEG Aldehyde (e.g., m-PEG-aldehyde, m-PEG-benzaldehyde, Ald-PEG-acid, Ald-PEG-amine, Ald-PEG-azide, Ald-PEG-NH-Boc, Ald-PEG-NHS ester, Ald-PEG-TFP ester, Ald-PEG-t-butyl ester), PEG Tosylate (e.g., Azido-PEG-Tos, Hydroxy-PEG-Tos, m-PEG-Tos, t-Boc-Aminooxy-PEG-Tos, Trifluoroethyl-PEG-Tos, Tos-PEG-acid, Tos-PEG-CH$_2$CO$_2$H, Tos-PEG-alkyne, Tos-PEG-t-butyl ester, Tos-PEG-CH$_2$CO$_2$tBu, Tos-PEG-Tos, S-acetyl-PEG6-Tos, N-Tos-N-(t-butoxycarbonyl)-aminooxy-PEG$_4$-Tos, Ms-PEG-Ms, Ms-PEG-t-butyl ester, PEG-Ms, Propargyl-PEG-Ms), Boc-PEG (e.g., Amino-PEG-t-Boc-Hydrazide, Azido-PEG-t-Boc-Hydrazide, Boc-NH-PEG-NH-Boc, Bromoacetamido-PEG-Boc-amine, m-PEG-ONHBoc, Mal-Alkyl-t-Boc-amine, N-Boc-PEG-alcohol, N-Boc-PEG-bromide, N-methyl-N-(t-Boc)-PEG-acid, t-Boc-N-amido-PEG-acid, t-Boc-N-amido-PEG-CH$_2$CO$_2$H, t-Boc-N-Amido-PEG-amine, t-Boc-N-amido-PEG-azide, t-Boc-N-amido-PEG-NHS ester, t-Boc-N-amido-PEG-sulfonic acid), PEG NHS ester (e.g., Acid-PEG-NHS ester, Azido-PEG-NHS ester, Bis-PEG-NHS, Fmoc-PEG-NHS ester, m-PEG-NHS ester, m-PEG-NHS Carbonate, Mal-PEG-NHS ester, Propargyl-PEG-NHS ester, t-Boc-N-amido-PEG-NHS ester, t-Butoxycarbonyl-PEG-NHS ester), Fmoc-PEG (e.g., Fmoc-N-amido-PEG-acid, Fmoc-NH-PEG-CH$_2$CO$_2$H, Fmoc-PEG-NHS ester), Biotin PEG (e.g., Biotin PEG-acid, Biotin PEG-alcohol, Biotin PEG-alkyne, Biotin PEG-amine, Biotin PEG-azide, Biotin PEG-DBCO, Biotin PEG-hydrazide, Biotin-PEG-Mal, Biotin-PEG-NHS, Biotin-EDA-PEG-NHS, Biotin-PEG-oxyamine, Biotin-PEG-PFP, Biotin-EDA-PEG-PFP, Biotin-PEG-Tetrazine, Biotin-PEG-TFP, Azide-SS-biotin, Biotin-PEG3-SS-azide, DBCO-S-S-PEG3-Biotin, Dde Biotin-PEG4-Alkyne, Dde Biotin-PEG$_4$-Azide, Dde Biotin-PEG$_4$-DBCO, Diazo Biotin-PEG$_3$-Alkyne, Diazo Biotin-PEG$_3$-Azide, Diazo Biotin-PEG3-DBCO, Diol Biotin-PEG$_3$-Alkyne, Diol Biotin-PEG$_3$-Azide, PC Biotin-PEG$_3$-Alkyne, PC-Biotin-PEG$_4$-PEG$_4$-Alkyne, PC-Biotin-PEG$_4$-PEG4-Alkyne, PC Biotin-PEG$_3$-Azide, PC-Biotin-PEG4-PEG3-Azide, PC-Biotin-PEG$_4$-NHS carbonate, PC DBCO-PEG$_3$-Biotin, WSPC Biotin-PEG$_3$-DBCO, Fmoc-Lys (biotin-PEG)-OH, Fmoc-N-amido-(PEG-biotin)-acid, TAMRA-Azide-PEG-Biotin), PEG Phosphonate, Aminooxy PEG (e.g., Aminooxy-PEG-acid, Aminooxy-PEG-alcohol, Aminooxy-PEG-azide, Aminooxy-PEG-bromide, Aminooxy-PEG-methane, Aminooxy-PEG-Propargyl, Aminooxy-PEG-t-butyl ester, Aminooxy-PEG-Thiol, Bis-(Aminooxy)-PEG, t-Boc-Aminooxy-PEG-acid, t-Boc-Aminooxy-PEG-alcohol, t-Boc-Aminooxy-PEG-amine, t-Boc-Aminooxy-PEG-Azide, t-Boc-Aminooxy-PEG-Bromide, t-Boc-aminooxy-PEG-Methane, t-Boc-aminooxy-PEG-Propargyl, t-Boc-aminooxy-PEG-S-Ac, t-Boc-Aminooxy-PEG-Thiol, t-Boc-Aminooxy-PEG-Tos, Fmoc-aminooxy-PEG-acid, Trifluoroethyl-PEG-Aminooxy), Alkyne PEG (e.g., endo-BCN-PEG, exo-BCN-PEG, Propargyl-PEG-acid, Propargyl-PEG-CH$_2$CO$_2$H, Propargyl-PEG-(CH$_2$)$_3$-acid, Propargyl-PEG-(CH$_2$)$_3$-methyl ester, Propargyl-PEG-Acrylate, Propargyl-PEG-alcohol, Propargyl-PEG-amine, Propargyl-PEG-methylamine, Aminooxy-PEG-Propargyl, Propargyl-PEG-azide, Propargyl-PEG-bromide, Propargyl-PEG-Maleimide, Propargyl-PEG-Ms, Propargyl-PEG-NHS ester, Propargyl-PEG-sulfonic acid, Propargyl-PEG-t-butyl ester, Propargyl-PEG-CH$_2$CO$_2$tBu, Propargyl-PEG-thiol, Propargyl-PEG-5-nitrophenyl carbonate, t-Boc-aminooxy-PEG-Propargyl, Bis-Propargyl-PEG, m-PEG-Propargyl), Azido PEG (e.g., Azido-PEG-acid, Azido-PEG-CH$_2$CO$_2$H, Azido-PEG-(CH$_2$)$_3$-methyl ester, Azido-PEG-Acrylate, Azido-PEG-alcohol, Azido-PEG-(CH$_2$)$_3$OH, Azido-PEG-amine, Azido-PEG-azide, Azido-PEG-Maleimide, Azido-PEG-methylamine, Azido-PEG-methyl ester, Azido-PEG-NHS ester, Azido-PEG-CH$_2$CO$_2$—NHS, Azido-PEG-oxazolidin-2-one, Azido-PEG-PFP ester, Azido-PEG-phosphonic acid, Azido-PEG-phosphonic acid ethyl ester, Azido-PEG-sulfonic acid, Azido-PEG-t-Boc-Hydrazide, Azido-PEG-t-butyl ester, Azido-PEG-CH$_2$CO$_2$-t-butyl ester, Azido-PEG-TFP ester, Azido-PEG-Tos, Aminooxy-PEG-azide, Bromo-PEG-azide, Bromoacetamido-PEG-azide, Carboxyrhodamine 110-PEG-Azide, Isothiocyanato-PEG-Azide, Isothiocyanato-PEG-Azide, m-PEG-azide, Propargyl-PEG-azide, TAMRA-PEG-Azide, t-Boc-N-Amido-PEG-Azide, t-Boc-Aminooxy-PEG-Azide, Thiol-PEG-Azide, Trifluoroethyl-PEG-Azide, Azido-PEG-amino acid, Azido-PEG$_4$-4-nitrophenyl carbonate, S-Acetyl-PEG$_3$-Azido, Azide, Trityl-PEG$_{10}$-Azide), Alkyne PEG, DBCO-PEG, BCN-PEG, Propargyl-PEG, Bis-PEG-acid, Bis-PEG-NHS, Bis-PEG-PFP, Bis-Propargyl-PEG, Amine-PEG-Amine, Azido-PEG-azide, Bromo-PEG, or Mal PEG may be used.

The linker between the anti-CAPRIN-1 antibody and the immune activator may be composed of a single linker or composed of a plurality of linkers.

A method for preparing the conjugate of the anti-CAPRIN-1 antibody and the immune activator according to the present invention includes a method which involves binding the immune activator using a ε-amino group at the lysine side chain of the antibody, and a method which involves binding the immune activator using thiol formed by the reduction treatment of a cysteine residue constituting the disulfide bond of the antibody.

In the case of using a ε-amino group at the lysine residue of the antibody, for example, a method is used which involves reacting active ester (e.g., N-hydroxysuccinimide ester) therewith to form an amide bond. In this case, since the antibody contains many lysine residues, the binding reaction proceeds nonspecifically.

In the case of using thiol constituting a disulfide bond present at the cysteine side chain of the antibody, a method is used which involves forming thiol from the disulfide bond on the antibody using a reducing agent such as mercaptoethanol, and reacting the thiol with maleimide or α-haloamide. For example, a method using sulfone phenyloxadiazole, a 4-cyanoethynyloxy derivative, or the like is used for stabilizing a thiol-mediated bond. These bonds are stable for a longer time than the bond based on the conjugate addition reaction of cysteine with maleimide. Also, a linker having an amino group near an imide group can be used because an imide ring with a thiol group added to maleimide is opened by hydrolysis so that stability is improved owing to the resulting amide bond. In the antibody, the thiols of cysteines form a disulfide bond. Thus, an alternative method involves binding the immune activator, etc. to between two thiols via the thiols. As an example, a cross-linked bond may be formed using a linker having two disulfide bond sites that can be formed from an amide group having two sulfones at the β position, or dibromomaleimide.

The conjugate of the present invention can be obtained by a method using, for example, the THIOMAB™ technique, which is a method capable of introducing a determined number of thiol groups at a particular site of an antibody (see Nature Biotechnology 26, 925-932 (2008)).

The conjugate of the present invention can be formed, for example, by reducing the antibody using a reducing agent dithiothreitol (DTT) in a phosphate buffer to obtain an antibody having a reactive thiol group, which is then conjugated with the immune activator. The conjugate can be obtained by adding a thiol group to primary amine at the lysine residue of the antibody by the introduction of a Traut's reagent (2-iminothiolane or N-succinimidyl S-acetylthioacetate (SATA)), instead of the method using a reducing agent.

The amount of the thiol added to the antibody can be determined, for example, by mixing a sample solution containing 5,5'-dithiobis(2-nitrobenzoic acid) (DTNB) and an SH group with a phosphate buffer solution (pH 8.0) and distilled water, adding a solution of DTNB dissolved in a phosphate buffer, a Good's buffer, or a Tris buffer to the mixture, and incubating the resulting mixture for a given time, followed by the measurement of absorbance at 412 nm (see G. L. Ellman, Arch. Biochem. Biophys., 82, 70 (1959)).

The thiol group added by the cleavage of the disulfide bond of the antibody through reduction treatment is preferably treated (capped) in order to prevent the formation of a disulfide bond again. The capping can employ, for example, N-ethylmaleimide (NEM) or 2-iodoacetamide (IAA).

The conjugate through can be constructed binding the immune activator to the antibody using the thiol group added to the antibody according to a method known in the art. Specifically, the binding can be carried out using, for example, a linker reagent having a maleimide group or a bromoacetamide group as a linker reagent specifically binding to the thiol group of the reduced antibody. For example, N-succinimidyl-4-(N-maleimidomethyl)-cyclohexane-1-carboxylate (SMCC) is used as the linker having a maleimide group. In this case, the N-succinimide group of SMCC can form an amide bond with an amino group present in the immune activator to obtain the conjugate.

In another embodiment, an amide bond is first formed at an amino group present in the activator using SMCC. Then, the maleimide group of the SMCC bound with the immune activator can be reacted with the thiol group added to the antibody to obtain the conjugate.

In an alternative embodiment, the conjugate of the antibody and the immune activator may be formed using two linkers. For example, a primary amino group present at the lysine residue of the antibody is bound to the N-succinimide group of SATA (N-succinimidyl-S-acetylthioacetate) via an amide bond to add a thiol group to the antibody. SMCC is reacted with the immune activator containing an amino group or with the immune activator having an amino group added thereto according to an ordinary method to form an amide bond with the N-succinimide group of the SMCC. The maleimide group of the SMCC bound with the immune activator can be reacted with the thiol group of the SATA bound with the antibody to obtain the conjugate.

In a further alternative embodiment, examples of the preparation of the conjugate of the antibody and the immune activator include a method using maleimidocaproyl-valine-citrulline-p-aminobenzyloxycarbonyl (MC-Val-Cit-PAB) as a linker. MC-val-Cit-PAB is a linker cleavable by intracellular protease (e.g., cathepsin B). A thiol group is added to the antibody dissolved in a phosphate bufferusing DTT or the like. Meanwhile, the immune activator having an amino group is reacted with the benzyloxycarbonyl (PAB) in MC-Val-Cit-PAB to prepare an immune activator bound with MC-val-Cit-PAB, which can then be reacted with the thiol-added antibody mentioned above to obtain the conjugate.

In a further alternative embodiment, SATA is bound to a primary amino group at the lysine residue of the antibody to add a thiol group thereto. Meanwhile, succinimidyl 3-(2-pyridyldithio)propionate (SPDP) is reacted with the immune activator having an amino group to form an amide bond with the N-succinimide group of the SPDP. In order to obtain a composition comprising the antibody bound with the linker, for example, a peak fraction of a higher molecular weight as compared with the antibody before the binding of the linker can be separated by the application of gel filtration chromatography or the like.

The number of molecules of the bound immune activator per antibody molecule in the conjugate of the anti-CAPRIN-1 antibody and the immune activator of the present invention can be characterized using a method such as mass spectrometry, ELISA, electrophoresis, or HPLC based on a method known in the art.

<Antitumor Effect of Conjugate>

The conjugate of the anti-CAPRIN-1 antibody and the immune activator of the present invention has cytotoxic activity in vitro or in vivo. Accordingly, the antitumor effect of the conjugate of the present invention may be determined by examining its cytotoxic activity against a cancer. The cytotoxic activity can be evaluated by: administering the conjugate to an organism having a cancer; and examining the size of the tumor over time via measuring the size of the tumor after the administration. The antitumor effect of the present invention can also be evaluated by examining a survival rate. Alternatively, the antitumor effect of the present invention may be evaluated by examining the ability to produce a cytokine or a chemokine. The antitumor effect of the conjugate of the present invention can be further determined by examining the prevention of a cancer, the prevention of metastasis, or the prevention of recurrence.

The conjugate of the present invention is expected to have a stronger antitumor effect, the higher binding affinity for the CAPRIN-1 protein on cancer cell surface the conjugate has. Its association constant (affinity constant) Ka (kon/koff) is preferably at least $10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, or at least $10^{13}$ $M^{-1}$.

The ability of the conjugate of the present invention to bind to CAPRIN-1 can be identified through the use of binding assay using, for example, ELISA, Western blot, immunofluorescence, or flow cytometry.

The conjugate of the present invention enhances the antitumor effect as compared with the anti-CAPRIN-1 antibody alone, as mentioned above. The rate of the enhancement is preferably 30% or more, more preferably 40% or more, further preferably 50% or more, still further preferably 55% or more, even further preferably 60% or more, furthermore preferably 65% or more, most preferably 70% or more. The rate of enhancement in antitumor effect by the conjugate of the present invention with respect to the anti-CAPRIN-1 antibody alone can be calculated by administering their respective effective amounts to cancer-bearing mice under the same conditions, and comparing tumor volumes 10 days or later after the start of the administration.

<Pharmaceutical Composition and Method for Treating and/or Preventing Cancer>

The target of the pharmaceutical composition for the treatment and/or prevention of a cancer of the present invention is not particularly limited as long as the target is cancer (cells) expressing the CAPRIN-1 protein.

The terms "tumor" and "cancer" used in the present specification mean malignant neoplasm and are used interchangeably with each other.

The cancer targeted in the present invention may be any cancer expressing the CAPRIN-1 protein on the cell membrane surface. The cancer is preferably breast cancer, kidney cancer, pancreatic cancer, colorectal cancer, lung cancer, brain tumor, stomach cancer, uterine cancer, ovary cancer, prostate cancer, bladder cancer, esophagus cancer, leukemia, lymphoma, liver cancer, gallbladder cancer, sarcoma, mastocytoma, melanoma, adrenal cortex cancer, Ewing's tumor, Hodgkin's lymphoma, mesothelioma, multiple myeloma, testicle cancer, thyroid cancer, or head and neck cancer as mentioned above.

More specifically, examples of these cancers include, but are not limited to, breast adenocarcinoma, complex-type breast adenocarcinoma, malignant mixed tumor of the mammary gland, intraductal papillary adenocarcinoma, lung adenocarcinoma, squamous cell cancer, small-cell cancer, large-cell cancer, glioma which is tumor of neuroepithelial tissue, glioblastoma, neuroblastoma, ependymoma, neuronal tumor, embryonal neuroectodermal tumor, neurilemmoma, neurofibroma, meningioma, chronic lymphocytic leukemia, lymphoma, gastrointestinal lymphoma, alimentary lymphoma, small to medium cell-type lymphoma, cecal cancer, ascending colon cancer, descending colon cancer, transverse colon cancer, sigmoid colon cancer, rectal cancer, epithelial ovarian cancer, germ cell tumor, stromal cell tumor, pancreatic ductal carcinoma, invasive pancreatic ductal carcinoma, pancreatic adenocarcinoma, acinar cell carcinoma, adenosquamous carcinoma, giant cell tumor, intraductal papillary-mucinous neoplasm, mucinous cystic neoplasm, pancreatoblastoma, islet-cell adenoma, Frants tumor, serous cystadenocarcinoma, solid-pseudopapillary tumor, gastrinoma, glucagonoma, insulinoma, multiple endocrine neoplasia type-1 (Wermer's syndrome), nonfunctional islet cell tumor, somatostatinoma, VIPoma, uterine cervix cancer, uterine body cancer, fibrosarcoma, sarcoma of bones or joints, Ewing's sarcoma, Wilms tumor, hepatoblastoma, soft tissue sarcoma, acute leukemia, chronic leukemia, spinal cord tumor, malignant soft tissue tumor, teratoma group tumor, and head and neck cancer including hypopharynx cancer, oropharynx cancer, tongue cancer, epipharynx cancer, oral cancer, lip cancer, sinus cancer, and throat cancer.

The subjects (patients) to be targeted are preferably mammals, for example, mammals including primates, pet animals, livestock, and sport animals and are particularly preferably humans, dogs, and cats.

In the case of using the conjugate used in the present invention in a pharmaceutical composition, the pharmaceutical composition can be formulated by a method known to those skilled in the art. For example, the pharmaceutical composition can be used in the form of a parenteral injection of an aseptic solution or suspension with water or any other pharmaceutically acceptable liquid. For example, the conjugate may be formulated in a unit dosage form required for generally accepted pharmaceutical practice, by mixing with pharmacologically acceptable carriers or media, specifically, sterilized water, physiological saline, a plant oil, an emulsifier, a suspending agent, a surfactant, a stabilizer, a fragrance, an excipient, a binder, etc in appropriate combination. The effective amount of the active ingredient in such a preparation is determined so that an appropriate dose within the prescribed range can be achieved.

An aseptic composition for injection can be formulated according to conventional pharmaceutical practice using a vehicle such as injectable distilled water. Examples of aqueous solutions for injection include physiological saline, isotonic solutions containing glucose and other auxiliary agents, for example, D-sorbitol, D-mannose, D-mannitol, and sodium chloride. These solutions may be used in combination with an appropriate solubilizer, for example, an alcohol (specifically, ethanol) or a polyalcohol (e.g., propylene glycol and polyethylene glycol), or a nonionic surfactant, for example, Polysorbate 80™ or HCO-60. Examples of oil solutions include sesame oil and soybean oil. These solutions may be used in combination with benzyl benzoate or benzyl alcohol as a solubilizer. The solutions may be further mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The injection solutions thus prepared are usually filled into appropriate ampules. Examples of oil solutions include sesame oil and soybean oil. These solutions may be used in combination with benzyl benzoate or benzyl alcohol as a solubilizer.

The administration is carried out orally or parenterally, preferably parenterally. Specific examples of its dosage forms include injections, intranasal administration preparations, transpulmonary administration preparations, and percutaneous administration preparations. Examples of the injections include intravenous injection, intramuscular injection, intraperitoneal injection, subcutaneous injection, and intratumoral administration, through which the pharmaceutical composition can be administered systemically or locally.

Also, the administration method can be appropriately selected in view of the age, weight, sex, symptoms, etc., of a patient. The dose of a pharmaceutical composition containing the antibody or a polynucleotide encoding the antibody can be selected within a range of, for example, 0.0001 to 1000 mg/kg of body weight per dose. Alternatively, the dose can be selected within a range of, for example, 0.001 to 100000 mg/body of a patient, though the dose is not necessarily limited to these numeric values. Although the dose and the administration method vary depending on the weight, age, sex, symptoms, etc., of a patient, those skilled in the art can appropriately select the dose and the method.

The pharmaceutical composition for the treatment and/or prevention of a cancer comprising the conjugate of the present invention as an active ingredient can be administered to a subject to treat and/or prevent the aforementioned cancer expressing CAPRIN-1 on the cell membrane surface, preferably breast cancer, kidney cancer, pancreatic cancer, colorectal cancer, lung cancer, brain tumor, stomach cancer, uterine cancer, ovary cancer, prostate cancer, bladder cancer, esophagus cancer, leukemia, lymphoma, liver cancer, gallbladder cancer, sarcoma, mastocytoma, melanoma, adrenal cortex cancer, Ewing's tumor, Hodgkin's lymphoma, mesothelioma, multiple myeloma, testicle cancer, thyroid cancer, or head and neck cancer.

EXAMPLES

Hereinafter, the present invention will be specifically described with reference to Examples. However, the scope of the present invention is not intended to be limited by these specific examples.

Example 1 Anti-CAPRIN-1 Polyclonal Antibody

In order to obtain anti-CAPRIN-1 polyclonal antibodies having immunological reactivity with the CAPRIN-1 protein to be used in conjugates, 1 mg of a recombinant human CAPRIN-1 protein of SEQ ID NO: 2 or SEQ ID NO: 4 produced according to Example 3 of WO2010/016526 was mixed with an equal volume of incomplete Freund's adjuvant (IFA) solution, and this mixture was subcutaneously administered to rabbits four times every 2 weeks. Then, blood was collected to obtain antiserum containing polyclonal antibodies. The obtained antiserum was purified using a (GE Healthcare Bio-Sciences Corp.) to prepare a polyclonal antibody against the CAPRIN-1 protein (anti-CAPRIN-1 polyclonal antibody #1). Also, the serum of a rabbit obtained without administering an antigen was purified using a protein G carrier in the same way as above and used as a rabbit control antibody.

The following polyclonal antibodies #2 to #6 against partial polypeptides of CAPRIN-1 were obtained in the same way as in the method for preparing the polyclonal antibody against the CAPRIN-1 protein.

Anti-CAPRIN-1 polyclonal antibody #2 against a partial CAPRIN-1 polypeptide represented by SEQ ID NO: 37 disclosed in WO2011/096528 (SEQ ID NO: 31 of the present specification), anti-CAPRIN-1 polyclonal antibody #3 against a partial polypeptide represented by SEQ ID NO: 5 disclosed in WO2013/018894 (SEQ ID NO: 32 of the present specification), anti-CAPRIN-1 polyclonal antibody #4 against a partial polypeptide represented by SEQ ID NO:

5 disclosed in WO2013/125654 (SEQ ID NO: 33 of the present specification), anti-CAPRIN-1 polyclonal antibody #5 against a partial polypeptide represented by SEQ ID NO: 37 disclosed in WO2011/096533 (SEQ ID NO: 34 of the present specification), and anti-CAPRIN-1 polyclonal antibody #6 against a partial polypeptide represented by SEQ ID NO: 37 disclosed in WO2011/096534 (SEQ ID NO: 35 of the present specification).

Example 2 Anti-CAPRIN-1 Monoclonal Antibody

The following anti-CAPRIN-1 monoclonal antibodies were used in the conjugate of the present invention.

The monoclonal antibody against CAPRIN-1 disclosed in WO2011/096528, wherein the antibody comprises CDR1, CDR2, and CDR3 of heavy chain variable region consisting of the amino acid sequences of SEQ ID NO: 36, SEQ ID NO: 37, and SEQ ID NO: 38, respectively, and CDR1, CDR2, and CDR3 of light chain variable region consisting of the amino acid sequences of SEQ ID NO: 40, SEQ ID NO: 41, and SEQ ID NO: 42, respectively (e.g., an antibody comprising the amino acid sequence of a heavy chain variable region represented by SEQ ID NO: 39 comprising the CDR1, CDR2, and CDR3 of heavy chain variable region, and the amino acid sequence of a light chain variable region represented by SEQ ID NO: 43 comprising the CDR1, CDR2, and CDR3 of light chain variable region).

The monoclonal antibody against CAPRIN-1 disclosed in WO2015/020212, wherein the antibody comprises CDR1, CDR2, and CDR3 of heavy chain variable region consisting of the amino acid sequences of SEQ ID NO: 44, SEQ ID NO: 45, and SEQ ID NO: 46, respectively, and CDR1, CDR2, and CDR3 of light chain variable region consisting of the amino acid sequences of SEQ ID NO: 48, SEQ ID NO: 49, and SEQ ID NO: 50, respectively (e.g., an antibody comprising the amino acid sequence of a heavy chain variable region represented by SEQ ID NO: 47 comprising the CDR1, CDR2, and CDR3 of heavy chain variable region, and the amino acid sequence of a light chain variable region represented by SEQ ID NO: 51 comprising the CDR1, CDR2, and CDR3 of light chain variable region).

The monoclonal antibody against CAPRIN-1 disclosed in WO2011/096519, wherein the antibody comprises CDR1, CDR2, and CDR3 of heavy chain variable region consisting of the amino acid sequences of SEQ ID NO: 52, SEQ ID NO: 53, and SEQ ID NO: 54, respectively, and CDR1, CDR2, and CDR3 of light chain variable region consisting of the amino acid sequences of SEQ ID NO: 56, SEQ ID NO: 57, and SEQ ID NO: 58, respectively (e.g., an antibody comprising the amino acid sequence of a heavy chain variable region represented by SEQ ID NO: 55 comprising the CDR1, CDR2, and CDR3 of heavy chain variable region, and the amino acid sequence of a light chain variable region represented by SEQ ID NO: 59 comprising the CDR1, CDR2, and CDR3 of light chain variable region).

The monoclonal antibody against CAPRIN-1 disclosed in WO2013/125654, wherein the antibody comprises CDR1, CDR2, and CDR3 of heavy chain variable region consisting of the amino acid sequences of SEQ ID NO: 60, SEQ ID NO: 61, and SEQ ID NO: 62, respectively, and CDR1, CDR2, and CDR3 of light chain variable region consisting of the amino acid sequences of SEQ ID NO: 64, SEQ ID NO: 65, and SEQ ID NO: 66, respectively (e.g., an antibody comprising the amino acid sequence of a heavy chain variable region represented by SEQ ID NO: 63 comprising the CDR1, CDR2, and CDR3 of heavy chain variable region, and the amino acid sequence of a light chain variable region represented by SEQ ID NO: 67 comprising the CDR1, CDR2, and CDR3 of light chain variable region).

The monoclonal antibody against CAPRIN-1 disclosed in WO2011/096517, wherein the antibody comprises the amino acid sequence of a heavy chain variable region represented by the amino acid sequence of SEQ ID NO: 68 and the amino acid sequence of a light chain variable region represented by the amino acid sequence of SEQ ID NO: 69.

The monoclonal antibody against CAPRIN-1 disclosed in WO2011/096528, wherein the antibody comprises the amino acid sequence of a heavy chain variable region represented by the amino acid sequence of SEQ ID NO: 70 and the amino acid sequence of a light chain variable region represented by the amino acid sequence of SEQ ID NO: 71; the antibody comprises the amino acid sequence of a heavy chain variable region represented by the amino acid sequence of SEQ ID NO: 72 and the amino acid sequence of a light chain variable region represented by the amino acid sequence of SEQ ID NO: 73; the antibody comprises the amino acid sequence of a heavy chain variable region represented by the amino acid sequence of SEQ ID NO: 74 and the amino acid sequence of a light chain variable region represented by the amino acid sequence of SEQ ID NO: 75; the antibody comprises the amino acid sequence of a heavy chain variable region represented by the amino acid sequence of SEQ ID NO: 76 and the amino acid sequence of a light chain variable region represented by the amino acid sequence of SEQ ID NO: 77; or the antibody comprises the amino acid sequence of a heavy chain variable region represented by the amino acid sequence of SEQ ID NO: 78 and the amino acid sequence of a light chain variable region represented by the amino acid sequence of SEQ ID NO: 79.

The monoclonal antibody against CAPRIN-1 disclosed in WO2011/096533, wherein the antibody comprises the amino acid sequence of a heavy chain variable region represented by the amino acid sequence of SEQ ID NO: 80 and the amino acid sequence of a light chain variable region represented by the amino acid sequence of SEQ ID NO: 81, or the antibody comprises the amino acid sequence of a heavy chain variable region represented by the amino acid sequence of SEQ ID NO: 82 and the amino acid sequence of a light chain variable region represented by the amino acid sequence of SEQ ID NO: 83.

The monoclonal antibody against CAPRIN-1 disclosed in WO2011/096534, wherein the antibody comprises the amino acid sequence of a heavy chain variable region represented by the amino acid sequence of SEQ ID NO: 84 and the amino acid sequence of a light chain variable region represented by the amino acid sequence of SEQ ID NO: 85, or the antibody comprises the amino acid sequence of a heavy chain variable region represented by the amino acid sequence of SEQ ID NO: 86 and the amino acid sequence of a light chain variable region represented by the amino acid sequence of SEQ ID NO: 87.

The monoclonal antibody against CAPRIN-1 disclosed in WO2010/016526, wherein the antibody comprises the amino acid sequence of a heavy chain variable region represented by the amino acid sequence of SEQ ID NO: 88 and the amino acid sequence of a light chain variable region represented by the amino acid sequence of SEQ ID NO: 89; the antibody comprises the amino acid sequence of a heavy chain variable region represented by the amino acid sequence of SEQ ID NO: 90 and the amino acid sequence of a light chain variable region represented by the amino acid sequence of SEQ ID NO: 91; the antibody comprises the amino acid sequence of a heavy chain variable region represented by the amino acid sequence of SEQ ID NO: 92 and the amino acid sequence of a light chain variable region represented by the amino acid sequence of SEQ ID NO: 93; the antibody comprises the amino acid sequence of a heavy chain variable region represented by the amino acid sequence of SEQ ID NO: 94 and the amino acid sequence of a light chain variable region represented by the amino acid sequence of SEQ ID NO: 95; the antibody comprises the amino acid sequence of a heavy chain variable region represented by the amino acid sequence of SEQ ID NO: 96 and the amino acid sequence of a light chain variable region represented by the amino acid sequence of SEQ ID NO: 97; the antibody comprises the amino acid sequence of a heavy chain variable region represented by the amino acid sequence of SEQ ID NO: 98 and the amino acid sequence of a light chain variable region represented by the amino acid sequence of SEQ ID NO: 99; or the antibody comprises the amino acid sequence of a heavy chain variable region represented by the amino acid sequence of SEQ ID NO: 100 and the amino acid sequence of a light chain variable region represented by the amino acid sequence of SEQ ID NO: 101.

The monoclonal antibody against CAPRIN-1 disclosed in WO2013/018894, wherein the antibody comprises the amino acid sequence of a heavy chain variable region represented by the amino acid sequence of SEQ ID NO: 102 and the amino acid sequence of a light chain variable region represented by the amino acid sequence of SEQ ID NO: 103, or the antibody comprises the amino acid sequence of a heavy chain variable region represented by the amino acid sequence of SEQ ID NO: 104 and the amino acid sequence of a light chain variable region represented by the amino acid sequence of SEQ ID NO: 105.

The monoclonal antibody against CAPRIN-1 disclosed in WO2013/018892, wherein the antibody comprises the amino acid sequence of a heavy chain variable region represented by the amino acid sequence of SEQ ID NO: 106 and the amino acid sequence of a light chain variable region represented by the amino acid sequence of SEQ ID NO: 107.

The monoclonal antibody against CAPRIN-1 disclosed in WO2013/018891, wherein the antibody comprises the amino acid sequence of a heavy chain variable region represented by the amino acid sequence of SEQ ID NO: 108 and the amino acid sequence of a light chain variable region represented by the amino acid sequence of SEQ ID NO: 109.

The monoclonal antibody against CAPRIN-1 disclosed in WO2013/018889, wherein the antibody comprises the amino acid sequence of a heavy chain variable region represented by the amino acid sequence of SEQ ID NO: 110 and the amino acid sequence of a light chain variable region represented by the amino acid sequence of SEQ ID NO: 111.

The monoclonal antibody against CAPRIN-1 disclosed in WO2013/018883, wherein the antibody comprises the amino acid sequence of a heavy chain variable region represented by the amino acid sequence of SEQ ID NO: 112 and the amino acid sequence of a light chain variable region represented by the amino acid sequence of SEQ ID NO: 113.

The monoclonal antibody against CAPRIN-1 disclosed in WO2013/125636, wherein the antibody comprises the amino acid sequence of a heavy chain variable region represented by the amino acid sequence of SEQ ID NO: 114 and the amino acid sequence of a light chain variable region represented by the amino acid sequence of SEQ ID NO: 115.

The monoclonal antibody against CAPRIN-1 disclosed in WO2013/125654, wherein the antibody comprises the amino acid sequence of a heavy chain variable region represented by the amino acid sequence of SEQ ID NO: 116 and the amino acid sequence of a light chain variable region represented by the amino acid sequence of SEQ ID NO: 117, or the antibody comprises the amino acid sequence of a heavy chain variable region represented by the amino acid sequence of SEQ ID NO: 118 and the amino acid sequence of a light chain variable region represented by the amino acid sequence of SEQ ID NO: 119.

The monoclonal antibody against CAPRIN-1 disclosed in WO2013/125630, wherein the antibody comprises the amino acid sequence of a heavy chain variable region represented by the amino acid sequence of SEQ ID NO: 120 and the amino acid sequence of a light chain variable region represented by the amino acid sequence of SEQ ID NO: 121.

The monoclonal antibody against CAPRIN-1 disclosed in WO2015/020212, wherein the antibody comprises the amino acid sequence of a heavy chain variable region represented by the amino acid sequence of SEQ ID NO: 122 and the amino acid sequence of a light chain variable region represented by the amino acid sequence of SEQ ID NO: 123; the antibody comprises the amino acid sequence of a heavy chain variable region represented by the amino acid sequence of SEQ ID NO: 124 and the amino acid sequence of a light chain variable region represented by the amino acid sequence of SEQ ID NO: 125; the antibody comprises the amino acid sequence of a heavy chain variable region represented by the amino acid sequence of SEQ ID NO: 126 and the amino acid sequence of a light chain variable region represented by the amino acid sequence of SEQ ID NO: 127; the antibody comprises the amino acid sequence of a heavy chain variable region represented by the amino acid sequence of SEQ ID NO: 128 and the amino acid sequence of a light chain variable region represented by the amino acid sequence of SEQ ID NO: 129; the antibody comprises the amino acid sequence of a heavy chain variable region represented by the amino acid sequence of SEQ ID NO: 130 and the amino acid sequence of a light chain variable region represented by the amino acid sequence of SEQ ID NO: 131; or the antibody comprises the amino acid sequence of a heavy chain variable region represented by the amino acid sequence of SEQ ID NO: 132 and the amino acid sequence of a light chain variable region represented by the amino acid sequence of SEQ ID NO: 133.

A nucleotide sequence was designed to express a heavy chain variable region comprising CDR1, CDR2, and CDR3 consisting of the amino acid sequences of SEQ ID NO: 36, SEQ ID NO: 37, and SEQ ID NO: 38, respectively, which are from one of the above-mentioned anti-CAPRIN-1 monoclonal antibodies, and framework region sequences of a human antibody. The nucleotide sequence was inserted into a mammalian expression vector with an insert encoding a heavy chain constant region of human IgG1. Similarly, a nucleotide sequence was designed to express a light chain variable region comprising CDR1, CDR2, and CDR3 consisting of the amino acid sequences of SEQ ID NO: 40, SEQ ID NO: 41, and SEQ ID NO: 42, respectively, and framework region sequences of a human antibody; and the nucleotide sequence was inserted into a mammalian expression vector with an insert encoding a light chain constant region of human IgG1. These two recombinant expression vectors were transferred to mammalian cells according to a conventional method, and a culture supernatant containing humanized monoclonal antibody #1 (humanized antibody #1) against CAPRIN-1 comprising CDR1, CDR2, and CDR3 of heavy chain variable region consisting of the amino acid sequences of SEQ ID NO: 36, SEQ ID NO: 37, and SEQ ID NO: 38, respectively, and CDR1, CDR2, and CDR3 of light chain variable region consisting of the amino acid sequences of SEQ ID NO: 40, SEQ ID NO: 41, and SEQ ID NO: 42, respectively, was obtained from the cells.

Similarly, a nucleotide sequence was designed to express a heavy chain variable region represented by SEQ ID NO: 47 comprising CDR1, CDR2, and CDR3 consisting of the amino acid sequences of SEQ ID NO: 44, SEQ ID NO: 45, and SEQ ID NO: 46, respectively, and framework region sequences of a human antibody; and the nucleotide sequence was inserted into a mammalian expression vector with an insert encoding a heavy chain constant region of human IgG1. Similarly, a nucleotide sequence was designed to express a light chain variable region represented by SEQ ID NO: 51 comprising CDR1, CDR2, and CDR3 consisting of the amino acid sequences of SEQ ID NO: 48, SEQ ID NO: 49, and SEQ ID NO: 50, respectively, and framework region sequences of a human antibody; and the nucleotide sequence was inserted into a mammalian expression vector with an insert encoding a heavy chain constant region of human IgG1. These two recombinant expression vectors were transferred to mammalian cells according to a conventional method, and a culture supernatant containing humanized anti-CAPRIN-1 monoclonal antibody #2 (humanized antibody #2) comprising CDR1, CDR2, and CDR3 of heavy chain variable region consisting of the amino acid sequences of SEQ ID NO: 44, SEQ ID NO: 45, and SEQ ID NO: 46, respectively, and CDR1, CDR2, and CDR3 of light chain variable region consisting of the amino acid sequences of SEQ ID NO: 48, SEQ ID NO: 49, and SEQ ID NO: 50, respectively, was obtained from the cells.

A culture supernatant containing humanized anti-CAPRIN-1 monoclonal antibody #3 (humanized antibody #3) comprising CDR1, CDR2, and CDR3 of heavy chain variable region consisting of the amino acid sequences of SEQ ID NO: 52, SEQ ID NO: 53, and SEQ ID NO: 54, respectively, and CDR1, CDR2, and CDR3 of light chain variable region consisting of the amino acid sequences of SEQ ID NO: 56, SEQ ID NO: 57, and SEQ ID NO: 58, respectively, was prepared in a similar way.

A culture supernatant containing humanized anti-CAPRIN-1 monoclonal antibody #4 (humanized antibody #4) comprising CDR1, CDR2, and CDR3 of heavy chain variable region consisting of the amino acid sequences of SEQ ID NO: 60, SEQ ID NO: 61, and SEQ ID NO: 62, respectively, and CDR1, CDR2, and CDR3 of light chain variable region consisting of the amino acid sequences of SEQ ID NO: 64, SEQ ID NO: 65, and SEQ ID NO: 66, respectively, was prepared in a similar way.

Culture supernatants containing the following humanized anti-CAPRIN-1 monoclonal antibodies #9 to #41 (humanized antibodies #9 to #41) were prepared in a similar way.

Humanized monoclonal antibody #9 (humanized antibody #9) comprising the amino acid sequence of a heavy chain variable region represented by the amino acid sequence of SEQ ID NO: 68 and the amino acid sequence of a light chain variable region represented by the amino acid sequence of SEQ ID NO: 69.

Humanized monoclonal antibody #10 (humanized antibody #10) comprising the amino acid sequence of a heavy chain variable region represented by the amino acid sequence of SEQ ID NO: 70 and the amino acid sequence of a light chain variable region represented by the amino acid sequence of SEQ ID NO: 71.

Humanized monoclonal antibody #11 (humanized antibody #11) comprising the amino acid sequence of a heavy chain variable region represented by the amino acid sequence of SEQ ID NO: 72 and the amino acid sequence of a light chain variable region represented by the amino acid sequence of SEQ ID NO: 73.

Humanized monoclonal antibody #12 (humanized antibody #12) comprising the amino acid sequence of a heavy chain variable region represented by the amino acid sequence of SEQ ID NO: 74 and the amino acid sequence of a light chain variable region represented by the amino acid sequence of SEQ ID NO: 75.

Humanized monoclonal antibody #13 (humanized antibody #13) comprising the amino acid sequence of a heavy chain variable region represented by the amino acid sequence of SEQ ID NO: 76 and the amino acid sequence of a light chain variable region represented by the amino acid sequence of SEQ ID NO: 77.

Humanized monoclonal antibody #14 (humanized antibody #14) comprising the amino acid sequence of a heavy chain variable region represented by the amino acid sequence of SEQ ID NO: 78 and the amino acid sequence of a light chain variable region represented by the amino acid sequence of SEQ ID NO: 79.

Humanized monoclonal antibody #15 (humanized antibody #15) comprising the amino acid sequence of a heavy chain variable region represented by the amino acid sequence of SEQ ID NO: 80 and the amino acid sequence of a light chain variable region represented by the amino acid sequence of SEQ ID NO: 81.

Humanized monoclonal antibody #16 (humanized antibody #16) comprising the amino acid sequence of a heavy chain variable region represented by the amino acid sequence of SEQ ID NO: 82 and the amino acid sequence of a light chain variable region represented by the amino acid sequence of SEQ ID NO: 83.

Humanized monoclonal antibody #17 (humanized antibody #17) comprising the amino acid sequence of a heavy chain variable region represented by the amino acid sequence of SEQ ID NO: 84 and the amino acid sequence of a light chain variable region represented by the amino acid sequence of SEQ ID NO: 85.

Humanized monoclonal antibody #18 (humanized antibody #18) comprising the amino acid sequence of a heavy chain variable region represented by the amino acid sequence of SEQ ID NO: 86 and the amino acid sequence of a light chain variable region represented by the amino acid sequence of SEQ ID NO: 87.

Humanized monoclonal antibody #19 (humanized antibody #19) comprising the amino acid sequence of a heavy chain variable region represented by the amino acid sequence of SEQ ID NO: 88 and the amino acid sequence of a light chain variable region represented by the amino acid sequence of SEQ ID NO: 89.

Humanized monoclonal antibody #20 (humanized antibody #20) comprising the amino acid sequence of a heavy chain variable region represented by the amino acid sequence of SEQ ID NO: 90 and the amino acid sequence of a light chain variable region represented by the amino acid sequence of SEQ ID NO: 91.

Humanized monoclonal antibody #21 (humanized antibody #21) comprising the amino acid sequence of a heavy chain variable region represented by the amino acid sequence of SEQ ID NO: 92 and the amino acid sequence of a light chain variable region represented by the amino acid sequence of SEQ ID NO: 93.

Humanized monoclonal antibody #22 (humanized antibody #22) comprising the amino acid sequence of a heavy chain variable region represented by the amino acid sequence of SEQ ID NO: 94 and the amino acid sequence of a light chain variable region represented by the amino acid sequence of SEQ ID NO: 95.

Humanized monoclonal antibody #23 (humanized antibody #23) comprising the amino acid sequence of a heavy chain variable region represented by the amino acid sequence of SEQ ID NO: 96 and the amino acid sequence of a light chain variable region represented by the amino acid sequence of SEQ ID NO: 97.

Humanized monoclonal antibody #24 (humanized antibody #24) comprising the amino acid sequence of a heavy chain variable region represented by the amino acid sequence of SEQ ID NO: 98 and the amino acid sequence of a light chain variable region represented by the amino acid sequence of SEQ ID NO: 99.

Humanized monoclonal antibody #25 (humanized antibody #25) comprising the amino acid sequence of a heavy chain variable region represented by the amino acid sequence of SEQ ID NO: 100 and the amino acid sequence of a light chain variable region represented by the amino acid sequence of SEQ ID NO: 101.

Humanized monoclonal antibody #26 (humanized antibody #26) comprising the amino acid sequence of a heavy chain variable region represented by the amino acid sequence of SEQ ID NO: 102 and the amino acid sequence of a light chain variable region represented by the amino acid sequence of SEQ ID NO: 103.

Humanized monoclonal antibody #27 (humanized antibody #27) comprising the amino acid sequence of a heavy chain variable region represented by the amino acid sequence of SEQ ID NO: 104 and the amino acid sequence of a light chain variable region represented by the amino acid sequence of SEQ ID NO: 105.

Humanized monoclonal antibody #28 (humanized antibody #28) comprising the amino acid sequence of a heavy chain variable region represented by the amino acid sequence of SEQ ID NO: 106 and the amino acid sequence of a light chain variable region represented by the amino acid sequence of SEQ ID NO: 107.

Humanized monoclonal antibody #29 (humanized antibody #29) comprising the amino acid sequence of a heavy chain variable region represented by the amino acid sequence of SEQ ID NO: 108 and the amino acid sequence of a light chain variable region represented by the amino acid sequence of SEQ ID NO: 109.

Humanized monoclonal antibody #30 (humanized antibody #30) comprising the amino acid sequence of a heavy chain variable region represented by the amino acid sequence of SEQ ID NO: 110 and the amino acid sequence of a light chain variable region represented by the amino acid sequence of SEQ ID NO: 111.

Humanized monoclonal antibody #31 (humanized antibody #31) comprising the amino acid sequence of a heavy chain variable region represented by the amino acid sequence of SEQ ID NO: 112 and the amino acid sequence of a light chain variable region represented by the amino acid sequence of SEQ ID NO: 113.

Humanized monoclonal antibody #32 (humanized antibody #32) comprising the amino acid sequence of a heavy chain variable region represented by the amino acid sequence of SEQ ID NO: 114 and the amino acid sequence of a light chain variable region represented by the amino acid sequence of SEQ ID NO: 115.

Humanized monoclonal antibody #33 (humanized antibody #33) comprising the amino acid sequence of a heavy chain variable region represented by the amino acid sequence of SEQ ID NO: 116 and the amino acid sequence of a light chain variable region represented by the amino acid sequence of SEQ ID NO: 117.

Humanized monoclonal antibody #34 (humanized antibody #34) comprising the amino acid sequence of a heavy chain variable region represented by the amino acid sequence of SEQ ID NO: 118 and the amino acid sequence of a light chain variable region represented by the amino acid sequence of SEQ ID NO: 119.

Humanized monoclonal antibody #35 (humanized antibody #35) comprising the amino acid sequence of a heavy chain variable region represented by the amino acid sequence of SEQ ID NO: 120 and the amino acid sequence of a light chain variable region represented by the amino acid sequence of SEQ ID NO: 121.

Humanized monoclonal antibody #36 (humanized antibody #36) comprising the amino acid sequence of a heavy chain variable region represented by the amino acid sequence of SEQ ID NO: 122 and the amino acid sequence of a light chain variable region represented by the amino acid sequence of SEQ ID NO: 123.

Humanized monoclonal antibody #37 (humanized antibody #37) comprising the amino acid sequence of a heavy chain variable region represented by the amino acid sequence of SEQ ID NO: 124 and the amino acid sequence of a light chain variable region represented by the amino acid sequence of SEQ ID NO: 125.

Humanized monoclonal antibody #38 (humanized antibody #38) comprising the amino acid sequence of a heavy chain variable region represented by the amino acid sequence of SEQ ID NO: 126 and the amino acid sequence of a light chain variable region represented by the amino acid sequence of SEQ ID NO: 127.

Humanized monoclonal antibody #39 (humanized antibody #39) comprising the amino acid sequence of a heavy chain variable region represented by the amino acid sequence of SEQ ID NO: 128 and the amino acid sequence of a light chain variable region represented by the amino acid sequence of SEQ ID NO: 129.

Humanized monoclonal antibody #40 (humanized antibody #40) comprising the amino acid sequence of a heavy chain variable region represented by the amino acid sequence of SEQ ID NO: 130 and the amino acid sequence of a light chain variable region represented by the amino acid sequence of SEQ ID NO: 131.

Humanized monoclonal antibody #41 (humanized antibody #41) comprising the amino acid sequence of a heavy chain variable region represented by the amino acid sequence of SEQ ID NO: 132 and the amino acid sequence of a light chain variable region represented by the amino acid sequence of SEQ ID NO: 133.

On the basis of humanized antibody #1 among these anti-CAPRIN-1 monoclonal antibodies, a nucleotide sequence was designed to express a heavy chain variable region comprising CDR1, CDR2, and CDR3 consisting of the amino acid sequences of SEQ ID NO: 36, SEQ ID NO: 37, and SEQ ID NO: 38, respectively, and framework region sequences of a human antibody. This nucleotide sequence was inserted into a mammalian expression vector with an insert encoding a heavy chain constant region of human IgG1 in which serine (Ser) at amino acid position 239 in EU numbering is substituted with aspartic acid (Asp), and isoleucine (Ile) at amino acid position 332 in EU numbering is substituted with glutamic acid (Glu). Also, a nucleotide sequence was designed to express the amino acid sequence of a light chain variable region comprising CDR1, CDR2, and CDR3 consisting of the amino acid sequences of SEQ ID NO: 40, SEQ ID NO: 41, and SEQ ID NO: 42, respectively, and framework region sequences of a human antibody, and the nucleotide sequence was inserted into a mammalian expression vector with an insert encoding a light chain constant region of human IgG1. These two recombinant expression vectors were transferred to mammalian cells according to a conventional method; and a culture supernatant containing humanized monoclonal antibody #5 (humanized antibody #5) against CAPRIN-1 composed of the full-length heavy chain amino acid sequence consisting of the heavy chain variable region designed above and the heavy chain constant region of human IgG1 in which serine (Ser) at amino acid position 239 in EU numbering is substituted with aspartic acid (Asp), and isoleucine (Ile) at amino acid position 332 in EU numbering is substituted with glutamic acid (Glu), and the full-length light chain amino acid sequence consisting of the light chain variable region designed above and the human light chain constant region, was obtained from the cells.

A culture supernatant containing humanized anti-CAPRIN-1 monoclonal antibody #6 (humanized antibody #6) comprising the amino acid sequence of the heavy chain variable region and the amino acid sequence of the light chain variable region of the humanized antibody #2 produced above was prepared in a similar way.

A culture supernatant containing humanized anti-CAPRIN-1 monoclonal antibody #7 (humanized antibody #7) comprising the amino acid sequence of the heavy chain variable region and the amino acid sequence of the light chain variable region of the humanized antibody #3 produced above was prepared in a similar way.

A culture supernatant containing humanized anti-CAPRIN-1 monoclonal antibody #8 (humanized antibody #8) comprising the amino acid sequence of the heavy chain variable region and the amino acid sequence of the light chain variable region of the humanized antibody #4 produced above was prepared in a similar way.

Culture supernatants containing each of humanized anti-CAPRIN-1 antibodies #42 to #74 (humanized antibodies #42 to #74) comprising the amino acid sequence of the heavy chain variable region and the amino acid sequence of the light chain variable region of each of the humanized antibodies #9 to #41 produced above were prepared in a similar way.

The obtained culture supernatants containing each of the humanized anti-CAPRIN-1 monoclonal antibodies #1 to #74 were subjected to purification using Hitrap Protein A Sepharose FF (GE Healthcare) according to a conventional method. The buffer was replaced with PBS(-). The resultant was filtered through a 0.22 μm filter (Merck Millipore Corp.) to prepare the humanized antibodies.

Example 3 Preparation of conjugate of anti-CAPRIN-1 antibody and immune activator Conjugates of anti-CAPRIN-1 polyclonal antibodies #1 to #6 described in Example 1 with resiquimod, an immune activator, were prepared using maleimidocaproyl-valine-citrulline-p-aminobenzyloxycarbonyl (MC-val-Cit-PAB) as a linker. The preparation of these conjugates was carried out with reference to the method described in WO2014/012479.

20 mg/mL of anti-CAPRIN-1 polyclonal antibody #0 described in Example 1 dissolved in PBS(-) was subjected to buffer replacement with a solution of 500 mM sodium borate and 500 mM sodium chloride (pH 8.0). After incubation of the antibody solution at 37° C. for 30 minutes with 100 mM dithiothreitol (DTT), the buffer was replaced with a PBS(-) solution containing 1 mM diethylenetriaminepentaacetic acid (DTPA) using Sephadex G25, and the resultant was cooled on ice to prepare "reduced" anti-CAPRIN-1 polyclonal antibody #0.

The amount of thiol per antibody molecule (thiol/antibody ratio) was determined by reacting the antibody with DTNB and measuring the absorbance at 412 nm and the absorbance at 280 nm.

Resiquimod (Enzo Life Sciences, Inc.) and MC-Val-Cit-PABC-PNP- (Medchem Express) were mixed in DMSO to allow the amino group of resiquimod to react with MC-Val-Cit-PABC-PNP-, thereby preparing a MC-val-Cit-PAB-bound resiquimod solution, which was then added to the reduced anti-CAPRIN-1 polyclonal antibody #1 prepared above for reaction thereof. After the reaction, an excess amount of maleimide was added to terminate the reaction, thereby preparing a solution containing a conjugate of anti-CAPRIN-1 polyclonal antibody #1 described in Example 1 with resiquimod. The obtained conjugate was concentrated by ultrafiltration and desalted using Sephadex G25 into a PBS (-) solution. The resultant was sterilized by filtration through a 0.22 μm filter to prepare a solution containing the conjugate of anti-CAPRIN-1 polyclonal antibody #1 and resiquimod (Conjugate 1).

A solution containing a conjugate of anti-CAPRIN-1 polyclonal antibody #2 and resiquimod (Conjugate 2), a solution of a conjugate of anti-CAPRIN-1 polyclonal antibody #3 and resiquimod (Conjugate 3), a solution of a conjugate of anti-CAPRIN-1 polyclonal antibody #4 and resiquimod (Conjugate 4), a solution of a conjugate of anti-CAPRIN-1 polyclonal antibody #5 and resiquimod (Conjugate 5), and a solution of a conjugate of anti-CAPRIN-1 polyclonal antibody #6 and resiquimod (Conjugate 6) were prepared in the same way as described above.

As for the rabbit control antibody described in Example 1 unreactive with the CAPRIN-1 protein, a solution containing a conjugate of the rabbit control antibody and resiquimod (Control conjugate 1) was also prepared in the same way as described above.

A solution containing a conjugate of humanized antibody #1, which is an anti-CAPRIN-1 monoclonal antibody described in Example 2, with the immune activator resiquimod (Conjugate 7) was prepared using the humanized antibody #1 in the same way as above.

A solution containing a conjugate of humanized antibody #2, which is an anti-CAPRIN-1 antibody described in Example 2, with the immune activator resiquimod (Conjugate 8) was prepared using the humanized antibody #2 in the same way.

A solution containing a conjugate of humanized antibody #3 described in Example 2 with the immune activator resiquimod (Conjugate 9); a solution containing a conjugate of humanized antibody #4 with the immune activator resiquimod (Conjugate 10); a solution containing a conjugate of humanized antibody #5 with the immune activator resiquimod (Conjugate 11); a solution containing a conjugate of humanized antibody #6 with the immune activator resiquimod (Conjugate 12); a solution containing a conjugate of humanized antibody #7 with the immune activator resiquimod (Conjugate 13); a solution containing a conjugate of humanized antibody #8 with the immune activator resiquimod (Conjugate 14); and solutions containing conjugates of humanized antibodies #9 to #74 with the immune activator resiquimod (Conjugates 45 to 110), were each prepared as described above.

The prepared solutions containing Conjugates 1 to 14, Conjugates 45 to 110, and Control conjugate 1 were each filtered through a 0.22 μm filter (Merck Millipore Corp.) to prepare the conjugates.

Example 4 Preparation of Conjugate of Anti-CAPRIN-1 Antibody and Immune Activator Conjugates of the anti-CAPRIN-1 polyclonal antibodies described in Example 1 with an immune activator were prepared by the following method. 1-(2 (2-aminoethoxy)-2-methylpropyl)-2-(ethoxymethyl)-1H-imidazo[4,5-c]quinolin-4-amine, a resiquimod derivative made by two-carbon homoligation of the tertiary hydroxy group of resiquimod and the addition of an amino group thereto, was prepared as an immune activator by synthesis according to an ordinary method.

Specifically, dry acetonitrile, triethylamine, and trityl chloride were added to resiquimod, and reacted in an argon atmosphere. After the reaction, the residue was purified by silica gel column chromatography. The purified product was dissolved in dehydrated DMF and reacted with added 3-Boc-1,2,3-oxathiazolidine 2,2-dioxide. The aqueous phase was subjected to extraction with ethyl acetate according to an ordinary method. The obtained organic phase was then purified by column chromatography to prepare the above-mentioned resiquimod derivative.

Next, the following procedure was carried out with reference to the method described in J. Med. Chem., (2008) 51, 6916-6926 in order to bind the obtained resiquimod derivative to succinimidyl 4-(N-maleimidomethyl)cyclohexane-1-carboxylate (SMCC), as a linker.

The resiquimod derivative was dissolved in dehydrated dichloromethane in an argon atmosphere. To the solution, diisopropylethylamine and SMCC were added. The mixture was allowed to react at room temperature for 2 hours. The reaction mixture was subjected to purification to obtain a condensate of resiquimod with SMCC.

A conjugate of the condensate of resiquimod with the linker SMCC and anti-CAPRIN-1 antibody was prepared according to an ordinary method with reference to the methods described in U.S. Pat. No. 8,951,528 and JIMD Reports-Case and Research Reports, 2012/5.

Specifically, to anti-CAPRIN-1 polyclonal antibody #1 dissolved in a phosphate buffer, N-succinimidyl S-acetylthioacetate (SATA) (Thermo Fischer Scientific, Inc.) dissolved in a 10-fold molar mass of DMSO relative to the antibody was added, and reacted at room temperature for 30 minutes at pH 8. Then, the buffer was replaced with a phosphate buffer containing 10 mM EDTA using a desalting column (Thermo Fischer Scientific, Inc.) to obtain a solution containing anti-CAPRIN-1 polyclonal antibody #1 bound with SATA. To the solution, a phosphate buffer containing 0.5 M hydroxylamine and 25 mM EDTA was added in a volume of 10% relative to the solution, and the mixture was deacetylated through reaction at room temperature for 2 hours. The buffer in the solution containing anti-CAPRIN-1 polyclonal antibody #1 bound with deacetylated SATA was replaced with a phosphate buffer using a desalting column as described above to prepare a solution containing a thiol group-added anti-CAPRIN-1 antibody.

The condensate prepared above, dissolved in a 10- to 50-fold molar mass of DMSO relative to such antibody, was added to the solution and the mixture was reacted at room temperature for 1 hour. After the reaction, the buffer was replaced with a PBS(−) solution using a desalting column, and the resultant was concentrated using an ultrafiltration column and sterilized by filtration through a 0.2 µm filter to obtain a solution containing a conjugate of anti-CAPRIN-1 polyclonal antibody #1 described in Example 1 with the resiquimod derivative (Conjugate 15).

In the same way as above, a solution containing a conjugate of anti-CAPRIN-1 polyclonal antibody #2 with the resiquimod derivative (Conjugate 16), a solution containing a conjugate of anti-CAPRIN-1 polyclonal antibody #3 with the immune activator (Conjugate 17), a solution containing a conjugate of anti-CAPRIN-1 polyclonal antibody #4 with the immune activator (Conjugate 18), a solution containing a conjugate of anti-CAPRIN-1 polyclonal antibody #5 with the immune activator (Conjugate 19), and a solution containing a conjugate of anti-CAPRIN-1 polyclonal antibody #6 with the immune activator (Conjugate 20) were prepared.

As for the rabbit control antibody described in Example 1 unreactive with the CAPRIN-1 protein, a solution containing a conjugate (Control conjugate 2) was also prepared in the same way as above using the rabbit control antibody.

A solution containing a conjugate of humanized antibody #1, which is one of the anti-CAPRIN-1 monoclonal antibodies described in Example 2, with the resiquimod derivative (Conjugate 21) was prepared in the same way as above.

A solution containing a conjugate of humanized antibody #2, which is one of the anti-CAPRIN-1 antibodies described in Example 2, with the resiquimod derivative (Conjugate 22) was obtained in the same way.

In the same way as above, a solution containing a conjugate of humanized antibody #3, which is an anti-CAPRIN-1 antibody described in Example 2, with the immune activator (Conjugate 23); a solution containing a conjugate of humanized antibody #4 with the immune activator (Conjugate 24); a solution containing a conjugate of humanized antibody #5 with the immune activator (Conjugate 25); a solution containing a conjugate of humanized antibody #6 with the immune activator (Conjugate 26); a solution containing a conjugate of humanized antibody #7 with the immune activator (Conjugate 27); and a solution containing a conjugate of humanized antibody #8 with the immune activator (Conjugate 28) were prepared.

In the same way as above, solutions containing conjugates of humanized antibodies #9 to #74 with the immune activator (Conjugates 111 to 176) were each prepared.

The prepared solutions containing Conjugates 15 to 28, Conjugates 111 to 176, and Control conjugate 2 were each filtered through a 0.22 µm filter (Merck Millipore Corp.) to prepare the conjugates.

Example 5 Specific Reactivity of Conjugate with CAPRIN-1 Protein and CAPRIN-1-Expressing Cancer Cell Conjugates 1 to 14 and Conjugates 45 to 110 prepared in Example 3 and Conjugates 15 to 28 and Conjugates 111 to 176 prepared in Example 4 were assayed for their specific reactivity with a CAPRIN-1 protein and their reactivity with the cell membrane surface of human cancer cells and mouse cancer cells which expressing a CAPRIN-1 protein.

The specific reactivity with the CAPRIN-1 protein was determined by ELISA. A 1 µg/mL CAPRIN-1 protein solution was added at 100 µL/well to a 96-well plate, and the plate was left to stand at 4° C. for 18 hours. Each well was washed with PBS-T three times. Then, a 0.5% bovine serum albumin (BSA) solution was added at 400 µL/well, and the plate was left to stand at room temperature for 3 hours. The solution was removed, and the wells were washed with 400 µL/well of PBS-T three times. Then, each of the solutions containing Conjugates 1 to 6, Conjugates 15 to 20, Control conjugate 1, and Control conjugate 2 was added at 100 µL/well, and the plate was left to stand at room temperature for 2 hours. Each well was washed with PBS-T three times.

Then, an HRP-labeled anti-rabbit antibody diluted 5000-fold with PBS was added at 100 µL/well, and left to stand at room temperature for 1 hour. Each well was washed with PBS-T three times. Then, a TMB substrate solution was added at 100 µL/well, and left to stand for 15 to 30 minutes for chromogenic reaction. After the color development, the reaction was terminated by the addition of 1 N sulfuric acid at 100 µL/well, and the absorbance values at 450 nm and 595 nm were measured using an absorption spectrometer. As a result, Conjugates 1 to 6 and Conjugates 15 to 20 exhibited a higher absorbance value than that of Control conjugates 1 and 2 as negative controls and were found to specifically react with the CAPRIN-1 protein.

Next, the reactivity with the cell membrane surface of CAPRIN-1-expressing cancer cells was verified by flow cytometry. Human breast cancer cells BT-474 (from ATCC) or mouse breast cancer cells 4T1 (from ATCC) were centrifuged in 1.5 mL microcentrifuge tubes ($2 \times 10^5$ cells per tube). 100 µL of the solutions containing each of Conjugates 1 to 6, Conjugates 15 to 20, Control conjugate 1, and Control conjugate 2 was then each added to separate tubes. The tube was left to stand on ice for 1 hour. After washing with PBS, Alexa 488-labeled anti-rabbit IgG (H+L) diluted 100-fold with PBS(-) containing 0.5% FBS (0.5% FBS-PBS(-)) was added thereto, and the tube was left to stand on ice for 1 hour. After washing with 0.5% FBS-PBS(-), the cells were suspended in 0.2 µg/mL propidium iodide and 0.5% FBS-PBS(-), and the fluorescence intensity was measured using FACSVerse™ (Becton, Dickinson and Company). As a result, Conjugates 1 to 6 and Conjugates 15 to 20, which were the conjugates of the anti-CAPRIN-1 polyclonal antibodies and the immune activator, were found to exhibit higher fluorescence intensity than that of Control conjugate 1 and Control conjugate 2 as negative controls, i.e., to strongly react with the cell surface of the human cancer cells BT474 and the mouse cancer cells 4T1 expressing CAPRIN-1.

The reactivity of the conjugates with the following various human cancer cells and mouse cancer cells was verified in a similar way: breast cancer cells (BT-474), colorectal cancer cells (HT-29), lung cancer cells (QG56 and H1650), stomach cancer cells (NCI-N87), uterine cancer cells (HEC-1-A), prostate cancer cells (22Rv1), pancreatic cancer cells (Panc10.5), liver cancer cells (Hep3B), ovary cancer cells (SKOV3), kidney cancer cells (Caki-2), brain tumor cells (U-87MG), bladder cancer cells (T24), esophagus cancer cells (OE33), leukemia cells (OCI-AMLS), lymphoma cells (Ramos), gallbladder cancer cells (TGBC14TKB), fibrosarcoma cells (HT-1080), and melanoma cells (G-361), which are human cancer cells found to express the CAPRIN-1 gene; and mouse kidney cancer cells (Renca) and mouse breast cancer cells (4T1), which are mouse cancer cells found to express the CAPRIN-1 gene. As a result of the verification, Conjugates 1 to 6 and Conjugates 15 to 20, which were the conjugates of the anti-CAPRIN-1 antibodies and the immune activator, exhibited stronger fluorescence intensities for all of the cancer cells than that of Control conjugate 1 and Control conjugate 2 as negative controls and were thus shown to strongly react with the cell membrane surface of the above cancer cells expressing CAPRIN-1.

Also, anti-CAPRIN-1 polyclonal antibodies #1 to #6 prepared in Example 1 which are unconjugated with the immune activator were similarly assayed. As a result of assaying their reactivity with the above cancer cells expressing CAPRIN-1 by flow cytometry, these antibodies exhibited fluorescence intensities equivalent to those of Conjugates 1 to 6 and Conjugates 15 to 20.

Next, Conjugates 7 to 14 and Conjugates 45 to 110, which were the conjugates of the anti-CAPRIN-1 monoclonal antibodies with the immune activator prepared in Example 3, and Conjugates 21 to 28 and Conjugates 111 to 176 prepared in Example 4 were assayed for their specific reactivity with the CAPRIN-1 protein and their reactivity with the cell membrane surface of human cancer cells and mouse cancer cells expressing CAPRIN-1, in the same way as above. As a result, Conjugates 7 to 14 and Conjugates 21 to 28 exhibited significantly higher absorbance values than a negative control with PBS(-) added and were therefore shown to specifically react with the CAPRN-1 protein.

Conjugates 7 to 14, Conjugates 45 to 110, Conjugates 21 to 28, and Conjugates 111 to 176 were further evaluated for their reactivity with the cell membrane surface of cancer cells expressing the CAPRIN-1 protein. As a result, these conjugates exhibited significantly stronger reactivity than that of a conjugate of the immune activator and human IgG unreactive with the CAPRIN-1 protein, and also exhibited strong reactivity equivalent to that of anti-CAPRIN-1 monoclonal antibodies #1 to #74 described in Example 2 which are unconjugated with the immune activator.

These results demonstrated that the conjugates of the anti-CAPRIN-1 antibodies and the immune activator prepared above (Conjugates 7 to 14, Conjugates 45 to 110, Conjugates 21 to 28, and Conjugates 111 to 176) specifically bind to the CAPRIN-1 protein and to the cell membrane surface of CAPRIN-1-expressing cancer cells.

Example 6 Antitumor Effect of Conjugate-1

Next, Conjugates 1 to 6 and Conjugates 15 to 20 prepared using anti-CAPRIN-1 polyclonal antibodies #1 to #6 and Conjugates 7 to 14 and Conjugates 21 to 28 prepared using anti-CAPRIN-1 monoclonal antibodies in Examples 3 and 4 were evaluated for their in vivo antitumor effects on cancer-bearing mice.

Specifically, the conjugates of the present invention were examined for their antitumor effect using NOD-SCID mice in which human-derived cancer cells expressing the CAPRIN-1 protein were transplanted. Human breast cancer cells BT474 were mixed with Matrigel (Sigma-Aldrich Corp.) and subcutaneously transplanted at $10^7$ cells/mouse to the mice, which were then grown until tumor became 180 mm³ or larger to prepare cancer-bearing mice. BT474 expresses the CAPRIN-1 protein on the cell membrane surface. As shown in Example 5, Conjugates 1 to 6 and Conjugates 15 to 20 prepared using anti-CAPRIN-1 polyclonal antibodies #1 to #6, and Conjugates 7 to 14 and Conjugates 21 to 28 prepared using anti-CAPRIN-1 monoclonal antibodies specifically bind to the cell membrane surface. Conjugates 1 to 28 were each administered at 10 mg/kg to the tail veins of 10 cancer-bearing mice.

A solution containing a conjugate of trastuzumab and resiquimod was prepared by the method described in Example 3 and administered as a comparative control in the same amount as above to the cancer-bearing mice. BT474 expresses HER2 protein, which is a target antigen of trastuzumab, on the cell membrane surface. The conjugate of trastuzumab and resiquimod specifically binds to BT474. The administration to the cancer-bearing mice was carried out once a week.

PBS(-) was administered to the cancer-bearing mice, for a negative control.

The tumor sizes of the cancer-bearing mice after the administration were measured using calipers over time, and tumor volumes were calculated according to an ordinary method based on the expression: (Length of the major axis of tumor)×(Length of the minor axis of tumor)$^2$×0.5. As a result of the evaluation, all the mice given Conjugates 1 to 6 prepared in Example 3 and Conjugates 15 to 20 prepared in Example 4 had less than 37% tumor volumes 50 days after the start of the administration relative to the tumor volume of the negative control (100%). All the mice given Conjugates 7 to 14 and Conjugates 21 to 28 had less than 15% tumor volumes. Cancer growth in the mice given Conjugates 11 to 14 and Conjugates 25 to 28 was suppressed early as compared with cancers in the mice given Conjugates 7 to 10 and Conjugates 21 to 24. As a result of similarly evaluating the in vivo antitumor effects of Conjugates 45 to 176 on cancer-bearing mice, all the mice had less than 20% tumor volumes.

On the other hand, the tumor volume of the mice given the solution containing the conjugate of trastuzumab and resiquimod as a comparative control was 54% relative to the negative control.

These evaluation results demonstrated that Conjugates 1 to 28 and Conjugates 45 to 176 prepared in Examples 3 and 4 using the antibodies against CAPRIN-1 exert a significantly stronger antitumor effect than that of the negative control. These results also demonstrated that Conjugates 1 to 28 and Conjugates 45 to 176 have a significantly stronger antitumor effect than that of the conjugate of trastuzumab and resiquimod prepared as a comparative control.

Example 7 Antitumor Effect of Conjugate-2

The conjugates of the anti-CAPRIN-1 antibodies and the immune activator (Conjugates 1 to 28) prepared in Examples 3 and 4 were evaluated for their in vivo antitumor effects on cancer-bearing mice.

Specifically, the conjugates of the present invention were examined for their antitumor effect using Balb/c nude mice in which human-derived cancer cells expressing CAPRIN-1 were transplanted. Human lung cancer cells H1650 were subcutaneously transplanted to the ventral regions of the mice, which were then grown until tumor became 180 mm$^3$ or larger to prepare cancer-bearing mice. The lung cancer cells H1650 express the CAPRIN-1 protein on the cell membrane surface. As shown in Example 5, Conjugates 1 to 28 specifically bind to CAPRIN-1 on the cell membrane surface of the lung cancer cells H1650. Conjugates 1 to 14 prepared in Example 3 and Conjugates 15 to 28 prepared in Example 4 were each administered at 10 mg/kg to the tail veins of 10 cancer-bearing mice.

A solution containing a conjugate of cetuximab and resiquimod was prepared by the method described in Example 3 and administered as a comparative control in the same amount as above to the cancer-bearing mice. The administration was carried out once a week a total of three times.

PBS(−) was administered to the cancer-bearing mice, for a negative control.

The tumor sizes of the cancer-bearing mice after the administration were measured using calipers over time, and tumor volumes were calculated according to an ordinary method based on the expression: (Length of the major axis of tumor)×(Length of the minor axis of tumor)$^2$×0.5. As a result, the mice given Conjugates 1 to 6 and Conjugates 15 to 20 had less than 22% tumor volumes 25 days after the start of the administration relative to the tumor volume of the negative control (100%). All the mice given Conjugates 7 to 14 and Conjugates 21 to 28 had less than 12% tumor volumes. Cancer growth in the mice given Conjugates 11 to 14 and Conjugates 25 to 28 was suppressed early as compared with cancers in the mice given Conjugates 7 to 10 and Conjugates 21 to 24. As a result of similarly evaluating the in vivo antitumor effects of Conjugates 45 to 176 on cancer-bearing mice, the mice had less than 16% tumor volumes.

On the other hand, the tumor volume of the mice given the solution containing the conjugate of cetuximab and resiquimod as a comparative control was 32% relative to the negative control.

These evaluation results demonstrated that Conjugates 1 to 28 and Conjugates 45 to 176 exert a significantly stronger antitumor effect than that of the negative control. These results also demonstrated that Conjugates 1 to 28 and Conjugates 45 to 176 have a significantly stronger antitumor effect than that of the conjugate of cetuximab and resiquimod as a comparative control.

Example 8 Preparation of Conjugate of Mouse Chimeric Anti-CAPRIN-1 Monoclonal Antibody and Immune Activator Mouse chimeric antibodies composed of a heavy chain comprising the heavy chain variable region of each anti-CAPRIN-1 monoclonal antibody and the heavy chain constant region of mouse IgG, and a light chain comprising the light chain variable region of the anti-CAPRIN-1 monoclonal antibody and the light chain constant region of mouse IgG were prepared, and then conjugates of the antibodies with the immune activator resiquimod were prepared in the same way as in Example 3. Also, the mouse chimeric antibodies were prepared, and then conjugates of the antibodies with the resiquimod derivative were prepared in the same way as in Example 4.

Specifically, the following antibodies were used in this Example as the mouse chimeric antibodies comprising the light chain variable regions of the anti-CAPRIN-1 monoclonal antibodies and the light chain constant region of mouse IgG.

The monoclonal antibody against CAPRIN-1 disclosed in WO2011/096528, wherein the antibody comprises CDR1, CDR2, and CDR3 of heavy chain variable region consisting of the amino acid sequences of SEQ ID NO: 36, SEQ ID NO: 37, and SEQ ID NO: 38, respectively, and CDR1, CDR2, and CDR3 of light chain variable region consisting of the amino acid sequences of SEQ ID NO: 40, SEQ ID NO: 41, and SEQ ID NO: 42, respectively, and wherein the antibody comprises the amino acid sequence of a heavy chain variable region represented by SEQ ID NO: 39 comprising the above-mentioned CDR1, CDR2, and CDR3 of heavy chain variable region, and the amino acid sequence of a light chain variable region represented by SEQ ID NO: 43 comprising the above-mentioned CDR1, CDR2, and CDR3 of light chain variable region.

The monoclonal antibody against CAPRIN-1 disclosed in WO2015/020212, wherein the antibody comprises CDR1, CDR2, and CDR3 of heavy chain variable region consisting of the amino acid sequences of SEQ ID NO: 44, SEQ ID NO: 45, and SEQ ID NO: 46, respectively, and CDR1, CDR2, and CDR3 of light chain variable region consisting of the amino acid sequences of SEQ ID NO: 48, SEQ ID NO: 49, and SEQ ID NO: 50, respectively, and wherein the antibody comprises the amino acid sequence of a heavy chain variable region represented by SEQ ID NO: 47 comprising the above-mentioned CDR1, CDR2, and CDR3 of heavy chain variable region, and the amino acid sequence of a light chain variable region represented by SEQ ID NO:

51 comprising the above-mentioned CDR1, CDR2, and CDR3 of light chain variable region.

The monoclonal antibody against CAPRIN-1 disclosed in WO2011/096519, wherein the antibody comprises CDR1, CDR2, and CDR3 of heavy chain variable region consisting of the amino acid sequences of SEQ ID NO: 52, SEQ ID NO: 53, and SEQ ID NO: 54, respectively, and CDR1, CDR2, and CDR3 of light chain variable region consisting of the amino acid sequences of SEQ ID NO: 56, SEQ ID NO: 57, and SEQ ID NO: 58, respectively, and wherein the antibody comprises the amino acid sequence of a heavy chain variable region represented by SEQ ID NO: 55 comprising the above-mentioned CDR1, CDR2, and CDR3 of heavy chain variable region, and the amino acid sequence of a light chain variable region represented by SEQ ID NO: 59 comprising the above-mentioned CDR1, CDR2, and CDR3 of light chain variable region.

The monoclonal antibody against CAPRIN-1 disclosed in WO2013/125654, wherein the antibody comprises CDR1, CDR2, and CDR3 of heavy chain variable region consisting of the amino acid sequences of SEQ ID NO: 60, SEQ ID NO: 61, and SEQ ID NO: 62, respectively, and CDR1, CDR2, and CDR3 of light chain variable region consisting of the amino acid sequences of SEQ ID NO: 64, SEQ ID NO: 65, and SEQ ID NO: 66, respectively, and wherein the antibody comprises the amino acid sequence of a heavy chain variable region represented by SEQ ID NO: 63 comprising the above-mentioned CDR1, CDR2, and CDR3 of heavy chain variable region, and the amino acid sequence of a light chain variable region represented by SEQ ID NO: 67 comprising the above-mentioned CDR1, CDR2, and CDR3 of light chain variable region.

The monoclonal antibody against CAPRIN-1 disclosed in WO2011/096517, the antibody comprising the amino acid sequence of a heavy chain variable region represented by the amino acid sequence of SEQ ID NO: 68 and the amino acid sequence of a light chain variable region represented by the amino acid sequence of SEQ ID NO: 69.

The monoclonal antibody against CAPRIN-1 disclosed in WO2011/096528, wherein the antibody comprises the amino acid sequence of a heavy chain variable region represented by the amino acid sequence of SEQ ID NO: 70 and the amino acid sequence of a light chain variable region represented by the amino acid sequence of SEQ ID NO: 71; the antibody comprises the amino acid sequence of a heavy chain variable region represented by the amino acid sequence of SEQ ID NO: 72 and the amino acid sequence of a light chain variable region represented by the amino acid sequence of SEQ ID NO: 73; the antibody comprises the amino acid sequence of a heavy chain variable region represented by the amino acid sequence of SEQ ID NO: 74 and the amino acid sequence of a light chain variable region represented by the amino acid sequence of SEQ ID NO: 75; the antibody comprises the amino acid sequence of a heavy chain variable region represented by the amino acid sequence of SEQ ID NO: 76 and the amino acid sequence of a light chain variable region represented by the amino acid sequence of SEQ ID NO: 77; or the antibody comprises the amino acid sequence of a heavy chain variable region represented by the amino acid sequence of SEQ ID NO: 78 and the amino acid sequence of a light chain variable region represented by the amino acid sequence of SEQ ID NO: 79.

The monoclonal antibody against CAPRIN-1 disclosed in WO2011/096533, wherein the antibody comprises the amino acid sequence of a heavy chain variable region represented by the amino acid sequence of SEQ ID NO: 80 and the amino acid sequence of a light chain variable region represented by the amino acid sequence of SEQ ID NO: 81, or the antibody comprises the amino acid sequence of a heavy chain variable region represented by the amino acid sequence of SEQ ID NO: 82 and the amino acid sequence of a light chain variable region represented by the amino acid sequence of SEQ ID NO: 83.

The monoclonal antibody against CAPRIN-1 disclosed in WO2011/096534, wherein the antibody comprises the amino acid sequence of a heavy chain variable region represented by the amino acid sequence of SEQ ID NO: 84 and the amino acid sequence of a light chain variable region represented by the amino acid sequence of SEQ ID NO: 85, or the antibody comprises the amino acid sequence of a heavy chain variable region represented by the amino acid sequence of SEQ ID NO: 86 and the amino acid sequence of a light chain variable region represented by the amino acid sequence of SEQ ID NO: 87.

The monoclonal antibody against CAPRIN-1 disclosed in WO2010/016526, wherein the antibody comprises the amino acid sequence of a heavy chain variable region represented by the amino acid sequence of SEQ ID NO: 88 and the amino acid sequence of a light chain variable region represented by the amino acid sequence of SEQ ID NO: 89; the antibody comprises the amino acid sequence of a heavy chain variable region represented by the amino acid sequence of SEQ ID NO: 90 and the amino acid sequence of a light chain variable region represented by the amino acid sequence of SEQ ID NO: 91; the antibody comprises the amino acid sequence of a heavy chain variable region represented by the amino acid sequence of SEQ ID NO: 92 and the amino acid sequence of a light chain variable region represented by the amino acid sequence of SEQ ID NO: 93; the antibody comprises the amino acid sequence of a heavy chain variable region represented by the amino acid sequence of SEQ ID NO: 94 and the amino acid sequence of a light chain variable region represented by the amino acid sequence of SEQ ID NO: 95; the antibody comprises the amino acid sequence of a heavy chain variable region represented by the amino acid sequence of SEQ ID NO: 96 and the amino acid sequence of a light chain variable region represented by the amino acid sequence of SEQ ID NO: 97; the antibody comprises the amino acid sequence of a heavy chain variable region represented by the amino acid sequence of SEQ ID NO: 98 and the amino acid sequence of a light chain variable region represented by the amino acid sequence of SEQ ID NO: 99; or the antibody comprises the amino acid sequence of a heavy chain variable region represented by the amino acid sequence of SEQ ID NO: 100 and the amino acid sequence of a light chain variable region represented by the amino acid sequence of SEQ ID NO: 101.

The monoclonal antibody against CAPRIN-1 disclosed in WO2013/018894, wherein the antibody comprises the amino acid sequence of a heavy chain variable region represented by the amino acid sequence of SEQ ID NO: 102 and the amino acid sequence of a light chain variable region represented by the amino acid sequence of SEQ ID NO: 103, or the antibody comprises the amino acid sequence of a heavy chain variable region represented by the amino acid sequence of SEQ ID NO: 104 and the amino acid sequence of a light chain variable region represented by the amino acid sequence of SEQ ID NO: 105.

The monoclonal antibody against CAPRIN-1 disclosed in WO2013/018892, the antibody comprising the amino acid sequence of a heavy chain variable region represented by the amino acid sequence of SEQ ID NO: 106 and the amino acid sequence of a light chain variable region represented by the amino acid sequence of SEQ ID NO: 107.

The monoclonal antibody against CAPRIN-1 disclosed in WO2013/018891, the antibody comprising the amino acid sequence of a heavy chain variable region represented by the amino acid sequence of SEQ ID NO: 108 and the amino acid sequence of a light chain variable region represented by the amino acid sequence of SEQ ID NO: 109.

The monoclonal antibody against CAPRIN-1 disclosed in WO2013/018889, the antibody comprising the amino acid sequence of a heavy chain variable region represented by the amino acid sequence of SEQ ID NO: 110 and the amino acid sequence of a light chain variable region represented by the amino acid sequence of SEQ ID NO: 111.

The monoclonal antibody against CAPRIN-1 disclosed in WO2013/018883, the antibody comprising the amino acid sequence of a heavy chain variable region represented by the amino acid sequence of SEQ ID NO: 112 and the amino acid sequence of a light chain variable region represented by the amino acid sequence of SEQ ID NO: 113.

The monoclonal antibody against CAPRIN-1 disclosed in WO2013/125636, the antibody comprising the amino acid sequence of a heavy chain variable region represented by the amino acid sequence of SEQ ID NO: 114 and the amino acid sequence of a light chain variable region represented by the amino acid sequence of SEQ ID NO: 115.

The monoclonal antibody against CAPRIN-1 disclosed in WO2013/125654, wherein the antibody comprises the amino acid sequence of a heavy chain variable region represented by the amino acid sequence of SEQ ID NO: 116 and the amino acid sequence of a light chain variable region represented by the amino acid sequence of SEQ ID NO: 117, or the antibody comprises the amino acid sequence of a heavy chain variable region represented by the amino acid sequence of SEQ ID NO: 118 and the amino acid sequence of a light chain variable region represented by the amino acid sequence of SEQ ID NO: 119.

The monoclonal antibody against CAPRIN-1 disclosed in WO2013/125630, the antibody comprising the amino acid sequence of a heavy chain variable region represented by the amino acid sequence of SEQ ID NO: 120 and the amino acid sequence of a light chain variable region represented by the amino acid sequence of SEQ ID NO: 121.

The monoclonal antibody against CAPRIN-1 disclosed in WO2015/020212, wherein the antibody comprises the amino acid sequence of a heavy chain variable region represented by the amino acid sequence of SEQ ID NO: 122 and the amino acid sequence of a light chain variable region represented by the amino acid sequence of SEQ ID NO: 123; the antibody comprises the amino acid sequence of a heavy chain variable region represented by the amino acid sequence of SEQ ID NO: 124 and the amino acid sequence of a light chain variable region represented by the amino acid sequence of SEQ ID NO: 125; the antibody comprises the amino acid sequence of a heavy chain variable region represented by the amino acid sequence of SEQ ID NO: 126 and the amino acid sequence of a light chain variable region represented by the amino acid sequence of SEQ ID NO: 127; the antibody comprises the amino acid sequence of a heavy chain variable region represented by the amino acid sequence of SEQ ID NO: 128 and the amino acid sequence of a light chain variable region represented by the amino acid sequence of SEQ ID NO: 129; the antibody comprises the amino acid sequence of a heavy chain variable region represented by the amino acid sequence of SEQ ID NO: 130 and the amino acid sequence of a light chain variable region represented by the amino acid sequence of SEQ ID NO: 131; or the antibody comprises the amino acid sequence of a heavy chain variable region represented by the amino acid sequence of SEQ ID NO: 132 and the amino acid sequence of a light chain variable region represented by the amino acid sequence of SEQ ID NO: 133.

The mouse chimeric antibodies were prepared by the following method.

Specifically, an amplification fragment of a gene encoding a heavy chain variable region having the amino acid sequence represented by SEQ ID NO: 39 according to the present invention was treated at its both ends with restriction enzymes, then purified, and inserted into a vector already comprising inserts of a human antibody-derived leader sequence and the heavy chain constant region of mouse IgG, according to an ordinary method. Further, an amplification fragment of a gene encoding a light chain variable region having the amino acid sequence represented by SEQ ID NO: 43 was treated at its both ends with restriction enzymes, then purified, and inserted into a vector already comprising inserts of a human antibody-derived leader sequence and the light chain constant region of mouse IgG, according to an ordinary method.

Next, the recombinant vector having a gene insert of the heavy chain variable region of the antibody against CAPRIN-1 as described above and the recombinant vector having a gene insert of the light chain variable region of the antibody, were transferred to mammalian cells according to an ordinary method, and a solution containing mouse chimeric antibody #1 composed of a heavy chain comprising the heavy chain variable region of the antibody against CAPRIN-1 represented by SEQ ID NO: 39 and the heavy chain constant region of mouse IgG, and a light chain comprising the light chain variable region represented by SEQ ID NO: 43 of the antibody against CAPRIN-1 and the light chain constant region of mouse IgG.

A solution containing mouse chimeric antibody #2 composed of a heavy chain comprising a heavy chain variable region having the amino acid sequence represented by SEQ ID NO: 47 and the heavy chain constant region of mouse IgG, and a light chain comprising a light chain variable region having the amino acid sequence represented by SEQ ID NO: 51 and the light chain constant region of mouse IgG was prepared in a similar way.

A solution containing mouse chimeric antibody #3 composed of a heavy chain comprising a heavy chain variable region having the amino acid sequence represented by SEQ ID NO: 55 and the heavy chain constant region of mouse IgG, and a light chain comprising a light chain variable region having the amino acid sequence represented by SEQ ID NO: 59 and the light chain constant region of mouse IgG was prepared in a similar way.

A solution containing mouse chimeric antibody #4 composed of a heavy chain comprising a heavy chain variable region having the amino acid sequence represented by SEQ ID NO: 63 and the heavy chain constant region of mouse IgG, and a light chain comprising a light chain variable region having the amino acid sequence represented by SEQ ID NO: 67 and the light chain constant region of mouse IgG was prepared in a similar way.

Solutions containing the following mouse chimeric antibodies #5 to #37 were prepared in a similar way.

Mouse chimeric antibody #5 composed of a heavy chain comprising the amino acid sequence of a heavy chain variable region represented by the amino acid sequence of SEQ ID NO: 68 and the heavy chain constant region of mouse IgG, and a light chain comprising the amino acid sequence of a light chain variable region represented by the amino acid sequence of SEQ ID NO: 69 and the light chain constant region of mouse IgG.

Mouse chimeric antibody #6 composed of a heavy chain comprising the amino acid sequence of a heavy chain variable region represented by the amino acid sequence of SEQ ID NO: 70 and the heavy chain constant region of mouse IgG, and a light chain comprising the amino acid sequence of a light chain variable region represented by the amino acid sequence of SEQ ID NO: 71 and the light chain constant region of mouse IgG.

A solution containing mouse chimeric antibody #7 composed of a heavy chain comprising the amino acid sequence of a heavy chain variable region represented by the amino acid sequence of SEQ ID NO: 72 and the heavy chain constant region of mouse IgG, and a light chain comprising the amino acid sequence of a light chain variable region represented by the amino acid sequence of SEQ ID NO: 73 and the light chain constant region of mouse IgG.

Mouse chimeric antibody #8 composed of a heavy chain comprising the amino acid sequence of a heavy chain variable region represented by the amino acid sequence of SEQ ID NO: 74 and the heavy chain constant region of mouse IgG, and a light chain comprising the amino acid sequence of a light chain variable region represented by the amino acid sequence of SEQ ID NO: 75 and the light chain constant region of mouse IgG.

Mouse chimeric antibody #9 composed of a heavy chain comprising the amino acid sequence of a heavy chain variable region represented by the amino acid sequence of SEQ ID NO: 76 and the heavy chain constant region of mouse IgG, and a light chain comprising the amino acid sequence of a light chain variable region represented by the amino acid sequence of SEQ ID NO: 77 and the light chain constant region of mouse IgG.

Mouse chimeric antibody #10 composed of a heavy chain comprising the amino acid sequence of a heavy chain variable region represented by the amino acid sequence of SEQ ID NO: 78 and the heavy chain constant region of mouse IgG, and a light chain comprising the amino acid sequence of a light chain variable region represented by the amino acid sequence of SEQ ID NO: 79 and the light chain constant region of mouse IgG.

Mouse chimeric antibody #11 composed of a heavy chain comprising the amino acid sequence of a heavy chain variable region represented by the amino acid sequence of SEQ ID NO: 80 and the heavy chain constant region of mouse IgG, and a light chain comprising the amino acid sequence of a light chain variable region represented by the amino acid sequence of SEQ ID NO: 81 and the light chain constant region of mouse IgG.

Mouse chimeric antibody #12 composed of a heavy chain comprising the amino acid sequence of a heavy chain variable region represented by the amino acid sequence of SEQ ID NO: 82 and the heavy chain constant region of mouse IgG, and a light chain comprising the amino acid sequence of a light chain variable region represented by the amino acid sequence of SEQ ID NO: 83 and the light chain constant region of mouse IgG.

Mouse chimeric antibody #13 composed of a heavy chain comprising the amino acid sequence of a heavy chain variable region represented by the amino acid sequence of SEQ ID NO: 84 and the heavy chain constant region of mouse IgG, and a light chain comprising the amino acid sequence of a light chain variable region represented by the amino acid sequence of SEQ ID NO: 85 and the light chain constant region of mouse IgG.

Mouse chimeric antibody #14 composed of a heavy chain comprising the amino acid sequence of a heavy chain variable region represented by the amino acid sequence of SEQ ID NO: 86 and the heavy chain constant region of mouse IgG, and a light chain comprising the amino acid sequence of a light chain variable region represented by the amino acid sequence of SEQ ID NO: 87 and the light chain constant region of mouse IgG.

Mouse chimeric antibody #15 composed of a heavy chain comprising the amino acid sequence of a heavy chain variable region represented by the amino acid sequence of SEQ ID NO: 88 and the heavy chain constant region of mouse IgG, and a light chain comprising the amino acid sequence of a light chain variable region represented by the amino acid sequence of SEQ ID NO: 89 and the light chain constant region of mouse IgG.

Mouse chimeric antibody #16 composed of a heavy chain comprising the amino acid sequence of a heavy chain variable region represented by the amino acid sequence of SEQ ID NO: 90 and the heavy chain constant region of mouse IgG, and a light chain comprising the amino acid sequence of a light chain variable region represented by the amino acid sequence of SEQ ID NO: 91 and the light chain constant region of mouse IgG.

Mouse chimeric antibody #17 composed of a heavy chain comprising the amino acid sequence of a heavy chain variable region represented by the amino acid sequence of SEQ ID NO: 92 and the heavy chain constant region of mouse IgG, and a light chain comprising the amino acid sequence of a light chain variable region represented by the amino acid sequence of SEQ ID NO: 93 and the light chain constant region of mouse IgG.

Mouse chimeric antibody #18 composed of a heavy chain comprising the amino acid sequence of a heavy chain variable region represented by the amino acid sequence of SEQ ID NO: 94 and the heavy chain constant region of mouse IgG, and a light chain comprising the amino acid sequence of a light chain variable region represented by the amino acid sequence of SEQ ID NO: 95 and the light chain constant region of mouse IgG.

Mouse chimeric antibody #19 composed of a heavy chain comprising the amino acid sequence of a heavy chain variable region represented by the amino acid sequence of SEQ ID NO: 96 and the heavy chain constant region of mouse IgG, and a light chain comprising the amino acid sequence of a light chain variable region represented by the amino acid sequence of SEQ ID NO: 97 and the light chain constant region of mouse IgG.

Mouse chimeric antibody #20 composed of a heavy chain comprising the amino acid sequence of a heavy chain variable region represented by the amino acid sequence of SEQ ID NO: 98 and the heavy chain constant region of mouse IgG, and a light chain comprising the amino acid sequence of a light chain variable region represented by the amino acid sequence of SEQ ID NO: 99 and the light chain constant region of mouse IgG.

Mouse chimeric antibody #21 composed of a heavy chain comprising the amino acid sequence of a heavy chain variable region represented by the amino acid sequence of SEQ ID NO: 100 and the heavy chain constant region of mouse IgG, and a light chain comprising the amino acid sequence of a light chain variable region represented by the amino acid sequence of SEQ ID NO: 101 and the light chain constant region of mouse IgG.

Mouse chimeric antibody #22 composed of a heavy chain comprising the amino acid sequence of a heavy chain variable region represented by the amino acid sequence of SEQ ID NO: 102 and the heavy chain constant region of mouse IgG, and a light chain comprising the amino acid sequence of a light chain variable region represented by the amino acid sequence of SEQ ID NO: 103 and the light chain constant region of mouse IgG.

Mouse chimeric antibody #23 composed of a heavy chain comprising the amino acid sequence of a heavy chain variable region represented by the amino acid sequence of SEQ ID NO: 104 and the heavy chain constant region of mouse IgG, and a light chain comprising the amino acid sequence of a light chain variable region represented by the amino acid sequence of SEQ ID NO: 105 and the light chain constant region of mouse IgG.

Mouse chimeric antibody #24 composed of a heavy chain comprising the amino acid sequence of a heavy chain variable region represented by the amino acid sequence of SEQ ID NO: 106 and the heavy chain constant region of mouse IgG, and a light chain comprising the amino acid sequence of a light chain variable region represented by the amino acid sequence of SEQ ID NO: 107 and the light chain constant region of mouse IgG.

Mouse chimeric antibody #25 composed of a heavy chain comprising the amino acid sequence of a heavy chain variable region represented by the amino acid sequence of SEQ ID NO: 108 and the heavy chain constant region of mouse IgG, and a light chain comprising the amino acid sequence of a light chain variable region represented by the amino acid sequence of SEQ ID NO: 109 and the light chain constant region of mouse IgG.

Mouse chimeric antibody #26 composed of a heavy chain comprising the amino acid sequence of a heavy chain variable region represented by the amino acid sequence of SEQ ID NO: 110 and the heavy chain constant region of mouse IgG, and a light chain comprising the amino acid sequence of a light chain variable region represented by the amino acid sequence of SEQ ID NO: 111 and the light chain constant region of mouse IgG.

Mouse chimeric antibody #27 composed of a heavy chain comprising the amino acid sequence of a heavy chain variable region represented by the amino acid sequence of SEQ ID NO: 112 and the heavy chain constant region of mouse IgG, and a light chain comprising the amino acid sequence of a light chain variable region represented by the amino acid sequence of SEQ ID NO: 113 and the light chain constant region of mouse IgG.

Mouse chimeric antibody #28 composed of a heavy chain comprising the amino acid sequence of a heavy chain variable region represented by the amino acid sequence of SEQ ID NO: 114 and the heavy chain constant region of mouse IgG, and a light chain comprising the amino acid sequence of a light chain variable region represented by the amino acid sequence of SEQ ID NO: 115 and the light chain constant region of mouse IgG.

Mouse chimeric antibody #29 composed of a heavy chain comprising the amino acid sequence of a heavy chain variable region represented by the amino acid sequence of SEQ ID NO: 116 and the heavy chain constant region of mouse IgG, and a light chain comprising the amino acid sequence of a light chain variable region represented by the amino acid sequence of SEQ ID NO: 117 and the light chain constant region of mouse IgG.

Mouse chimeric antibody #30 composed of a heavy chain comprising the amino acid sequence of a heavy chain variable region represented by the amino acid sequence of SEQ ID NO: 118 and the heavy chain constant region of mouse IgG, and a light chain comprising the amino acid sequence of a light chain variable region represented by the amino acid sequence of SEQ ID NO: 119 and the light chain constant region of mouse IgG.

Mouse chimeric antibody #31 composed of a heavy chain comprising the amino acid sequence of a heavy chain variable region represented by the amino acid sequence of SEQ ID NO: 120 and the heavy chain constant region of mouse IgG, and a light chain comprising the amino acid sequence of a light chain variable region represented by the amino acid sequence of SEQ ID NO: 121 and the light chain constant region of mouse IgG.

Mouse chimeric antibody #32 composed of a heavy chain comprising the amino acid sequence of a heavy chain variable region represented by the amino acid sequence of SEQ ID NO: 122 and the heavy chain constant region of mouse IgG, and a light chain comprising the amino acid sequence of a light chain variable region represented by the amino acid sequence of SEQ ID NO: 123 and the light chain constant region of mouse IgG.

Mouse chimeric antibody #33 composed of a heavy chain comprising the amino acid sequence of a heavy chain variable region represented by the amino acid sequence of SEQ ID NO: 124 and the heavy chain constant region of mouse IgG, and a light chain comprising the amino acid sequence of a light chain variable region represented by the amino acid sequence of SEQ ID NO: 125 and the light chain constant region of mouse IgG.

Mouse chimeric antibody #34 composed of a heavy chain comprising the amino acid sequence of a heavy chain variable region represented by the amino acid sequence of SEQ ID NO: 126 and the heavy chain constant region of mouse IgG, and a light chain comprising the amino acid sequence of a light chain variable region represented by the amino acid sequence of SEQ ID NO: 127 and the light chain constant region of mouse IgG.

Mouse chimeric antibody #35 composed of a heavy chain comprising the amino acid sequence of a heavy chain variable region represented by the amino acid sequence of SEQ ID NO: 128 and the heavy chain constant region of mouse IgG, and a light chain comprising the amino acid sequence of a light chain variable region represented by the amino acid sequence of SEQ ID NO: 129 and the light chain constant region of mouse IgG.

Mouse chimeric antibody #36 composed of a heavy chain comprising the amino acid sequence of a heavy chain variable region represented by the amino acid sequence of SEQ ID NO: 130 and the heavy chain constant region of mouse IgG, and a light chain comprising the amino acid sequence of a light chain variable region represented by the amino acid sequence of SEQ ID NO: 131 and the light chain constant region of mouse IgG.

Mouse chimeric antibody #37 composed of a heavy chain having the amino acid sequence of a heavy chain variable region represented by the amino acid sequence of SEQ ID NO: 132 and the heavy chain constant region of mouse IgG, and a light chain having the amino acid sequence of a light chain variable region represented by the amino acid sequence of SEQ ID NO: 133 and the light chain constant region of mouse IgG.

The prepared culture supernatant containing each of mouse chimeric antibodies #1 to #37 was purified according to a conventional method using Hitrap Protein A Sepharose FF (GE Healthcare Japan Corp.). The buffer was replaced with PBS(-), and the resultant was filtered through a 0.22 μm filter (Merck Millipore Corp.) to prepare the mouse chimeric antibodies.

Conjugates with resiquimod were prepared in the same way as the method described in Example 3 using mouse chimeric antibodies #1 to #37 prepared above. Solutions containing a conjugate of mouse chimeric antibody #1 with resiquimod (Conjugate 29), a conjugate of mouse chimeric antibody #2 with resiquimod (Conjugate 30), a conjugate of mouse chimeric antibody #3 with resiquimod (Conjugate 31), a conjugate of mouse chimeric antibody #4 with resiquimod (Conjugate 32), a conjugate of mouse chimeric antibody #5 with resiquimod (Conjugate 177), a conjugate of mouse chimeric antibody #6 with resiquimod (Conjugate 178), a conjugate of mouse chimeric antibody #7 with resiquimod (Conjugate 179), a conjugate of mouse chimeric antibody #8 with resiquimod (Conjugate 180), a conjugate of mouse chimeric antibody #9 (Conjugate 181), a conjugate of mouse chimeric antibody #10 with resiquimod (Conjugate 182), a conjugate of mouse chimeric antibody #11 with resiquimod (Conjugate 183), a conjugate of mouse chimeric antibody #12 with resiquimod (Conjugate 184), a conjugate of mouse chimeric antibody #13 with resiquimod (Conjugate 185), a conjugate of mouse chimeric antibody #14 with resiquimod (Conjugate 186), a conjugate of mouse chimeric antibody #15 with resiquimod (Conjugate 187), a conjugate of mouse chimeric antibody #16 with resiquimod (Conjugate 188), a conjugate of mouse chimeric antibody #17 with resiquimod (Conjugate 189), a conjugate of mouse chimeric antibody #18 with resiquimod (Conjugate 190), a conjugate of mouse chimeric antibody #19 with resiquimod (Conjugate 191), a conjugate of mouse chimeric antibody #20 with resiquimod (Conjugate 192), a conjugate of mouse chimeric antibody #21 with resiquimod (Conjugate 193), a conjugate of mouse chimeric antibody #22 with resiquimod (Conjugate 194), a conjugate of mouse chimeric antibody #23 with resiquimod (Conjugate 195), a conjugate of mouse chimeric antibody #24 with resiquimod (Conjugate 196), a conjugate of mouse chimeric antibody #25 with resiquimod (Conjugate 197), a conjugate of mouse chimeric antibody #26 with resiquimod (Conjugate 198), a conjugate of mouse chimeric antibody #27 with resiquimod (Conjugate 199), a conjugate of mouse chimeric antibody #28 with resiquimod (Conjugate 200), a conjugate of mouse chimeric antibody #29 with resiquimod (Conjugate 201), a conjugate of mouse chimeric antibody #30 with resiquimod (Conjugate 202), a conjugate of mouse chimeric antibody #31 with resiquimod (Conjugate 203), a conjugate of mouse chimeric antibody #32 with resiquimod (Conjugate 204), a conjugate of mouse chimeric antibody #33 with resiquimod (Conjugate 205), a conjugate of mouse chimeric antibody #34 with resiquimod (Conjugate 206), a conjugate of mouse chimeric antibody #35 with resiquimod (Conjugate 207), a conjugate of mouse chimeric antibody #36 with resiquimod (Conjugate 208), and a conjugate of mouse chimeric antibody #37 with resiquimod (Conjugate 209) were prepared.

Further, conjugates with the resiquimod derivative were prepared in the same way as the method described in Example 4 using mouse chimeric antibodies #1 to #37 prepared above. Solutions containing a conjugate of mouse chimeric antibody #1 with the resiquimod derivative (Conjugate 33), a conjugate of mouse chimeric antibody #2 with the resiquimod derivative (Conjugate 34), a conjugate of mouse chimeric antibody #3 with the resiquimod derivative (Conjugate 35), and a conjugate of mouse chimeric antibody #4 with the resiquimod derivative (Conjugate 36) were prepared. Solutions containing conjugates of mouse chimeric antibodies #5 to #37 with the resiquimod derivative (Conjugates 210 to 242) were prepared in a similar way.

The prepared solutions containing Conjugates 29 to 36, Conjugates 177 to 242, and Control conjugate 2 were each filtered through a 0.22 μm filter (manufactured by Merck Millipore Corp.) to prepare the conjugates.

Conjugates 29 to 36 and Conjugates 177 to 242 were assayed for their specific reactivity with the CAPRIN-1 protein in the same way as in Example 5 using the prepared solutions containing Conjugates 29 to 36 and Conjugates 177 to 242. As a result, the solutions containing Conjugates 29 to 36 and Conjugates 177 to 242 each exhibited specific reactivity with the CAPRN-1 protein.

Further, Conjugates 29 to 36 and Conjugates 177 to 242 were assayed for their reactivity with cancer cells by flow cytometry using the cancer cells expressing CAPRIN-1 on the cell membrane surface. As a result, all the conjugates exhibited stronger fluorescence intensity than that of the negative control. Also, the conjugates were found to exhibit strong reactivity equivalent to that of the anti-CAPRIN-1 monoclonal antibodies described in mouse chimeric antibodies #1 to #37 prepared above, unconjugated with the immune activator.

Example 9 Antitumor Effect of Conjugate of Mouse Chimeric Anti-CAPRIN-1 Monoclonal Antibody and Immune Activator The conjugates of the mouse chimeric anti-CAPRIN-1 monoclonal antibodies and the immune activator (Conjugates 29 to 36 and conjugates 177 to 242) prepared in Example 8 were evaluated for their in vivo antitumor effects of the antibodies on cancer-bearing mice.

Specifically, the conjugates of the present invention were examined for their antitumor effect using Balb/c mice in which mouse-derived cancer cells expressing CAPRIN-1 were transplanted. Mouse breast cancer cells 4T1 were subcutaneously transplanted at $10^4$ cells/mouse to the ventral regions of the mice, which were then grown until tumor became 30 $mm^3$ or larger to prepare cancer-bearing mice. As shown in Example 5, the breast cancer cells 4T1 are cells expressing the CAPRIN-1 protein on the cell membrane surface. The solutions containing Conjugates 29 to 36 prepared in Example 8 each specifically bind to CAPRIN-1 on the cell membrane surface of the breast cancer cells 4T1. Conjugates 29 to 36 prepared in Example 8 were each administered at 8 mg/kg to the tail veins of 10 cancer-bearing mice. Mouse chimeric antibodies #1 to #4 were each administered as a comparative control in the same amount as above to the cancer-bearing mice. The administration was carried out twice a week a total of four times. PBS(−) was administered to cancer-bearing mice, for a negative control. The tumor sizes of the cancer-bearing mice after the administration were measured using calipers over time, and tumor volumes were calculated according to an ordinary method based on the expression: (Length of the major axis of tumor)×(Length of the minor axis of tumor)$^2$×0.5. As a result, all the mice given Conjugates 29 to 36 had 0% tumor volume 20 days after the start of the administration relative to the tumor volume of the negative control (100%). Also, the mice given mouse chimeric antibodies #1 to #4 alone had 69% tumor volume on average relative to the tumor volume of the negative control mice (100%). These evaluation results demonstrated that the conjugates of resiquimod and the mouse chimeric anti-CAPRIN-1 antibodies (mouse chimeric antibodies) (Conjugates 29 to 32) and the conjugates of the resiquimod derivative and these antibodies (Conjugates 33 to 36) prepared in Example 8 exert a stronger antitumor effect as compared with the negative control and the case of administering the anti-CAPRIN-1 antibody alone to cancer-bearing mice. As a result of similarly evaluating Conjugates 177 to 242 for their antitumor effects, all the mice given Conjugates 29 to 36 had 0% tumor volume relative to the tumor volume of the negative control (100%). The mice given mouse chimeric antibodies #5 to #37 alone had 69% tumor volume on average relative to the tumor volume of the negative control (100%).

Example 10 Antitumor Effect of Conjugate-3

An in vivo antitumor effect on cancer-bearing mice was compared between Conjugates 7 to 14, Conjugates 21 to 28, and Conjugates 45 to 179 prepared in Example 4 using the anti-CAPRIN-1 monoclonal antibodies, and a trastuzumab conjugate prepared in the same way as in Example 4 using the existing antibody drug trastuzumab for a cancer, or trastuzumab.

The trastuzumab conjugate is a conjugate prepared in the same way as in Example 4 using trastuzumab and the immune activator. The conjugate of trastuzumab and the immune activator was prepared by the following method.

With reference to J. Med. Chem. 2008, 51, 6916-6926, succinimidyl 4-(N-maleimidomethyl)cyclohexane-1-carboxylate (SMCC) was condensed with 1-(2 (2-aminoethoxy)-2-methylpropyl)-2-(ethoxymethyl)-1H-imidazo[4,5-c]quinolin-4-amine, a resiquimod derivative made by two-carbon homoligation of the tertiary hydroxy group of resiquimod and the addition of an amino group thereto to obtain a condensate of resiquimod bound with SMCC, as the immune activator.

Meanwhile, trastuzumab was used in the preparation of the conjugate after removing a formulation composition contained in a solution using an ultrafilter, or affinity-purifying only trastuzumab using a protein A carrier and adding the trastuzumab to a phosphate buffer. A conjugate of the condensate of resiquimod with the linker SMCC as described above and an anti-CAPRIN-1 antibody was prepared according to an ordinary method with reference to the methods described in U.S. Pat. No. 8,951,528 and JIMD Reports-Case and Research Reports, 2012/5. Using the trastuzumab dissolved in a phosphate buffer, a solution containing SATA-added trastuzumab was obtained in the same way as in Example 4. This solution was further reacted with the condensate prepared above to prepare a solution containing a conjugate of trastuzumab and the resiquimod derivative (trastuzumab conjugate). The obtained trastuzumab conjugate was verified by flow cytometry to exhibit reactivity with human breast cancer cells used in the antitumor effect evaluation. It was further verified by mass spectrometry that the prepared trastuzumab conjugate to be compared, and Conjugates 7 to 14, Conjugates 21 to 28, and Conjugates 45 to 179 prepared in Example 4 using the anti-CAPRIN-1 monoclonal antibodies, have comparable molecule numbers of the immune activator bound therein and the verified conjugates were used in the following evaluation.

For the comparison of the antitumor effect, human breast cancer cells BT474 were mixed with Matrigel (Sigma-Aldrich Corp.) and subcutaneously transplanted at $10^7$ cells/mouse to the mice, which were then grown until tumor became 150 mm³ or larger to prepare cancer-bearing mice. BT474 has been found to express the CAPRIN-1 protein and HER2, which is a target antigen of trastuzumab, on the cell membrane surface.

The conjugates of the anti-CAPRIN-1 antibody (Conjugates 7 to 14, Conjugates 21 to 28, and Conjugates 45 to 179) and the trastuzumab conjugate prepared above were each administered at 10 mg/kg to the tail veins of 10 cancer-bearing mice. The administration was carried out twice a week a total of 13 times. For comparison, the anti-CAPRIN-1 antibodies used in the preparation of the conjugates of the anti-CAPRIN-1 antibody (Conjugates 7 to 14, conjugates 21 to 28, and conjugates 45 to 179), and trastuzumab were administered in the same way as above. PBS(−) was administered to cancer-bearing mice, for a negative control.

The tumor sizes of the cancer-bearing mice after the administration were measured using calipers over time, and tumor volumes were calculated according to an ordinary method based on the expression: (Length of the major axis of tumor)×(Length of the minor axis of tumor)²×0.5. As a result of the evaluation, all the mice given Conjugates 11 and 25 had less than 15% tumor volumes 45 days after the start of the administration relative to the tumor volume of the negative control (100%). The mice given the unconjugated anti-CAPRIN-1 antibodies to be compared had less than 50% tumor volume. From these results, it was shown that the conjugation of the immune activator to the anti-CAPRIN-1 antibody enhanced the antitumor effect of the antibody by 77%. The rate of enhancement was calculated based on the expression: 1−(Tumor volume determined with conjugate/Tumor volume determined with antibody alone)×100(%).

On the other hand, the mice given the trastuzumab conjugate and the mice given the unconjugated trastuzumab to be compared had 53% and 74% tumor volumes, respectively, relative to the tumor volume of the negative control (100%). Thus, the rate of enhancement in antitumor effect by the conjugation of the immune activator to trastuzumab was only less than 29%.

Example 11 Preparation of Conjugate of Anti-CAPRIN-1 Antibody and Immune Activator and Antitumor Effect of the Conjugate Conjugates of humanized antibodies #1 to #8 which were the anti-CAPRIN-1 monoclonal antibodies described in Example 2 with an immune activator DSR-6434 (6-amino-2(butylamino)-9-[[6-[2-(dimethylamino)ethoxy]-3-pyridinyl]methyl]-7,9-dihydro-8H-purin-8-one) (Conjugate 37 to 44) were prepared. Specifically, a condensate of DSR-6434 with succinimidyl 4-(N-maleimidomethyl)cyclohexane-1-carboxylate (SMCC) via the amino group of DSR-6434 was first synthesized, and then, solutions containing conjugates of humanized antibodies #1 to #8 and the immune activator RSR-6434 (Conjugates 37 to 44) were prepared basically according to the method described in Example 4.

The prepared solutions containing Conjugates 37 to 44 were each filtered through a 0.22 μm filter (Merck Millipore Corp.) to prepare the conjugates. The conjugates were assayed for their specific reactivity with the CAPRIN-1 protein in the same way as in Example 5. As a result, the solutions containing Conjugates 37 to 44 each exhibited specific reactivity with the CAPRN-1 protein.

Conjugates 37 to 44 were further assayed for their reactivity with cancer cells by flow cytometry using cancer cells expressing the CAPRIN-1 protein on the cell membrane surface. As a result, all the conjugates exhibited stronger fluorescence intensity than that of the negative control. The conjugates were found to exhibit fluorescence intensity similar to that of the antibodies alone used in the conjugates.

Conjugates 37 to 44 were evaluated for their antitumor effects on cancer-bearing mice. The conjugates of anti-CAPRIN-1 antibody (Conjugates 37 to 44) were each administered at 10 mg/kg to the tail veins of 10 cancer-bearing mice in the same way as the method described in Example 10. The administration was carried out twice a week a total of 16 times. The anti-CAPRIN-1 antibodies used in the preparation of the conjugates were administered in the same way as above. PBS (−) was administered to cancer-bearing mice, for a negative control.

The tumor sizes of the cancer-bearing mice after the administration were measured using calipers over time, and tumor volumes were calculated according to an ordinary method based on the expression: (Length of the major axis of tumor)×(Length of the minor axis of tumor)$^2$×0.5. As a result of the evaluation, all the mice given Conjugates 37 to 44 had less than 32% tumor volumes 50 days after the start of the administration relative to the tumor volume of the negative control (100%). The mice given the unconjugated anti-CAPRIN-1 antibodies to be compared had less than 50% tumor volume. From these results, the conjugation of the immune activator to the anti-CAPRIN-1 antibody was shown to enhance the antitumor effect by more than 35%. The rate of enhancement was calculated based on the expression: 1−(Tumor volume determined with conjugate/Tumor volume determined with antibody alone)×100(%).

The invention claimed is:

1. A conjugate of an antibody linked to an immune activator,
wherein the antibody or the fragment thereof has immunological reactivity with a CAPRIN-1 protein of any of even-numbered SEQ ID NOs among SEQ ID NO: 2 to 30, wherein the immune activator is an imidazoquinoline compound which is a TLR7- or TLR8-binding ligand or agonist, and
wherein the antibody is linked to the immune activator via a linker;
wherein said imidazoqjuinoline compound is 4-amino-2-(ethoxymethyl)-a,a-dimethyl-1H-imidazo[r4,5-c]quinoline-1-ethanol or 1-(2(2-aminoethoxy)-2-methylpropyl)-2-(ethoxymethyl)-1H-imidazo[4,5-c~quinolin-4-amine; and
wherein said linker is maleimidocaproyl-valine-citrulline-p-aminobenzyloxycarbonyl (MC-val-Cit-PAB) or succinimidyl 4-(N-maleimidomethyl)cyclohexane-1-carboxylate (SMCC).

2. The conjugate according to claim 1, wherein:
i) said imidazoquinoline compound is 4-amino-2-(ethoxymethyl)-a,a-dimethyl-1H-imidazo[4,5-c]quinoline-1-ethanol, and said linker is MC-val-Cit-PAB; or
ii) said imidazoquinoline compound is 1-(2(2-aminoethoxy)-2-methylpropyl)-2-(ethoxymethyl)-1H-imidazo[4,5-c]quinoline-4-amine, and said linker is SMCC.

3. The conjugate according to claim 1, wherein the antibody has immunological reactivity with a partial polypeptide of the CAPRIN-1 protein, wherein the partial polypeptide consists of any of SEQ ID NO: 31 to 35 and 296 to 299, 308, and 309.

4. The conjugate according to claim 1, wherein the antibody is a monoclonal antibody or a polyclonal antibody.

5. The conjugate according to claim 1, wherein the antibody is a humanized antibody or a chimeric antibody.

6. The conjugate according to claim 1, wherein the antibody is any of the following (A) to (M):
(A) an antibody, which comprises a heavy chain variable region comprising complementarity-determining regions of SEQ ID NO: 36, 37, and 38 (CDR1, CDR2, and CDR3, respectively) and a light chain variable region comprising complementarity-determining regions of SEQ ID NO: 40, 41, and 42 (CDR1, CDR2, and CDR3, respectively) and has immunological reactivity with the CAPRIN-1 protein,
(B) an antibody, which comprises a heavy chain variable region comprising complementarity-determining regions of SEQ ID NO: 44, 45, and 46 (CDR1, CDR2, and CDR3, respectively) and a light chain variable region comprising complementarity-determining regions of SEQ ID NO: 48, 49, and 50 (CDR1, CDR2, and CDR3, respectively) and has immunological reactivity with the CAPRIN-1 protein,
(C) an antibody, which comprises a heavy chain variable region comprising complementarity-determining regions of SEQ ID NO: 52, 53, and 54 (CDR1, CDR2, and CDR3, respectively) and a light chain variable region comprising complementarity-determining regions of SEQ ID NO: 56, 57, and 58 (CDR1, CDR2, and CDR3, respectively) and has immunological reactivity with the CAPRIN-1 protein, (D) an antibody, which comprises a heavy chain variable region comprising complementarity-determining regions of SEQ ID NO: 60, 61, and 62 (CDR1, CDR2, and CDR3, respectively) and a light chain variable region comprising complementarity-determining regions of SEQ ID NO: 64, 65, and 66 (CDR1, CDR2, and CDR3, respectively) and has immunological reactivity with the CAPRIN-1 protein, (E) an antibody, which comprises a heavy chain variable region comprising complementarity-determining regions of SEQ ID NO: 170, 171, and 172 (CDR1, CDR2, and CDR3, respectively) and a light chain variable region comprising complementarity-determining regions of SEQ ID NO: 173, 174, and 175 (CDR1, CDR2, and CDR3, respectively) and has immunological reactivity with the CAPRIN-1 protein, (F) an antibody, which comprises a heavy chain variable region comprising complementarity-determining regions of SEQ ID NO: 176, 177, and 178 (CDR1, CDR2, and CDR3, respectively) and a light chain variable region comprising complementarity-determining regions of SEQ ID NO: 179, 180, and 181 (CDR1, CDR2, and CDR3, respectively) and has immunological reactivity with the CAPRIN-1 protein, (G) an antibody, which comprises a heavy chain variable region comprising complementarity-determining regions of SEQ ID NO: 182, 183, and 184 (CDR1, CDR2, and CDR3, respectively) and a light chain variable region comprising complementarity-determining regions of SEQ ID NO: 185, 186, and 187 (CDR1, CDR2, and CDR3, respectively) and has immunological reactivity with the CAPRIN-1 protein, (H) an antibody, which comprises a heavy chain variable region comprising complementarity-determining regions of SEQ ID NO: 188, 189, and 190 (CDR1, CDR2, and CDR3, respectively) and a light chain variable region comprising complementarity-determining regions of SEQ ID NO: 191, 192, and 193 (CDR1, CDR2, and CDR3, respectively) and has immunological reactivity with the CAPRIN-1 protein, (I) an antibody, which comprises a heavy chain variable region comprising complementarity-determining regions of SEQ ID NO: 146, 147, and 148 (CDR1, CDR2, and CDR3, respectively) and a light chain variable region comprising complementarity-determining regions of SEQ ID NO: 149, 150, and 151 (CDR1, CDR2, and CDR3, respectively) and has immunological reactivity with the CAPRIN-1 protein, (J) an antibody, which comprises a heavy chain variable region comprising complementarity-determining regions of SEQ ID NO: 272, 273, and 274 (CDR1, CDR2, and CDR3, respectively) and a light chain variable region comprising complementarity-determining regions of SEQ ID NO: 275, 276, and 277 (CDR1, CDR2, and CDR3, respectively) and has immunological reactivity with the CAPRIN-1 protein, (K) an antibody, which comprises a heavy chain variable region comprising complementarity-determining regions of SEQ ID NO: 290, 291, and 292 (CDR1, CDR2, and CDR3, respectively) and a light chain variable region comprising complementarity-determining regions of SEQ ID NO: 293, 294, and 295 (CDR1, CDR2, and CDR3, respectively) and has immunological reactivity with the CAPRIN-1 protein, (L) an antibody, which comprises a heavy chain variable region comprising complementarity-determining regions of SEQ ID NO: 300, 301, and 302 (CDR1, CDR2, and CDR3, respectively) and a light chain variable region comprising complementarity-determining regions of SEQ ID NO: 304, 305, and 306 (CDR1, CDR2, and CDR3, respectively) and has immunological reactivity with the CAPRIN-1 protein, and (M) an antibody, which comprises a heavy chain variable region comprising complementarity-determining regions of SEQ ID NO: 134, 135, and 136 (CDR1, CDR2, and CDR3, respectively) and a light chain variable region comprising complementarity-determining regions of SEQ ID NO: 137, 138, and 139 (CDR1, CDR2, and CDR3, respectively) and has immunological reactivity with the CAPRIN-1 protein.

7. The conjugate according to claim 1, wherein the antibody is any of the following (a) to (al):

(a) an antibody, comprising a heavy chain variable region comprising the amino acid sequence of SEQ ID NO: 39 and a light chain variable region comprising the amino acid sequence of SEQ ID NO: 43, (b) an antibody, comprising a heavy chain variable region comprising the amino acid sequence of SEQ ID NO: 47 and a light chain variable region comprising the amino acid sequence of SEQ ID NO: 51, (c) an antibody, comprising a heavy chain variable region comprising the amino acid sequence of SEQ ID NO: 55 and a light chain variable region comprising the amino acid sequence of SEQ ID NO: 59, (d) an antibody, comprising a heavy chain variable region comprising the amino acid sequence of SEQ ID NO: 63 and a light chain variable region comprising the amino acid sequence of SEQ ID NO: 67, (e) an antibody, comprising a heavy chain variable region comprising the amino acid sequence of SEQ ID NO: 68 and a light chain variable region comprising the amino acid sequence of SEQ ID NO: 69, (f) an antibody, comprising a heavy chain variable region comprising the amino acid sequence of SEQ ID NO: 70 and a light chain variable region comprising the amino acid sequence of SEQ ID NO: 71, (g) an antibody, comprising a heavy chain variable region comprising the amino acid sequence of SEQ ID NO: 72 and a light chain variable region comprising the amino acid sequence of SEQ ID NO: 73, (h) an antibody, comprising a heavy chain variable region comprising the amino acid sequence of SEQ ID NO: 74 and a light chain variable region comprising the amino acid sequence of SEQ ID NO: 75, (i) an antibody, comprising a heavy chain variable region comprising the amino acid sequence of SEQ ID NO: 76 and a light chain variable region comprising the amino acid sequence of SEQ ID NO: 77, (j) an antibody, comprising a heavy chain variable region comprising the amino acid sequence of SEQ ID NO: 78 and a light chain variable region comprising the amino acid sequence of SEQ ID NO: 79, (k) an antibody, comprising a heavy chain variable region comprising the amino acid sequence of SEQ ID NO: 80 and a light chain variable region comprising the amino acid sequence of SEQ ID NO: 81, (l) an antibody, comprising a heavy chain variable region comprising the amino acid sequence of SEQ ID NO: 82 and a light chain variable region comprising the amino acid sequence of SEQ ID NO: 83,
(m) an antibody, comprising a heavy chain variable region comprising the amino acid sequence of SEQ ID NO: 84 and a light chain variable region comprising the amino acid sequence of SEQ ID NO: 85,
(n) an antibody, comprising a heavy chain variable region comprising the amino acid sequence of SEQ ID NO: 86 and a light chain variable region comprising the amino acid sequence of SEQ ID NO: 87,
(o) an antibody, comprising a heavy chain variable region comprising the amino acid sequence of SEQ ID NO: 88 and a light chain variable region comprising the amino acid sequence of SEQ ID NO: 89,
(p) an antibody, comprising a heavy chain variable region comprising the amino acid sequence of SEQ ID NO: 90 and a light chain variable region comprising the amino acid sequence of SEQ ID NO: 91,
(q) an antibody, comprising a heavy chain variable region comprising the amino acid sequence of SEQ ID NO: 92 and a light chain variable region comprising the amino acid sequence of SEQ ID NO: 93,
(r) an antibody, comprising a heavy chain variable region comprising the amino acid sequence of SEQ ID NO: 94 and a light chain variable region comprising the amino acid sequence of SEQ ID NO: 95,
(s) an antibody, comprising a heavy chain variable region comprising the amino acid sequence of SEQ ID NO: 96 and a light chain variable region comprising the amino acid sequence of SEQ ID NO: 97,
(t) an antibody, comprising a heavy chain variable region comprising the amino acid sequence of SEQ ID NO: 98 and a light chain variable region comprising the amino acid sequence of SEQ ID NO: 99,
(u) an antibody, comprising a heavy chain variable region comprising the amino acid sequence of SEQ ID NO: 100 and a light chain variable region comprising the amino acid sequence of SEQ ID NO: 101,
(v) an antibody, comprising a heavy chain variable region comprising the amino acid sequence of SEQ ID NO: 102 and a light chain variable region comprising the amino acid sequence of SEQ ID NO: 103,
(w) an antibody, comprising a heavy chain variable region comprising the amino acid sequence of SEQ ID NO: 104 and a light chain variable region comprising the amino acid sequence of SEQ ID NO: 105,
(x) an antibody or a fragment thereof, comprising a heavy chain variable region comprising the amino acid sequence of SEQ ID NO: 106 and a light chain variable region comprising the amino acid sequence of SEQ ID NO: 107,
(y) an antibody, comprising a heavy chain variable region comprising the amino acid sequence of SEQ ID NO: 108 and a light chain variable region comprising the amino acid sequence of SEQ ID NO: 109,
(z) an antibody, comprising a heavy chain variable region comprising the amino acid sequence of SEQ ID NO: 110 and a light chain variable region comprising the amino acid sequence of SEQ ID NO: 111,
(aa) an antibody, comprising a heavy chain variable region comprising the amino acid sequence of SEQ ID NO: 112 and a light chain variable region comprising the amino acid sequence of SEQ ID NO: 113,
(ab) an antibody, comprising a heavy chain variable region comprising the amino acid sequence of SEQ ID NO: 114 and a light chain variable region comprising the amino acid sequence of SEQ ID NO: 115,
(ac) an antibody, comprising a heavy chain variable region comprising the amino acid sequence of SEQ ID NO: 116 and a light chain variable region comprising the amino acid sequence of SEQ ID NO: 117,
(ad) an antibody, comprising a heavy chain variable region comprising the amino acid sequence of SEQ ID NO: 118 and a light chain variable region comprising the amino acid sequence of SEQ ID NO: 119,
(ae) an antibody, comprising a heavy chain variable region comprising the amino acid sequence of SEQ ID NO: 120 and a light chain variable region comprising the amino acid sequence of SEQ ID NO: 121,
(af) an antibody, comprising a heavy chain variable region comprising the amino acid sequence of SEQ ID NO: 122 and a light chain variable region comprising the amino acid sequence of SEQ ID NO: 123,
(ag) an antibody, comprising a heavy chain variable region comprising the amino acid sequence of SEQ ID NO: 124 and a light chain variable region comprising the amino acid sequence of SEQ ID NO: 125,
(ah) an antibody, comprising a heavy chain variable region comprising the amino acid sequence of SEQ ID NO: 126 and a light chain variable region comprising the amino acid sequence of SEQ ID NO: 127,
(ai) an antibody, comprising a heavy chain variable region comprising the amino acid sequence of SEQ ID NO: 128 and a light chain variable region comprising the amino acid sequence of SEQ ID NO: 129,
(aj) an antibody, comprising a heavy chain variable region comprising the amino acid sequence of SEQ ID NO: 130 and a light chain variable region comprising the amino acid sequence of SEQ ID NO: 131,
(ak) an antibody, comprising a heavy chain variable region comprising the amino acid sequence of SEQ ID NO: 132 and a light chain variable region comprising the amino acid sequence of SEQ ID NO: 133, and
(al) an antibody, comprising a heavy chain variable region comprising the amino acid sequence of SEQ ID NO: 303 and a light chain variable region comprising the amino acid sequence of SEQ ID NO: 307.

8. A pharmaceutical composition comprising the conjugate according to claim 1 as an active ingredient and a pharmaceutically acceptable carrier.

9. The pharmaceutical composition according to claim 8, wherein the cancer is a cancer expressing a CAPRIN-1 protein on the cell membrane surface.

10. The pharmaceutical composition according to claim 8, wherein the cancer is breast cancer, kidney cancer, pancreatic cancer, colorectal cancer, lung cancer, brain tumor, stomach cancer, uterine cancer, ovary cancer, prostate cancer, bladder cancer, esophagus cancer, leukemia, lymphoma, liver cancer, gallbladder cancer, sarcoma, mastocytoma, melanoma, adrenal cortex cancer, Ewing's tumor, Hodgkin's lymphoma, mesothelioma, multiple myeloma, testicle cancer, thyroid cancer, or head and neck cancer.

11. A method for treating a cancer expressing a CAPRIN-1 protein on the cell membrane surface, comprising administering an effective amount of the conjugate according to claim 1 or a pharmaceutical composition comprising the conjugate as an active ingredient and a pharmaceutically acceptable carrier to a subject in need thereof.

* * * * *